(12) United States Patent
Gardiner et al.

(10) Patent No.: US 8,852,600 B2
(45) Date of Patent: Oct. 7, 2014

(54) **CODON-OPTIMIZED DNA MOLECULES ENCODING THE RECEPTOR BINDING DOMAINS OF *CLOSTRIDIUM DIFFICILE* TOXINS A AND B, AND METHODS OF USE THEREOF**

(75) Inventors: David F. Gardiner, Wayne, PA (US); Yaoxing Huang, Brooklyn, NY (US)

(73) Assignees: The Rockefeller University, New York, NY (US); Cornell University, Ithaca, NY (US)

( * ) Notice: Subject to any disclaimer, the term of this patent is extended or adjusted under 35 U.S.C. 154(b) by 1183 days.

(21) Appl. No.: 12/308,150

(22) PCT Filed: Jun. 7, 2007

(86) PCT No.: PCT/US2007/013535
§ 371 (c)(1),
(2), (4) Date: Apr. 8, 2009

(87) PCT Pub. No.: WO2007/146139
PCT Pub. Date: Dec. 21, 2007

(65) Prior Publication Data
US 2010/0278868 A1      Nov. 4, 2010

Related U.S. Application Data

(60) Provisional application No. 60/812,489, filed on Jun. 8, 2006.

(51) Int. Cl.
*A61K 39/00* (2006.01)
*A61K 39/38* (2006.01)
*A61K 39/08* (2006.01)
*C12N 15/00* (2006.01)
*C12N 1/20* (2006.01)
*C07H 21/04* (2006.01)
*C07K 14/33* (2006.01)

(52) U.S. Cl.
CPC ..................................... *C07K 14/33* (2013.01)
USPC ................. 424/184.1; 424/239.1; 424/247.1; 435/320.1; 435/252.7; 536/23.7

(58) Field of Classification Search
None
See application file for complete search history.

(56) References Cited

U.S. PATENT DOCUMENTS 6,635,260 B1 * 10/2003 Gerding ..................... 424/247.1
6,733,760 B1 *  5/2004 Wilkins et al. ............. 424/247.1

OTHER PUBLICATIONS

Dove et al., Infection and Immunity, 1990; 58(2): 480-488.*
Hoppner (Horm Re. 2002, 58 Suppl. 3:7-15).*

* cited by examiner

*Primary Examiner* — Gary Nickol
*Assistant Examiner* — Lakia Tongue
(74) *Attorney, Agent, or Firm* — Hoffmann & Baron, LLP

(57) ABSTRACT

In one aspect, the invention provides a DNA molecule. The DNA molecule includes a nucleotide sequence that encodes the receptor-binding domain of *Clostridium difficile* toxin A or toxin B in which at least about 10% of the in-frame codons for each amino acid residue has a higher percentage use in the human genome than the corresponding in-frame codons of *C. difficile* toxin A or toxin B having a known sequence. Methods for generating antibodies to *Clostridium difficile* toxin A or toxin B, methods for reducing the risk of a *C. difficile* infection, and methods for treating a *C. difficile* are also provided.

1 Claim, 43 Drawing Sheets

Figure 1.

```
   1 msliskeeli klaysirpre neyktiltnl deynklttnn nenkylqlkk lnesidvfmn
  61 kyktssrnra lsnlkkdilk eviliknsnt spveknlhfv wiggevsdia leyikqwadi
 121 naeyniklwy dseaflvntl kkaivesstt ealqlleeei qnpqfdnmkf ykkrmefiyd
 181 rqkrfinyyk sqinkptvpt iddiikshlv seynrdetvl esyrtnslrk insnhgidir
 241 anslfteqel lniysqelln rgnlaaasdi vrllalknfg gvyldvdmlp gihsdlfkti
 301 srpssigldr wemikleaim kykkyinnyt senfdkldqq lkdnfkliie sksekseifs
 361 klenlnvsdl eikiafalgs vinqaliskq gsyltnlvie qvknryqfln qhlnpaiesd
 421 nnftdttkif hdslfnsata ensmfltkia pylqvgfmpe arstislsgp gayasayydf
 481 inlqentiek tlkasdlief kfpennlsql teqeinslws fdqasakyqf ekyvrdytgg
 541 slsedngvdf nkntaldkny llnnkipsnn veeagsknyv hyiiqlqgdd isyeatcnlf
 601 sknpknsiii qrnmnesaks yflsddgesi lelnkyripe rlknkekvkv tfighgkdef
 661 ntsefarlsv dslsneissf ldtikldisp knvevnllgc nmfsydfnve etypgkllls
 721 imdkitstlp dvnknsitig anqyevrins egrkellahs gkwinkeeai msdlsskeyi
 781 ffdsidnklk aksknipgla sisediktll ldasvspdtk filnnlklni essigdyiyy
 841 eklepvknii hnsiddlide fnllenvsde lyelkklnnl dekylisfed isknnstysv
 901 rfinksnges vyvetekeif skysehitke istiknsiit dvngnlldni qldhtsqvnt
 961 lnaaffiqsl idyssnkdvl ndlstsvkvq lyaqlfstgl ntiydsiqlv nlisnavndt
1021 invlptiteg ipivstildg inlgaaikel ldehdpllkk eleakvgvla inmslsiaat
1081 vasivgigae vtifllpiag isagipslvn nelilhdkat svvnyfnhls eskkygplkt
1141 eddkilvpid dlviseidfn nnsiklgtcn ilameggsgh tvtgnidhff sspsisship
1201 slsiysaigi etenldfskk immlpnapsr vfwwetgavp glrslendgt rlldsirdly
1261 pgkfywrfya ffdyaittlk pvyedtniki kldkdtrnfi mptittneir nklsysfdga
1321 ggtyslllss ypistninls kddlwifnid nevreisien gtikkgklik dvlskidink
1381 nkliignqti dfsgdidnkd ryifltceld dkisliiein lvaksysll1 sgdknylisn
1441 lsntiekint lgldskniay nytdesnnky fgaisktsqk siihykkdsk nilefyndst
1501 lefnskdfia edinvfmkdd intitgkyyv dnntdksidf sislvsknqv kvnglylnes
1561 vyssyldfvk nsdghhntsn fmnlfldnis fwklfgfeni nfvidkyftl vgktnlgyve
1621 ficdnnknid iyfgewktss skstifsgng rnvvvepiyn pdtgedists ldfsyeplyg
1681 idryinkvli apdlytslin intnyysney ypeiivlnpn tfhkkvninl dsssfeykws
1741 tegsdfilvr yleesnkkil qkirikgils ntqsfnkmsi dfkdikklsl gyimsnfksf
1801 nseneldrdh lgfkiidnkt yyydedsklv kglininnsl fyfdpiefnl vtgwqtingk
1861 kyyfdintga altsykiing khfyfnndgv mqlgvfkgpd gfeyfapant qnnniegqai
1921 vyqskfltln gkkyyfdnns kavtgwriin nekyyfnpnn aiaavglqvi dnnkyyfnpd
1981 taiiskgwqt vngsryyfdt dtaiafngyk tidgkhfyfd sdcvvkigvf stsngfeyfa
2041 pantynnnie gqaivyqskf ltlngkkyyf dnnskavtgl qtidskkyyf ntntaeaatg
2101 wqtidgkkyy fntntaeaat gwqtiidgkky yfntntaias tgytiingkh fyfntdgimq
2161 igvfkgpngf eyfapantda nniegqaily qnefltlngk kyyfgsdska vtgwriinnk
2221 kyyfnpnnai aaihlctinn dkyyfsydgi lqngyitier nnfydanne skmvtgvfkg
2281 pngfeyfapa nthnnniegq aivyqnkflt lngkkyyfdn dskavtgwqt idgkkyyfnl
2341 ntaeaatgwq tidgkkyyfn lntaeaatgw qtidgkkyyf ntntfiastg ytsingkhfy
2401 fntdgimqig vfkgpngfey fapantdann ieggailyqn kfltlngkky yfgsdskavt
2461 glrtidgkky yfntntavav tgwqtingkk yyfntntsia stgytiisgk hfyfntdgim
2521 qigvfkgpdg feyfapantd anniegqair yqnrflylhd niyyfgnnsk aatgwvtidg
2581 nryyfepnta mgangyktid nknfyfrngl pqigvfkgsn gfeyfapant danniegqai
2641 ryqnrflhll gkiyyfgnns kavtgwqtin gkvyyfmpdt amaaagglfe idgviyffgv
2701 dgvkapgiyg (SEQ. ID. NO.: 1)
```

Figure 2.

```
   1 msliskeeli klaysirpre neyktiltnl deynklttnn nenkylqlkk lnesidvfmn
  61 kyktssrnra lsnlkkdilk eviliknsnt spveknlhfv wiggevsdia leyikqwadi
 121 naeyniklwy dseaflvntl kkaivesstt ealqlleeei qnpqfdnmkf ykkrmefiyd
 181 rqkrfinyyk sqinkptvpt iddiikshlv seynrdetvl esyrtnslrk insnhgidir
 241 anslfteqel lniysqelln rgnlaaasdi vrllalknfg gvyldvdmlp gihsdlfkti
 301 srpssigldr wemikleaim kykkyinnyt senfdkldqq lkdnfkliie sksekseifs
 361 klenlnvsdl eikiafalgs vinqaliskq gsyltnlvie qvknryqfln qhlnpaiesd
 421 nnftdttkif hdslfnsata ensmfltkia pylqvgfmpe arstislsgp gayasayydf
 481 inlqentiek tlkasdlief kfpennlsql teqeinslws fdqasakyqf ekyvrdytgg
 541 slsedngvdf nkntaldkny llnnkipsnn veeagsknyv hyiiqlqgdd isyeatcnlf
 601 sknpknsiii qrnmnesaks yflsddgesi lelnkyripe rlknkekvkv tfighgkdef
 661 ntsefarlsv dslsneissf ldtikldisp knvevnllgc nmfsydfnve etypgkllls
 721 imdkitstlp dvnknsitig anqyevrins egrkellahs gkwinkeeai msdlsskeyi
 781 ffdsidnklk aksknipgla sisediktll ldasvspdtk filnnlklni essigdyiyy
 841 eklepvknii hnsiddlide fnllenvsde lyelkklnnl dekylisfed isknnstysv
 901 rfinksnges vyvetekeif skysehitke istiknsiit dvngnlldni qldhtsqvnt
 961 lnaaffiqsl idyssnkdvl ndlstsvkvq lyaqlfstgl ntiydsiqlv nlisnavndt
1021 invlptiteg ipivstildg inlgaaikel ldehdpllkk eleakvgvla inmslsiaat
1081 vasivgigae vtifllpiag isagipslvn nelilhdkat svvnyfnhls eskkygplkt
1141 eddkilvpid dlviseidfn nnsiklgtcn ilameggsgh tvtgnidhff sspsisship
1201 slsiysaigi etenldfskk immlpnapsr vfwwetgavp glrslendgt rlldsirdly
1261 pgkfywrfya ffdyaittlk pvyedtniki kldkdtrnfi mptittneir nklsysfdga
1321 ggtysllls ypistninls kddlwifnid nevreisien gtikkgklik dvlskidink
1381 nkliignqti dfsgdidnkd ryifltceld dkisliiein lvaksyslll sgdknylisn
1441 lsntiekint lgldskniay nytdesnnky fgaisktsqk siihykkdsk nilefyndst
1501 lefnskdfia edinvfmkdd intitgkyyv dnntdksidf sislvsknqv kvnglylnes
1561 vyssyldfvk nsdghhntsn fmnlfldnis fwklfgfeni nfvidkyftl vgktnlgyve
1621 ficdnnknid iyfgewktss skstifsgng rnvvvepiyn pdtgedists ldfsyeplyg
1681 idryinkvli apdlytslin intnyysney ypeiivlnpn tfhkkvninl dsssfeykws
1741 tegsdfilvr yleesnkkil qkirikgils ntqsfnkmsi dfkdikklsl gyimsnfksf
1801 nseneldrdh lgfkiidnkt yyydedsklv kglininnsl fyfdpiefnl vtgwqtingk
1861 kyyfdintga altsykiing khfyfnndgv mqlgvfkgpd gfeyfapant qnnniegqai
1921 vyqskfltln gkkyyfdnns kavtgwriin nekyyfnpnn aiaavglqvi dnnkyyfnpd
1981 taiiskgwqt vngsryyfdt dtaiafngyk tidgkhfyfd sdcvvkigvf stsngfeyfa
2041 pantynnnie gqaivyqskf ltlngkkyyf dnnskavtgw qtidskkyyf ntntaeaatg
2101 wqtidgkkyy fntntaeaat gwqtidgkky yfntntaias tgytiingkh fyfntdgimq
2161 igvfkgpngf eyfapantda nniegqaily qnefltlngk kyyfgsdska vtgwriinnk
2221 kyyfnpnnai aaihlctinn dkyyfsydgi lqngyitier nnfyfdanne skmvtgvfkg
2281 pngfeyfapa nthnnniegq aivyqnkflt lngkkyyfdn dskavtgwqt idgkkyyfnl
2341 ntaeaatgwq tidgkkyyfn lntaeaatgw qtidgkkyyf ntntfiastg ytsingkhfy
2401 fntdgimqig vfkgpngfey fapantdann iegqailyqn kfltlngkky yfgsdskavt
2461 glrtidgkky yfntntavav tgwqtingkk yyfntntsia stgytiisgk hfyfntdgim
2521 qigvfkgpdg feyfapantd anniegqair yqnrflylhd niyyfgnnsk aatgwvtidg
2581 nryyfepnta mgangyktid nknfyfrngl pqigvfkgsn gfeyfapant danniegqai
2641 ryqnrflhll gkiyyfgnns kavtgwqtin gkvyyfmpdt amaaagglfe idgviyffgv
2701 dgvkapgiyg (SEQ. ID. NO.: 3)
```

Figure 3.

```
   1 msliskeeli klaysirpre neyktiltnl deynklttnn nenkylqlkk lnesidvfmn
  61 kyktssrnra lsnlkkdilk eviliknsnt spveknlhfv wiggevsdia leyikqwadi
 121 naeyniklwy dseaflvntl kkaivesstt ealqlleeei qnpqfdnmkf ykkrmefiyd
 181 rqkrfinyyk sqinkptvpt iddiikshlv seynrdetvl esyrtnslrk insnhgidir
 241 anslfteqel lniysqelln rgnlaaasdi vrllalknfg gvyldvdmlp gihsdlfkti
 301 srpssigldr wemikleaim kykkyinnyt senfdkldqq lkdnfkliie sksekseifs
 361 klenlnvsdl eikiafalgs vinqaliskq gsyltnlvie qvknryqfln qhlnpaiesd
 421 nnftdttkif hdslfnsata ensmfltkia pylqvgfmpe arstislsgp gayasayydf
 481 inlqentiek tlkasdlief kfpennlsql teqeinslws fdqasakyqf ekyvrdytgg
 541 slsedngvdf nkntaldkny llnnkipsnn veeagsknyv hyiiqlqgdd isyeatcnlf
 601 sknpknsiii qrnmnesaks yflsddgesi lelnkyripe rlknkekvkv tfighgkdef
 661 ntsefarlsv dslsneissf ldtikldisp knvevnllgc nmfsydfnve etypgkllls
 721 imdkitstlp dvnknsitig anqyevrins egrkellahs gkwinkeeai msdlsskeyi
 781 ffdsidnklk aksknipgla sisediktll ldasvspdtk filnnlklni essigdyiyy
 841 eklepvknii hnsiddlide fnllenvsde lyelkklnnl dekylisfed isknnstysv
 901 rfinksnges vyvetekeif skysehitke istiknsiit dvngnlldni qldhtsqvnt
 961 lnaaffiqsl idyssnkdvl ndlstsvkvq lyaqlfstgl ntiydsiqlv nlisnavndt
1021 invlptiteg ipivstildg inlgaaikel ldehdpllkk eleakvgvla inmslsiaat
1081 vasivgigae vtifllpiag isagipslvn nelilhdkat svvnyfnhls eskkygplkt
1141 eddkilvpid dlviseidfn nnsiklgtcn ilameggsgh tvtgnidhff sspsisship
1201 slsiysaigi etenldfskk immlpnapsr vfwwetgavp glrslendgt rlldsirdly
1261 pgkfywrfya ffdyaittlk pvyedtniki kldkdtrnfi mptittneir nklsysfdga
1321 ggtyslllss ypistninls kddlwifnid nevreisien gtikkgklik dvlskidink
1381 nkliignqti dfsgdidnkd ryifltceld dkisliiein lvaksyslll sgdknylisn
1441 lsntiekint lgldskniay nytdesnnky fgaisktsqk siihykkdsk nilefyndst
1501 lefnskdfia edinvfmkdd intitgskyv dnntdksidf sislvsknqv kvnglylnes
1561 vyssyldfvk nsdghhntsn fmnlfldnis fwklfgfeni nfvidkyftl vgktnlgyve
1621 ficdnnknid iyfgewktss skstifsgng rnvvvepiyn pdtgedists ldfsyeplyg
1681 idryinkvli apdlytslin intnyysney ypeiivlnpn tfhkkvninl dsssfeykws
1741 tegsdfilvr yleesnkkil qkirikgils ntqsfnkmsi dfkdikklsl gyimsnfksf
1801 nseneldrdh lgfkiidnkt yyydedsklv kglininnsl fyfdpiefnl vtgwqtingk
1861 kyyfdintga altsykiing khfyfnndgv mqlgvfkgpd gfeyfapant qnnniegqai
1921 vyqskfltln gkkyyfdnns kavtgwriin nekyyfnpnn aiaavglqvi dnnkyyfnpd
1981 taiiskgwqt vngsryyfdt dtaiafngyk tidgkhfyfd sdcvvkigvf stsngfeyfa
2041 pantynnnie gqaivyqskf ltlngkkyyf dnnskavtgw qtidskkyyf ntntaeaatg
2101 wqtidgkkyy fntntaeaat gwqtidgkky yfntntaias tgytiingkh fyfntdgimq
2161 igvfkgpngf eyfapantda nniegqaily qnefltlngk kyyfgsdska vtgwriinnk
2221 kyyfnpnnai aaihlctinn dkyyfsydgi lqngyitier nnfyfdanne skmvtgvfkg
2281 pngfeyfapa nthnnniegq aivyqnkflt lngkkyyfdn dskavtgwqt idgkkyyfnl
2341 ntaeaatgwq tidgkkyyfn lntaeaatgw qtidgkkyyf ntntfiastg ytsingkhfy
2401 fntdgimqig vfkgpngfey fapantdann iegqailyqn kfltlngkky yfgsdskavt
2461 glrtidgkky yfntntavav tgwqtiisgk yyfntntsia stgytiisgk hfyfntdgim
2521 qigvfkgpdg feyfapantd anniegqair yqnrflylhd niyyfgnnsk aatgwvtidg
2581

Figure 4.

```
   1 msliskeeli klaysirpre neyktiltnl deynklttnn nenkylqlkk lnesidvfmn
  61 kyktssrnra lsnlkkdilk eviliknsnt spveknlhfv wiggevsdia leyikqwadi
 121 naeyniklwy dseaflvntl kkaivesstt ealqlleeei qnpqfdnmkf ykkrmefiyd
 181 rqkrfinyyk sqinkptvpt iddiikshlv seynrdetvl esyrtnslrk insnhgidir
 241 anslfteqel lniysqelln rgnlaaasdi vrllalknfg gvyldvdmlp gihsdlfkti
 301 srpssigldr wemikleaim kykkyinnyt senfdkldqq lkdnfkliie sksekseifs
 361 klenlnvsdl eikiafalgs vinqaliskq gsyltnlvie qvknryqfln qhlnpaiesd
 421 nnftdttkif hdslfnsata ensmfltkia pylqvgfmpe arstislsgp gayasayydf
 481 inlqentiek tlkasdlief kfpennlsql teqeinslws fdqasakyqf ekyvrdytgg
 541 slsedngvdf nkntaldkny llnnkipsnn veeagsknyv hyiiqlqgdd isyeatcnlf
 601 sknpknsiii qrnmnesaks yflsddgesi lelnkyripe rlknkekvkv tfighgkdef
 661 ntsefarlsv dslsneissf ldtikldisp knvevnllgc nmfsydfnve etypgkllls
 721 imdkitstlp dvnknsitig anqyevrins egrkellahs gkwinkeeai msdlsskeyi
 781 ffdsidnklk aksknipgla sisediktll ldasvspdtk filnnlklni essigdyiyy
 841 eklepvknii hnsiddlide fnllenvsde lyelkklnnl dekylisfed isknnstysv
 901 rfinksnges vyvetekeif skysehitke istiknsiit dvngnlldni qldhtsqvnt
 961 lnaaffiqsl idyssnkdvl ndlstsvkvq lyaqlfstgl ntiydsiqlv nlisnavndt
1021 invlptiteg ipivstildg inlgaaikel ldehdpllkk eleakvgvla inmslsiaat
1081 vasivgigae vtifllpiag isagipslvn nelilhdkat svvnyfnhls eskkygplkt
1141 eddkilvpid dlviseidfn nnsiklgtcn ilameggsgh tvtgnidhff sspsisship
1201 slsiysaigi etenldfskk immlpnapsr vfwwetgavp glrslendgt rlldsirdly
1261 pgkfywrfya ffdyaittlk pvyedtniki kldkdtrnfi mptittneir nklsysfdga
1321 ggtyslllss ypistninls kddlwifnid nevreisien gtikkgklik dvlskidink
1381 nkliignqti dfsgdidnkd ryifltceld dkisliiein lvaksyslll sgdknylisn
1441 lsntiekint lgldskniay nytdesnnky fgaisktsqk siihykkdsk nilefyndst
1501 lefnskdfia edinvfmkdd intitgkyyv dnntdksidf sislvsknqv kvnglylnes
1561 vyssyldfvk nsdghhntsn fmnlfldnis fwklfgfeni nfvidkyftl vgktnlgyve
1621 ficdnnknid iyfgewktss skstifsgng rnvvvepiyn pdtgedists ldfsyeplyg
1681 idryinkvli apdlytslin intnyysney ypeiivlnpn tfhkkvninl dsssfeykws
1741 tegsdfilvr yleesnkkil qkirikgils ntqsfnkmsi dfkdikklsl gyimsnfksf
1801 nseneldrdh lgfkiidnkt yyydedsklv kglininnsl fyfdpiefnl vtgwqtingk
1861 kyyfdintga altsykiing khfyfnndgv mqlgvfkgpd gfeyfapant qnnniegqai
1921 vyqskfltln gkkyyfdnns kavtgwriin nekyyfnpnn aiaavglqvi dnnkyyfnpd
1981 taiiskgwqt vngsryyfdt dtaiafngyk tidgkhfyfd sdcvvkigvf stsngfeyfa
2041 pantynnnie gqaivyqskf ltlngkkyyf dnnskavtgl qtidskkyyf ntntaeaatg
2101 wqtidgkkyy fntntaeaat gwqtidgkky yfntntaias tgytiingkh fyfntdgimq
2161 igvfkgpngf eyfapantda nniegqaily qnefltlngk kyyfgsdska vtgwriinnk
2221 kyyfnpnnai aaihlctinn dkyyfsydgi lqngyitier nnfyfdanne skmvtgvfkg
2281 pngfeyfapa nthnnniegq aivyqnkflt lngkkyyfdn dskavtgwqt idgkkyyfnl
2341 ntaeaatgwq tidgkkyyfn lntaeaatgw qtidgkkyyf ntntfiastg ytsingkhfy
2401 fntdgimqig vfkgpngfey fapantdann iegqailyqn kfltlngkky yfgsdskavt
2461 glrtidgkky yfntntavav tgwqtingkk yyfntntsia stgytiisgk hfyfntdgim
2521 qigvfkgpdg feyfapantd annieggair yqnrflylhd niyyfgnnsk aatgwvtidg
2581 nryyfepnta mgangyktid nknfyfrngl pqigvfkgsn gfeyfapant dannieggai
2641 ryqnrflhll gkiyyfgnns kavtgwqtin gkvyyfmpdt amaaagglfe idgviyffgv
2701 dgvkapgiyg (SEQ. ID. NO.: 7)
```

Figure 5.

```
AGCCTGTTCTACTTCGACCCCATCGAGTTCAACCTGGTGACCGGCTGGCAGACCATCAACGGCAAGAAGTACTAC
TTCGACATCAACACCGGCGCCGCCCTGACCAGCTACAAGATCATCAACGGCAAGCACTTCTACTTCAACAACGAC
GGCGTGATGCAGCTGGGCGTGTTCAAGGGCCCCGACGGCTTCGAGTACTTCGCCCCCGCCAACACCCAGAACAAC
AACATCGAGGGCCAGGCCATCGTGTACCAGAGCAAGTTCCTGACCCTGAACGGCAAGAAGTACTACTTCGACAAC
AACAGCAAGGCCGTGACCGGCTGGAGAATCATCAACAACGAGAAGTACTACTTCAACCCCAACAACGCCATCGCC
GCCGTGGGCCTGCAGGTGATCGACAACAACAAGTACTACTTCAACCCCGACACCGCCATCATCAGCAAGGGCTGG
CAGACCGTGAACGGCAGCAGATACTACTTCGACACCGACACCGCCATCGCCTTCAACGGCTACAAGACCATCGAC
GGCAAGCACTTCTACTTCGACAGCGACTGTGTGGTGAAGATCGGCGTGTTCAGCACCAGCAACGGCTTCGAGTAC
TTCGCCCCCGCCAACACCTACAACAACAACATCGAGGGCCAGGCCATCGTGTACCAGAGCAAGTTCCTGACCCTG
AACGGCAAGAAGTACTACTTCGACAACAACAGCAAGGCCGTGACCGGCCTGCAGACCATCGACAGCAAGAAGTAC
TACTTCAACACCAACACCGCCGAGGCCGCCACCGGCTGGCAGACCATCGACGGCAAGAAGTACTACTTCAACACC
AACACCGCCGAGGCCGCCACCGGCTGGCAGACCATCGACGGCAAGAAGTACTACTTCAACACCAACACCGCCATC
GCCAGCACCGGCTACACCATCATCAACGGCAAGCACTTCTACTTCAACACCGACGGCATCATGCAGATCGGCGTG
TTCAAGGGCCCCAACGGCTTCGAGTACTTCGCCCCCGCCAACACCGACGCCAACAACATCGAGGGCCAGGCCATC
CTGTACCAGAACGAGTTCCTGACCCTGAACGGCAAGAAGTACTACTTCGGCAGCGACAGCAAGGCCGTGACCGGC
TGGAGAATCATCAACAACAAGAAGTACTACTTCAACCCCAACAACGCCATCGCCGCCATCCACCTGTGTACCATC
AACAACGACAAGTACTACTTCAGCTACGACGGCATCCTGCAGAACGGCTACATCACCATCGAGAGAAACAACTTC
TACTTCGACGCCAACAACGAGAGCAAGATGGTGACCGGCGTGTTCAAGGGCCCCAACGGCTTCGAGTACTTCGCC
CCCGCCAACACCCACAACAACAACATCGAGGGCCAGGCCATCGTGTACCAGAACAAGTTCCTGACCCTGAACGGC
AAGAAGTACTACTTCGACAACGACAGCAAGGCCGTGACCGGCTGGCAGACCATCGACGGCAAGAAGTACTACTTC
AACCTGAACACCGCCGAGGCCGCCACCGGCTGGCAGACCATCGACGGCAAGAAGTACTACTTCAACCTGAACACC
GCCGAGGCCGCCACCGGCTGGCAGACCATCGACGGCAAGAAGTACTACTTCAACACCAACACCTTCATCGCCAGC
ACCGGCTACACCAGCATCAACGGCAAGCACTTCTACTTCAACACCGACGGCATCATGCAGATCGGCGTGTTCAAG
GGCCCCAACGGCTTCGAGTACTTCGCCCCCGCCAACACCGACGCCAACAACATCGAGGGCCAGGCCATCCTGTAC
CAGAACAAGTTCCTGACCCTGAACGGCAAGAAGTACTACTTCGGCAGCGACAGCAAGGCCGTGACCGGCCTGAGA
ACCATCGACGGCAAGAAGTACTACTTCAACACCAACACCGCCGTGGCCGTGACCGGCTGGCAGACCATCAACGGC
AAGAAGTACTACTTCAACACCAACACCAGCATCGCCAGCACCGGCTACACCATCATCAGCGGCAAGCACTTCTAC
TTCAACACCGACGGCATCATGCAGATCGGCGTGTTCAAGGGCCCCGACGGCTTCGAGTACTTCGCCCCCGCCAAC
ACCGACGCCAACAACATCGAGGGCCAGGCCATCAGATACCAGAACAGATTCCTGTACCTGCACGACAACATCTAC
TACTTCGGCAACAACAGCAAGGCCGCCACCGGCTGGGTGACCATCGACGGCAACAGATACTACTTCGAGCCCAAC
ACCGCCATGGGCGCCAACGGCTACAAGACCATCGACAACAAGAACTTCTACTTCAGAAACGGCCTGCCCCAGATC
GGCGTGTTCAAGGGCAGCAACGGCTTCGAGTACTTCGCCCCCGCCAACACCGACGCCAACAACATCGAGGGCCAG
GCCATCAGATACCAGAACAGATTCCTGCACCTGCTGGGCAAGATCTACTACTTCGGCAACAACAGCAAGGCCGTG
ACCGGCTGGCAGACCATCAACGGCAAGGTGTACTACTTCATGCCCGACACCGCCATGGCCGCCGCCGGCGGCCTG
TTCGAGATCGACGGCGTGATCTACTTCTTCGGCGTGGACGGCGTGAAGGCCCCCGGCATCTACGGCtaa (SEQ.
ID. NO.: 9)                                                          stop
                                                                     codon
```

Figure 6.

ATGWQTIDGKKYYFNTNTAEAATGWQTIDGKKYYFNTNTAIAST (SEQ. ID. NO.: 10)

Figure 7.

Base-pairs (bp) corresponding to design features

| | |
|---|---|
| 1-6 | NheI restriction site |
| 5-13 | Kozak sequence |
| 14-16 | Methionine "ATG" start codon (in bold) |
| 14-106 | tissue plasminogen activator (tPA) signal peptide (published) |
| 107-112 | BamHI restriction site (in bold) |
| 113-2731 | Toxin A codon optimized gene |
| 2732-2737 | EcoRI restriction site |

```
                    14
                    |
                    | Met
     kozak          | Start      tPA
  _____  ▼         _____→
  gctagccgccaccATGGAcGCcATGCTgCGCGGACTgTGcTGcGTgCTgCTgCTgTGc BamH1 (in bold)   113   Toxin
                              _____    |    _____→
                                                ▼
  GGcGCCGTgTTcGTgagcCCcagccgcagacgcaagaagcgcgccggaggatccAGCCTGTTCTACTTC
  GACCCCATCGAGTTCAACCTGGTGACCGGCTGGCAGACCATCAACGGCAAGAAG
  TACTACTTCGACATCAACACCGGCGCCGCCCTGACCAGCTACAAGATCATCAACG
  GCAAGCACTTCTACTTCAACAACGACGGCGTGATGCAGCTGGGCGTGTTCAAGG
  GCCCCGACGGCTTCGAGTACTTCGCCCCCGCCAACACCCAGAACAACAACATCG
  AGGGCCAGGCCATCGTGTACCAGAGCAAGTTCCTGACCCTGAACGGCAAGAAGT
  ACTACTTCGACAACAACAGCAAGGCCGTGACCGGCTGGAGAATCATCAACAACG
  AGAAGTACTACTTCAACCCCAACAACGCCATCGCCGCCGTGGGCCTGCAGGTGA
  TCGACAACAACAAGTACTACTTCAACCCCGACACCGCCATCATCAGCAAGGGCT
  GGCAGACCGTGAACGGCAGCAGATACTACTTCGACACCGACACCGCCATCGCCT
  TCAACGGCTACAAGACCATCGACGGCAAGCACTTCTACTTCGACAGCGACTGTGT
  GGTGAAGATCGGCGTGTTCAGCACCAGCAACGGCTTCGAGTACTTCGCCCCCGCC
  AACACCTACAACAACAACATCGAGGGCCAGGCCATCGTGTACCAGAGCAAGTTC
  CTGACCCTGAACGGCAAGAAGTACTACTTCGACAACAACAGCAAGGCCGTGACC
  GGCCTGCAGACCATCGACAGCAAGAAGTACTACTTCAACACCAACACCGCCGAG
  GCCGCCACCGGCTGGCAGACCATCGACGGCAAGAAGTACTACTTCAACACCAAC
  ACCGCCGAGGCCGCCACCGGCTGGCAGACCATCGACGGCAAGAAGTACTACTTC
  AACACCAACACCGCCATCGCCAGCACCGGCTACACCATCATCAACGGCAAGCAC
  TTCTACTTCAACACCGACGGCATCATGCAGATCGGCGTGTTCAAGGGCCCCAACG
  GCTTCGAGTACTTCGCCCCCGCCAACACCGACGCCAACAACATCGAGGGCCAGG
  CCATCCTGTACCAGAACGAGTTCCTGACCCTGAACGGCAAGAAGTACTACTTCGG
  CAGCGACAGCAAGGCCGTGACCGGCTGGAGAATCATCAACAACAAGAAGTACTA
  CTTCAACCCCAACAACGCCATCGCCGCCATCCACCTGTGTACCATCAACAACGAC
  AAGTACTACTTCAGCTACGACGGCATCCTGCAGAACGGCTACATCACCATCGAG
  AGAAACAACTTCTACTTCGACGCCAACAACGAGAGCAAGATGGTGAC
```

Figure 7 (continued)

CGGCGTGTTCAAGGGCCCCAACGGCTTCGAGTACTTCGCCCCCGCCAACACCCAC
AACAACAACATCGAGGGCCAGGCCATCGTGTACCAGAACAAGTTCCTGA
CCCTGAACGGCAAGAAGTACTACTTCGACAACGACAGCAAGGCCGTGACCGGCT
GGCAGACCATCGACGGCAAGAAGTACTACTTCAACCTGAACACCGCCGAGGCCG
CCACCGGCTGGCAGACCATCGACGGCAAGAAGTACTACTTCAACCTGAACACCG
CCGAGGCCGCCACCGGCTGGCAGACCATCGACGGCAAGAAGTACTACTTCAACA
CCAACACCTTCATCGCCAGCACCGGCTACACCAGCATCAACGGCAAGCACTTCTA
CTTCAACACCGACGGCATCATGCAGATCGGCGTGTTCAAGGGCCCCAACGGCTTC
GAGTACTTCGCCCCCGCCAACACCGACGCCAACAACATCGAGGGCCAGGCCATC
CTGTACCAGAACAAGTTCCTGACCCTGAACGGCAAGAAGTACTACTTCGGCAGC
GACAGCAAGGCCGTGACCGGCCTGAGAACCATCGACGGCAAGAAGTACTACTTC
AACACCAACACCGCCGTGGCCGTGACCGGCTGGCAGACCATCAACGGCAAGAAG
TACTACTTCAACACCAACACCAGCATCGCCAGCACCGGCTACACCATCATCAGCG
GCAAGCACTTCTACTTCAACACCGACGGCATCATGCAGATCGGCGTGTTCAAGGG
CCCCGACGGCTTCGAGTACTTCGCCCCCGCCAACACCGACGCCAACAACATCGA
GGGCCAGGCCATCAGATACCAGAACAGATTCCTGTACCTGCACGACAACATCTA
CTACTTCGGCAACAACAGCAAGGCCGCCACCGGCTGGGTGACCATCGACGGCAA
CAGATACTACTTCGAGCCCAACACCGCCATGGGCGCCAACGGCTACAAGACCAT
CGACAACAAGAACTTCTACTTCAGAAACGGCCTGCCCCAGATCGGCGTGTTCAA
GGGCAGCAACGGCTTCGAGTACTTCGCCCCCGCCAACACCGACGCCAACAACAT
CGAGGGCCAGGCCATCAGATACCAGAACAGATTCCTGCACCTGCTGGGCAAGAT
CTACTACTTCGGCAACAACAGCAAGGCCGTGACCGGCTGGCAGACCATCAACGG
CAAGGTGTACTACTTCATGCCCGACACCGCCATGGCCGCCGCCGGCGGCCTGTTC
GAGATCGACGGCGTGATCTACTTCTTCGGCGTGGACGGCGTGAAGGC stop  EcoRl
CCCCGGCATCTACGGCtaaGAATTCta (SEQ. ID. NO.: 11)

Figure 8.

```
           kozak   Met   BamH1    Toxin
                   Start
gctagccgccaccATGggatccGCCTGTTCTACTTCGACCCCATCGAGTTCAACCTGGTGAC
CGGCTGGCAGACCATCAACGGCAAGAAGTACTACTTCGACATCAACACCGGCGC
CGCCCTGACCAGCTACAAGATCATCAACGGCAAGCACTTCTACTTCAACAACGAC
GGCGTGATGCAGCTGGGCGTGTTCAAGGGCCCCGACGGCTTCGAGTACTTCGCCC
CCGCCAACACCCAGAACAACAACATCGAGGGCCAGGCCATCGTGTACCAGAGCA
AGTTCCTGACCCTGAACGGCAAGAAGTACTACTTCGACAACAACAGCAAGGCCG
TGACCGGCTGGAGAATCATCAACAACGAGAAGTACTACTTCAACCCCAACAACG
CCATCGCCGCCGTGGGCCTGCAGGTGATCGACAACAACAAGTACTACTTCAACCC
CGACACCGCCATCATCAGCAAGGGCTGGCAGACCGTGAACGGCAGCAGATACTA
CTTCGACACCGACACCGCCATCGCCTTCAACGGCTACAAGACCATCGACGGCAA
GCACTTCTACTTCGACAGCGACTGTGTGGTGAAGATCGGCGTGTTCAGCACCAGC
AACGGCTTCGAGTACTTCGCCCCCGCCAACACCTACAACAACAACATCGAGGGC
CAGGCCATCGTGTACCAGAGCAAGTTCCTGACCCTGAACGGCAAGAAGTACTAC
TTCGACAACAACAGCAAGGCCGTGACCGGCCTGCAGACCATCGACAGCAAGAAG
TACTACTTCAACACCAACACCGCCGAGGCCGCCACCGGCTGGCAGACCATCGAC
GGCAAGAAGTACTACTTCAACACCAACACCGCCGAGGCCGCCACCGGCTGGCAG
ACCATCGACGGCAAGAAGTACTACTTCAACACCAACACCGCCATCGCCAGCACC
GGCTACACCATCATCAACGGCAAGCACTTCTACTTCAACACCGACGGCATCATGC
AGATCGGCGTGTTCAAGGGCCCCAACGGCTTCGAGTACTTCGCCCCCGCCAACAC
CGACGCCAACAACATCGAGGGCCAGGCCATCCTGTACCAGAACGAGTTCCTGAC
CCTGAACGGCAAGAAGTACTACTTCGGCAGCGACAGCAAGGCCGTGACCGGCTG
GAGAATCATCAACAACAAGAAGTACTACTTCAACCCCAACAACGCCATCGCCGC
CATCCACCTGTGTACCATCAACAACGACAAGTACTACTTCAGCTACGACGGCATC
CTGCAGAACGGCTACATCACCATCGAGAGAAACAACTTCTACTTCGACGCCAAC
AACGAGAGCAAGATGGTGACCGGCGTGTTCAAGGGCCCCAACGGCTTCGAGTAC
TTCGCCCCCGCCAACACCCACAACAACAACATCGAGGGCCAGGCCATCGTGTAC
CAGAACAAGTTCCTGACCCTGAACGGCAAGAAGTACTACTTCGACAACGACAGC
AAGGCCGTGACCGGCTGGCAGACCATCGACGGCAAGAAGTACTACTTCAACCTG
AACACCGCCGAGGCCGCCACCGGCTGGCAGACCATCGACGGCAAGAAGTACTAC
TTCAACCTGAACACCGCCGAGGCCGCCACCGGCTGGCAGACCATCGACGGCAAG
AAGTACTACTTCAACACCAACACCTTCATCGCCAGCACCGGCTACACCAGCATCA
ACGGCAAGCACTTCTACTTCAACACCGACGGCATCATGCAGATCGGCGTGTTCAA
GGGCCCCAACGGCTTCGAGTACTTCGCCCCCGCCAACACCGACGCCAACAACAT
CGAGGGCCAGGCCATCCTGTACCAGAACAAGTTCCTGACCCTGAACGGCAAGAA
GTACTACTTCGGCAGCGACAGCAAGGCCGTGACCGGCCTGAGAACCATCGACGG
CAAGAAGTACTACTTCAACACCAACACCGCCGTGGCCGTGACCGGCTGGCAGAC
CATCAACGGCAAGAAGTACTACTTCAACACCAACACCAGCATCGCCAGCACCGG
CTACACCATCATCAGCGGCAAGCACTTCTACTTCAACACCGACGGCATCATGCAG
ATCGGCGTGT
```

Figure 8 (continued)

TCAAGGGCCCCGACGGCTTCGAGTACTTCGCCCCCGCCAACACCGACGCCAA
CAACATCGAGGGCCAGGCCATCAGATACCAGAACAGATTCCTGTACCTGCACGA
CAACATCTACTACTTCGGCAACAACAGCAAGGCCGCCACCGGCTGGGTGACCAT
CGACGGCAACAGATACTACTTCGAGCCCAACACCGCCATGGGCGCCAACGGCTA
CAAGACCATCGACAACAAGAACTTCTACTTCAGAAACGGCCTGCCCCAGATCGG
CGTGTTCAAGGGCAGCAACGGCTTCGAGTACTTCGCCCCCGCCAACACCGACGCC
AACAACATCGAGGGCCAGGCCATCAGATACCAGAACAGATTCCTGCACCTGCTG
GGCAAGATCTACTACTTCGGCAACAACAGCAAGGCCGTGACCGGCTGGCAGACC
ATCAACGGCAAGGTGTACTACTTCATGCCCGACACCGCCATGGCCGCCGCCGGC
GGCCTGTTCGAGATCGACGGCGTGATCTACTTCTTCGGCGTGGACGGCGTGAAGG
C stop EcoR1
CCCCGGCATCTACGGCtaaGAATTCta (SEQ. ID. NO.: 12)

Figure 9.

```
TCATTATTCTATTTTGATCCTATAGAATTTAACTTAGTAACTGGATGGCAAACTATCAATGGTAAAAAATATTAT
TTTGATATAAATACTGGAGCAGCTTTAACTAGTTATAAAATTATTAATGGTAAACACTTTTATTTTAATAATGAT
GGTGTGATGCAGTTGGGAGTATTTAAAGGACCTGATGGATTTGAATATTTTGCACCTGCCAATACTCAAAATAAT
AACATAGAAGGTCAGGCTATAGTTTATCAAAGTAAATTCTTAACTTTGAATGGCAAAAAATATTATTTTGATAAT
AACTCAAAAGCAGTCACTGGATGGAGAATTATTAACAATGAGAAATATTACTTTAATCCTAATAATGCTATTGCT
GCAGTCGGATTGCAAGTAATTGACAATAATAAGTATTATTTCAATCCTGACACTGCTATCATCTCAAAAGGTTGG
CAGACTGTTAATGGTAGTAGATACTACTTTGATACTGATACCGCTATTGCCTTTAATGGTTATAAAACTATTGAT
GGTAAACACTTTTATTTTGATAGTGATTGTGTAGTGAAAATAGGTGTGTTTAGTACCTCTAATGGATTTGAATAT
TTTGCACCTGCTAATACTTATAATAATAACATAGAAGGTCAGGCTATAGTTTATCAAAGTAAATTCTTAACTTTG
AATGGTAAAAAATATTACTTTGATAATAACTCAAAAGCAGTTACCGGATGGCAAACTATTGATAGTAAAAAATAT
TACTTTAATACTAACACTGCTGAAGCAGCTACTGGATGGCAAACTATTGATGGTAAAAAATATTACTTTAATACT
AACACTGCTGAAGCAGCTACTGGATGGCAAACTATTGATGGTAAAAAATATTACTTTAATACTAACACTGCTATA
GCTTCAACTGGTTATACAATTATTAATGGTAAACATTTTTATTTTAATACTGATGGTATTATGCAGATAGGAGTG
TTTAAAGGACCTAATGGATTTGAATATTTTGCACCTGCTAATACGGATGCTAACAACATAGAAGGTCAAGCTATA
CTTTACCAAAATGAATTCTTAACTTTGAATGGTAAAAAATATTACTTTGGTAGTGACTCAAAAGCAGTTACTGGA
TGGAGAATTATTAACAATAAGAAATATTACTTTAATCCTAATAATGCTATTGCTGCAATTCATCTATGCACTATA
AATAATGACAAGTATTACTTTAGTTATGATGGAATTCTTCAAAATGGATATATTACTATTGAAAGAAATAATTTC
TATTTTGATGCTAATAATGAATCAAAATGGTAACAGGAGTATTTAAAGGACCTAATGGATTTGAGTATTTTGCA
CCTGCTAATACTCACAATAATAACATAGAAGGTCAGGCTATAGTTTACCAGAACAAATTCTTAACTTTGAATGGC
AAAAAATATTATTTTGATAATGACTCAAAAGCAGTTACTGGATGGCAAACCATTGATGGTAAAAAATATTACTTT
AATCTTAACACTGCTGAAGCAGCTACTGGATGGCAAACTATTGATGGTAAAAAATATTACTTTAATCTTAACACT
GCTGAAGCAGCTACTGGATGGCAAACTATTGATGGTAAAAAATATTACTTTAATACTAACACTTTCATAGCCTCA
ACTGGTTATACAAGTATTAATGGTAAACATTTTTATTTTAATACTGATGGTATTATGCAGATAGGAGTGTTTAAA
GGACCTAATGGATTTGAATACTTTGCACCTGCTAATACGGATGCTAACAACATAGAAGGTCAAGCTATACTTTAC
CAAAATAAATTCTTAACTTTGAATGGTAAAAAATATTACTTTGGTAGTGACTCAAAAGCAGTTACCGGACTGCCGA
ACTATTGATGGTAAAAAATATTACTTTAATACTAACACTGCTGTTGCAGTTACTGGATGGCAAACTATTAATGGT
AAAAAATACTACTTTAATACTAACACTTCTATAGCTTCAACTGGTTATACAATTATTAGTGGTAAACATTTTTAT
TTTAATACTGATGGTATTATGCAGATAGGAGTGTTTAAAGGACCTGATGGATTTGAATACTTTGCACCTGCTAAT
ACAGATGCTAACAATATAGAAGGTCAAGCTATACGTTATCAAAATAGATTCCTATATTTACATGACAATATATAT
TATTTTGGTAATAATTCAAAAGCGGCTACTGGTTGGGTAACTATTGATGGTAATAGATATTACTTCGAGCCTAAT
ACAGCTATGGGTGCGAATGGTTATAAAACTATTGATAATAAAAATTTTTACTTTAGAAATGGTTTACCTCAGATA
GGAGTGTTTAAAGGGTCTAATGGATTTGAATACTTTGCACCTGCTAATACGGATGCTAACAATATAGAAGGTCAA
(SEQ. ID. NO.: 13)
```

Figure 12. Amino acid sequence of C. difficile toxin B (GenBank Accession no. P18177, (SEQ. ID. NO.: 15).

```
   1 mslvnrkqle kmanvrfrtq edeyvailda leeyhnmsen tvvekylklk dinsltdiyi
  61 dtykksgrnk alkkfkeylv tevlelknnn ltpveknlhf vwiggqindt ainyinqwkd
 121 vnsdynvnvf ydsnaflint lkktvvesai ndtlesfren lndprfdynk ffrkrmeily
 181 dkqknfinyy kaqreenpel iiddivktyl sneyskeide lntyicesln kitqnsgndv
 241 rnfeefknge sfnlyeqelv erwnlaaasd ilrisalkei ggmyldvdml pgiqpdlfes
 301 iekpssvtvd fwemtkleai mkykeyipey tsehfdmlde evqssfesvl asksdkseif
 361 sslgdmeasp levkiafnsk giinqglisv kdsycsnliv kqienrykil nnslnpaise
 421 dndfntttnt fidsimaean adngrfmmel gkylrvgffp dvkttinlsg peayaaayqd
 481 llmfkegsmn ihlieadlrn feisktnisq steqemaslw sfddarakaq feeykrnyfe
 541 gslgeddnld fsqnivvdke yllekissla rssergyihy ivqlqgdkis yeaacnlfak
 601 tpydsvlfqk niedseiayy ynpgdgeiqe idkykipsii sdrpkikltf ighgkdefnt
 661 difagfdvds lsteieaaid lakedispks ieinllgcnm fsysinveet ypgklllkvk
 721 dkiselmpsi sqdslivsan qyevrinseg rrelldhsge winkeesiik disskeyisf
 781 npkenkitvk sknlpelstl lqeirnnsns sdieleekvm lteceinvis nidtqiveer
 841 ieeaknltsd sinyikdefk liesisdalc dlkqqneled shfisfedis etdegfsirf
 901 inketgesif vetektifse yanhiteeis kikgtifdtv ngklvkkvnl dtthevntln
 961 aaffiqslie ynsskeslsn lsvamkvqvy aqlfstglnt itdaakvvel vstaldetid
1021 llptlseglp iiatiidgvs lgaaikelse tsdpllrqei eakigimavn lttattaiit
1081 sslgiasgfs illvplagis agipslvnne lvlrdkatkv vdyfkhvslv etegvftlld
1141 dkimmpqddl viseidfnnn sivlgkceiw rmeggsghtv tddidhffsa psityrephl
1201 siydvlevqk eeldlskdlm vlpnapnrvf awetgwtpgl rslendgtkl ldrirdnyeg
1261 efywryfafi adalittlkp ryedtnirin ldsntrsfiv piitteyire klsysfygsg
1321 gtyalslsqy nmginielse sdvwiidvdn vvrdvtiesd kikkgdlieg ilstlsieen
1381 kiilnshein fsgevngsng fvsltfsile ginaiievdl lsksykllis gelkilmlns
1441 nhiqqkidyi gfnselqkni pysfvdsegk engfingstk eglfvselpd vvliskvymd
1501 dskpstgyys nnlkdvkvit kdnvniltgy ylkddikisl sltlqdekti klnsvhldes
1561 gvaeilkfmn rkgntntsds lmsflesmni ksifvnflqs nikfildanf iisgttsigq
1621 feficdendn iqpyfikfnt letnytlyvg nrqnmivepn ydlddsgdis stvinfsqky
1681 lygidscvnk vvispniytd einitpvyet nntypevivl danyinekin vnindlsiry
1741 vwsndgndfi lmstseenkv sqvkirfvnv fkdktlankl sfnfsdkqdv pvseiilsft
1801 psyyedglig ydlglvslyn ekfyinnfgm mvsgliyind slyyfkppvn nlitgfvtvg
1861 ddkyyfnpin ggaasigeti iddknyyfnq sgvlqtgvfs tedgfkyfap antldenleg
1921 eaidftgkli ideniyyfdd nyrgavewke ldgemhyfsp etgkafkgln qigdykyyfn
1981 sdgvmqkgfv sindnkhyfd dsgvmkvgyt eidgkhfyfa engemqigvf ntedgfkyfa
2041 hhnedlgnee geeisysgil nfnnkiyyfd dsftavvgwk dledgskyyf dedtaeayig
2101 lslindgqyy fnddgimqvg fvtindkvfy fsdsgiiesg vqniddnyfy iddngivqig
2161 vfdtsdgyky fapantvndn iygqaveysg lvrvgedvyy fgetytietg wiydmenesd
2221 kyyfnpetkk ackginlidd ikyyfdekgi mrtglisfen nnyyfnenge mqfgyinied
2281 kmfyfgedgv mqigvfntpd gfkyfahqnt ldenfegesi nytgwldlde kryyftdeyi
2341 aatgsviidg eeyyfdpdta qlvise
```

Figure 13. Nucleotide sequence (SEQ. ID. NO.: 17) for a naturally occurring receptor binding domain of *C. difficile* toxin B.

```
AGTGAAGAAA ATAAGGTGTC ACAAGTTAAA ATAAGATTCG TTAATGTTTT TAAAGATAAG ACTTTGGCAA ATAAGCTATC
TTTTAACTTT AGTGATAAAC AAGATGTACC TGTAAGTGAA ATAATCTTAT CATTTACACC TTCATATTAT GAGGATGGAT
TGATTGGCTA TGATTTGGGT CTAGTTTCTT TATATAATGA GAAATTTTAT ATTAATAACT TTGGAATGAT GGTATCTGGA
TTAATATATA TTAATGATTC ATTATATTAT TTTAAACCAC CAGTAAATAA TTTGATAACT GGATTTGTGA CTGTAGGCGA
TGATAAATAC TACTTTAATC CAATTAATGG TGGAGCTGCT TCAATTGGAG AGACAATAAT TGATGACAAA AATTATTATT
TCAACCAAAG TGGAGTGTTA CAAACAGGTG TATTTAGTAC AGAAGATGGA TTTAAATATT TTGCCCCAGC TAATACACTT
GATGAAAACC TAGAAGGAGA AGCAATTGAT TTTACTGGAA AATTAATTAT TGACGAAAAT ATTTATTATT TTGATGATAA
TTATAGAGGA GCTGTAGAAT GGAAAGAATT AGATGGTGAA ATGCACTATT TTAGCCCAGA AACAGGTAAA GCTTTTAAAG
GTCTAAATCA AATAGGTGAT TATAAATACT ATTTCAATTC TGATGGAGTT ATGCAAAAAG GATTTGTTAG TATAAATGAT
AATAAACACT ATTTTGATGA TTCTGGTGTT ATGAAAGTAG GTTACACTGA AATAGATGGC AAGCATTTCT ACTTTGCTGA
AAACGGAGAA ATGCAAATAG GAGTATTTAA TACAGAAGAT GGATTTAAAT ATTTTGCTCA TCATAATGAA GATTTAGGAA
ATGAAGAAGG TGAAGAAATC TCATATTCTG GTATATTAAA TTTCAATAAT AAAATTTACT ATTTTGATGA TTCATTTACA
GCTGTAGTTG GATGGAAAGA TTTAGAGGAT GGTTCAAAGT ATTATTTTGA TGAAGATACA GCAGAAGCAT ATATAGGTTT
GTCATTAATA AATGATGGTC AATATTATTT TAATGATGAT GGAATTATGC AAGTTGGATT TGTCACTATA AATGATAAAG
TCTTCTACTT CTCTGACTCT GGAATTATAG AATCTGGAGT ACAAAACATA GATGACAATT ATTTCTATAT AGATGATAAT
GGTATAGTTC AAATTGGTGT ATTTGATACT TCAGATGGAT ATAAATATTT TGCACCTGCT AATACTGTAA ATGATAATAT
TTACGGACAA GCAGTTGAAT ATAGTGGTTT AGTTAGAGTT GGGGAAGATG TATATTATTT TGGAGAAACA TATACAATTG
AGACTGGATG GATATATGAT ATGGAAAATG AAAGTGATAA ATATTATTTC AATCCAGAAA CTAAAAAAGC ATGCAAAGCT
A
```

Figure 14. (SEQ. ID. NO.: 19)

5'GCTAGCCGCCACCATGGGATCCAGCCTGTTCTACTTCGACCCCATCGAGTTCAACCTGGTGACCGGCTGGCAGACCATCAACGGCAAGAAG
TACTACTTCGACATCAACACCGGCGCCGCCCTGACCAGCTACAAGATCATCAACGGCAAGCACTTCTACTTCAACAACGACGGCGTGATGCAG
CTGGGCGTGTTCAAGGGCCCCGACGGCTTCGAGTACTTCGCCCCCGCCAACACCCAGAACAACAACATCGAGGGCCAGGCCATCGTGTACCAG
AGCAAGTTCCTGACCCTGAACGGCAAGAAGTACTACTTCGACAACAACAGCAAGGCCGTGACCGGCTGGAGAATCATCAACAACGAGAAGTAC
TACTTCAACCCCAACAACGCCATCGCCGCCGTGGGCCTGCAGGTGATCGACAACAACAAGTACTACTTCAACCCCGACACCGCCATCATCAGC
AAGGGCTGGCAGACCGTGAACGGCAGCAGATACTACTTCGACACCGACACCGCCATCGCCTTCAACGGCTACAAGACCATCGACGGCAAGCAC
TTCTACTTCGACAGCGACTGTGTGGTGAAGATCGGCGTGTTCAGCACCAGCAACGGCTTCGAGTACTTCGCCCCCGCCAACACCTACAACAAC
AACATCGAGGGCCAGGCCATCGTGTACCAGAGCAAGTTCCTGACCCTGAACGGCAAGAAGTACTACTTCGACAACAACAGCAAGGCCGTGACC
GGCCTGCAGACCATCGACAGCAAGAAGTACTACTTCAACACCAACACCGCCGAGGCCGCCACCGGCTGGCAGACCATCGACGGCAAGAAGTAC
TACTTCAACACCAACACCGCCGAGGCCGCCACCGGCTGGCAGACCATCGACGGCAAGAAGTACTACTTCAACACCAACACCGCCATCGCCAGC
ACCGGCTACACCATCATCAACGGCAAGCACTTCTACTTCAACACCGACGGCATCATGCAGATCGGCGTGTTCAAGGGCCCCAACGGCTTCGAG
TACTTCGCCCCCGCCAACACCGACGCCAACAACATCGAGGGCCAGGCCATCCTGTACCAGAACGAGTTCCTGACCCTGAACGGCAAGAAGTAC
TACTTCGGCAGCGACAGCAAGGCCGTGACCGGCTGGAGAATCATCAACAACAAGAAGTACTACTTCAACCCCAACAACGCCATCGCCGCCATC
CACCTGTGTACCATCAACAACGACAAGTACTACTTCAGCTACGACGGCATCCTGCAGAACGGCTACATCACCATCGAGAGAAACAACTTCTAC
TTCGACGCCAACAACGAGAGCAAGATGGTGACCGGCGTGTTCAAGGGCCCCAACGGCTTCGAGTACTTCGCCCCCGCCAACACCCACAACAAC
AACATCGAGGGCCAGGCCATCGTGTACCAGAACAAGTTCCTGACCCTGAACGGCAAGAAGTACTACTTCGACAACGACAGCAAGGCCGTGACC
GGCTGGCAGACCATCGACGGCAAGAAGTACTACTTCAACCTGAACACCGCCGAGGCCGCCACCGGCTGGCAGACCATCGACGGCAAGAAGTAC
TACTTCAACCTGAACACCGCCGAGGCCGCCACCGGCTGGCAGACCATCGACGGCAAGAAGTACTACTTCAACACCAACACCTTCATCGCCAGC
ACCGGCTACACCAGCATCAACGGCAAGCACTTCTACTTCAACACCGACGGCATCATGCAGATCGGCGTGTTCAAGGGCCCCAACGGCTTCGAG
TACTTCGCCCCCGCCAACACCGACGCCAACAACATCGAGGGCCAGGCCATCCTGTACCAGAACAAGTTCCTGACCCTGAACGGCAAGAAGTACT
ACTTCGGCAGCGACAGCAAGGCCGTGACCGGCCTGAGAACCATCGACGGCAAGAAGTACTACTTCAACACCAACACCGCCGTGGCCGTGACCG
GCTGGCAGACCATCAACGGCAAGAAGTACTACTTCAACACCAACACCAGCATCGCCAGCACCGGCTACACCATCATCAGCGGCAAGCACTTCT
ACTTCAACACCGACGGCATCATGCAGATCGGCGTGTTCAAGGGCCCCGACGGCTTCGAGTACTTCGCCCCCGCCAACACCGACGCCAACAACA
TCGAGGGCCAGGCCATCAGATACCAGAACAGATTCCTGTACCTGCACGACAACATCTACTACTTCGGCAACAACAGCAAGGCCGCCACCGGCT
GGGTGACCATCGACGGCAACAGATACTACTTCGAGCCCAACACCGCCATGGGCGCCAACGGCTACAAGACCATCGACAACAAGAACTTCTACT
TCAGAAACGGCCTGCCCCAGATCGGCGTGTTCAAGGGCAGCAACGGCTTCGAGTACTTCGCCCCCGCCAACACCGACGCCAACAACATCGAGG
GCCAGGCCATCAGATACCAGAACAGATTCCTGCACCTGCTGGGCAAGATCTACTACTTCGGCAACAACAGCAAGGCCGTGACCGGCTGGCAGA
CCATCAACGGCAAGGTGTACTACTTCATGCCCGACACCGCCATGG

Figure 14 (Con't).

CCGCCGCCGGCGGCCTCTTCGAGATCGACGGCGTGATCTACTTCTTCGGCGTGGACGGCGTGAAGGCCCCCGGCATCTACGGCTAAGAATTCT
A-3` (SEQ. ID. NO.: 19)

Enzymatic Domain | Receptor Binding Domain (RBD)

NH₂— | ⋈ | | ▬▬▬▬▬ ▨▨▨▨ —COOH

Vaccine Sequence

"TxA-RBD"    [CMV] [TxA-RBD ➤] [BGH pA]

"tPA-TxA-RBD"    [CMV|tPA] [TxA-RBD ➤] [BGH pA]

B.

TxA-RBD plasmid: pUC ori, CMV, TxA-RBD, BGH pA, Kanamycin tPA-TxA-RBD plasmid: pUC ori, CMV, tPA, TxA-RBD, BGH pA, Kanamycin Kozak sequence, ATG start Figure 16. Nucleotide sequence of tPA-TxB-RBD (SEQ. ID. NO.: 20)

```
GCTAGCCGCCACCATGGACGCCATGCTGCGCGGACTGTGCTGCGTGCTGCTGCTGTGCGGCGCCGTGTTCGTGAGCCCCAGC
CGCAGACGCAAGAAGCGCGCCGGAGGATCCAGCGAGGAGAACAAGGTGAGCCAAGTGAAGATTAGATTCGTGAACGTGTTC
AAGGACAAGACACTGGCCAACAAGCTGAGCTTCAACTTCAGCGACAAGCAAGACGTGCCTGTGAGCGAGATTATTCTGAGC
TTCACACCTAGCTATTATGAGGACGGCCTGATTGGCTATGACCTGGGCCTGGTGAGCCTGTATAACGAGAAGTTCTATATTAA
CAACTTCGGCATGATGGTGAGCGGCCTGATTTATATTAACGACAGCCTGTACTACTTCAAGCCTCCTGTGAACAACCTGATCA
CCGGCTTCGTGACCGTGGGCGACGACAAGTACTACTTCAACCCTATCAACGGCGGCGCaGCCAGCATCGGCGAGACCATCAT
CGACGACAAGAACTACTACTTCAACCAGAGCGGCGTGCTGCAGACCGGCGTGTTCAGCACCGAGGACGGCTTCAAGTACTTC
GCCCCTGCCAACACCCTGGACGAGAACCTGGAGGGCGAGGCCATCGACTTCACCGGCAAGCTGATCATCGACGAGAACATC
TACTACTTCGACGACAACTACAGAGGCGCCGTGGAGTGGAAGGAGCTGGACGGCGAGATGCATTACTTCAGCCCTGAGACC
GGCAAGGCCTTCAAGGGCCTGAACCAGATCGGCGACGACAAGTACTACTTCAACAGCGACGGCGTGATGCAGAAGGGCTTC
GTGAGCATCAACGACAACAAGCATTACTTCGACGACAGCGGCGTGATGAAGGTGGGCTACACCGAGATCGACGGCAAGCAT
TTCTACTTCGCCGAGAACGGCGAGATGCAGATCGGCGTGTTCAACACCGAGGACGGCTTCAAGTACTTCGCCCATCATAACG
AGGACCTGGGCAACGAGGAGGGCGAGGAGATCAGCTACAGCGGCATCCTGAACTTCAACAACAAGATCTACTACTTCGACG
ACAGCTTCACCGCCGTGGTGGGCTGGAAGGACCTGGAGGACGGCAGCAAGTACTACTTCGACGAGGACACCGCCGAGGCCT
ACATCGGCCTGAGCCTGATCAACGACGGCCAGTACTACTTCAACGACGACGGCATCATGCAGGTGGGCTTCGTGACCATCAA
CGACAAGGTGTTCTACTTCAGCGACAGCGGCATCATCGAGAGCGGCGTGCAGAACATCGACGACAACTACTTCTACATCGAC
GACAACGGCATCGTGCAGATCGGCGTGTTCGACACCAGCGACGGCTACAAGTACTTCGCCCCTGCCAACACCGTGAACGACA
ACATCTACGGCCAGGCCGTGGAGTACAGCGGCCTGGTGAGAGTGGGCGAGGACGTGTACTACTTCGGCGAGACCTACACCA
TCGAGACCGGCTGGATCTACGACATGGAGAACGAGAGCGACAAGTACTACTTCAACCCTGAGACCAAGAAGGCCTGCAAGG
GCATCAACCTGATCGACGACATCAAGTACTACTTCGACGAGAAGGGCATCATGAGAACCGGCCTGATCAGCTTCGAGAATAA
CAACTACTACTTCAACGAGAACGGCGAGATGCAGTTCGGCTACATCAACATCGAGGACAAGATGTTCTACTTCGGCGAGGAC
GGCGTGATGCAGATCGGCGTGTTCAACACCCCTGACGGCTTCAAGTACTTCGCCCATCAGAACACCCTGGACGAGAACTTCG
AGGGCGAGAGCATCAACTACACCGGCTGGCTGGACCTGGACGAGAAGAGATACTACTTCACCGACGAGTACATCGCCGCCA
CCGGCAGCGTGATCATCGACGGCGAGGAGTACTACTTCGACCCTGACACCGCCCAGCTGGTGATCAGCGAGtaaGAATTC-1957
``` base pair (bp) notations refer to the position *ahead* of number
bp 1-6 = NHE1 restriction site
bp 5-13 = Kozak sequence
bp 14-16 = ATG start
bp 17-106 = tPA signal sequence
bp 107-112 = BamH1 restriction site
bp 113 - 1951 = TxB-RBD
bp 1952-1957 = EcoR1 restriction site

Figure 17

Expression Cassettes pVAX Toxin B 4803 bp — pUC ori, pCMV, Toxin B, BGH pA, Kanamycin tPA-Toxin B 4893 bp — pUC ori, pCMV, tPA, Toxin B, BGH pA, Kanamycin

- Kozak sequence, ATG start
- Eukaryotic CHO signals retained*

Figure 18.

```
1000000
100000          ▨  ▲
 10000    ◇     ▨
  1000    ◇◇◇   ▨
   100 ●  ◇     ▨
    10
     1 ▲  ●●●
       Vector  tPA-TxB  TxB-RBD  tPA-TxB  TxB-RBD
       Control -RBD-IM  -IM      -RBD-EP  -EP
```

Anti-toxin B IgG antibody titer

Figure 22.

Balb/c TxA-TxB Survival

(Survival curves)
- TxA & TxB RBD (4/5)
- TxA-RBD-Only (1/5)
- Vector Only (0/5)
- TxB-RBD-Only (0/5)

Challenge → A, B

X-axis: Time Post Toxin Challenge (Hours)
Y-axis: Percent (Survival)

Figure 23.
Hamster Anti-Toxin A ELISA
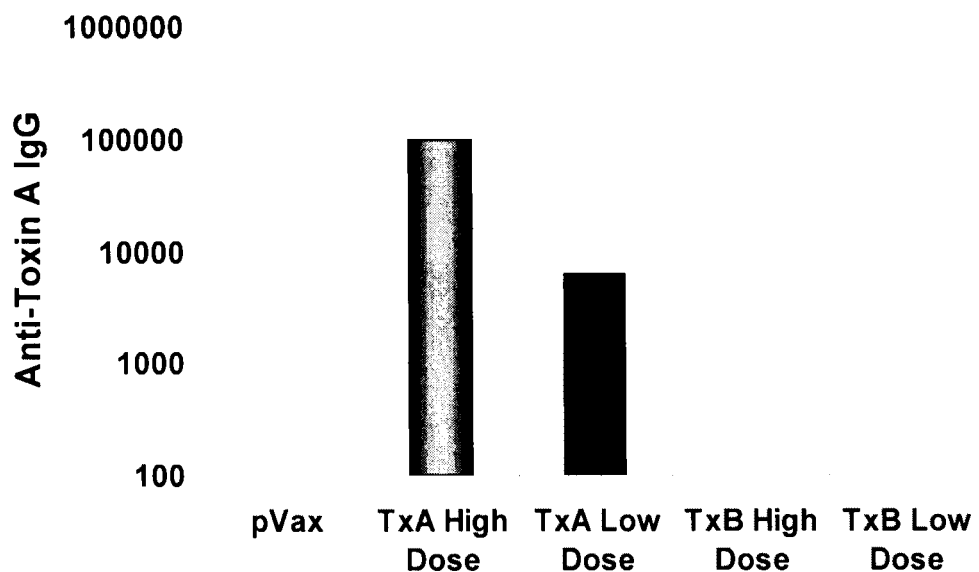
Hamster Anti-Toxin B ELISA
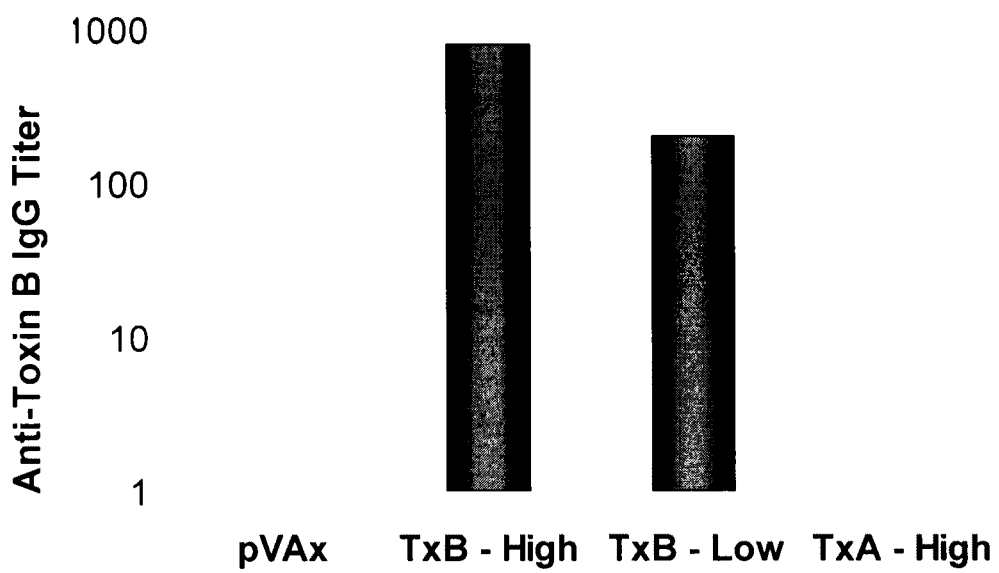

Figure 24. (SEQ. ID. NO.: 21)    M30307 10% optimized (positions 4-267, in bold, lowercase)

TCActgttttactttgatccaattgagtttaatctggtgaccggctggcagaccattaatgcaaaaatactactttgatattaataccggcgcccgccagctacaaaat
tattaatgcaaacacttacttaataatgatggcgtgatgcagctgggcgtgtttaaggcccagatggcccagcaataccagaataatattga
gggccaggccattgtgtaccagagcaaatttctgACTTTGAATGGCAAAAATATTATTTGATAATAACTCAAAGCAGTCACTGG
ATGGAGAATTATTAACAATGAGAAATATTTACTTTAATCCTAATAATGCTATTGCTGCAGTCGCAGATTGCAAGTAATTGACA
ATAATAAGTATTATTTCAATCCTGACACTGCTATCATCTCAAAAGGTTGGCAGACTGTTAATGGTAGTAGATACTACTTT
GATACTGATACCGCTATTGCCTTTAGTACCTCTAATGGATTTGAATATTTTGCACCTGCTAATACTTATAATAATAACATAGAAGGTC
GAAAATAGGTGTGTTTATCAAAGTAAATTCTAACTTTGAATGGTAAAAATATTCTGAAGCAGCTACTGGATGGCAAACTATTGA
AGGCTATAGTTATCAAAGTAAATTCTAACTTTGAATGGTAAAAATATTCTGAAGCAGCTACTGGATGGCAAACTATTGA
GGATGGCAAACTATTGATAGTAAAAATATTACTTAATACTGCTGAAGCAGTCAAACTATTGATGGTAAAAATATTACT
TGGTAAAAATATAACACTGCTATAGCTTCAACTGGTATACAATTATTAATGGTAAACATTTTATTTAATACTGATGGTATT
TAATACTAACACTGCTATAGCTTCAACTGGTATACAATTGAATGGATTTGAAAGGACCTAATTCTTGTGCAATTCATCATGCACTATA
ATGCAGATAGGAGTGTTTACCAAGATATTAACAATGAATTCTTAAAGGACCTAATTCTTGTGCAATTCATCTATGCACTATA
CTGGATGGGAGAATTATTACTTAGTATGATGGAATTCTTAAAGGACCTAATTCTTGCACCTGCTAATA
AATAATGACAAGTATTACTTGAATCTAAATGGTAACAGGAGTATTTAAAGGACCTAATTCTTGCACCTGCTAATA
TGATGCTAATAATAACATAGAAGGTCAGCTAGTTACTGGATGCAAACAAATTCTTAACTTTGAATGGCAAAAATATTATTT
CTCACAATAATAACATAGAAGGTCAGCTAGTTACTGGATGCAAACAAATTCTTAACTTTGAATGGCAAAAATATTATTT
GATAATGACTCAAAGCAGTACTGGATGGCAAACATTGATGGTAAAAATATTACTTAACACTGCTGAAGCAGCTACTGGATGGCAAA
AGCTACTGGATGGCAAACTATTGATGGTAAAAATATTACTTAACACTGCTGAAGCAGCTACTGGATGGCAAA
CTATTGATGGTAAAAATATTACTTAATACTGCAGATAGGAGTGTTTATGCAGATAGGAGTATTGAATACTTTGCACCTGCTAA
TTTATTTAATACTGATGGTATTATGCAGATAGGAGTATTATGCAGATAGGAGTTTAAAGGACCTAATTGAATACTTTGCACCTGCTAA
TACGGATGCTAACAACATAGAAGGTCAAGCTATACTTGCGAACTGCGAACTGCTGAACTATTGATGGTAAAAATAAATTAACACTGCTGTT
TGGTAGTGACTCAAAAGCAGTCACCGGACTCAAGCTATTACTGGAACTGCTGAACTATTGATGGTAAAAATAAATTAACACTGCTGTT
GCAGTTACTGGATGGCAAACATTAATAAATACTGGTAAATACTGGTATATGCAGAATAGGAGTATACGTATGGTAACTGGTTATAC
AATTATTAGTGGTAAACATTTTATTTAATACAGATGCTAATAATTGGTAATAATACTTCAAAGGACCTGATGGATTTG
AATACTTTGCACCTGCTAATAATTTGGTAATAATACTTCAAAGGAGCTACTGGGTAACTATTGATGGTAATAGATATTACTT
CATGACAATATACAGCTATGGGTGCGAATGGTCTAATGGGTGCGAATGGTCTAATTCCTACATTTACTTGGAAAATATTTGGTAATAATCAAAGGAGCTACTGGGTAACTATTGATGGTAATAGATATTACTT
CGAGCCTAATACAGCTATGGGTGCGAATGGTCTAATGGGTGCGAATGGTCTAATTCCTACATTTACTTGGAAAATATTTACTTAGAAATGGTTACCTC
AGATAGGAGTGTTTATCAAAATAGATTTGGTTAAAGTATATTACTTATGCCTGATACTGCTATGCCTGATACTGCTGCTATGCGCAGCGTACTGG
GCTATACGTTATCAAAATAGATTGGTTAAAGTATATTACTTATGCCTGATACTGCTATGCCTGATACTGCTGCTATGCGCAGCGTACTGG
ATGGCAAACTATTAATGGTAAAAGCCCCTGGGAGTAAAAGCCCCTGGGATATATGGCTAA
ATGGTGTTATATATTCTTGGTGTTGATGGAGTAAAAGCCCCTGGGATATATGGCTAA Figure 25. (SEQ. ID. NO.: 22) M30307 20% optimized (positions 154 - 681, in bold, lowercase)

TCATTATTCTATTTGATCCTATAGAATTAACTTAGTAACTGGATGGCAAACTATCAATGGTAAAAAATATTATTTGA
TATAAATACTGGAGCAGCTTTAACTAGTTATAAAATTATTAATGGTAAACACTTTATTTAATAATGATGGTgtgatgcagctgggcgtg
ttcaagggccccgacggcttcgagtacttcgccccgcaacaccagaacaacaacatcgagggcaggcaggctactgtgtaccagagcaagttcctgacctgaacggc
agaagtactacttcgacaacaacaacagcaaggccgtgacggctgagaatcatcaacaacgagaagtactacttcaacccaacaacgcattgacaccgcctgggcctg
caggtgatcgacaacaacaagtactacttcaaccccgacaccgcacttctacttcgacagcaaggctgcagaccgtgaaccgcagcagatactacttgacaccgacaccgcc
atcgccttcaacggctacaagaccatcgacggcaagcacttctacttcgacagcaagaagtgcggtgaagatcggcgttcagcaccagcaacgcttcgagtacttcgc
cccgccaacacctacaacaacaacatcgagggcaggcaggctactgtgtaccagagcaagcAAAAAATATTACTTTGATAATAACTC
AAAAGCAGTTACCGGATGGCAAACTATTAATACTACTTAATACTACTAACACTGCTGAAGCAGCTACTGGATGGCAA
ACTATTGATGGTAAAAATACTACTTAATACTACTGGTTACAATTAATGGTAACACATTTTATTTTATACTGATGGTATATGCA
CTTTAATACTACTGCTATAGCTTCAACTGCTATAGCTTCAACCTAATTGGATTTGAATATTTGCACCTGCTAATACGATTGTGTAGGAAGTCAAGCTATA
GATAGGAGTGTTAAAGGACCTAATTCTTAACTTTGAATGGTAAAATATTCTTAATACTACTGGATGCTAACACATAGAAGGTCAAGCTATA
CTTTACCAAAATGAATTCTTAACTTTGAATGGTAAAATATGCTATTGCTGCAATTCATCTATGACCACTATAAATAATGACAAGTATTACTTTAG
TAACAATAAGAAATATTACTTAATCCTAATAATGCTATTGAAAGAAATAATTCTATTGATGCTAATAATACATAGAAGGTCAAGCTAAAATGGTAAC
TTATGATGGAATTCTTCAAAATGGATATATACTATTGAGTATTTGCACCTGCTAATACTCACATATTGTGCTATAATACAGTTCAGGCTATAGTT
AGGAGTAGTATTTAAAAGGACCTAATTCTTAACTTTGAATGGCAAAAATATGCTGAAGCAGCTGCTGATGGCAAAACCATTGA
TACCAGAACAACAAATTCTTAACTTTAATCTTTAATCTAACACTGCTGAAGCAGCTACTGGATGGCAACTGCAAACCATTTAATC
TGGTAAACACCTCTGAAGCAGCTACTGGATGCTAATACGATTAGTGATGCTAATAGGAGTGTTAAGGACCTAATGGATT
TAACACTGCTGAAGCAGTATTTAATGCAGCACTTATTTGATGGTAAAAATATTACTTAATACTACTTAATACTACTTTCATAGCCTCAACT
GGTTATACAAGTATTAATGGTAACATACGATGCTAATACGATTATGCAGATAGAAGGTCAGATATACTTACCAAAAATAAATTCTTAACTTTGAATG
TGAATATCTGGCACCTGGTAGTGACTGCAAAGCAGTTACCGGACTGCAAACTATTGATGGTAAAAATATTACTTAATACTACTTAATACTAAC
GTAAAAATATTACTTCTTGATGGTAAAGTATTCCTATATGCCTGATACTGCTATGGCTGCAGCTGTGACTTTCAAAGCAGTTACTGG
ACTGCTGTTGCAGTAGTGGTAAACATTTTATTTAATACGATGCTAACAATATAATGACTGATTATGCAGATAGAAGGTGTTTAAAGGACCTGATGGATTG
TACAATTATTAGTGGTAAACATTTTATTTATTAATACGCTAACAATATAAAGCGGCTACTGGTTGGGTAACTATTGATGGTAATA Figure 26. (SEQ. ID. NO.: 23) M30307 30% optimized (positions 667 - 1458, in bold, lowercase)

TCATTATTCTATTTGATCCTATAGAATTAACTTAGTAACTGGATGGCAAACTATCAATGGTAAAAATATTATTTGA
TATAAATACTGGAGCAGCTTTAACTAGTTATAAATTATTAATGGTAAACACTTTATTTAATAATGATGGTGTGATGC
AGTTGGGAGTATTTAAAGGACCTGATGGATTTGAATATTTGCACCTGCCAATACTCAAATAATAACATAGAAGGTCAG
GCTATAGTTTATCAAAGTAAATTCTTAACTTTGATAATTATTTTGATAATAACTCAAAAGCAGTCACTGG
ATGGAGAATATTAACAATGAGAAATATTACTTAATCCTAATAATGCTATTGCTGCAGACTGTTAAGGTTGCAAGTAATTGACA
ATAATAAGTATTATTTCAATCCTGACACTGCTATCATCTCAAAAGGTTGGCAGACTGTTAAGGTAGTAGATACTACTTT
GATACTGATACCGCTATTGCCTTTAATGGCTATAAAACTATTGATGGTAAACACTTTATTTGATGATTGTGTAGT
GAAAATAGGTGTGTTAGTACCTCTAATGGATTTGAATATTTTGCACCTGCTAATACTTATATAATAACATAGAAGGTC
AGGCTATAGTTTATCAAAGTAAATTCctgacctgcaacggcaagaagtactacttgataacaacagcaaggccgtgaccggctggcagaccatcgata
gcaagaagtactacttcaacaccaacagcgcgaggcgccaccggtgcagaccatcgatggcaagaagtactacttcaacaccaacagcgcgaggccgcc
accggctggcagaccatcgatgcaagaagtactacttcaacaccaacagcgctacaccatcatcaacggcaagcacttcacttcaaca
ccgatggcatcatgcagaccatcgatcggcgtgttcaaggccccaacggcttcgagtacttcgccccccgccaacaccgatggccaacacatcgaggcaggccatcctgta
ccagaacgagttcgacccctgaccgtgcaacggcaagaaggcaaggtactacttcggcagcagagaagtactacttcggcgagatagcaagtactacttcaacaacaagataagtactacttcgagcagcagaaactcaacaagaagtactcaac
cccaacaacgccatcgccgccatccacctgtgcaacaacgagagagcaagatggtgaccggcgtgttcaagggccccaacggcttcaagggcccaacggcttcgagtacttcggcgtgttcaaggccccaacgcttcgagtacttcgataacgcttgataacgcttgataacggcaaggccGTTACTGGTAAAAATATTA
atcgaggccaggccatcgtgtaccagaacaagttcctgacctgtgtaccagaacaagttcctgacctgtgaacggcaagaagtactacttcgataacggcaagaagtactacttcgataacgatagcaaggccGTTACTGGTAAAAATATTA
CATTGATGGTAAAAATATTACTTAATCTTAACACTGCTGAAGCAGCTACTGGATGGCAAACTATTGATGGTAAAAATATTA
CTTAATCTTAACACTGCTGAAGCAGCTACTGGATGGCAAACTATTTAATACTGATGGTAAACATTTAATACTGATGGTATTATGCAGATAGGAGTGTTAAGG
AGCCTCAACTGGTTATACAAGTATTAATGGTAAACATTTAATACTGATGGTAAACATTTAATACTGATGGTATTATGCAGATAGGAGTGTTAAGG
ACCTAATGGATTTGAATACTTTGCACCTGCTAATACTTTGGTAGTGACTCAAAAGCAGTTACCGGACTGCGAACTATTAATGGTAAAAATACTACTTTAATACTGATGGTATTATGCAGATAGGAGTGTTAAG
TCTTAACTTTGATAATGGTAAAAATACTGCTGTGCAGTTACTGATGGTAAAAATACTACTTTAATCTACTTAATACTACT
TATTACTTAATACTACTTGGTAACTGGTTATACAATTAGTGGTAAACATTTTATTTAATACAGATGCTAACAATAGAAGGTCAACTATAGAGAAGGTCAACTATAGAGAAGGTTATCAAAAT
CTATAGCTTCAACTGGTTATACAATTTGCACCTGGTGCAGTTACTGATGGTAAACATTTTATTTAATACAGATGCTAACAATAGAAGGTCAACTATAGAGAAGGTTATCAAAAT
AAGGACCTGATGGATTTGAATACTTTGCACCTGCTAATACTTTGGTATAAAAGCGGCTACTGGTTGGTAACTATTTGATGGTAAT
AGATTCCTATATATTACATGACAATATATATTTGGTAACATGGCCTATGGGTGCGAATGGTGCAAATGGTTATAAAAATTTACTTTTAGAAATGGT
AGATATTACTTCGAGCCTAATACAGCCTATGGGTGCGAATGGTCTAATGGTTTAAAGGGTCTAATGTTAAAGGGTCTAATGTTAAAGGGTCTAATGTTTGAATACTTTGCACCTGCTAACACTACTAGAAGG
TACCTCAGATAGGAGTGTTAAAGGGTCTAATGTTTGAATACTTTGCACCTGCTAACACTACTAGAAGG
TCAAGCTATACGTTATCAAAATAGATTCCTACATTACTTTATGCCTGATCTGCTATGGCTGCAGCTGTTGTTCAGCTGGACTTTCGAGATTG
ATGGCAAACTATTGATTTAATGGTAAGTATATTACTTTATGCCTGATCTGCTATGGCTGCAGCTGTTGTTCAGCTGGACTTTCGAGATTG
ATGGTGTATATAATTTCTTTGGTTGATGGAGTAAAAGCCCCCTGGGATATATGGCTAA Figure 27. (SEQ. ID. NO.: 24) M30307 40% optimized (positions 769 - 1824, in bold, lowercase)

TCATTATTCTATTTGATCCTATAGAATTAACTAGTAACTGGATGGCAAACTATCAATGGTAAAAATATTATTTGA
TATAAATACTGGAGCAGCTTAACTAGTTATAAAATTATTAATGGTAAACACTTTATTTTAATAATGATGGTGATGC
AGTTGGGAGTATTAAAGGACCTGATGGATTTGAATATTTGCACCTGCCAATACTCAAATACTCAAAGCAGTCAG
GCTATAGTTTATCAAAGTAAATTCTTAACTTTGAATGGCAAAAAATATTATTTGATAATAACTCAAAAGCAGTCACTGG
ATGGAGAATTATTAACAATGAGAAATATTACTTAATCCTAATAATGCTATTGCTGCAGACTGTAAGGTTGCAAGTAATTGACA
ATAATAAGTATTATTTCAATCCTGACACTGCTATCATCTCAAAAGGTTGGCAGACTGTAATGGTAGTAGATACTACTTT
GATACTGATACCGCTATTGCC

Figure 28. (SEQ. ID. NO.: 25) M30307 50% optimized (positions 31 - 1350, in bold, lowercase)

TCATTATTCTATTTGATCCTATAGAATTTaacctgtgtgaccggctggcagaccatcaacggcaagaagtactacttgacatcaacaccggcgccgccct
gaccagctgacatcaagatcatcaacgacgcaagcatttctacttcaacaacgacggcttgatgcagctggcgtgttcaaggcgtttcaagggcttcgagtacttcgccctgcca
acaccagaacaacaacatcgagggccaggccatcgtgtaccagagcaagtactcgacctgaacgagcaagttcctgaccaacaacagcaaggccgtgac
cggctggagaatcatcagcaacggctggcagaccgtgaacgcagcagatactacttcgacaccgcgacctgcttcaacggctacaagaccatcgacggcaag
cacggccatcatcagcaacggcgactgtgtggtgaagatcggcgtgttcagcacgcaacgcgttttcagcaacagcttcgccctgcaacacctacaacaacatcgagggcca
ggccatcgtgtaccacagagacagtttcctgaccgtgaacgcagcaagttcctcaacaacacagcaagaagtactacttcgacacccaaggccgtgagacagcaagaagt
actacttcaacacaaccacccgcgagccgccaccggctgcagaccatcgccagcaaccggctacaccatcatcaacggccaagaagtactcttcaacaccgacggcatcat
agacaatcgacggaagaagtactacttcaaggggcctacttcgccctgcagtactccaacggccatcttgtaccagaagaacgagttcct
gcagatcggcgtgttcaagggccaagaagtactacttcggcagcagcagaaccggccagcagcagcacgcctgcacaacacaacacgccatcg
gacctgaaccgcaagaagtactacttcggcagcagcagcagaagcaagagccgtgacccagcagcaaagaagtactcaacaacaaggtactcgacctgaacgcgcatg
ccgccatcatctgtaccatcaacaacgacagacagtactacttcagcttcagccgccgtaacggccctcagaaacgcctacgacaacgctacttcgacgc
aacaacggagagcaagatggtgaccggctgtcaagggccctaacggccttgagacttcgccacgcctgtaatactactccccTCTAATACTACATAGAAGGTCA
GGCTATAGTTTACCAGAACAAATTCTTAACTTTAATCTATTACTTTGAATGCAAACAAATTGATAATGACTCAAAGCAGTATACTACGTGGATGG
CAAACCATTGAATACTTAACACTGCTGAAGCAGCTACTGGATGCAAACTATTGATGGGCAAACTATTGATACTTTAATACTACTTC
ATTACTTTAATCTCAACTGGTTATACAGTATACAGTATACGATGCAAGAGGTTAAAATACTTTATTATGCAGATAGGAGTGTTTAAAG
ATAGCCTCAACTGGTTATACAGTTGAATACTTTGCACCTGCTAATACGGATGCTAAAACATAGCAGTTACCGGACTGCGAACTATTGATGTGAAAAATAT
GACCTAATGGATTTGAATGGTAAAAAATATTACTTTGCACCTGCTAATACGGATGCTAACTTTGTAATACCAAATATAAGGATTGATGGAAAAATAT
CTAACTTTAATACTAACACTGCTGTGTCCAGTATGACAGTTAACTACTATAAGCGGGTAAAAACTATTAATGCTGATGGTATTATGCAGATAGGGTGTTAAGGA
AGCTTCAACTGGATTTGAATACTTTGCACCTGCTAACATATACAGATGCTAACATGCTAAAAGATGCGCTACTGGTGCGGGTAACTATTGATGGGAATAGTATATCC
CCCTGATGGATTTTGAATACTTTGCACCTGCTAACATATACAGATGCTAACATGCTAAAAAGATGCGCTACTGGGTGAATGCGTTATCAAATAGATTCC
TATATTTACAGACAATATAATTTGTGGTGCGAATAGGTTGCGAATGGTTATAAAACTATTGATAAAAATTTTTTACTTTAGAATATAAGGTTTACCTCAGA
TTCGAGCCTAATACGTGGTTGATGCTATGGGCGAATGTCTAATGCATTGAATACTTGCACCTGCTAATACGGATGCGAATAATATAAGGTTCAAGCTATAC
TAGGAGTGTTAAAGGGTCTAATGGTTAAGCTCAACCTGCTATTTGAATACTTTGGTAATATTACTTGAAAAATATATTGGTAATATTACTTGAAAAATATGTAATAATATATTGTAATATTACTTGAAAAATATATATTGTAATATTACTTGAAAAATATATATTGGAATAATATATATTGGTAATATTACTTTGGTAATACAGCATGAAAGCAGTACGATGCAAACTATT
GTTATCAAAAGTATATTACTTGGAAAAATATATTGTCTGATGCCTATGCCTGCGAGCTGCTATGCCTATGCCTATGGGACTTTTCGAGACTTTCGAGACTTTCGAGATTGATTGGTGTTATATTTCT
AATGGTAAAGTATATTACTTGGAAAAATATATTGCCTGATACCTATGCCTGCGAGCTGCTATGCCTATGCCTATGGGACTTTTCGAGACTTTCGAGATTGATGATTGGTGTTATATTTCT
TTGGTGTTGATGGAGTAAAAGCCCCTGGGATATATGGCTAA Figure 29. (SEQ. ID. NO.: 26)    M30307 60% optimized (positions 415 - 1998, in bold, lowercase)

TCATTATTCTATTTGATCCTATAGAATTAACTTAGTAACTGGATGGCAAACTATCAATGGTAAAAATATTATTTTGATATAAATA
CTGGAGCAGCTTAACTAGTTATAAAATTATTAATGGTAAACACTTTATTTAATAATGATGGTGTGATGCAGTTGGGAGTATTA
AAGGACCTGATGGATTTGAATATTTGCACCTGCCAATACTCAAAATAATAACTCAAAAGCAGTCACTGGATGGAGAATTATTAACAATGAGAAATAT
TCTTAACTTGAATGGCAAAAATATATTTGATAATAACTCAAAAGCAGTCACTGGATGGAGAATTATTAACAATGAGAAATAT
TACTTAATCCTAATAATGCTATT

Figure 30. (SEQ. ID. NO.: 27)    M30307 70% optimized (positions 226 - 2073, in bold, lowercase)

```
TCATTATTCTATTTGATCCTATAGAATTTAACTTAGTAACTGGATGCTAAAAAATATTATTTGATATAA
ATACTGGAGCAGCTTAACTAGTATAAAATTATTAATGGTAAACACTTTATTTAATAATGATGGTGTGATGCAGTTGGGAT
ATTTAAAGGACCTGATGGATTTGAATATTTTGCACCTGCCAATACTCAAAATAATaacatcgagggcaggcaagaagtactattcaaccaacaacg
ttcctgaccctgaacggcaagaaggtactacttcgacaacaacagcagtacttcaacagaagatcatcaaacagagaagtactactcaacccaacaacg
ccatcgccgcgtggcctgcaggtgatcgacaacaacaagtactacttcaaccctgaccccgacaccgccatcatcagcagcagcaaggctggcagaccgtgaaccgcagcagat
actacttcgacaccgacaccgccatcgccttcaacgctacaagagaccatgacgcaagcagcatttctacttgacagcagcatttcacttacttgacaggggtgtttcagca
ccagcaacgcgttcgagtactacttcgacaaacagcaaggccgtgaccgtgaccgtgaccatcgacagccagcaagttcctgacctgaacggcaaga
agtactacttcgacaaacagcaaccgctgtgaccggcgtacaacaccaacaccgcgaagaagtactacttcaacaccaacac
cagaccatcgacgtgaccgcagcagccaacaccgccaggcaggcatttctacttcaacaccgcgaagatcgatcgtggcagaccgtgttcaaggcccccaacgcttcgagt
acttcgaccgcagcagcaacaccggctacatcctgagtacttcgccccgccaacaacaatcaacacccaaacaacatcgagggccaggcaggccatcgacgacgtaccaacaagagagccaacaacgagacaa
aacaaggccgtgacgacgcacgggcttcgacaacagcagcagcaagaagagtactacttcgagaatcatcgagaagaatcaccaaagcagaacaacttctacttcgagggcaaacggatcaacatgcagcacgccacc
gtactacttcagtcgacagcgcatcctgagtacttcgcccccgccaacactcaacctgaacaacatcaaacaagagaaacaacaactgaccagaacaacaagcagccaggcaaccgcagcagcagccgaggccgccacc
gcaagaagtactacttcgacaaacagcgaagaagtactacttcaacctgaccgacggcaagaagtactacttcaacac
ggctggcagaccgacgaagagtactacttcaacctgaaccgtggccgtgaccagaagtactcgtggccgtgaccgccaagaagtactcgtggccgtgaccgccaagaagtactacttcaacac
caacacccttcatcgccagcagcaccggcaagaagtactacttcaacctgaccgcagcagccatcatcgacgccaaagaagagtactacttcaaggcccgtgttcaagggccccaacgct
tcgagtacttcgccccgccaacagcaaggcgtgacgacgcagcagcggcaagaagtactacttcaacaccatcagcgccaagcatttctacttcaacaccaccgcaagcatttctacttcaaccatcagcaagcatttctacttcaacaccgcaagcatttctacttcaacaccgcaagcatttctacttcaacaccatcagcggcaaacggaccatcaac
cagcgacgacagcaaggccgtgaccgcagcagcaccatcgccagcagcaagtactcaccaccatcatcgagggccaagcatttctacttcaacaccgcaagcatttctacttcaacatcagcgacgccaagaatttctacttcaacaccgcaagcatttctacttcaacaccgcaagcatttctacttcaaccccgcaagcaagcatttctacttcaaccccgcaagcatttcgaccgtggccgtggcagaccatcaac
ggcaagacagcaaggcgtgaccaccaacaacaccgctgagaacaccagcatcgccagcagcaagtactccaccaccatcatcgagggccaagcatttctacttcaacaccgcaagcatttctacttcaactccctgcaagcatttcgaccgtggccgtggcagaccatcagatcg
gcgtgttcaagggccccgacGGATTGAATACTTTGCACCTGCTAATACTCAAAAAGGCTAAGATGCTAACAATATAGAAGGTCAAGCTACTCAAGCTATC
AAAATAGATTCCTATATTACTTCGAGCCTAATACTGACAATATACAGCCTATGGGTGCGAATGGTCTATGGATGTTAAAGGTCTAATGATTGATATAAAATTTTACTTTAGAA
GTAATAGATATTACTTCGAGATAGGAGTGTTATCAAAATAGATTCCTACACTTTACTTTGCACCCTGCTAATACGGATGCTAACAATATA
ATGGTTACCTCAGATAGGAGTGTTATCAAAATAGATTCCTACACATTTACTTGGAAAATATATTTGGTAATAATTCAAAAGCAGTT
GAAGGTCAAGCTATACGTTATCAAAATAGATTCCTACACTTTACTTGGAAAATATATTTGGTAATAATTCAAAAGCAGTT
ACTGGATGGCAAACTATTAATATTTCTTGGTGTTGATGGAGTGAGTAAAAGCCCCTGGGATATATGGCTAA
```

Figure 31. (SEQ. ID. NO.: 28)    M30307 80% optimized (positions 193 - 2112, in bold, lowercase)

TCATTATTCTATTTGATCCTATAGAATTTAACTTAGTAACTGGATGGCAAACTATCAATGGTAAAAAATATTATTTGATATAAATA
CTGGAGCAGCTTTAACTAGTTATAAATTATTAAATGGTAAACACTTTATTTAATTAATGATGGTGTGATGCAGTTGGGAGTATTA
AAGGACCTGATGGATTT**gagtacttcgccccagccaacggccaacaccaacacatcgagggccaggccatcgtgtaccagagcaagttcctgacccgtgaacggc
aagaagtactacttcgacaacaacagtactacttcaaccggcgtgaccggctggagagcaagttcatcaaccaaaacaacgccatcgccgccgtgggcctgc
agttgatgacaacaacaagtactacttcaacccggctacaagaccatcgacggcaagcacttctacttcgacagcgacttcgacagcgacgctgttgaagatcggcgtgttgtgaagcaagtgcgagcgtgcaagcttcgagcaccagcaacggcttcgagtacttcgccc
agccaacacctacaacgacaacacatcgagggccaggccatcgagcgcgtgaccgtgctcgacgaccgtacaccatcatcaacggca
gaccggctggcagacgcgaggccgcctggcagaccgggcaagaagtactacttcaacaacaaccggcgcaagaagtactactcgagcca
caacacgccgagggccaggccatcgacgacagcaaccaaaccggcgcaccaccgcaacaccgacgcaacatcgagggc
agcacttcacttcaaacaccgacgcgcttccaaaccggcttcgccaacacccggctgttcaaggcccgagtttcgagtactcgcccccagccaacacatgagggc
caggccatcctgtaccagagcaagttcctgacccgtgaacggcaagcagagcaagaagtactacttcggcagcgacagcaaggccgtgaccatcatcaacaacaacaagaagt
actacttcaaaccaacttcaaacgccgccaacacctgtgaccatcaacacgacacaagctacagtactcaagccgtgaccatcaccgaatcaacaaccggcttctacaacgccggctacatcaccatcg
agagaaacaacttctacttcgacgccaacaacgagagcaagaagttcctgacccctgaacggcgtgttcaaggcgagaagtactacttcgacaacaacgcctacatccgcaacacgcaccacaacacaa
caacatcgagggcaaggccatcgtaccagagcaagaagttcctgaccgtgaacggcaagaagtactacttcgacggcaagaagttcaacggcaagtactcgaggccg
ccacggctggcagaccatcgagaccggcaagaagtactacttcaacaaccaacacccttcaacggcaaagacttcgacggcaagcagcttctacttcaaccaaccacc
gacggcatcatgaacgggcgttcaaggcgagtgaccatcgagtgacaagaagttcctgacaagaagttctgcgagcgcgagcaaggccaggccatcaccgaagaagtactacttcgatcctcctgaccag
aacaagttcctgacctgaacggcgtgaccggctgaaggcaagaagtactacttcaacacggcaagaagtactacttcaaccaacaaca
cggcgtgacggctgtgaccggctgcagaccatcaaacggcgtgaccaccgacacagccaccgccatctacaacaaccagcgacaagcact
tctagatgatagaccaagatcctgtacggcgcaagcgctacaagagcaagacggtgacgccgtgggtgacctgacggcaaaccaacacatcagcggccaagcagc
catcgagataccggctgaccatcgtaccatgagccaggacagccgtgcgtaccgcgtgcgtacgatcctacaagaacatcaaggccaacatggctacaagagcaacagatactactt
cgagcaacaaccgccatgggcgccaacggcgccaacgcgctacaagagcaactcAGAAATGGTTACCTCAGATAGGAGTGTTAAGG**
GTCTAATGGATTTGAATACTTGCACCTGCTAATACGGATGCTAACAATATAGAAGGTCAAGCTATACGTTATCAAAATAGATTCC
TACATTACTTGGAAAAATATATTACTTTGGTAATAATTCAAAAGCAGTTACTGGATGGCAAACTATTAATGGTAAAGTATATTACT
TTATGCCTGATACTGCTATGGCTGCTGCAGTTGAAGATTCCTGTACCTGCAGTGGACTTTTCGAGATTGTTATATATTTCTTTGGTGTTGATGGAGTAAAA
GCCCCTGGGATATATGGCTAA Figure 32. (SEQ. ID. NO.: 29)   M30307 90% optimized (positions 16 - 2391, in bold, lowercase)

TCATTATTCTATTTTgacccatgagttcaacctggtgaccggctggcagaccatcaacggcaagaagtactacttgacatcaacaccggccgccctgacca
gctacaagatcatcaacgacggcaagcacttctacttcaacaacgacgcgtgatgcagctgccctgaccggcttgaagggccccgacgcttcgagtacttcgccccgccaacacc
cagaacaacaacatcgagggccaggccaggctacttcgacaacaacatcgtgtaccagagacaacaagccatcgccgccgtgggcctgacccgccatcgccgagcaagtccgtgaccggcggctgg
agaatcatcaacaacgagagattacttcaacccccaacaacaaagtactacttcaacaacaagtactacttcaaccccgacaccgccat
catcagcaagggctggcagaccgtgaacgacgcagcagatactacttgacaccgccttcaacgcttcgagtacttcgccccgcaacactcaacaacatcaacggcttcgacaccaagaccatcgagtgtac
acagcgactgtgtgtgaagatcggcgtgttcagcaacgacaagaagtactacttcgacaacaacaacatcgacgcaagaagtactacttcaacacca
cagagcaagttcctgacctgaacggcagacctcgccacccaggccgtgcagacacacaccgccgaggcgtgcaggcgtgcaggccatcgacagaccatcgacggttcaa
gaagtactacttcaacacaccaacaaggccgtacaccatcatcaacggcacgccaccgacggcatcatgcagatcgccgtgtgttcaa
gggccccaacggcttcgagtactttgccccgccaacaccgacggcaagccaggccatcctgaccagaacgagttctgacctgacccactgtgtacca
gtactacttggcagcgacagcaaggccgtgaccggcatctcgagatgctacgacggcccccaacaagccatgagaacctactttgacgccaacaacgagagcaagttcctgaccc
tcaaacgacagaagtactacttcaagggccccaacagcttcgagtacttgcccccgccaacaaggccgtgaccggccagacccgtgaccggaatcaacaccaacaacctactctgagggcaaaaaaacaactactgagggcagcgatcgtgtaccagaacaacgagagcaagttctgaccc
accggcgtgttcaagaacctacttcgacaacgcaacgcacagaagtactacttcaacctgacaccgccgacggcaagagtactacttcaaacctgaacaccgccgaggccgca
tgaacggcagacagcaaggccgtgaccggcaacgacagcaagtactacttcaacctgacggcaagagtactacttgacagaccatcgacggcgtgttcaagggcccaacggcttcgag
ccggctggcagacagcaccatcgacggcaacctgacggcgctacaacaccgccgaagccaccttctacttcaacaacggcaagagtactacttcgacggcaagagtactacttcgagagaccatcgacggccgtgttcaagggccccaacggcttcgag
acaccttcatcgcagcagcccgccaacaccgagggccaggccaagagtactacttgacctgaccctgacctgtaccagaacaagccgccgtgaccggcgctgttcaagggccccaacggcttcggagcgagcagacagcaaggccgtgaccggcaacctgtaccagaacaagccgccgtgaccggcgctgttcaagggccccaacggcttcgag
tacttgcccccgccaacaaggccgtgaccggcaacaaggccgtgacccgtgagaacatcgaagggcaagagtactacttcggcagcgaca
gcaaggccgtgaccggcctgagaacatcgccagccaccatcgacggcagaagtactacttcaacacgcaagaagtactacttgaccggcaagaagagaccatcaacggcaagaagtact
acttcaacacaccaacaccaccagccagcacgccaggccacgccaacatcagcagcggcaagcagatactacttgagccaacaacaccgccgaacagattcctgacctgacctacctgacgacaacaccatcaagaagtactacttgcaggggcccc
gacggcttcgagtacttcgccccgccaacaccgacggcgtgttcaagggcagcaacggcttcgagtacttcgccccgccaacaccgacggcgtgttcaagggccccaacaaccatctactt
cggcaacaacagcaaggccgtgaccggctgggtgacccagatcggctacccatgaccatcgacggcaacaccagatacttcgagccaacacgacggctacaacagcctgagccaacgacggcggcgtacaagccatcgaca
acaagaacttctacttcaagaacggcctgtgccccagatgaaaatagattcctacattgttttcaagggcagcaacgcaacgcaacaacagaaaatcgtgtacaagagtactcaaacaacaacatcGAAG
GTCAAGCTATACGTTATCAAAATAGATTCCTACATTTACTTGGAAAAATATATTACTTTGGTAATAATTCAAAGCAGTACTGGAT
GGCAAACTATTAATGGTAAGTATATTACTTTATGCCTGATACTGCTATGCCTATGCCTGGCTGCAGCTGTGGTGGACTTTTCGAGATTTCGAGATTGATGGTGTT
ATATATTCTTTGGGTGTTGATGGAGTAAAAGCCCCTGGGATATATGGCTAA Figure 33. (SEQ. ID. NO.: 30) X53138 10% optimized (positions 1075 – 1260, in bold, lowercase)

AGTGAAGAAATAAGGTGTCACAAGTTAAAATAAGATTCGTTAATGTTTTAAAGATAAGACTTTGGCAAATAAGCTATCTTTAAC
TTAGTGATAAACAAGATGTACCTGTAAGTGAAATAATCTTATCATTACACCTTCATATTATGAGGATGGATTGATTGGCTATGAT
TGGGTCTAGTTTCTTTATATGAGAAATTTATATAATAACTTGGAATGATGGTATCTGGATTAATACTACTTAATCCAATAATG
TATATTATTTAAACCACCAGTAAATTTGATAACTGGATTTGTGACTGTAGGCGATGATAAATACTACTTAATCCAATAATG
GTGGAGCTGCTCAATTGGAGAGAGACAATAATATTTCAACCAAAGTGGAGTGTTACAAACAGGTGTATT
AGTACAGAAGATGGATTAAATATTTGCCCCAGCTAATACACTGATGAAAACCTAGAAGGAGAAGCAATTGATTTTACTGGAAA
ATTAATTATTGACGAAATATTTATTATTTGATGATAATTATAGAGGAGCTGTAGAATGGAAAGAATTAGATGGTGAAATGCACTA
TTTAGCCCCAGAAACAGGTAAAGCTTTAAAGGTCTAAATCAAACTATTTGATGATTCTGTTATGCAAAGATGGATTAAATACTATTTCAATTCTGATGGAGTTATGCA
AAAAGGATTTGTAGTATAAATGGAGAAACGGAGAGAAATGCAAATAGGAGTATTAATACAGAAGATGGATTTAATATATTTGCTCATCATATGA
GCATTTCTACTTTGCTGAAAACGGAGAAGAAATCTCATATTCTGGTATATTAAAATTTCAATATAAAATTTACTATTTGATGATTCATTT
AGATTTAGGAAATGAAGAAGGTGAAAGATTTAGAGAGATGGTCAAAGTATTATTTGATGAAGATACACAGAAGACAGAGACAGAAGCATATAGGTTT
ACAGCTGTAGTGGATGGAAAGATTCAATATATTTTAATgatgatgaatcatgcaggtgaattgtgacaatcaatgataaagtgtttactttagcgatagcggaatc
GTCATTAATAATGATGGTCAATATATTTTAATgatgatgaatcatgcaggtgaattgtgacaatcaatgataaagtgtttactttagcgatagcggaatc
atcgagagcggagtgcagaatatcgatgataatattacttacatcgatgataatgaatcgtgcagatcggagtgttagagttagagttGGGGAAGATGTATATTATTTTGGAGAA
ATACTGTAAATGATAATATTGAGACTGATGGATATGATATAAAATATTGGAAAATGAAAGTGATAAATTATTCAATCCAGAAACTAAAAAGCATG
ACATATACAATTGAGACTGGATGGATATGATATAAAATATTGGAAAATGAAAGTGATAAATTATTCAATCCAGAAACTAAAAAGCATG
CAAAGGTATTATTACTTAATGAGAATGGTCAATTGTGAATGCAATAGATAGAAGATAAGATGTTCTATTTGGTGAAGATGGTGT
TAATTATTATTACTTAATGAGAATGGTGAATGCAATAGATAGAAGATAAGATGTTCTATTTGGTGAAGATGGTGT
CATGCAGATTGGAGTATTAATACACCAGATTAGATTGAAAAGAGATATTTACAGATGAATATTGCAGCAACTGGTTCAGTTATTA
CAATAAACTATACTGGTTAGATTTTGATCCTGATACAGCTCAATTAGTGATTAGTGAATAG Figure 34. (SEQ. ID. NO.: 31) X53138 20% optimized (positions 16 - 387, in bold, lowercase)

AGTGAAGAAATAAGgtgagcaagtgaagatcagatttgtgaacgtgtttaaggataagaccctggcaaacaagctgagcttaactttagcgataagcaag
atgtgcccgtgagcgaaatcatcctgagctttaccccagctactacgaagatgactgatcggatacgatcggatcggtgagcctgtgcaacgaaaagttttacat
caacaacttggaatgatggtgagcgactgagcgactgatcaacgatactgtactactttaagcccgtgaacaacctgatcaccgatttgtgaccgtgggagat
gataagtactactttaacccatcaacgaggagcagcaagcatcggagaaaccatcatcgatgatAAAATTATTATTTCAACCAAAGTGGAGTGTT
ACAAACAGGTGATTTACTGAAATTAATTATTGACGAAAATATTATTTGCCCCAGCTAATACACTTGATGAAACCTAGAAGGAGAA
GCAATTGATTTACTGGAAATAATTATTGACGAAAATAATTATTTGATGATAATATAGAGGAGCTGTAGAATGGAAA
GAATTAGATGGTGAAATGCACTATTTAGCCCAGAAACAGGTAAAGCTTTAAAGGTCTAAATCAAATAGGTGATTATAAATA
CTATTTCAATTCTGATGGAGTTATGCAAAAGGATTGTAGTATAAATGATAATAAACACTATTTGATGATTCTGGTGTAT
GAAAGTAGGTACACTGAAATAGATGGCAAGCATTTCTACTTTGCTGAAAATGAAGAAGGTCAAATAGGAGTATTAATACA
GAAGATGGATTTAAATATTTGCTCATCATAATGAAGATTAGGAAATGAAGAAGATTTAGAGGATGGTTCAAAGT
AAATTTCAATAATAAAATTACTATTTGATGATTCATTTACAGCTGTAGTTGTCATTAATAAATGATGGTCAATATTATTTAATGATGATGGA
ATTATTTGATGAAGATACAGCAGAAGCATATAAATGATGATAAAGTCTCTACTCTCTGGAATTATAGAATCTGGAGTACAAAA
ATTATGCAAGTTGGATTGTCACTATTCTATATAGATGATAATATTACGGACAAGCAGTTGAATATAGTGGTTTAGTAGAGTTGGGAAGATGTA
CATAGATGACAATTATTCTATATAGATGATAATATTACGGACAAGCAGTTGAATATAGTGGTTTAGTAGAGTTGGGAAGATGTA
TGCACCTGCTAATACTGTAAATGATAATATACAATTGAGACTGGATATATGAGTGATATAAATATTTCAATCC
TATTATTTGGAGAAACATATACAATTGAGACTGGATTAATTGATGATATAAAATATTTGATGAGAAGGGCATAATGAGAACGG
AGAAACTAAAAAGCATGCAAAGGTATTAATTAATTACTTTAATGAAATGGTGAAATGCAATTTGGTTATATAAATAGAAGATAAGA
GTCTTATATCATTTGAAAATAATAATTACTTTCATGCAAGGTGTCTCAGATTGGAGTATTTAAATACTTTGCACATCAAAT
TGTTCTATTTGGTGAAGATGGTGTCATGCAAGGAGATGGTGTCATGCAAGAATAACTATACTGGTTGGTTAGATTAGATGAAAAGAGATTTTACAGA
ACTTTGATGAGAATTTGAGGAGAATCAATAAACTATACTGGTTGGTTAGATTAGATGAAAAGAGATATTTTACAGA
TGAATATATTGCAGCAACTGGTTCAGTTATTATTGATGGTGAGGAGTATTATTTGATCCTGATACAGCTCAATTAGTGATTA
GTGAATAG Figure 35. (SEQ. ID. NO.: 32) X53138 30% optimized (positions 145 - 372, in bold, lowercase)

AGTGAAGAAATAAGGTGTCACAAGTTAAAATAAGATTCGTTAATGTTTTAAAGATAAGCTTTGGCAAATAAGCTATCTTTTAAC
TTTAGTGATAAACAAGATGTACCTGTAAGTGAAATAATCTTATCATTTACACCTTCAtactatgaggatggactgataggctatgacctggcctg
gtttcattgtataatgagaagtttacatcaacaatttggatgatggtctctggctaatctacatcaatgattcgcttactatttaaccccctgtgaacaatctgattactgttt
cgttacagtgggggacgataaatactatttcaacccaataaacggcggagccgctagtatggagaaactatcatagatgacaagaactactatttcaatcagtccggatgct
ccagacagaggtctttagcaccgaagatggcttcaagtatttcgccccgcgaataccctgatgagaacctgaggggagccattgatttcacgggcaagctgatcatt
gacgaaaacattactatttgacgataactacagagaggtgcagtggaggagttagacggcgagatgcattacttagcccgaaaccggtaaagcttttaaaggatt
gaatcaaatcggtgactacaagtactatttaactctgacggggtgatgcagaagggcttcgtatcatcaacgacaataagcactacTTTGATGATTCTGGTGTAT
GAAAGTAGGTTACACTGAAATAGATGGCAAGCATTCTACTTGCTGAAAACGGAGAAATGAAGAATCTCATATTCTGTATATTAAATTC
GATGGATTTAAAATAAATTTGCTCATCATGATTAGGAAATGAAGAGGTGAAGAGATTAGAGGATGGTTCAAGTATTATTTTGAT
AATAATAAAATTTACTATTTTGTCACTTCTGACTCTGAATTATAGAATCTGAGTACAAACATAGATGACAATATT
GAAGATACAGCAGAAGCAGATATAAGTCTTCTACTTCTGACTCTGAATTGGTGTATTCAGATGCGATATAAATATTTGCACCTGCTAATACTGTAAA
ATTTGTCACTATAAATGATAAATGGTATAGTGAAATTGGTATAGCGAGCAGTGATATAAGTGGTTAGAGTTGGGGAAGATGTATATTATTTTGGAGAAAACATATACAA
CTATATATATTACGGACAAGCAGTGAATATATGGAAATGAAAGTGATAAATATATTCAATCCAGAAACTAAAAAGCATGCAAAGGT
TGAGACTGGATGGATATGATAAAATATATTTGATGAGAAGGCATAATGAGAACGGGTCTTATCATTTGAAAATAA
ATTAATTAATTGATGATATAAAATATATTTGATGAGAAGGCATAATGAGAACGGGTCTTATCATTTGTGAAG
TAATTATTACTTTAATGAATGGTGAAATGCAATTGGTTATATAAATATAGAAGATAAGATGTTCTATTTTGGTGAAG
ATGGTGTCATGCAGATTGGAGTATTAATACACCAGATGATTAAATACTTTGCACATCAAATACTTTGGATGAGAAT
TTGAGGGAGAATCAATAAACTATACTGGTTGGTTAGATTAGATGAAAAGAGATATTATTTTACAGATGAATATTGC
AGCAACTGGTTCAGTTATTATTGATGGTGAGGAGTATTATTTGATCCTGATACAGCTCAATTAGTGATTAGTGAATAG Figure 36. (SEQ. ID. NO.: 33) X53138 40% optimized (positions 325 - 1098, in bold, lowercase)

AGTGAAGAAAATAAGGTGTCACAAGTTAAAATAAGATTCGTTAATGTTTTAAAGATAAGACTTTGGCAAATAAGCTATCTTTTAAC
TTAGTGATAAACAAGATGTACCTGTAAGTGAAATCTTATCATTTACACCTTCATATTATGAGGATGGATTGATTGGCTATGAT
TGGGTCTAGTTCTTCTTATATAATGAGAAATTTATATTAATAACTTTGGAATGATGGTATCTGGATTAATATATATTAATGATTCAT
TATATTATTTAAACCACCAGTAAATAATTGATAACTGGATTTGTGACTGTAGGCGATGAaagtattacttcaatcctattaacggcggggcg
gcttcaatcgggaaaccataattgacgataagaactactatttcaaccaatccgggtcctgcagacaggagtgttttctaccgaggatgttcaaatacttttgctcccgcc
aacacattagacgagaaatcagagggcgaagccattgatttacaggaaactcatcatttcgatgacaattacagagggcgccgtcgaatgaa
agagctcgacggtgagatgcattactttagcccagagacggtaaagccttcaaaggactgaaccagatggcgactacaagtattaacagtgatgagtgatgcag
aaggtttcgtgtcaataatgacaataacattacttttgacgatagcggtgtaatgaaggttggctacactgaaatcgatggcaagcacttctatttgcagaaaacggcgaga
tgcagataggcgtgtttaacacggaggatgatttaagtacttcgcccacaccacaatggaaatgaggaaggtgaagagatttctattcggggatcttgaactttaa
caataaaatttactatttcgatgacagcttcaccgcagtcgttggtgggtgaagacctggaagacgggtcaagtattacttcgatgaggacactgcagaggcttatatcggact
gagtcttatcaatgacggccagtattatttcaatgatgaataCATGGCTTTGTCACTATAAATGATAAAGTCTTCTACTTCTCTGACTCTGG
AATTATAGAATCTGGAGTACAAAACATAGATGACAATTATTTCTATATAGATGATAATGTTCAAATTGGTATAGTTCAAATTGGTATTGATAC
TTCAGATGGATATAAATATTTGCACCTGCTAATACTGTAAATGATAATATTACGGACAAGCAGTTGAATATAGTGGTTAGTTAG
AGTTGGGGAAGATGTATATTTGGAGAAAACATGCAAAGGTATTAATTAATTATTACTTTAATGAGAATGTGCAATTGGTTATAAAATATTTGATGAGAAGGGCATAA
ATATTTCAATCAGGGTCTTATATCATTTGGTGAAGATGGTGTCATGCAGATTGGAGTATTAATACACCAGATGGATTTAAATACTTTGCACATCAA
ATAAGATGTTCTATTTGGTGAGAATTTGAGGGAGAATCAATAAACTATACTGGTTGGTTAGATTTAGATGAAAAGAGATATATTTACAGAT
AATACTTGGATGAGCAACTGGTTCAGTTATTGATGGTGAGGAGTATTATTGATCCTGATACAGCTCAATTAGTGATTAGTGA
ATAG Figure 37. (SEQ. ID. NO.: 34) X53138 50% optimized (positions 448 - 1377, in bold, lowercase)

AGTGAAGAAATAAGGTGTCACAAGTTAAAATAAGATTCGTTAATGTTTTAAAGATAAGACTTTGGCAAATAAGCTATCTTTA
ACTTAGTGATAAACAAGATGTACCTGTAAGTGAAATAATCTTATCATTTACACCTTCATATTGAGGATGGATTGATTGGCTA
TGATTGGGTCTAGTTCTTTATATAATGAGAAATTTATATTAATAACTTGGAATGATGGTATCTGATTAATATATATAATG
ATTCATTATATATTTAAACCACCAGTAAATAATTTGATAACTGGATTGTGACTGTAGGCGATGATAAATACTACTTAATCC
AATTAATGGTGGAGCTGCTTCAATTGGAGAGACAATAATTGATGACAAAATTATTATTCAACCAAAGTGGAGTGTTACAAAC
AGGTGTATTTAGTACAGAAGATaatatttactatttgatgacaactataggggcgagtggagtggaagaactggatggagagatgcactatttagcctga
aacaggcaaagcattcaagggattaaaccaaattgggactacaaatactatttcaatagcgacggagtaatgcagaaggggttcgtctccatcaatgataacaagcatt
actttgacgattcaggcgttatgaacgtgggctatactgagatcgatgggaagcacttctacttttgctgagaacgcgaaatgcagattggtgttcaatactgaagacg
gttttaaatatttcgcacatcacaatgaggatcttgcaatgaagaggagagattaagtttactctggtatcctgaacttcaacaataaatctactattcgacgattcgt
tcaccgccgtggtcggatggaaggaccttgaagatgggagcaagtattacttgacgaagatacagccgaggctgaggcgtatattggcctcagtcgattaacgacgacagta
ttactttaacgacgatggcatcatgacaatggtcgtgacaatcaatgacaaggtattttacttttctgactctgaataatcgaatcaggagtgcagaacaattgacgata
actactttacatcgatgacaatgacatcgtccagatggcgtcgtgtttgacacatccgacgggtataagtacttcgcccagtaacactgttaacgacaacacttacggcca
agccgttgagtattccggtcagtgagagtgggaggaggacgtctactattcggtgagactacaccatagagacggggtgatttatgatgaaaatgaaagtgata
aatatttcaatccagaaaaagcatgcaaaggtattaattaattgatgatataaatatATTTGATGAGAAGGGCATAATGAGAACGGTCTT
ATATCATTTGAAATAATAATTATTACTTTAATGAGAATGTGAATGCAATTGGTTATATAAATACTTTGCACATCAAATACTTTGGA
TTTGGTGAAGATGTGTCATGCAGATTGGAGTATTTAATACACCAGATGGATTTAATATGTGAAATGCAATGGATTAAATACTTTGGA
TGAGAATTTTGAGGGAGAATCAATAAACTATACTGGTTAGATTAGATGAAAAGAAGATATTATTTTACAGATGAATATATT
GCAGCAACTGGTTCAGTTATTATTGATGGTGAGGAGTATTATTTGATCCTGATACAGCTCAATTAGTGATTAGTGAATAG Figure 38. (SEQ. ID. NO.: 35) X53138 60% optimized (676 – 1836 positions, in bold, lowercase)

```
AGTGAAGAAATAAGGTGTCACAAGTTAAAATAAGATTCGTTAATGTTTTAAAGATAAGACTTTGGCAAATAAGCTATCTTTA
ACTTTAGTGATAAACAAGATGTACCTGTAAGTGAAATAATCTTATCATTTACACCTTCATATTATGAGGATGGATTGGCTA
TGATTGGGTCTAGTTCTTTATATATGAGAAATTTATATAATAACTTTGGAATGATGTATCTGGATTAATATATATTAATG
ATTCATTATATTATTTAAACCACCAGTAAATAATTTGATAACTGGATTTGTGACTGTAGGCGATGATAAATACTACTTAATCC
AATTAATGGTGGAGCTGCTTCAATTGGAGAGACAATAATTGATGACAAAATTATTATTCAACCAAAGTGGAGTGTTACAAAC
AGGTGTATTAGTACAGAAGATGGATTTAAATATTTGCCCCAGCTAATACACTTGATGAAAACCTAGAAGGAGAAGCAATTG
ATTTACTGGAAAATAATTATTGACGAAAATATTATTTGATGATAATTATAGAGGAGCTGTAGAATGGAAAGAATTAGA
TGGTGAAATGCACTATTTAGCCCAGAAACAGGTAAAGCTTTAAAGGTCTAAATCAAATAGGTGATTATAAATACTATTTCaac
agtgacggggttatgcagaaggtttcgtgagtattaatgacaataagcattatttcgacgatagcggagtgatgaaggtcggctacaccgaaatcgatgggaaacacttt
tactttgcagaaatgagaaatgcaaatggcgtgttcaatacccgagatgcttcaagtattcgcacaccataatgaggatctgggaacgaagaagagggggaggaa
ataagctattctgcatcctcaacttaacaataagattactattcgacgattcgttcaccgccgttgtcgctgaaagactagaggatggctctaaatactatttcgatg
aggacacggccgaggcgtatatcggcctgctcactcattcaatgaccgccagtactatttcaatgatgacgggatcatgcagggattcatcagtggggttgtctgactattaacgataaagtttt
ctactttccgatagcggaatcatagaatccggagtcgaaatcgtgaacgacagaatccaccattatgacagccgtggagtagcggtttggtacgggtgggcgaagatgtgtactatttggagaga
gatacaaatactttgccccagctaacaccgtaacgacacaatatttatgacgacgacaatattgacgaacgacaggcgtgagtagcggtttggtacgggtgggcgaagatgtgtactatttggagaga
cttacaccattgagaccgggtgattatgacgaggaataatgaggactgactgttatcggagacaaaaggcttgcaagggcatcaacctgatcgatgac
atcaaatactatttgacgagaaggaataatgaggactgactttatatcatttgaaaacaataactactatttgcacaccaaaacacgcgacgaaaacttcga
aggataagatgttttacttttggcgaagatgttggatgcagattggtgtgtcagattggtcaagtattcgacaccaaaacacgcgacgaaaacttcga
gggcgagtccatcaattacactgttggctcgacctagtaatgaggatgaagtacttcacagatgagtacttcattgacggtgaggaata
ctacttcgaccctgacacagtcagctcagtgatccagagTAG
```

Figure 39. (SEQ. ID. NO.: 36) X53138 70% optimized (196 – 1497 positions, in bold, lowercase)

AGTGAAGAAATAAGGTGTCACAAGTTAAAATAAGATTCGTTAATGTTTTAAAGATAAGACTTTGGCAAATAAGCTATCTTTA
ACTTAGTGATAAACAAGATGTACCTGTAAGTGAAATAATCTTATCATTTACACCTTCATATTATGAGGATGGATTGATTGGCTA
TGATTTGGGTCTAGTTTCTTTATATaacgaaaaaatttacattaataacttggatgatggtgtcaggcttatctacatcaacgactccctgattactttaagc
cgcccgtcaacaatttaatcacgggattcgtcactgtcgggacgataaatactatttcaaccaattaacggcgggcagcctctataggtgagactatcattgacgata
agaattactactatttcaatcagagagcgggtgctacaaaccgtgtcactgttagcactgaggacgtgttagcactgaggacgttgatgcactgaggacgaaaacctgaagga
gaggccatcgatttcactggtaaggcgttaagggacttaatcagataggggattataaatcagataggggattataaatcagataggggattataaacatttcaactccgacgagtaatgcagaaaggctttgtgagcatcaatgata
cttctcctgaaactggtaaggcgattcaggcgtgatgaaagtgggctacacagaaattgacggcaagcactttacttcgctgagaacgttgagatcggcgtctcaaca
ataaacattattttgacgatttaaatatttcgctcaccataatgagaccttgaattttaacataagatttattacttt
cagaagacggattaaatatttcgctcgttggctgaagatctggaagatctggaagatctgaagatcacatcggggctcagttgataaacg
gatgacagcttcacagctgtcgttggctgaagatctggaagatctgaagataggcttcgtgaccattaatgacaaggtgttctacttctctgatagcggaattatcgagagtggtgtgcagaat
acgggcaatattacttcaatgatgacggataggcttcgtgaccattaatgacaaggtgttctacttctctgatagcggaattatcgagagtggtgtgcagaat
atcgacgataactattttatattgacgataacgggatagtcagatcggcgtgtttgatacctcggatggataccaagtactcgcgccagctaataccgtaatgacaacat
ctacggccaggcgttgaatatagtggtctcgtgagagtaggcgaggacgttattacttggcgagaccggctgatgagaccgtgatacgacatggagaatg
aatccgataagtattacttcaatcctgagaccaaaaggcatgcaagggaataaacctgatcgatgacatcaagtattatttgatgagaaggtattatgcggacaGGT
CTTATATCATTGAAAATAATAATTATTACTTTAATGAATGGTGAAATGCAATTGGTTATATAATATAGAAGATAAGATGTT
CTATTTGGTGAAGATTGGTGTCATGCAGATTGGAGTATTAATACACCAGATGATTAAATACTTTGCACATCAAATACTTT
GGATGAGAATTTGAGGGAGAATCAATAAACTATACTGGTTAGATGAAAAGAGATATTATTTACAGATGAATA
TATTGCAGCAACTGGTTCAGTTATTATTGATGGTGAGGAGTATTATTTGATCCTGATACAGCTCAATTAGTGATTAGTGAATA
G Figure 40. (SEQ. ID. NO.: 37) X53138 80% optimized (22 - 1509 positions, in bold, lowercase)

AGTGAAGAAAATAAGGTGTCAcaagtgaagatcagattcgtgaatgttttaaagacaaaacgttggcgaacaagctttcattcaactttagtgacaaacaaga
cgtgcccgtgtccgaaataatcctgagcttcacccagcttacgaggacggacttatcgagaacgttgactggtatcctttatataacgagaaattctatattaac
aattttgggatgatggtctccggcctgatttacataatgacagtctatattactttaagcgccgtcaacaatctcatcacggcttcgtaactgtcgcgacgataagta
tacttttaacctatcaacggagggcagctagtaggggacgatcattgatgacaaaattactattttaatcagtctggagttctccagacaggcgtgttcaaca
gaagacgggttcaagtacttcgcaccagctacaacacattgatgaaggagctcgatgagaaggagctcactttctctctgaaacaggcaaggcctcaaagggctcaatcagattggag
cgatgacaactatcggggtgccgttgaatggaaggagctcgatgatgcgtgatcaaaaggttttgtctattaatgacaacaagcactatttgatgactctggcgttatgaaggtaggctacacagag
actataaatactatttcaactccgatgcgtgatcaaaaggttttgtctattaatgacaacaagcactatttgatgactctggcgttatgaaggtaggctacacagag
atcgatggcaagcattctatttcgcagaaaacggcagaatcgagcaagatcaagatctgcgaagctcaccgccgtttgggttggaaagatttagaagatgg
tgaggaaggcgaagagagataagctatagaccgcgagaaacctcagagccattcaacataagatctctcctgataaacgacggtcagtactatttcaatgacagcttcataggacgtcagtggggttttgtc
gtcgaaatactatttgatgaagatactcttttagtgattcaggaattacgagacggggtcagaatatcgacgataataattctacatcgacgataatgaatcgtccagatcgg
accattaacgataaggtcttttattttagtgattcaggaattacgagacggggtcagaatatcgacgataataattctacatcgacgataatgaatcgtccagatcgg
agtattgacacttccgatgctacaaatacttcgctccagcaacaccgttaacgacacatatctacgacaggccgtggaatactctggtcgtgcgtgcgag
gacgtgactactattggtgaaacctacactattgagaccgcggatctacgacatggagaagaatcagacaagtactatttcaacctgagactaagaagcatgcaa
gggcattaacctgatagacgacattaaatactacttgacgagaaggaattatgaggaacaggctaattagcTTTGAAAATAATAATTACTTTAATGA
GAATGGTGAAATGCAATTTGGTTATATAAATACTTTGTCTATTTGGTGAAGATGGTGTCATGCAGATTGGAG
TATTTAATACACCAGATGCAATTTAAATACTTTGCACATCAAAATACTTTGGATGAGAATTTGAGGGAGAATCAATAAACTATA
CTGGTTGGTTAGATTAGATGAAAAGAGATATATTTACAGATGAATATTGCAGCAACTGGTTCAGTTATTATTGATGGTG
AGGAGTATTATTTTGATCCTGATACAGCTCAATTAGTGATTAGTGAATAG Figure 41. (SEQ. ID. NO.: 38) X53138 90% optimized (70 – 1743 positions, in bold, lowercase)

AGTGAAGAAAATAAGGTGTCACAAGTTAAAATAAGATTCGTTAATGTTTTAAAGATAAGACTTTGGCAaataagctttcattcaacttca
gcgataaacaggacgtcccggtatccgaaattatcctgtccttacccccagctactatgaggacgcctgatcgatatgatcgatcagggctagggcgtgtcattatacaatgaga
agtttacatcaacaatttcggaatgatgtgagtgtctgatctacatcaatgatagccttactatttcaagcctccccgttaataacctataaccggatttgtaacagtgggc
gatgacaaatactatttaacccaatcaacgaggtgccgcatcgataggggaaaactattatagacgataaaaactattacttcaatcaaagtggcgtgttgcaaactggc
gtgtttagcacggaggatggttcaagtactttgctcccgctaacacactgacgaaaacctcgagggtgaggcgattgattttacagggaagctgatcattgacgagaa
catttattacttcgacgataattacagggggtgccgttgaatgaagagttacagggagttagacggcgaggcattcacctgaaacgggaaggcattcaaagactcaatca
gatcggggattacaagtattactttaacagtgatgcgtcatgcagagaacggagaaattgagtctttaatacagagaggatgcttaagtatttcgcccaccataacgaggac
tatacgaaaatagacgggaagcatttctatttgcagagaacgagaaatgcaaattggagtcttaatacagagaggatgcttaagtatttcgcgtggtaggtggaaagacctgga
agatggatctaaatactatttgacgaggagacagcccgaggctagagcgcccagaggctacgatccagagtacattcaacgacgatgggatcatgcggcattgtgca
attcgtcaccatcaatgacaaagtgttctactttagcgatagcggcgtccaaaacattgaatcaggcgatcaaacattttatcgacgataacaacattatatcgcggatctgaggttgat
gataggtgtgtcgacacctcggatgggtacaaaatattcgctcctgcgaacaccgttaatgataatagtgagaatacatggccaggcgtagaatacagtggcctcgtgaagttggt
gagacgtgtattacttggagagaaccatatcatcgagactgctggattatgacatgagagaatgagtctgacaaatattcttgaaacaataactatttacttcaatgagaatggcga
agggaatcaacttgattgatgacattaagtactattgagtcttgacgaagaacagagttctactttcggtgaagacgcgtgcgtgttaacacccagatgggctttaagtatttcgcaca
ccagaatactcttgatgaaaacttcgaaggcgaaagcataattaacaccgggtgctgatctcgatgagaagcggtattacttcACAGATGAATATATTGCAG
CAACTGGTTCAGTTATTATTGATGGTGAGGAGTATTATTTGATCCTGATACAGCTCAATTAGTGATTAGTGAATAG

US 8,852,600 B2

CODON-OPTIMIZED DNA MOLECULES ENCODING THE RECEPTOR BINDING DOMAINS OF *CLOSTRIDIUM DIFFICILE* TOXINS A AND B, AND METHODS OF USE THEREOF

This invention was made with government support from the National Institute of Health under Grant No. 5K08AI58747-03. The U.S. Government has certain rights in this invention.

This application asserts priority to U.S. Provisional Application Ser. No. 60/812,489 filed on Jun. 8, 2006, the specification of which is hereby incorporated by reference in its entirety.

BACKGROUND OF THE INVENTION

*Clostridium difficile* is a gram-positive anaerobic bacterium whose clinical manifestations include diarrhea, pseudomembraneous colitis, sepsis, and death. Progression from colonization to infection and recrudescent disease reflects a failure to mount an effective antibody response against the toxins released by the bacterium.

Common treatments for *C. difficile*-associated diseases include terminating the original antibiotic treatment and administering either metronidazole or vancomycin. Both metronidazole and vancomycin, however, have particular disadvantages. Vancomycin, the only therapy approved by the United States Food and Drug Administration, (USFDA) is associated with selection of resistant gram positive pathogens, while metronidazole appears less effective than vancomycin for severe *C. difficile* disease. Both agents do not prevent relapse of *C. difficile* infection after termination of treatment, a situation also associated with poor anti-toxin immune responses and one that can be very difficult to treat.

Therefore, there is a need for new, more effective approaches to treating and preventing *C. difficile*-associated diseases.

BRIEF DESCRIPTION OF THE DRAWINGS

FIG. 1. Amino acid sequence of *Clostridium difficile* toxin A (GenBank Accession no. CAA63564, SEQ. ID. NO.: 1). The receptor-binding domain of *Clostridium difficile* toxin A occurs at amino acid residues from positions 1839-2710 (SEQ. ID. NO.: 2).

FIG. 2. Amino acid sequence of *Clostridium difficile* toxin A (GenBank Accession no. A37052, SEQ. ID. NO.: 3). The receptor-binding domain of *Clostridium difficile* toxin A occurs at amino acid residues from positions 1839-2710 (SEQ. ID. NO.: 4).

FIG. 3. Amino acid sequence of *Clostridium difficile* toxin A (GenBank Accession no. AAA23283, SEQ. ID. NO.: 5). The receptor-binding domain of *Clostridium difficile* toxin A occurs at amino acid residues from positions 1839-2710 (SEQ. ID. NO.: 6).

FIG. 4. Amino acid sequence of *Clostridium difficile* toxin A (GenBank Accession no. P16154, SEQ. ID. NO.: 7). The receptor-binding domain of *Clostridium difficile* toxin A occurs at amino acid residues from positions 1839-2710 (SEQ. ID. NO.: 8).

FIG. 5. Nucleotide sequence (SEQ. ID. NO.: 9) encoding a receptor-binding domain of *Clostridium difficile* toxin A wherein at least about 10% of the in-frame codons for each amino acid residue has a higher percentage use in the human genome according to table 1 than the corresponding in-frame codons of *Clostridium difficile* toxin A having SEQ. ID. NO.: 13.

FIG. 6. Amino acid sequence (SEQ. ID. NO.: 10) of an epitope of *Clostridium difficile* toxin A.

FIG. 7. DNA molecule (SEQ. ID. NO.: 11) containing a nucleotide sequence (SEQ. ID. NO.: 9) encoding a receptor-binding domain *Clostridium difficile* toxin A wherein at least about 10% of the in-frame codons for each amino acid residue has a higher percentage use in the human genome according to table 1 than the corresponding in-frame codons of *Clostridium difficile* toxin A having SEQ. ID. NO.: 13 and further containing a Kozak sequence, a tPA leader sequence, and an EcoRI restriction site.

FIG. 8. DNA molecule (SEQ. ID. NO.: 12) containing a nucleotide sequence (SEQ. ID. NO.: 9) encoding a receptor-binding domain *Clostridium difficile* toxin A wherein at least about 10% of the in-frame codons for each amino acid residue has a higher percentage use in the human genome according to table 1 than the corresponding in-frame codons of *Clostridium difficile* toxin A having SEQ. ID. NO.: 13 and further containing a Kozak sequence and an EcoRI restriction site.

FIG. 9. Nucleotide sequence (SEQ. ID. NO.: 13) for a naturally occurring receptor binding domain of *Clostridium difficile* toxin A. The sequence is nucleotide positions 5515-7914 (SEQ. ID. NO.: 14) of GenBank Accession no. M30307.

FIG. 10. Schematic of a plasmid containing a "tPA-TxA-RBD" DNA molecule of the claimed invention.

FIG. 11. Serum IgG antibody titers to *C. difficile* toxin A measured in BALB/c mice. The mice were immunized with one of the following: pVAX (25 ug into each rear limb intramuscularly); TxA-RBD (25 ug into each rear limb intramuscularly); tPA-TxA-RBD (25 ug into each rear limb intramuscularly); TxA-RBD (25 ug into each rear limb by electroporation-enhanced (EP) intramuscular injection); or tPA-TxA-RBD (25 ug into each rear limb by electroporation-enhanced (EP) intramuscular injection). Mice were injected at week 0 and 2. The mice were bled 6 weeks after immunization and were challenged with *C. difficile* toxin A at week 8. Antibody titers were determined by ELISA.

FIG. 12. Amino acid sequence of *Clostridium difficile* toxin B (GenBank Accession no. P18177, SEQ. ID. NO.: 15). The receptor-binding domain of *Clostridium difficile* toxin B occurs at amino acid residues from positions 1755-2367 (SEQ. ID. NO.: 16).

FIG. 13. Nucleotide sequence for a naturally occurring receptor binding domain of *Clostridium difficile* toxin B (SEQ. ID. NO.: 17). The sequence is nucleotide positions 5263-7101 (SEQ. ID. NO.: 18) of GenBank Accession no. X53138.

FIG. 14. Nucleotide sequence (SEQ. ID. NO.: 19) encoding a receptor-binding domain *Clostridium difficile* toxin B wherein at least about 10% of the in-frame codons for each amino acid residue has a higher percentage use in the human genome according to table 1 than the corresponding in-frame codons of *Clostridium difficile* toxin B having SEQ. ID. NO.: 17. Gene composition by nucleic acid residue positions: nucleic acid residue positions 1-6 is Nhe1 restriction site (GCT AGC); nucleic acid residue positions 5-13 is Kozak sequence (GCC GCC ACC); nucleic acid residue positions 14-16 is ATG start; nucleic acid residue positions 17-22 is BamH1 restriction site (GGA TCC); nucleic acid residue positions 23-1861 is toxin B receptor binding domain; nucleic acid residue positions 1862-1867 is EcoR1 restriction site (GAA TTC).

FIG. 15. Schematic of plasmids "TxA-RBD" and "tPA-TxA-RBD."

FIG. 16. DNA molecule (SEQ. ID. NO.: 20) containing a nucleotide sequence (SEQ. ID. NO.: 19) encoding a receptor-binding domain *Clostridium difficile* toxin A wherein at least about 10% of the in-frame codons for each amino acid residue has a higher percentage use in the human genome according to table 1 than the corresponding in-frame codons of *Clostridium difficile* toxin B having SEQ. ID. NO.:17 and further containing a tPA leader sequence.

FIG. 17. Schematic of plasmids "TxB-RBD" and "tPA-TxB-RBD."

FIG. 18. Serum IgG antibody titers to *C. difficile* toxin B measured in BALB/c mice. The mice were immunized with one of the following: pVAX (25 ug into each rear limb intramuscularly); TxB-RBD (25 ug into each rear limb intramuscularly); tPA-TxB-RBD (25 ug into each rear limb intramuscularly); TxB-RBD (25 ug into each rear limb by electroporation-enhanced (EP) intramuscular injection); or tPA-TxB-RBD (25 ug into each rear limb by electroporation-enhanced (EP) intramuscular injection). The mice were bled 6 weeks after immunization and were challenged with *C. difficile* toxin B at week 8. Antibody titers were determined by ELISA.

FIG. 22. Survival curve plots for BALB/c mice following *C. difficile* toxin A and toxin B challenge. The mice were immunized with one of the following: pVAX (25 ug into each rear limb intramuscularly); TxA-RBD (25 ug into each rear limb intramuscularly); TxB-RBD (25 ug into each rear limb intramuscularly); or a combination of TxA-RBD and TxB-RBD ("TxA-TxB") (25 ug of each plasmid into each rear limb intramuscularly). Toxin challenges were performed as described.

FIG. 23. Serum IgG antibody titers to *C. difficile* toxin A and B measured in hamsters. The hamsters were immunized by electroporation-enhanced (EP) intramuscular injection with one of the following: pVAX (100 ug into each rear limb); TxA-RBD (100 ug ("High") into each rear limb); TxA-RBD (11 ug ("Low") into each rear limb); TxB-RBD (100 ug ("High") into each rear limb; or TxB-RBD (11 ug ("Low") into each rear limb). The hamsters were bled 10 weeks after immunization and antibody titers determined by ELISA.

FIG. 24. Nucleotide sequence (SEQ. ID. NO.: 21) encoding a receptor-binding domain of *Clostridium difficile* toxin A wherein at least about 10% of the in-frame codons for each amino acid residue has a higher percentage use in the human genome according to table 1 than the corresponding in-frame codons of *Clostridium difficile* toxin A having SEQ. ID. NO.: 13. Nucleotide sequence SEQ. ID. NO.:21 contains 2619 nucleotides, in which positions 1-2619 corresponds to nucleotide positions 5675-8293 (SEQ. ID. NO.:39) of GenBank Accession no. M30307. Positions 4-267 in the figure represent in-frame codons having a higher percentage use in the human genome according to table 1 than the corresponding in-frame codons of *C. difficile* toxin A.

FIG. 25. Nucleotide sequence (SEQ. ID. NO.: 22) encoding a receptor-binding domain of *Clostridium difficile* toxin A wherein at least about 20% of the in-frame codons for each amino acid residue has a higher percentage use in the human genome according to table 1 than the corresponding in-frame codons of *Clostridium difficile* toxin A having SEQ. ID. NO.: 13. Nucleotide sequence SEQ. ID. NO.:22 contains 2619 nucleotides, in which positions 1-2619 corresponds to nucleotide positions 5675-8293 (SEQ. ID. NO.:39) of GenBank Accession no. M30307. Positions 154-681 in the figure represent in-frame codons having a higher percentage use in the human genome according to table 1 than the corresponding in-frame codons of *C. difficile* toxin A.

FIG. 26. Nucleotide sequence (SEQ. ID. NO.: 23) encoding a receptor-binding domain of *Clostridium difficile* toxin A wherein at least about 30% of the in-frame codons for each amino acid residue has a higher percentage use in the human genome according to table 1 than the corresponding in-frame codons of *Clostridium difficile* toxin A having SEQ. ID. NO.: 13. Nucleotide sequence SEQ. ID. NO.:23 contains 2619 nucleotides, in which positions 1-2619 corresponds to nucleotide positions 5675-8293 (SEQ. ID. NO.:39) of GenBank Accession no. M30307. Positions 667-1458 in the figure represent in-frame codons having a higher percentage use in the human genome according to table 1 than the corresponding in-frame codons of *C. difficile* toxin A.

FIG. 27. Nucleotide sequence (SEQ. ID. NO.: 24) encoding a receptor-binding domain of *Clostridium difficile* toxin A wherein at least about 40% of the in-frame codons for each amino acid residue has a higher percentage use in the human genome according to table 1 than the corresponding in-frame codons of *Clostridium difficile* toxin A having SEQ. ID. NO.: 13. Nucleotide sequence SEQ. ID. NO.:24 contains 2619 nucleotides, in which positions 1-2619 corresponds to nucleotide positions 5675-8293 (SEQ. ID. NO.:39) of GenBank Accession no. M30307. Positions 769-1824 in the figure represent in-frame codons having a higher percentage use in the human genome according to table 1 than the corresponding in-frame codons of *C. difficile* toxin A.

FIG. 28. Nucleotide sequence (SEQ. ID. NO.: 25) encoding a receptor-binding domain of *Clostridium difficile* toxin A wherein at least about 50% of the in-frame codons for each amino acid residue has a higher percentage use in the human genome according to table 1 than the corresponding in-frame codons of *Clostridium difficile* toxin A having SEQ. ID. NO.: 13. Nucleotide sequence SEQ. ID. NO.:25 contains 2619 nucleotides, in which positions 1-2619 corresponds to nucleotide positions 5675-8293 (SEQ. ID. NO.:39) of GenBank Accession no. M30307. Positions 31-1350 in the figure represent in-frame codons having a higher percentage use in the human genome according to table 1 than the corresponding in-frame codons of *C. difficile* toxin A.

FIG. 29. Nucleotide sequence (SEQ. ID. NO.: 26) encoding a receptor-binding domain of *Clostridium difficile* toxin A wherein at least about 60% of the in-frame codons for each amino acid residue has a higher percentage use in the human genome according to table 1 than the corresponding in-frame codons of *Clostridium difficile* toxin A having SEQ. ID. NO.: 13. Nucleotide sequence SEQ. ID. NO.:26 contains 2619 nucleotides, in which positions 1-2619 corresponds to nucleotide positions 5675-8293 (SEQ. ID. NO.:39) of GenBank Accession no. M30307. Positions 415-1998 in the figure represent in-frame codons having a higher percentage use in the human genome according to table 1 than the corresponding in-frame codons of *C. difficile* toxin A.

FIG. 30. Nucleotide sequence (SEQ. ID. NO.: 27) encoding a receptor-binding domain of *Clostridium difficile* toxin A wherein at least about 70% of the in-frame codons for each amino acid residue has a higher percentage use in the human genome according to table 1 than the corresponding in-frame codons of *Clostridium difficile* toxin A having SEQ. ID. NO.: 13. Nucleotide sequence SEQ. ID. NO.:27 contains 2619 nucleotides, in which positions 1-2619 corresponds to nucleotide positions 5675-8293 (SEQ. ID. NO.:39) of GenBank Accession no. M30307. Positions 226-2073 in the figure represent in-frame codons having a higher percentage use in the human genome according to table 1 than the corresponding in-frame codons of *C. difficile* toxin A.

FIG. 31. Nucleotide sequence (SEQ. ID. NO.: 28) encoding a receptor-binding domain of *Clostridium difficile* toxin A wherein at least about 80% of the in-frame codons for each amino acid residue has a higher percentage use in the human genome according to table 1 than the corresponding in-frame codons of *Clostridium difficile* toxin A having SEQ. ID. NO.: 13. Nucleotide sequence SEQ. ID. NO.:28 contains 2619 nucleotides, in which positions 1-2619 corresponds to nucleotide positions 5675-8293 (SEQ. ID. NO.:39) of GenBank Accession no. M30307. Positions 193-2112 in the figure represent in-frame codons having a higher percentage use in the human genome according to table 1 than the corresponding in-frame codons of *C. difficile* toxin A.

FIG. 32. Nucleotide sequence (SEQ. ID. NO.: 29) encoding a receptor-binding domain of *Clostridium difficile* toxin A wherein at least about 90% of the in-frame codons for each amino acid residue has a higher percentage use in the human genome according to table 1 than the corresponding in-frame codons of *Clostridium difficile* toxin A having SEQ. ID. NO.: 13. Nucleotide sequence SEQ. ID. NO.:29 contains 2619 nucleotides, in which positions 1-2619 corresponds to nucleotide positions 5675-8293 (SEQ. ID. NO.:39) of GenBank Accession no. M30307. Positions 16-2391 in the figure represent in-frame codons having a higher percentage use in the human genome according to table 1 than the corresponding in-frame codons of *C. difficile* toxin A.

FIG. 33. Nucleotide sequence (SEQ. ID. NO.: 30) encoding a receptor-binding domain of *Clostridium difficile* toxin B wherein at least about 10% of the in-frame codons for each amino acid residue has a higher percentage use in the human genome according to table 1 than the corresponding in-frame codons of *Clostridium difficile* toxin B having SEQ. ID. NO.: 17. Nucleotide sequence SEQ. ID. NO.:30 contains 1839 nucleotides, in which positions 1-1839 corresponds to nucleotide positions 5661-7499 (SEQ. ID. NO.:40) of GenBank Accession no. X53138. Positions 1075-1260 in the figure represent in-frame codons having a higher percentage use in the human genome according to table 1 than the corresponding in-frame codons of *C. difficile* toxin B.

FIG. 34. Nucleotide sequence (SEQ. ID. NO.: 31) encoding a receptor-binding domain of *Clostridium difficile* toxin B wherein at least about 20% of the in-frame codons for each amino acid residue has a higher percentage use in the human genome according to table 1 than the corresponding in-frame codons of *Clostridium difficile* toxin B having SEQ. ID. NO.: 17. Nucleotide sequence SEQ. ID. NO.:31 contains 1839 nucleotides, in which positions 1-1839 corresponds to nucleotide positions 5661-7499 (SEQ. ID. NO.:40) of GenBank Accession no. X53138. Positions 16-387 in the figure represent in-frame codons having a higher percentage use in the human genome according to table 1 than the corresponding in-frame codons of *C. difficile* toxin B.

FIG. 35. Nucleotide sequence (SEQ. ID. NO.: 32) encoding a receptor-binding domain of *Clostridium difficile* toxin B wherein at least about 30% of the in-frame codons for each amino acid residue has a higher percentage use in the human genome according to table 1 than the corresponding in-frame codons of *Clostridium difficile* toxin B having SEQ. ID. NO.: 17. Nucleotide sequence SEQ. ID. NO.:32 contains 1839 nucleotides, in which positions 1-1839 corresponds to nucleotide positions 5661-7499 (SEQ. ID. NO.:40) of GenBank Accession no. X53138. Positions 145-372 in the figure represent in-frame codons having a higher percentage use in the human genome according to table 1 than the corresponding in-frame codons of *C. difficile* toxin B.

FIG. 36. Nucleotide sequence (SEQ. ID. NO.: 33) encoding a receptor-binding domain of *Clostridium difficile* toxin B wherein at least about 40% of the in-frame codons for each amino acid residue has a higher percentage use in the human genome according to table 1 than the corresponding in-frame codons of *Clostridium difficile* toxin B having SEQ. ID. NO.: 17. Nucleotide sequence SEQ. ID. NO.:33 contains 1839 nucleotides, in which positions 1-1839 corresponds to nucleotide positions 5661-7499 (SEQ. ID. NO.:40) of GenBank Accession no. X53138. Positions 325-1098 in the figure represent in-frame codons having a higher percentage use in the human genome according to table 1 than the corresponding in-frame codons of *C. difficile* toxin B.

FIG. 37. Nucleotide sequence (SEQ. ID. NO.: 34) encoding a receptor-binding domain of *Clostridium difficile* toxin B wherein at least about 50% of the in-frame codons for each amino acid residue has a higher percentage use in the human genome according to table 1 than the corresponding in-frame codons of *Clostridium difficile* toxin B having SEQ. ID. NO.: 17. Nucleotide sequence SEQ. ID. NO.:34 contains 1839 nucleotides, in which positions 1-1839 corresponds to nucleotide positions 5661-7499 (SEQ. ID. NO.:40) of GenBank Accession no. X53138. Positions 448-1377 in the figure represent in-frame codons having a higher percentage use in the human genome according to table 1 than the corresponding in-frame codons of *C. difficile* toxin B.

FIG. 38. Nucleotide sequence (SEQ. ID. NO.: 35) encoding a receptor-binding domain of *Clostridium difficile* toxin B wherein at least about 60% of the in-frame codons for each amino acid residue has a higher percentage use in the human genome according to table 1 than the corresponding in-frame codons of *Clostridium difficile* toxin B having SEQ. ID. NO.: 17. Nucleotide sequence SEQ. ID. NO.:35 contains 1839 nucleotides, in which positions 1-1839 corresponds to nucleotide positions 5661-7499 (SEQ. ID. NO.:40) of GenBank Accession no. X53138. Positions 676-1836 in the figure represent in-frame codons having a higher percentage use in the human genome according to table 1 than the corresponding in-frame codons of *C. difficile* toxin B.

FIG. 39. Nucleotide sequence (SEQ. ID. NO.: 36) encoding a receptor-binding domain of *Clostridium difficile* toxin B wherein at least about 70% of the in-frame codons for each amino acid residue has a higher percentage use in the human genome according to table 1 than the corresponding in-frame codons of *Clostridium difficile* toxin B having SEQ. ID. NO.: 17. Nucleotide sequence SEQ. ID. NO.:36 contains 1839 nucleotides, in which positions 1-1839 corresponds to nucleotide positions 5661-7499 (SEQ. ID. NO.:40) of GenBank Accession no. X53138. Positions 196-1497 in the figure represent in-frame codons having a higher percentage use in the human genome according to table 1 than the corresponding in-frame codons of *C. difficile* toxin B.

FIG. 40. Nucleotide sequence (SEQ. ID. NO.: 37) encoding a receptor-binding domain of *Clostridium difficile* toxin B wherein at least about 80% of the in-frame codons for each amino acid residue has a higher percentage use in the human genome according to table 1 than the corresponding in-frame codons of *Clostridium difficile* toxin B having SEQ. ID. NO.: 17. Nucleotide sequence SEQ. ID. NO.:37 contains 1839 nucleotides, in which positions 1-1839 corresponds to nucleotide positions 5661-7499 (SEQ. ID. NO.:40) of GenBank Accession no. X53138. Positions 22-1509 in the figure represent in-frame codons having a higher percentage use in the human genome according to table 1 than the corresponding in-frame codons of *C. difficile* toxin B.

FIG. 41. Nucleotide sequence (SEQ. ID. NO.: 38) encoding a receptor-binding domain of *Clostridium difficile* toxin B wherein at least about 90% of the in-frame codons for each amino acid residue has a higher percentage use in the human genome according to table 1 than the corresponding in-frame codons of *Clostridium difficile* toxin B having SEQ. ID. NO.: 17. Nucleotide sequence SEQ. ID. NO.:38 contains 1839 nucleotides, in which positions 1-1839 corresponds to nucleotide positions 5661-7499 (SEQ. ID. NO.:40) of GenBank Accession no. X53138. Positions 70-1743 in the figure represent in-frame codons having a higher percentage use in the human genome according to table 1 than the corresponding in-frame codons of *C. difficile* toxin B.

INCORPORATION OF SEQUENCE LISTING

Figure 19:
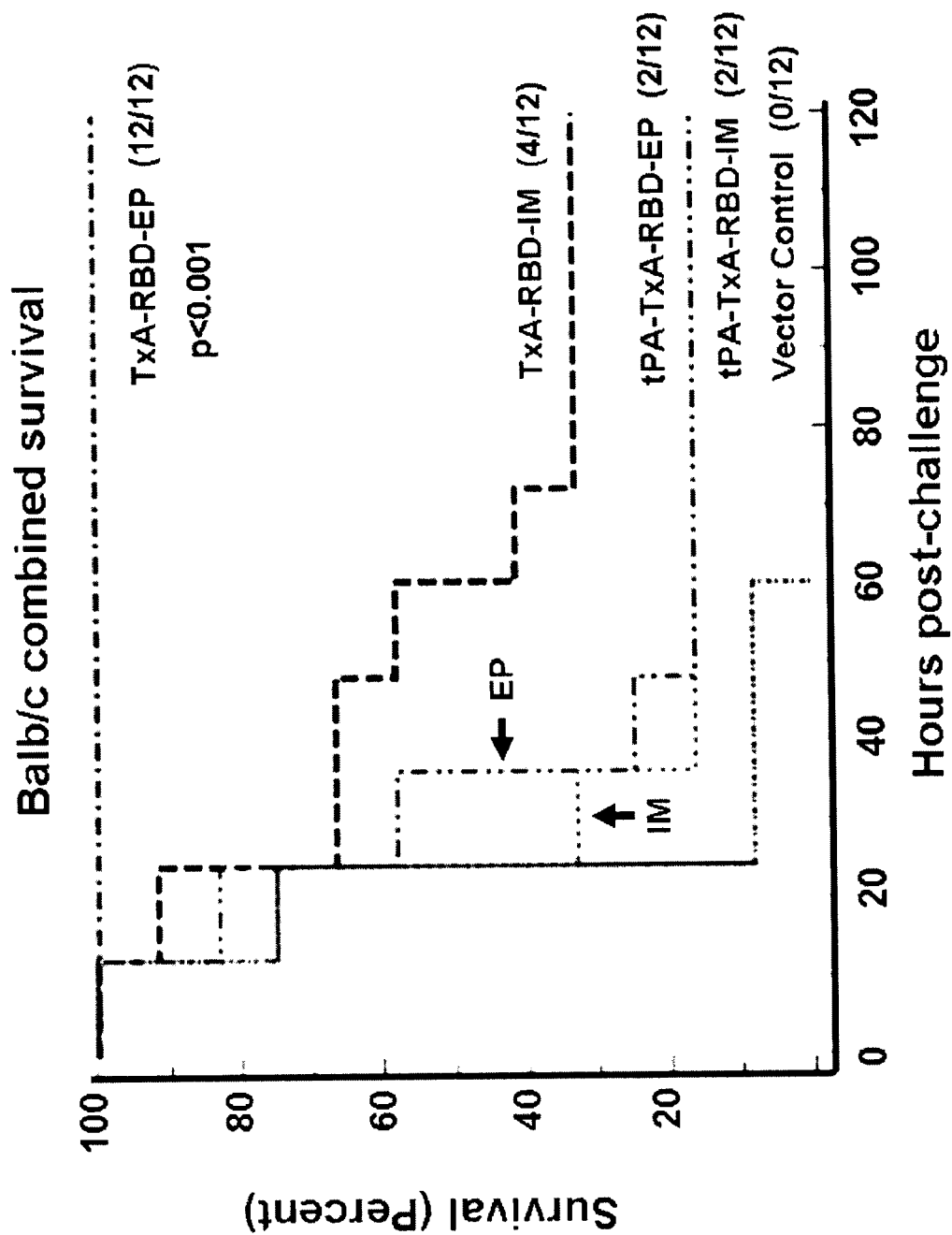
FIG. 19. Survival curve plots for BALB/c mice administered with pVAX vector (EP), tPA-TxA-RBD (IM), tPA-TxA-RBD (EP), TxA-RBD (IM), or TxA-RBD (EP) after *C. difficile* toxin A challenge. Animals were challenged with 300 ng of active, purified *C. difficile* toxin A, from strain VPI 10463 in 100 μl of sterile saline by intraperitoneal injection.

Incorporated herein by reference in its entirety is the Sequence Listing for the application. The Sequence Listing is disclosed on a computer-readable ASCII text file titled, "substitute_sequence_listing_2.txt", created on Apr. 24, 2014. The file is 236 kb in size.

SUMMARY OF THE INVENTION

The present invention provides a DNA molecule comprising a nucleotide sequence that encodes the receptor-binding domain of *Clostridium difficile* toxin A, wherein at least about 10% of the in-frame codons for each amino acid residue has a higher percentage use in the human genome according to table 1 than the corresponding in-frame codons of *Clostridium difficile* toxin A having SEQ. ID. NO.: 13.

In another embodiment, the invention provides a method for generating antibodies to *Clostridium difficile* toxin A in a mammal. The method comprises administering to the mammal an effective amount of a DNA of the claimed invention incorporated into a vector.

In a further embodiment, the invention provides a method for reducing the risk of a *Clostridium difficile* infection in a human. The method comprises administering to the human an effective amount of a DNA molecule of the claimed invention incorporated into a vector.

In yet another embodiment, a method for treating a *Clostridium difficile* infection in a human in need thereof, the method comprising administering to the human an effective amount of a DNA molecule of the claimed invention incorporated into a vector.

In another aspect, the invention provides a DNA molecule comprising a nucleotide sequence that encodes the receptor-binding domain of *Clostridium difficile* toxin B, wherein at least about 10% of the in-frame codons for each amino acid residue has a higher percentage use in the human genome according to table 1 than the corresponding in-frame codons of *Clostridium difficile* toxin B having SEQ. ID. NO.:17.

In another embodiment, the invention provides a method for generating antibodies to *Clostridium difficile* toxin B in a mammal. The method comprises administering to the mammal an effective amount of a DNA of the claimed invention incorporated into a vector.

In a further embodiment, the invention provides a method for reducing the risk of a *Clostridium difficile* infection in a human. The method comprises administering to the human an effective amount of a DNA molecule of the claimed invention incorporated into a vector.

In yet another embodiment, a method for treating a *Clostridium difficile* infection in a human in need thereof, the method comprising administering to the human an effective amount of a DNA molecule of the claimed invention incorporated into a vector.

DISCLOSURE OF INVENTION

DNA Molecule

In one aspect, the invention provides a modified DNA molecule comprising a nucleotide sequence that encodes the receptor-binding domain (RBD) of *Clostridium difficile* toxin A. The nucleotide sequence of a naturally occurring receptor binding domain of *C. difficile* toxin A is shown in FIG. 9 (SEQ. ID. NO.:13). The amino acid sequence for *C. difficile* toxin A is shown in FIGS. 1 through 4 (SEQ. ID. NOs: 1, 3, 5, and 7, respectively). The amino acid sequences for the receptor binding domain of *C. difficile* toxin A is set forth in SEQ. ID. NOs: 2, 4, 6 and 8.

In another aspect, the invention provides a DNA molecule comprising a nucleotide sequence that encodes the receptor-binding domain (RBD) of *Clostridium difficile* toxin B. The nucleotide sequence of a naturally occurring receptor binding domain of *C. difficile* toxin B is shown in FIG. 14 (SEQ. ID. NO.:17). The amino acid sequence for *C. difficile* toxin B is shown in FIG. 12 (SEQ. ID. NO.: 15). The amino acid sequence for the receptor binding domain of *C. difficile* toxin B is set forth in SEQ. ID. NO.: 16.

In yet another aspect, the invention provides a DNA molecule comprising a nucleotide sequence that encodes the receptor-binding domain of *Clostridium difficile* toxin A and toxin B. The DNA molecule includes a nucleotide sequence that encodes the receptor-binding domain of *C. difficile* toxin A, wherein at least about 10% of the in-frame codons for each amino acid residue has a higher percentage use in the human genome according to table 1 than the corresponding in-frame codons of *Clostridium difficile* toxin A having SEQ. ID. NO.: 13, and it includes a nucleotide sequence that encodes the receptor-binding domain of *C. difficile* toxin B, wherein at least about 10% of the in-frame codons for each amino acid residue has a higher percentage use in the human genome according to table 1 than the corresponding in-frame codons of *Clostridium difficile* toxin B having SEQ. ID. NO.: 17.

The term, "DNA molecule," as used herein, refers to a strand of deoxyribonucleotides. The term, "DNA molecule" is equivalent to "DNA chain," or "a DNA," or "DNA polymer," or "DNA sequence." A "recombinant DNA molecule" is a DNA molecule which is comprised of segments of DNA joined together by means of molecular biological techniques.

*C. difficile* toxin A and toxin B are major *C. difficile* virulence factors. Toxin A and toxin B are large (250 to 310 kDa) polypeptides with structures that possess multiple functional domains. The N-terminal domains of both toxins contain glucosyltransferase activity. The central domain is a hydrophobic region, important for translocating the toxins across the cell membrane. The C-terminal domains of the toxins, herein referred to as receptor binding domains, are primarily responsible for binding to receptors expressed on a target cell surface.

The nucleotide sequences useful in the DNA molecules of the present invention include those that encode the full length receptor-binding domain of *C. difficile* toxin A or *C. difficile* toxin B. An example of a nucleotide sequence useful in the DNA molecule of the claimed invention that encodes the full length of the receptor-binding domain of *C. difficile* toxin A is set forth in SEQ. ID. NO.:9 (FIG. 5). An example of a nucleotide sequence that encodes the full length of the receptor-binding domain of *C. difficile* toxin B is set forth in SEQ. ID. NO.:19 (FIG. 14).

As used herein, the term "nucleotide sequence encoding the receptor-binding domain of *Clostridium difficile* toxin A or *Clostridium difficile* toxin B" includes fragments thereof. The minimum number of amino acids for the fragment of the receptor-binding domain of *C. difficile* toxin A or toxin B is about 44 amino acids, preferably about 50 amino acids, and more preferably about 60 amino acids. Thus, the minimum number of nucleotides in the nucleotide sequence of the DNA molecule of the claimed invention is about 132 nucleotides, preferably about 150 nucleotides, and more preferably about 180 nucleotides.

The maximum number of amino acids for the fragment of the receptor-binding domain of *C. difficile* toxin A or toxin B is at most about 870, about 860, about 850 or about 840 amino acids. Thus, the maximum number of nucleotides in the nucleotide sequence of the DNA molecule of the claimed invention is about 2610, about 2580 nucleotides, about 2550 nucleotides, or about 2520 nucleotides.

A unique feature of the receptor binding domain of *C. difficile* toxin A and toxin B is the presence of clostridial repeat oligopeptides of 21-, 30-, or 50-amino acid residues. The sequence of the receptor binding domain of toxin A contains between 30 and 38 clostridial repeat oligopeptides. In the sequence of the receptor binding domain of toxin B, there are about 19 to 24 clostridial repeat oligopeptides.

For example, *C. difficile* toxin A contains a clostridial repeat oligopeptide at the following amino acid residues in SEQ. ID. NO.:5 (FIG. 3): 1810-1829; 1851-1870; 1872-1891; 1923-1942; 1943-1962; 1964-1983; 1985-2004; 2006-2025; 2057-2076; 2077-2096; 2098-2117; 2119-2138; 2140-2159; 2191-2210; 2211-2230; 2232-2251; 2252-2271; 2305-2324; 2325-2344; 2346-2365; 2367-2386; 2388-2407; 2439-2458; 2459-2478; 2480-2499; 2501-2520; 2552-2571; 2572-2591; 2593-2612; 2643-2662; 2663-2682; 2685-2704.

*C. difficile* toxin B contains a clostridial repeat oligopeptide at the following amino acid residues in SEQ. ID. NO.:15 (FIG. 12): 1832-1851; 1853-1872; 1875-1894; 1925-1944; 1966-1985; 1986-2005; 2006-2025; 2056-2075; 2076-2096; 2098-2117; 2118-2137; 2138-2157; 2208-2230; 2232-2251; 2252-2271; 2272-2291; 2322-2341; 2342-2361.

A nucleotide sequence that encodes a fragment of the receptor-binding domain of *C. difficile* toxin A or of *C. difficile* toxin B may encode clostridial repeat oligopeptides.

The nucleotide sequence that encodes a fragment of the receptor-binding domain of *C. difficile* toxin A may encode a minimum number of 1 clostridial repeat oligopeptide, 2 clostridial repeat oligopeptides, 5 clostridial repeat oligopeptides, 10 clostridial repeat oligopeptides, or 15 clostridial repeat oligopeptides.

The nucleotide sequence that encodes a fragment of the receptor-binding domain of *C. difficile* toxin A may include a maximum number of all of the clostridial repeat oligopeptides of *C. difficile* toxin A, about 35 repeating clostridial repeat oligopeptides, about 25 clostridial repeat oligopeptides, or about 15 clostridial repeat oligopeptides.

The nucleotide sequence that encodes a fragment of the receptor-binding domain of *C. difficile* toxin B may encode a minimum number of 1 clostridial repeat oligopeptide, 2 clostridial repeat oligopeptides, 5 clostridial repeat oligopeptides, 10 clostridial repeat oligopeptides, or 15 clostridial repeat oligopeptides.

The nucleotide sequence that encodes a fragment of the receptor-binding domain of *C. difficile* toxin B may include a maximum number of all of the clostridial repeat oligopeptides of *C. difficile* toxin B, about 20 repeating clostridial repeat oligopeptides, about 15 clostridial repeat oligopeptides, or about 10 clostridial repeat oligopeptides.

Nucleotide sequences that encode the receptor binding domain of *C. difficile* toxin A or of *C. difficile* toxin B may include nucleotides located beyond the termini of the clostridial repeat oligopeptides. In addition, nucleotide sequences that encode a fragment of the receptor binding domain of *C. difficile* toxin A or of *C. difficile* toxin B may include nucleotides located beyond the termini of the clostridial repeat oligopeptides.

For example, in one embodiment, the nucleotide sequence preferably encodes a fragment of the receptor-binding domain of *C. difficile* toxin A containing the epitope set forth in SEQ. ID. NO.: 10 (FIG. 6). The amino acid sequence of the epitope is also shown at residues 2098-2141 in SEQ. ID. NO.: 5 (FIG. 3).

The amino acid sequence of the epitope includes two *C. difficile* toxin A clostridial repeat oligopeptides located at residues 2098-2117 and at residues 2119-2138 in SEQ. ID. NO.: 5 (FIG. 3). Residues 2118 and 2139-2141 in SEQ. ID. NO.: 5 represent residues beyond the termini of clostridial repeat oligopeptides that are included in the fragment of the receptor-binding domain of *C. difficile* toxin A.

Accordingly, the corresponding nucleotide sequence of the epitope includes nucleotides located beyond the termini of clostridial repeat oligopeptides. Nucleotides at positions 778-909 in SEQ. ID. NO.: 13 (FIG. 9) and in SEQ. ID. NO.: 9 (FIG. 5) encode the epitope set forth in the amino acid sequence shown in SEQ. ID. NO.: 10 (FIG. 6).

In another preferred embodiment, the nucleotide sequence encodes a fragment of the receptor-binding domain of *Clostridium difficile* toxin A containing the epitope at amino acid residues 2456-2710 of SEQ. ID. NO.:7 (FIG. 4). The last 762 nucleotides in SEQ. ID. NO.: 13 (FIG. 9) encode amino acid residues at positions 2456-2710 of SEQ. ID. NO.:7.

In the DNA molecules of the claimed invention, at least about 10% of the in-frame codons for each amino acid residue have a higher percentage use in the human genome according to table 1 (hereafter, percentage use) than the corresponding in-frame codons either of *C. difficile* toxin A having SEQ. ID. NO.: 13 or *C. difficile* toxin B having SEQ. ID. NO.: 17.

TABLE 1

Human Codon Usage Table. Numbers represent percent usage for each codon in the human genome.

| AMINO ACID | CODON | PERCENT USAGE IN THE HUMAN GENOME |
|---|---|---|
| PHE (F) | TTC | 20.4 |
|  | TTT | 17.4 |
| LEU (L) | CTG | 39.9 |
|  | CTC | 19.7 |

TABLE 1-continued

Human Codon Usage Table. Numbers represent percent usage for each codon in the human genome.

| AMINO ACID | CODON | PERCENT USAGE IN THE HUMAN GENOME |
|---|---|---|
| | CTT | 13.1 |
| | TTG | 12.8 |
| | TTA | 7.6 |
| | CTA | 7.1 |
| ILE (I) | ATC | 20.9 |
| | ATT | 15.8 |
| | ATA | 7.4 |
| MET (M) | AUG | 22.1 |
| VAL (V) | GTG | 28.3 |
| | GTC | 14.5 |
| | GTT | 11.0 |
| | GTA | 7.1 |
| SER (S) | AGC | 19.4 |
| | TCC | 17.7 |
| | TCT | 15.1 |
| | TCA | 12.2 |
| | AGT | 12.1 |
| | TCG | 4.5 |
| PRO (P) | CCC | 19.9 |
| | CCT | 17.4 |
| | CCA | 16.9 |
| | CCG | 7.0 |
| THR (T) | ACC | 19.0 |
| | ACA | 15.0 |
| | ACT | 13.0 |
| | ACG | 6.1 |
| ALA (A) | GCC | 28.0 |
| | GCT | 18.5 |
| | GCA | 15.9 |
| | GCG | 7.5 |
| TYR (Y) | TAC | 15.3 |
| | TAT | 12.1 |
| HIS (H) | CAC | 15.1 |
| | CAT | 10.8 |
| GLN (Q) | CAG | 34.2 |
| | CAA | 12.2 |
| ASN (N) | AAC | 19.1 |
| | AAT | 16.8 |
| LYS (K) | AAG | 32.0 |
| | AAA | 24.2 |
| ASP (D) | GAC | 25.2 |
| | GAT | 21.7 |
| GLU (E) | GAG | 39.6 |
| | GAA | 28.7 |
| CYS (C) | TGC | 12.6 |
| | TGT | 10.5 |
| TRP (W) | TGG | 13.2 |
| ARG (R) | AGA | 12.0 |
| | AGG | 11.9 |
| | CGG | 11.5 |
| | CGC | 10.6 |
| | CGA | 6.2 |
| | CGT | 4.6 |
| GLY (G) | GGC | 22.4 |
| | GGA | 16.5 |

TABLE 1-continued

Human Codon Usage Table. Numbers represent percent usage for each codon in the human genome.

| AMINO ACID | CODON | PERCENT USAGE IN THE HUMAN GENOME |
|---|---|---|
| | GGG | 16.5 |
| | GGT | 10.8 |

For example, if one of the in-frame codons in SEQ. ID. NO.: 13 (FIG. 9) is TTG, which has a percentage use in the human genome of 12.8 and encodes the amino acid leucine, then the corresponding in-frame codon in the nucleotide sequence that is useful in the DNA molecule can be replaced with any of the codons for leucine that has a higher percentage use. Such codons for leucine having a higher percentage use than 12.8 are CTG, CTC, and CTT.

Preferably, at least about 20%, more preferably at least about 30%, even more preferably at least about 40%, and most preferably at least about 50% of the in-frame codons for each amino acid residue in the DNA molecule of the invention have a higher percentage use than the corresponding in-frame codons of *C. difficile* toxin A having SEQ. ID. NO.: 13 or of *C. difficile* toxin B having SEQ. ID. NO.: 17.

Optimally, at least about 50%, more optimally at least about 75%, and most optimally 100% of the in-frame codons selected for each amino acid in the nucleotide sequence is the codon having the highest percentage use.

The wild type nucleic acid sequence for *C. difficile* toxin A and *C. difficile* toxin B have about 30% guanine (G) and cytosine (C) content. Using codons with a higher percentage use in humans generally results in an increase in the GC content. In an embodiment, the nucleic acid sequence useful in the DNA molecule contains codons with a higher GC content than the corresponding wild type codon for *C. difficile* toxin A or toxin B. Preferably, the GC content of the nucleotide sequence is at least about 40%, more preferably at least about 50%, and most preferably at least about 60%.

The nucleotide sequence can be synthesized by any method known to those in the art. For example, the nucleotide sequence can be divided into oligonucleotides of standard length (e.g., 100 nucleotides). Oligonucleotides can be designed with complementary overhanging regions and bound to a solid phase matrix. In groups, oligonucleotides can be permitted to hybridize via their overlapping regions and covalently linked to provide the final nucleotide sequence.

Alternatively, commercial companies, such as Blue Heron Biotechnology, Inc., Bothell, Wash. can be employed for synthesis of nucleotide sequences.

The DNA molecule of the claimed invention optionally comprises one or more additional nucleotides. Any nucleotide can be added to those described above. The additional nucleotide can be added to the 5' or 3' end of the nucleotide sequence encoding the receptor-binding domain of *C. difficile* toxin A or toxin B. There is no upper limit to the additional number of nucleotides. Typically, no more than about 10,000 nucleotides, preferably no more than about 5,000 nucleotides, more preferably no more than about 3,000 nucleotides, even more preferably no more than about 1,000 nucleotides are added to the DNA molecule.

In one embodiment, the additional nucleotides comprise the gene for a leader sequence. A "gene" as used herein refers to a nucleic acid sequence encoding a given amino acid sequence. Leader sequences include secretion signals and signal peptide sequences. A leader sequence is generally added to the 5' end of the nucleotide sequence encoding the receptor-binding domain of *C. difficile* toxin A or toxin B.

Examples of nucleotide sequences useful in a leader sequence include signal peptide of tPA, etc.

In another embodiment, the additional nucleotides comprise a Kozak sequence. A Kozak sequence preferably includes the nucleotide sequence ACCATGG and (GCC)RCCATGG where R is a purine (A or G).

An example of a DNA molecule of the claimed invention containing a Kozak sequence and nucleotide sequence of the receptor-binding domain of *C. difficile* toxin A is shown in FIG. 8 (SEQ. ID. NO.:12). In this embodiment, the DNA molecule is the sequence set forth in SEQ. ID. NO.: 12.

An example of a DNA molecule of the claimed invention containing a Kozak sequence and nucleotide sequence of the receptor-binding domain of *C. difficile* toxin B is shown in FIG. 14 (SEQ. ID. NO.: 19). In this embodiment, the DNA molecule is the sequence set forth in SEQ. ID. NO.: 19.

An example of a DNA molecule of the claimed invention containing a Kozak sequence, the gene for the signal peptide of tPA, and nucleotide sequence of the receptor-binding domain of *C. difficile* toxin A is shown in FIG. 7 (SEQ. ID. NO.: 11). In this embodiment, the DNA molecule is the sequence set forth in SEQ. ID. NO.: 11.

An example of a DNA molecule of the claimed invention containing a Kozak sequence, the gene for the signal peptide of tPA, and nucleotide sequence of the receptor-binding domain of *C. difficile* toxin B is shown in FIG. 16 (SEQ. ID. NO.: 20). In this embodiment, the DNA molecule is the sequence set forth in SEQ. ID. NO.: 20.

In a further embodiment, the additional nucleotides can comprise the gene of any bacterial sequence or non-bacterial sequence. For example, the bacterial sequence can be from pathogenic or non-pathogenic bacteria. Examples of bacteria include *E. coli, Mycobacterium, Streptococcus*, etc.

The non-bacterial sequence can be from a virus (e.g., HIV, CMV, HBV, HCV, etc) and epitopes from immune cells (e.g., $CD4^+$ cells).

In yet another embodiment, the additional nucleotides comprise a poly A tail. A poly A tail is generally added to the 3' end of the nucleotide sequence encoding the receptor-binding domain of *C. difficile* toxin A or toxin B.

In one embodiment, the DNA molecule of the claimed invention can be incorporated into a vector. For example, a vector can be employed for replicating or amplifying the DNA molecule, or for expressing the encoded protein. The vector may comprise segments of chromosomal, non-chromosomal and synthetic DNA sequences.

The vector may be any recombinant vector. Recombinant vectors have an origin of replication from which copying of the vector and incorporated DNA molecule is initiated. Examples of recombinant vectors include plasmids, cosmids and phages.

Plasmids are typically circular double-stranded DNA molecules capable of autonomous replication. Typically a plasmid contains the information needed for gene expression by a cell, such as a promoter, Kozak sequence, methionine start, poly A tail. Examples of plasmids include pVAX™ and pUC. pVAX™ is commercially available from Invitrogen, Carlsbad, Calif. pUC is commercially available from New England BioLabs, Ipswich, Mass.

The vector may further include a selectable marker, such as for instance a drug resistance marker, a detectable gene marker, an origin of replication, and/or multiple cloning sites for ease of manipulation of the inserted DNA molecule, as is well known in the art. Examples of drug resistance markers include tetracycline, ampicillin, and kanamycin. Examples of detectable gene markers include β-galactosidase and lacZ.

A multiple cloning site is generally a segment of DNA containing one or more restriction sites. Examples of restriction sites include BamHI, EcoRI, PstI sites.

An origin of replication is generally a DNA sequence at which DNA replication begins. Typically, an origin of replication is AT rich.

Method for Generating Antibodies to *Clostridium difficile* Toxin A or Toxin B

In one aspect, the invention provides a method for generating antibodies to *Clostridium difficile* toxin A in a mammal. In another aspect, the invention provides a method for generating antibodies to *C. difficile* toxin B in a mammal. In both of these embodiments, the method comprises administering to the mammal an effective amount of a DNA molecule as described above incorporated into a vector.

In yet another aspect, the invention provides a method for generating antibodies to *C. difficile* toxin A and B in a mammal. The method comprises administering to the mammal an effective amount of a DNA molecule comprising a nucleotide sequence that encodes the receptor-binding domain of *Clostridium difficile* toxin A and toxin B as described above.

In yet a further aspect, the invention provides another method for generating antibodies to *C. difficile* toxin A and B in a mammal. The method comprises administering to the mammal an effective amount of both a DNA molecule as described above that encodes the receptor-binding domain of *C. difficile* toxin A and a DNA molecule as described above that encodes the receptor-binding domain of *C. difficile* toxin B. Accordingly, the DNA molecules described above can be administered to the mammal separately or in combination.

The DNA molecule-vector complex can be administered to any mammal Mammals include, for example, humans, baboons, and other primates, as well as pet animals such as dogs and cats, laboratory animals such as rats and mice, and farm animals such as horses, sheep, and cows.

The antibodies generated in a mammal can be purified, immobilized to a solid support and used as probes for *C. difficile*. Alternatively, the antibodies can be administered to a human as a therapeutic composition.

In an embodiment, the mammal is a human. The DNA molecule-vector complex can be administered to a human as a therapeutic composition at any time. For example, the DNA molecule-vector complex can be administered to a human prior to, or after, potential exposure to or infection with *C. difficile*.

Method for Reducing Risk of a *Clostridium difficile* Infection

In another aspect, the invention provides a method for reducing the risk of a *Clostridium difficile* infection in a human. Any human can be at risk for a *C. difficile* infection. *C. difficile* infection is generally a nosocomial pathogen. Thus, one example of a human at risk for a *C. difficile* infection includes those humans who are or will be patients of a hospital or hospital-like setting. Examples of hospital-like settings include a nursing home, assisted living facility, etc.

Other examples of a human at risk for a *Clostridium difficile* infection include humans that have had, or are having, or are about to have an enema, nasogastric tube insertion and gastrointestinal tract surgery.

Humans in whom the normal intestinal flora is altered are also at risk for a *C. difficile* infection. For example, the use of antibiotics, such as penicillin, ampicillin, clindamycin and cephalosporins may alter the normal intestinal flora and increase the risk of *C. difficile* infection.

In addition, *C. difficile* is also associated with disease in patients undergoing chemotherapy with such compounds as methotrexate, 5-fluorouracil, cyclophosphamide, and doxorubicin. Patients undergoing or are about to undergo such chemotherapies are also examples of a human at risk of *C. difficile* infection.

A frequent complication of *C. difficile* infection is recurrent or relapsing disease. Relapse may be characterized clinically as antibiotic-associated diarrhea (AAD), antibiotic-associated colitis (AAC), or pseudomembranous colitis (PMC). Patients who relapse once are more likely to relapse again. Accordingly, patients who have or had a recurrent or relapsing *C. difficile* infection are examples of a human at risk.

The method for reducing the risk of a *C. difficile* infection in a human comprises administering to the human an effective amount of a DNA molecule described above incorporated in a vector. In another aspect, the method for reducing the risk of a *C. difficile* infection in a human comprises administering to the human an effective amount of a DNA molecule incorporated in a vector as described above for toxin A and a DNA molecule incorporated in a vector for toxin B. Accordingly, the DNA molecules described above can be administered to the human separately or in combination.

In yet another aspect, the method for reducing the risk of a *C. difficile* infection in a human comprises administering to the human an effective amount of a DNA molecule comprising a nucleotide sequence that encodes the receptor-binding domain of both *Clostridium difficile* toxin A and toxin B as described above.

The DNA molecule-vector complex can be administered at any time prior to the human's potential exposure to risk of *C. difficile* infection. For instance, the DNA molecule-vector complex can be administered up to one day, up to two days, preferably up to one week, more preferably up to two weeks, even more preferably up to one month, and still more preferably up to two months or more prior to potential exposure to risk of *C. difficile* infection.

The amount that the risk is reduced generally varies among humans, and depends on such factors as the amount of DNA molecule administered, the risk factors (e.g., hospital setting, factors altering normal intestinal flora, etc.). Generally, the risk of *C. difficile* infection is reduced by at least about 10%, more generally at least about 25%, more generally at least about 50%, even more generally at least about 75%, still more generally at least about 90%. Optimally, the risk for *C. difficile* infection is completely eliminated.

Method for Treating *Clostridium difficile* Infection

In yet another aspect, the invention provides a method for treating a *Clostridium difficile* infection in a human in need thereof. Any human infected with *C. difficile* is in need of treatment in accordance with the method of the claimed invention. Generally, a human in need of treatment is one diagnosed by a physician or clinician as having a *C. difficile* infection.

The method for treating a *C. difficile* infection in the human includes administering to the human an effective amount of a DNA molecule as described above incorporated into a vector. In another aspect, the method for treating a *C. difficile* infection in the human includes administering to the human an effective amount of a DNA molecule as described above incorporated into a vector for toxin A and a DNA molecule as described above incorporated into a vector for toxin B. Accordingly, the DNA molecules described above can be administered to the human separately or in combination.

In another aspect, the method for treating a *C. difficile* infection in a human includes administering to the human an effective amount of a DNA molecule comprising a nucleotide sequence that encodes the receptor-binding domain of both *Clostridium difficile* toxin A and toxin B as described above.

The DNA molecule-vector complex can be administered at any time during the *C. difficile* infection. Preferably, the DNA molecule-vector complex is administered as soon as possible after infection with *C. difficile*.

For example, the DNA molecule-vector complex of the claimed invention is administered within about one month after infection, preferably within about two weeks, more preferably within about one week, even more preferably within about two weeks, more preferably within about one week, even more preferably within about two days, yet even more preferably within about one day after infection with *Clostridium difficile*.

Administration

The DNA molecule described above is incorporated into a vector, herein referred to as "DNA molecule-vector complex," as described above. Examples of vectors useful for administration nucleic acids include the viral and bacterial vectors disclosed in Dietrich et al., *Curr. Opin. Mol. Ther.*, 2003, 5:10-19 and Liu et al., *PNAS*, 2004, 101:14567-14571. An example of a plasmid containing a DNA molecule is illustrated in FIG. 10.

Any method known to those skilled in the art may be used to administer the DNA molecule-vector complex. For example, the DNA molecule-vector complex may be administered enterally or parenterally, e.g., intravenously; intramuscularly; subcutaneously, as injectable solutions or suspensions; or intraperitoneally.

For example, the DNA molecule-vector complex can be administered by in vivo electroporation. Briefly, in vivo electroporation involves the contemporaneous application of an electrical pulse to the tissues of a human at the time of injection of the DNA molecule-vector complex. Generally, administration by in vivo electroporation increases the amount of DNA molecule-vector complex taken into a cell.

Alternatively, the DNA molecule-vector complex can be administered by a DNA biojector. Briefly, a biojector is a needle-free injection technology that works by forcing compounds suspended in a liquid at high speed through a tiny orifice that is held against the skin. A biojector can deliver intramuscular or subcutaneous injections. Biojectors are commercially available from Bioject Medical Technologies, Inc, Tualatin, Oreg.

Another method for administering the DNA molecule-vector complex by means of a gene gun. The in vivo administration of a gene by a gene gun is disclosed in Frelin, et al. *Gene Ther.*, 2004, 11:522-533. The relevant section regarding in vivo administration by a gene gun is hereby incorporated by reference. Gene guns are commercially available from Bio-Rad Laboratories, Inc., Hercules, Calif.

The molecule-vector complex is administered in an amount that is effective to generate antibodies in a human, or otherwise cause an immune response. The actual effective amounts of the DNA molecule-vector complex will vary according to, for example, the particular nucleotide sequence that encodes the receptor-binding domain used, the plasmid, the mode of administration, the particular sites of administration, and the subject being treated (e.g. age, gender, size, etc.). Such effective amounts can be readily determined by physicians and clinicians during pre-clinical and clinical trials.

The DNA molecule-vector complex can be formulated in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The DNA molecule-vector complex can be formulated into a composition containing one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the DNA molecule-vector complex.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent. Suitable salts include, for example, sodium or potassium chloride. Suitable buffers include, for example, sodium or potassium bicarbonate or biphosphate. Preferably, the buffering agent maintains the pH of the DNA molecule-vector complex formulation in the range of about 5.5 to about 7.5. The salt and/or buffering agent is also useful to maintain the osmolality at a level suitable for administration. Preferably the salt or buffering agent is present at a roughly isotonic concentration of about 150 mM to about 300 mM.

The DNA molecule-vector complex can be formulated into a composition which may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anesthetic agent such as for example a morphine derivative; or an isotonic agent etc., such as described above. As a further precaution against oxidation or other spoilage, the composition may be stored under nitrogen gas in vials sealed with impermeable stoppers.

EXAMPLES

Example 1

Antibody Generation

Endotoxin-free plasmid preparations were obtained from Aldevron Inc, Fargo N. Dak. Plasmids were diluted in sterile saline to a concentration of 100|xg in 50 ul of saline. Five groups of 3 BALB/c mice (Charles River Laboratories) were obtained and injected with DNA. Group 1 received pVAX™ (Invitrogen, Carlsbad, Calif.) vector; Group 2 received TxA-RBD alone, standard intramuscular (IM) injection; Group 3 received tPA-TxARBD, IM injection; Group 4 received TxA-RBD alone, IM electroporation; Group 5 received tPA-TxA-RBD, IM electroporation.

Mice were vaccinated at weeks 0 and 2 with 100 μg in 50 μl of saline in the right rear limb. Blood was drawn and serum isolated at prevaccination (week 0) and at conclusion of study, week six.

Serum was analyzed by ELISA using commercial toxin A as the binding antigen on high protein binding Costar Plates, and commercial anti-mouse horseradish-peroxidase (HRP) as the secondary antigen. ELISA was developed using the DAKO development system.

FIG. 11 shows that both TxA-RBD and tPA-TxA-RBD are immunogenic. TxA-RBD alone provides 10 fold higher IgG responses than tPA-TxA-RBD. Electroporation augments the IgG response by 100 fold for both plasmids.

Example 2

Plasmid Design for TxA-RBD and tPA-TxA-RBD Plasmids

The following plasmids were constructed using standard techniques for cloning (Sambrook, et al., *Molecular Cloning: A Laboratory Manual* (1989)).

The full length amino acid sequence corresponding to the toxin A protein of *C. difficile* strain VPI 10463 (Gen-Bank Accession No. AAA23283, see FIG. 3) was assessed and residues corresponding to the putative receptor-binding domain that occupy the carboxy-terminal third of the protein was identified (FIG. 16A). The amino-acid sequence of the RBD was back-translated in silico to a novel genetic sequence using those codons most commonly employed by human cells (www.entelechon.com). A Nhel restriction sequence, kozak sequence, and methionine start site occupy base-pairs 1-16 of SEQ. ID. NO.: 12 (FIG. 8). The optimized gene is comprised of base pairs 23-2641 of SEQ. ID. NO.: 12 (FIG. 8). Finally, an EcoRl restriction sequence was included at the 3' end and a BamH1 restriction site was incorporated into positions 17-22 of SEQ. ID. NO.: 12 (FIG. 8) to permit future modifications. This gene was then submitted for commercial synthesis (BlueHeron Biotechnology, Seattle, Wash.). The gene insert was digested (Nhel/EcoRl, New England Biolabs) and ligated into the commercial vector, pVAX™ (Invitrogen, Carlsbad, Calif.), a plasmid which meets United States Food and Drug Administration guideline for human use. The insert was also digested (BamH1/EcoRl) and inserted into a pVAX™ vector with a previously positioned tissue plasminogen activator (tPA) sequence as well as the Nhe1, kozak, and ATG start codon as described (FIG. 16B).

Following restriction digestion and overnight ligation using T4 ligase (Roche), ligation products were transformed into TOP10 chemically competent *E. coli* cells (Invitrogen, Carlsbad, Calif.). Positive clones selected following plating on Luria-Bertani (LB) plates supplemented with Kanamycin. Gene insertion was confirmed by restriction digestion and DNA sequencing (GeneWiz, North Brunswick, N.J.). The two plasmids (TxA-RBD and tPA-TxA-RBD) differ only in the presence or absence of a tPA leader sequence following the ATG start codon.

Example 3

In Vitro Expression of TxA-RBD 293T cells were split twenty-four hours prior to transfection and plated in a 12 well dish at a concentration of $5\times10^5$ cells per well in DMEM with 10% inactivated FBS (v/v) (Gibco) and 1% Penicillin-Streptomycin (Gibco). Twenty-four hours post plating, cells were transfected with 2 μg of plasmid DNA, TxA-RBD, TxB-RBD, tPA-TxA-RBD, tPA-TxB-RBD, or pVAX™-GFP (as a negative control) using Lipofectamine™ 2000 (Invitrogen, Carlsbad, Calif.) per the manufacturer's instructions.

Forty-eight hours post-transfection, supernatant and/or cell lysates were collected. Supernatant was clarified by centrifugation at 22,000×g for 30 minutes prior to immunoblot. Samples were stored at −20° C. until assay performance.

Immunoblots were performed using the Invitrogen SURE-LOCK™ (Invitrogen, Carlsbad, Calif.) system according to the manufacturer's recommendations. Briefly, 32.5 ul of sample was added to 12|×l NuPAGE LDS loading buffer and 5|×l of reducing agent and heated to 70° C. for 10 minutes. Samples were subjected to electrophoresis in a 10% BisTris gel (Invitrogen, Carlsbad, Calif.) at a constant voltage of 200V. Samples were transferred to polyvinylidene difluoride (PVDF) membranes and blocked for two hours in blocking buffer (5% dry milk, 0.5% bovine albumin in phosphate-buffered saline (PBS) (Gibco)). Membranes were incubated with primary antibody (goat polyclonal anti-toxin A (List Biological Laboratories, Inc.) 1:2000 in blocking buffer overnight at 4° C. Membranes were then washed with wash buffer (PBS with 0.05% Tween™, Sigma) and horseradish-peroxidase (HRP)-conjugated antigoat secondary antibody (1:8000) (Sigma Inc., St. Louis, Mo.) was added at the indicated dilutions in blocking buffer for 1 hour. Membranes were washed as above and developed using the Amersham ECL development system (GE Healthcare, Piscataway, N.J.).

Example 4

Animal Inoculations and *C. difficile* Toxin Challenge

For an immunogenicity study, 6-8 week old inbred BALB/c mice (6 mice per group) and out bred CD-1, Swiss-Webster mice (5 mice per group) were obtained (Charles River Laboratories, Wilmington, Mass.) and housed at the Laboratory Animal Research Center of The Rockefeller University. All procedures were carried out under protocols approved by the Animal Care and Use Committee of The Rockefeller University.

Endotoxin free (<100 IU) plasmid DNA for vaccination was obtained (Aldevron Inc., Fargo, N. Dak.). Five groups of mice, 5-10 animals per group, were vaccinated at weeks 0 and 2 with 50 µg of plasmid DNA divided into two doses delivered by either standard syringe intramuscular injection (IM) or electroporation-enhanced (EP) intramuscular injection into each of the rear limbs.

For *C. difficile* toxin A challenge experiments, Group 1 received pVAX™ alone; Group 2 received TxA-RBD (IM); Group 3 received tPA-TxA-RBD (IM); Group 4 received TxA-RBD (EP); and Group 5 received tPA-TxA-RBD (EP). See FIG. 11.

For *C. difficile* toxin B challenge experiments, Group 1 received pVAX™ alone; Group 2 received TxB-RBD (IM); Group 3 received tPA-TxB-RBD (IM); Group 4 received TxB-RBD (EP); and Group 5 received tPA-TxB-RBD (EP). See FIG. 18.

Serum was obtained at week 6 post injection for immunologic evaluation prior to toxin challenge.

Figure 20:
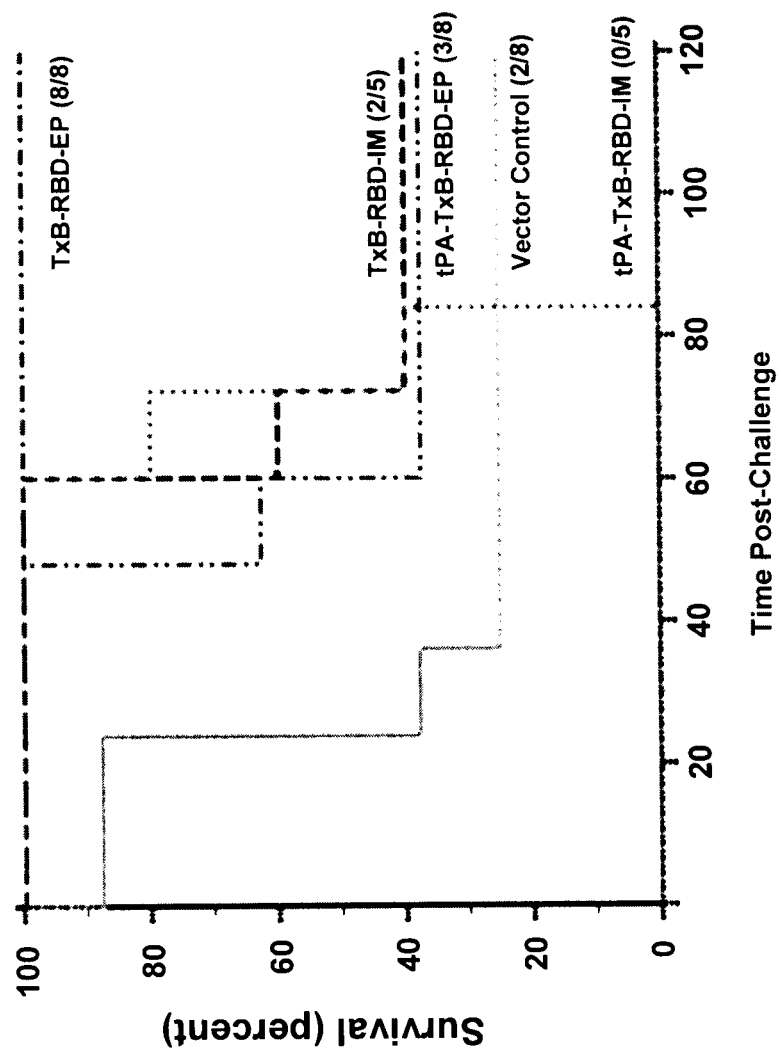
FIG. 20. Survival curve plots for BALB/c mice administered with pVAX vector (EP), TxB-RBD (IM), or TxB-RBD (EP) after *C. difficile* toxin B challenge. Animals were challenged with 400 ng of active, purified *C. difficile* toxin B, from strain VPI 10463 in 50 μl of sterile saline by intravenous tail vein injection.
Figure 21:
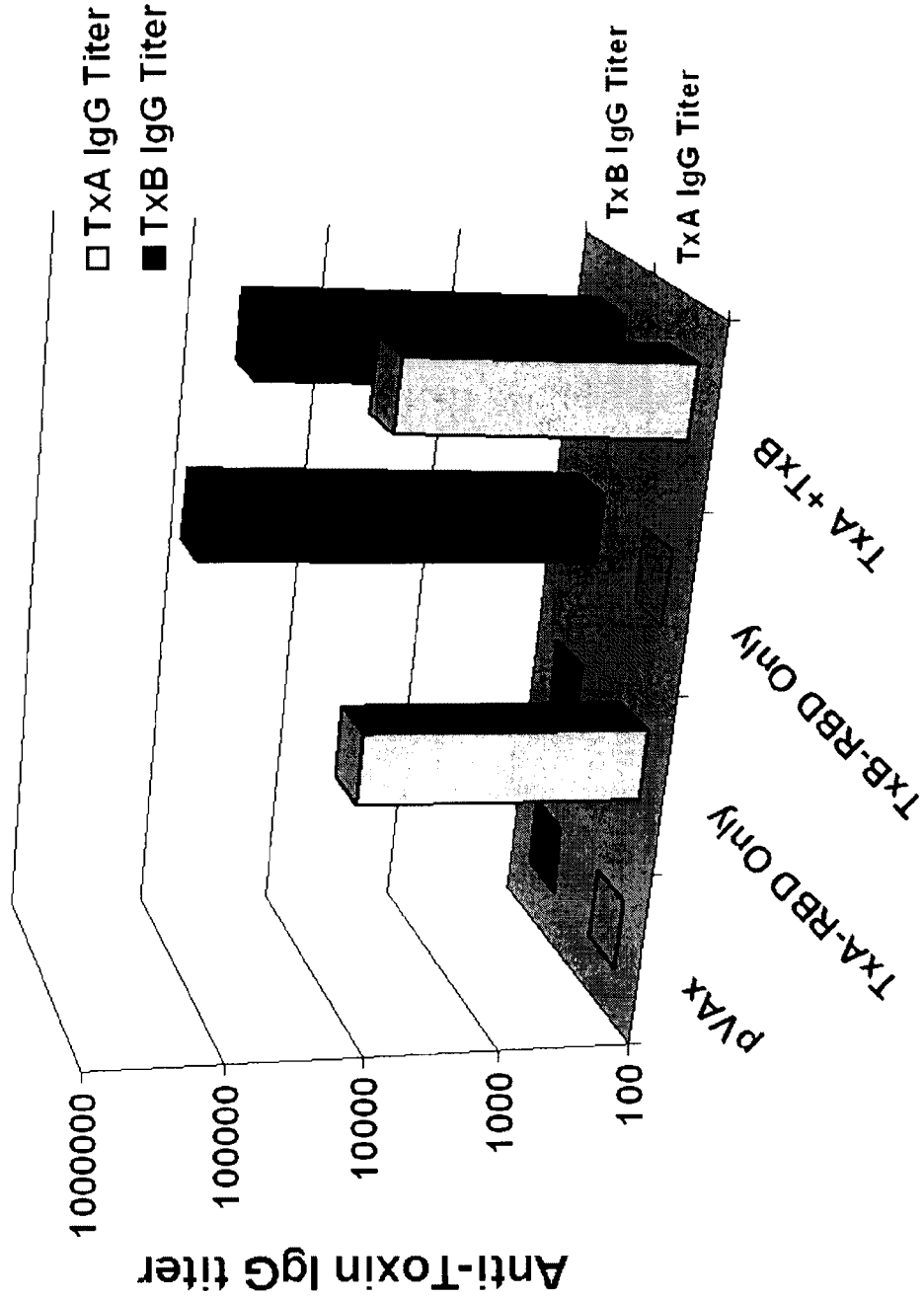
FIG. 21. Serum IgG antibody titers to *C. difficile* toxin A and to *C. difficile* toxin B measured in BALB/c mice. The mice were immunized with one of the following: pVAX (25 ug into each rear limb intramuscularly); TxA-RBD (25 ug into each rear limb intramuscularly); TxB-RBD (25 ug into each rear limb intramuscularly); or TxA-RBD and TxB-RBD ("TxA-TxB") (25 ug into each rear limb intramuscularly). Mice were injected at weeks 0 and 2. The mice were bled 6 weeks after immunization and were challenged with *C. difficile* toxin A or toxin B at week 8. Antibody titers were determined by ELISA.

Animals were monitored for symptoms or death for 90 hours after *C. difficile* toxin A challenge (FIG. 19), and after *C. difficile* toxin B challenge (FIG. 20).

Example 5

Anti-Toxin ELISA IgG Titers 96-well high protein-binding polystyrene EIA plates (Costar 9018, Corning Inc., Corning, N.Y.) were coated with either 0.5 µg purified, whole *C. difficile* toxin A or 0.5 µg purified, whole *C. difficile* toxin B in 1M $NaHCO_3$ buffer overnight at 4° C. The next day, plates were blocked for 1.5 hours with blocking buffer (PBS-T, 5% dry milk w/v, 0.5% bovine serum albumin w/v). Serum samples obtained from the protocol of example 4 were added in duplicate at the indicated dilutions and incubated for 2 hours at 37° C. Plates were washed five times with wash buffer (PBS-0.05% Tween 20™) and incubated for one hour with alkaline phosphatase (AKP)-conjugated rat anti-mouse secondary antibody (1:10,000 in blocking buffer).

Plates were developed using the AMPAK ELISA development kit according to manufacturer's specifications (DAKO Corporation, Carpinteria, Calif.). Optical density of plate wells was determined at 490 nm (Dynex Technologies, Chantilly, Va.). The end-point antibody titers represent the reciprocal dilution of the last dilution providing an O.D. 2-fold higher than the O.D. of sera controls at the lowest performed dilution. See FIGS. 11, 18, 21, and 23.

Example 6

Plasmid Design for TxB-RBD and tPA-TxB-RBD Plasmids

The following plasmids were constructed using standard techniques for cloning (Sambrook, et al., *Molecular Cloning: A Laboratory Manual* (1989)).

The full length amino acid sequence corresponding to the toxin B protein of *C. difficile* strain VPI 10463 (Gen-Bank Accession No. P18177, see FIG. 12) was assessed and residues corresponding to the putative receptor-binding domain that occupy the carboxy-terminal third of the protein was identified (FIG. 17). The amino-acid sequence of the RBD was back-translated in silico to a novel genetic sequence using those codons most commonly employed by human cells (www.entelechon.com). A NheI restriction sequence, kozak sequence, and methionine start site occupy base pairs 1-16 of SEQ. ID. NO.: 19 (FIG. 14). The optimized gene is comprised of base pairs 23-1861 of SEQ. ID. NO.: 19 (FIG. 14). Finally, an EcoRl restriction sequence was included at the 3' end and a BamH1 restriction site was incorporated into positions 17-22 of SEQ. ID. NO.: 19 (FIG. 14) to permit future modifications. This gene was then submitted for commercial synthesis (BlueHeron Biotechnology, Seattle, Wash.). The gene insert was digested (NheI/EcoRI, New England Biolabs) and ligated into the commercial vector, pVAX™ (Invitrogen, Carlsbad, Calif.), a plasmid which meets United States Food and Drug Administration guideline for human use. The insert was also digested (BamH1/EcoRI) and inserted into a pVAX™ vector with a previously positioned tissue plasminogen activator (tPA) sequence as well as the NheI, kozak, and ATG start codon as described (FIG. 17).

Following restriction digestion and overnight ligation using T4 ligase (Roche), ligation products were transformed into TOP10 chemically competent *E. coli* cells (Invitrogen, Carlsbad, Calif.). Positive clones selected following plating on Luria-Bertani (LB) plates supplemented with kanamycin. Gene insertion was confirmed by restriction digestion and DNA sequencing (GeneWiz, North Brunswick, N.J.). The two plasmids (TxB-RBD and tPA-TxB-RBD) differ only in the presence or absence of a tPA leader sequence following the ATG start codon.

Example 7

Combination Vaccine Immunogenicity Protocol

BALB/c mice, 5 per group were vaccinated with DNA encoding pVAX™, TxA-RBD, TxB-RBD, or a combination of TxA-RBD and TxB-RBD (herein referred to as "TxA-TxB") at weeks 0 and 2.

DNA was provided in the following doses: 50 µg/100 µl of sterile saline divided between both rear limbs for pVAX, TxA-RBD, and TxB-RBD. For TxA-TxB co-delivery, DNA was adjusted to 50 µg/50 µl sterile saline for each DNA plasmid (i.e., for TxA-RBD plasmid and TxB-RBD plasmid), then mixed to provide 50 µg/100 µl for each plasmid in a single injection.

Blood was collected by retro-orbital puncture following sedation with ketamine/xylazine by intraperitoneal injection.

ELISA was performed according to prior protocols described in example 5. See results in FIG. 21.

Animals were challenged eight weeks following initiation of the experiment with 300 ng of purified *C. difficile* toxin A in 100 µl of sterile saline by intraperitoneal (IP) injection and followed every 12 hours for symptoms or death. See results in FIG. 22.

Animals remaining were challenged with 400 ng of purified *C. difficile* toxin B in 50 µl of sterile saline by intravenous injection and followed every 12 hours for symptoms or death. See results in FIG. 22.

Example 8

Hamster Immunogenicity Experiment

Hamsters (Syrian golden, 5 per group) were vaccinated with pVAX™, TxA-RBD, or TxB-RBD. All inoculations were provided with electroporation (EP)-enhanced intramuscular injection using the 3.0 mm TriGrid-EP array as directed by Ichor Medical Systems, Inc.

TxA-RBD or TxB-RBD was provided in two doses: 1) 200 µg/100 µl of sterile saline divided between both rear limbs or, 2) 22 µg in 25 µl of sterile saline into a single rear limb. Animals were injected at weeks 0 and 4 and serum harvested for anti-toxin ELISA by retro-orbital puncture. All procedures on animals were performed under protocols approved by the Institutional Care and Use Committee of the Rockefeller University.

96-well high protein-binding polystyrene EIA plates (Costar 9018, Corning Inc., Corning, N.Y.) were coated with either 50 ng purified, whole *C. difficile* toxin A or 50 ng purified, whole *C. difficile* toxin B in PBS overnight at 4° C. The next day, plates were blocked for 1.5 hours with blocking buffer (PBS-T, 5% dry milk w/v, 0.5% BSA w/v). Serum samples were added in duplicate following serial dilution in blocking buffer and incubated for two hours at 37° C. Plates were washed five times with wash buffer (PBS-0.05% Tween 20) and incubated for one hour with AKP-conjugated anti-hamster secondary antibody.

Plates were developed using the AMPAK ELISA development kit according to manufacturer's specifications (DAKO Corporation, Carpinteria, Calif.). Optical density of plate wells was determined at 490 nm (Dynex Technologies, Chantilly, Va.). See FIG. 23. The end-point antibody titers represent the reciprocal dilution of the last dilution providing an O.D. 2-fold higher than the O.D. of sera controls at the lowest performed dilution.

SEQUENCE LISTING

```
<160> NUMBER OF SEQ ID NOS: 41

<210> SEQ ID NO 1
<211> LENGTH: 2710
<212> TYPE: PRT
<213> ORGANISM: Clostridium difficile

<400> SEQUENCE: 1

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
```

```
              180                 185                 190
Ile Asn Lys Pro Thr Val Pro Thr Ile Asp Asp Ile Ile Lys Ser His
            195                 200                 205
Leu Val Ser Glu Tyr Asn Arg Asp Glu Thr Val Leu Glu Ser Tyr Arg
210                 215                 220
Thr Asn Ser Leu Arg Lys Ile Asn Ser Asn His Gly Ile Asp Ile Arg
225                 230                 235                 240
Ala Asn Ser Leu Phe Thr Glu Gln Glu Leu Leu Asn Ile Tyr Ser Gln
            245                 250                 255
Glu Leu Leu Asn Arg Gly Asn Leu Ala Ala Ala Ser Asp Ile Val Arg
        260                 265                 270
Leu Leu Ala Leu Lys Asn Phe Gly Gly Val Tyr Leu Asp Val Asp Met
    275                 280                 285
Leu Pro Gly Ile His Ser Asp Leu Phe Lys Thr Ile Ser Arg Pro Ser
        290                 295                 300
Ser Ile Gly Leu Asp Arg Trp Glu Met Ile Lys Leu Glu Ala Ile Met
305                 310                 315                 320
Lys Tyr Lys Lys Tyr Ile Asn Asn Tyr Thr Ser Glu Asn Phe Asp Lys
                325                 330                 335
Leu Asp Gln Gln Leu Lys Asp Asn Phe Lys Leu Ile Ile Glu Ser Lys
            340                 345                 350
Ser Glu Lys Ser Glu Ile Phe Ser Lys Leu Glu Asn Leu Asn Val Ser
        355                 360                 365
Asp Leu Glu Ile Lys Ile Ala Phe Ala Leu Gly Ser Val Ile Asn Gln
    370                 375                 380
Ala Leu Ile Ser Lys Gln Gly Ser Tyr Leu Thr Asn Leu Val Ile Glu
385                 390                 395                 400
Gln Val Lys Asn Arg Tyr Gln Phe Leu Asn Gln His Leu Asn Pro Ala
                405                 410                 415
Ile Glu Ser Asp Asn Asn Phe Thr Asp Thr Thr Lys Ile Phe His Asp
            420                 425                 430
Ser Leu Phe Asn Ser Ala Thr Ala Glu Asn Ser Met Phe Leu Thr Lys
        435                 440                 445
Ile Ala Pro Tyr Leu Gln Val Gly Phe Met Pro Glu Ala Arg Ser Thr
    450                 455                 460
Ile Ser Leu Ser Gly Pro Gly Ala Tyr Ala Ser Ala Tyr Tyr Asp Phe
465                 470                 475                 480
Ile Asn Leu Gln Glu Asn Thr Ile Glu Lys Thr Leu Lys Ala Ser Asp
                485                 490                 495
Leu Ile Glu Phe Lys Phe Pro Glu Asn Asn Leu Ser Gln Leu Thr Glu
            500                 505                 510
Gln Glu Ile Asn Ser Leu Trp Ser Phe Asp Gln Ala Ser Ala Lys Tyr
        515                 520                 525
Gln Phe Glu Lys Tyr Val Arg Asp Tyr Thr Gly Gly Ser Leu Ser Glu
    530                 535                 540
Asp Asn Gly Val Asp Phe Asn Lys Asn Thr Ala Leu Asp Lys Asn Tyr
545                 550                 555                 560
Leu Leu Asn Asn Lys Ile Pro Ser Asn Asn Val Glu Glu Ala Gly Ser
                565                 570                 575
Lys Asn Tyr Val His Tyr Ile Ile Gln Leu Gln Gly Asp Asp Ile Ser
            580                 585                 590
Tyr Glu Ala Thr Cys Asn Leu Phe Ser Lys Asn Pro Lys Asn Ser Ile
        595                 600                 605
```

```
Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
                660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
                740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
                820                 825                 830

Ser Ile Gly Asp Tyr Ile Tyr Tyr Glu Lys Leu Glu Pro Val Lys Asn
        835                 840                 845

Ile Ile His Asn Ser Ile Asp Asp Leu Ile Asp Glu Phe Asn Leu Leu
850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
                900                 905                 910

Val Glu Thr Glu Lys Glu Ile Phe Ser Lys Tyr Ser Glu His Ile Thr
        915                 920                 925

Lys Glu Ile Ser Thr Ile Lys Asn Ser Ile Ile Thr Asp Val Asn Gly
930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
                980                 985                 990

Ala Gln Leu Phe Ser Thr Gly Leu  Asn Thr Ile Tyr Asp  Ser Ile Gln
        995                 1000                1005

Leu Val  Asn Leu Ile Ser Asn  Ala Val Asn Asp Thr  Ile Asn Val
    1010                1015                1020
```

```
Leu Pro Thr Ile Thr Glu Gly Ile Pro Ile Val Ser Thr Ile Leu
    1025                1030                1035

Asp Gly Ile Asn Leu Gly Ala Ala Ile Lys Glu Leu Leu Asp Glu
    1040                1045                1050

His Asp Pro Leu Leu Lys Lys Glu Leu Glu Ala Lys Val Gly Val
    1055                1060                1065

Leu Ala Ile Asn Met Ser Leu Ser Ile Ala Ala Thr Val Ala Ser
    1070                1075                1080

Ile Val Gly Ile Gly Ala Glu Val Thr Ile Phe Leu Leu Pro Ile
    1085                1090                1095

Ala Gly Ile Ser Ala Gly Ile Pro Ser Leu Val Asn Asn Glu Leu
    1100                1105                1110

Ile Leu His Asp Lys Ala Thr Ser Val Val Asn Tyr Phe Asn His
    1115                1120                1125

Leu Ser Glu Ser Lys Lys Tyr Gly Pro Leu Lys Thr Glu Asp Asp
    1130                1135                1140

Lys Ile Leu Val Pro Ile Asp Asp Leu Val Ile Ser Glu Ile Asp
    1145                1150                1155

Phe Asn Asn Asn Ser Ile Lys Leu Gly Thr Cys Asn Ile Leu Ala
    1160                1165                1170

Met Glu Gly Gly Ser Gly His Thr Val Thr Gly Asn Ile Asp His
    1175                1180                1185

Phe Phe Ser Ser Pro Ser Ile Ser Ser His Ile Pro Ser Leu Ser
    1190                1195                1200

Ile Tyr Ser Ala Ile Gly Ile Glu Thr Glu Asn Leu Asp Phe Ser
    1205                1210                1215

Lys Lys Ile Met Met Leu Pro Asn Ala Pro Ser Arg Val Phe Trp
    1220                1225                1230

Trp Glu Thr Gly Ala Val Pro Gly Leu Arg Ser Leu Glu Asn Asp
    1235                1240                1245

Gly Thr Arg Leu Leu Asp Ser Ile Arg Asp Leu Tyr Pro Gly Lys
    1250                1255                1260

Phe Tyr Trp Arg Phe Tyr Ala Phe Phe Asp Tyr Ala Ile Thr Thr
    1265                1270                1275

Leu Lys Pro Val Tyr Glu Asp Thr Asn Ile Lys Ile Lys Leu Asp
    1280                1285                1290

Lys Asp Thr Arg Asn Phe Ile Met Pro Thr Ile Thr Thr Asn Glu
    1295                1300                1305

Ile Arg Asn Lys Leu Ser Tyr Ser Phe Asp Gly Ala Gly Gly Thr
    1310                1315                1320

Tyr Ser Leu Leu Leu Ser Ser Tyr Pro Ile Ser Thr Asn Ile Asn
    1325                1330                1335

Leu Ser Lys Asp Asp Leu Trp Ile Phe Asn Ile Asp Asn Glu Val
    1340                1345                1350

Arg Glu Ile Ser Ile Glu Asn Gly Thr Ile Lys Lys Gly Lys Leu
    1355                1360                1365

Ile Lys Asp Val Leu Ser Lys Ile Asp Ile Asn Lys Asn Lys Leu
    1370                1375                1380

Ile Ile Gly Asn Gln Thr Ile Asp Phe Ser Gly Asp Ile Asp Asn
    1385                1390                1395

Lys Asp Arg Tyr Ile Phe Leu Thr Cys Glu Leu Asp Asp Lys Ile
    1400                1405                1410

Ser Leu Ile Ile Glu Ile Asn Leu Val Ala Lys Ser Tyr Ser Leu
```

```
                1415                1420                1425
Leu Leu Ser Gly Asp Lys Asn Tyr Leu Ile Ser Asn Leu Ser Asn
        1430                1435                1440
Thr Ile Glu Lys Ile Asn Thr Leu Gly Leu Asp Ser Lys Asn Ile
        1445                1450                1455
Ala Tyr Asn Tyr Thr Asp Glu Ser Asn Asn Lys Tyr Phe Gly Ala
        1460                1465                1470
Ile Ser Lys Thr Ser Gln Lys Ser Ile Ile His Tyr Lys Lys Asp
        1475                1480                1485
Ser Lys Asn Ile Leu Glu Phe Tyr Asn Asp Ser Thr Leu Glu Phe
        1490                1495                1500
Asn Ser Lys Asp Phe Ile Ala Glu Asp Ile Asn Val Phe Met Lys
        1505                1510                1515
Asp Asp Ile Asn Thr Ile Thr Gly Lys Tyr Tyr Val Asp Asn Asn
        1520                1525                1530
Thr Asp Lys Ser Ile Asp Phe Ser Ile Ser Leu Val Ser Lys Asn
        1535                1540                1545
Gln Val Lys Val Asn Gly Leu Tyr Leu Asn Glu Ser Val Tyr Ser
        1550                1555                1560
Ser Tyr Leu Asp Phe Val Lys Asn Ser Asp Gly His His Asn Thr
        1565                1570                1575
Ser Asn Phe Met Asn Leu Phe Leu Asp Asn Ile Ser Phe Trp Lys
        1580                1585                1590
Leu Phe Gly Phe Glu Asn Ile Asn Phe Val Ile Asp Lys Tyr Phe
        1595                1600                1605
Thr Leu Val Gly Lys Thr Asn Leu Gly Tyr Val Glu Phe Ile Cys
        1610                1615                1620
Asp Asn Asn Lys Asn Ile Asp Ile Tyr Phe Gly Glu Trp Lys Thr
        1625                1630                1635
Ser Ser Ser Lys Ser Thr Ile Phe Ser Gly Asn Gly Arg Asn Val
        1640                1645                1650
Val Val Glu Pro Ile Tyr Asn Pro Asp Thr Gly Glu Asp Ile Ser
        1655                1660                1665
Thr Ser Leu Asp Phe Ser Tyr Glu Pro Leu Tyr Gly Ile Asp Arg
        1670                1675                1680
Tyr Ile Asn Lys Val Leu Ile Ala Pro Asp Leu Tyr Thr Ser Leu
        1685                1690                1695
Ile Asn Ile Asn Thr Asn Tyr Tyr Ser Asn Glu Tyr Tyr Pro Glu
        1700                1705                1710
Ile Ile Val Leu Asn Pro Asn Thr Phe His Lys Lys Val Asn Ile
        1715                1720                1725
Asn Leu Asp Ser Ser Ser Phe Glu Tyr Lys Trp Ser Thr Glu Gly
        1730                1735                1740
Ser Asp Phe Ile Leu Val Arg Tyr Leu Glu Glu Ser Asn Lys Lys
        1745                1750                1755
Ile Leu Gln Lys Ile Arg Ile Lys Gly Ile Leu Ser Asn Thr Gln
        1760                1765                1770
Ser Phe Asn Lys Met Ser Ile Asp Phe Lys Asp Ile Lys Lys Leu
        1775                1780                1785
Ser Leu Gly Tyr Ile Met Ser Asn Phe Lys Ser Phe Asn Ser Glu
        1790                1795                1800
Asn Glu Leu Asp Arg Asp His Leu Gly Phe Lys Ile Ile Asp Asn
        1805                1810                1815
```

```
                                -continued

Lys Thr Tyr Tyr Tyr Asp Glu Asp Ser Lys Leu Val Lys Gly Leu
1820                1825                1830

Ile Asn Ile Asn Asn Ser Leu Phe Tyr Phe Asp Pro Ile Glu Phe
1835                1840                1845

Asn Leu Val Thr Gly Trp Gln Thr Ile Asn Gly Lys Lys Tyr Tyr
1850                1855                1860

Phe Asp Ile Asn Thr Gly Ala Ala Leu Thr Ser Tyr Lys Ile Ile
1865                1870                1875

Asn Gly Lys His Phe Tyr Phe Asn Asn Asp Gly Val Met Gln Leu
1880                1885                1890

Gly Val Phe Lys Gly Pro Asp Gly Phe Glu Tyr Phe Ala Pro Ala
1895                1900                1905

Asn Thr Gln Asn Asn Asn Ile Glu Gly Gln Ala Ile Val Tyr Gln
1910                1915                1920

Ser Lys Phe Leu Thr Leu Asn Gly Lys Lys Tyr Tyr Phe Asp Asn
1925                1930                1935

Asn Ser Lys Ala Val Thr Gly Trp Arg Ile Ile Asn Asn Glu Lys
1940                1945                1950

Tyr Tyr Phe Asn Pro Asn Asn Ala Ile Ala Ala Val Gly Leu Gln
1955                1960                1965

Val Ile Asp Asn Asn Lys Tyr Tyr Phe Asn Pro Asp Thr Ala Ile
1970                1975                1980

Ile Ser Lys Gly Trp Gln Thr Val Asn Gly Ser Arg Tyr Tyr Phe
1985                1990                1995

Asp Thr Asp Thr Ala Ile Ala Phe Asn Gly Tyr Lys Thr Ile Asp
2000                2005                2010

Gly Lys His Phe Tyr Phe Asp Ser Asp Cys Val Val Lys Ile Gly
2015                2020                2025

Val Phe Ser Thr Ser Asn Gly Phe Glu Tyr Phe Ala Pro Ala Asn
2030                2035                2040

Thr Tyr Asn Asn Asn Ile Glu Gly Gln Ala Ile Val Tyr Gln Ser
2045                2050                2055

Lys Phe Leu Thr Leu Asn Gly Lys Lys Tyr Tyr Phe Asp Asn Asn
2060                2065                2070

Ser Lys Ala Val Thr Gly Leu Gln Thr Ile Asp Ser Lys Lys Tyr
2075                2080                2085

Tyr Phe Asn Thr Asn Thr Ala Glu Ala Ala Thr Gly Trp Gln Thr
2090                2095                2100

Ile Asp Gly Lys Lys Tyr Tyr Phe Asn Thr Asn Thr Ala Glu Ala
2105                2110                2115

Ala Thr Gly Trp Gln Thr Ile Asp Gly Lys Lys Tyr Tyr Phe Asn
2120                2125                2130

Thr Asn Thr Ala Ile Ala Ser Thr Gly Tyr Thr Ile Ile Asn Gly
2135                2140                2145

Lys His Phe Tyr Phe Asn Thr Asp Gly Ile Met Gln Ile Gly Val
2150                2155                2160

Phe Lys Gly Pro Asn Gly Phe Glu Tyr Phe Ala Pro Ala Asn Thr
2165                2170                2175

Asp Ala Asn Asn Ile Glu Gly Gln Ala Ile Leu Tyr Gln Asn Glu
2180                2185                2190

Phe Leu Thr Leu Asn Gly Lys Lys Tyr Tyr Phe Gly Ser Asp Ser
2195                2200                2205
```

```
Lys Ala Val Thr Gly Trp Arg Ile Ile Asn Asn Lys Lys Tyr Tyr
2210                2215                2220

Phe Asn Pro Asn Asn Ala Ile Ala Ala Ile His Leu Cys Thr Ile
2225                2230                2235

Asn Asn Asp Lys Tyr Tyr Phe Ser Tyr Asp Gly Ile Leu Gln Asn
2240                2245                2250

Gly Tyr Ile Thr Ile Glu Arg Asn Asn Phe Tyr Phe Asp Ala Asn
2255                2260                2265

Asn Glu Ser Lys Met Val Thr Gly Val Phe Lys Gly Pro Asn Gly
2270                2275                2280

Phe Glu Tyr Phe Ala Pro Ala Asn Thr His Asn Asn Asn Ile Glu
2285                2290                2295

Gly Gln Ala Ile Val Tyr Gln Asn Lys Phe Leu Thr Leu Asn Gly
2300                2305                2310

Lys Lys Tyr Tyr Phe Asp Asn Asp Ser Lys Ala Val Thr Gly Trp
2315                2320                2325

Gln Thr Ile Asp Gly Lys Lys Tyr Tyr Phe Asn Leu Asn Thr Ala
2330                2335                2340

Glu Ala Ala Thr Gly Trp Gln Thr Ile Asp Gly Lys Lys Tyr Tyr
2345                2350                2355

Phe Asn Leu Asn Thr Ala Glu Ala Ala Thr Gly Trp Gln Thr Ile
2360                2365                2370

Asp Gly Lys Lys Tyr Tyr Phe Asn Thr Asn Thr Phe Ile Ala Ser
2375                2380                2385

Thr Gly Tyr Thr Ser Ile Asn Gly Lys His Phe Tyr Phe Asn Thr
2390                2395                2400

Asp Gly Ile Met Gln Ile Gly Val Phe Lys Gly Pro Asn Gly Phe
2405                2410                2415

Glu Tyr Phe Ala Pro Ala Asn Thr Asp Ala Asn Asn Ile Glu Gly
2420                2425                2430

Gln Ala Ile Leu Tyr Gln Asn Lys Phe Leu Thr Leu Asn Gly Lys
2435                2440                2445

Lys Tyr Tyr Phe Gly Ser Asp Ser Lys Ala Val Thr Gly Leu Arg
2450                2455                2460

Thr Ile Asp Gly Lys Lys Tyr Tyr Phe Asn Thr Asn Thr Ala Val
2465                2470                2475

Ala Val Thr Gly Trp Gln Thr Ile Asn Gly Lys Lys Tyr Tyr Phe
2480                2485                2490

Asn Thr Asn Thr Ser Ile Ala Ser Thr Gly Tyr Thr Ile Ile Ser
2495                2500                2505

Gly Lys His Phe Tyr Phe Asn Thr Asp Gly Ile Met Gln Ile Gly
2510                2515                2520

Val Phe Lys Gly Pro Asp Gly Phe Glu Tyr Phe Ala Pro Ala Asn
2525                2530                2535

Thr Asp Ala Asn Asn Ile Glu Gly Gln Ala Ile Arg Tyr Gln Asn
2540                2545                2550

Arg Phe Leu Tyr Leu His Asp Asn Ile Tyr Tyr Phe Gly Asn Asn
2555                2560                2565

Ser Lys Ala Ala Thr Gly Trp Val Thr Ile Asp Gly Asn Arg Tyr
2570                2575                2580

Tyr Phe Glu Pro Asn Thr Ala Met Gly Ala Asn Gly Tyr Lys Thr
2585                2590                2595

Ile Asp Asn Lys Asn Phe Tyr Phe Arg Asn Gly Leu Pro Gln Ile
```

```
                    2600              2605              2610
Gly Val Phe Lys Gly Ser Asn Gly Phe Glu Tyr Phe Ala Pro Ala
        2615              2620              2625

Asn Thr Asp Ala Asn Asn Ile Glu Gly Gln Ala Ile Arg Tyr Gln
        2630              2635              2640

Asn Arg Phe Leu His Leu Leu Gly Lys Ile Tyr Tyr Phe Gly Asn
        2645              2650              2655

Asn Ser Lys Ala Val Thr Gly Trp Gln Thr Ile Asn Gly Lys Val
        2660              2665              2670

Tyr Tyr Phe Met Pro Asp Thr Ala Met Ala Ala Ala Gly Gly Leu
        2675              2680              2685

Phe Glu Ile Asp Gly Val Ile Tyr Phe Phe Gly Val Asp Gly Val
        2690              2695              2700

Lys Ala Pro Gly Ile Tyr Gly
        2705              2710

<210> SEQ ID NO 2
<211> LENGTH: 872
<212> TYPE: PRT
<213> ORGANISM: Clostridium difficile

<400> SEQUENCE: 2

Ser Leu Phe Tyr Phe Asp Pro Ile Glu Phe Asn Leu Val Thr Gly Trp
1               5                   10                  15

Gln Thr Ile Asn Gly Lys Lys Tyr Tyr Phe Asp Ile Asn Thr Gly Ala
                20                  25                  30

Ala Leu Thr Ser Tyr Lys Ile Ile Asn Gly Lys His Phe Tyr Phe Asn
            35                  40                  45

Asn Asp Gly Val Met Gln Leu Gly Val Phe Lys Gly Pro Asp Gly Phe
        50                  55                  60

Glu Tyr Phe Ala Pro Ala Asn Thr Gln Asn Asn Asn Ile Glu Gly Gln
65                  70                  75                  80

Ala Ile Val Tyr Gln Ser Lys Phe Leu Thr Leu Asn Gly Lys Lys Tyr
                85                  90                  95

Tyr Phe Asp Asn Asn Ser Lys Ala Val Thr Gly Trp Arg Ile Ile Asn
            100                 105                 110

Asn Glu Lys Tyr Tyr Phe Asn Pro Asn Asn Ala Ile Ala Ala Val Gly
        115                 120                 125

Leu Gln Val Ile Asp Asn Asn Lys Tyr Tyr Phe Asn Pro Asp Thr Ala
    130                 135                 140

Ile Ile Ser Lys Gly Trp Gln Thr Val Asn Gly Ser Arg Tyr Tyr Phe
145                 150                 155                 160

Asp Thr Asp Thr Ala Ile Ala Phe Asn Gly Tyr Lys Thr Ile Asp Gly
                165                 170                 175

Lys His Phe Tyr Phe Asp Ser Asp Cys Val Val Lys Ile Gly Val Phe
            180                 185                 190

Ser Thr Ser Asn Gly Phe Glu Tyr Phe Ala Pro Ala Asn Thr Tyr Asn
        195                 200                 205

Asn Asn Ile Glu Gly Gln Ala Ile Val Tyr Gln Ser Lys Phe Leu Thr
    210                 215                 220

Leu Asn Gly Lys Lys Tyr Tyr Phe Asp Asn Asn Ser Lys Ala Val Thr
225                 230                 235                 240

Gly Leu Gln Thr Ile Asp Ser Lys Lys Tyr Tyr Phe Asn Thr Asn Thr
                245                 250                 255
```

-continued

```
Ala Glu Ala Ala Thr Gly Trp Gln Thr Ile Asp Gly Lys Lys Tyr Tyr
            260                 265                 270

Phe Asn Thr Asn Thr Ala Glu Ala Ala Thr Gly Trp Gln Thr Ile Asp
        275                 280                 285

Gly Lys Lys Tyr Tyr Phe Asn Thr Asn Thr Ala Ile Ala Ser Thr Gly
    290                 295                 300

Tyr Thr Ile Ile Asn Gly Lys His Phe Tyr Phe Asn Thr Asp Gly Ile
305                 310                 315                 320

Met Gln Ile Gly Val Phe Lys Gly Pro Asn Gly Phe Glu Tyr Phe Ala
                325                 330                 335

Pro Ala Asn Thr Asp Ala Asn Asn Ile Glu Gly Gln Ala Ile Leu Tyr
            340                 345                 350

Gln Asn Glu Phe Leu Thr Leu Asn Gly Lys Lys Tyr Tyr Phe Gly Ser
        355                 360                 365

Asp Ser Lys Ala Val Thr Gly Trp Arg Ile Ile Asn Asn Lys Lys Tyr
    370                 375                 380

Tyr Phe Asn Pro Asn Asn Ala Ile Ala Ala Ile His Leu Cys Thr Ile
385                 390                 395                 400

Asn Asn Asp Lys Tyr Tyr Phe Ser Tyr Asp Gly Ile Leu Gln Asn Gly
                405                 410                 415

Tyr Ile Thr Ile Glu Arg Asn Asn Phe Tyr Phe Asp Ala Asn Asn Glu
            420                 425                 430

Ser Lys Met Val Thr Gly Val Phe Lys Gly Pro Asn Gly Phe Glu Tyr
        435                 440                 445

Phe Ala Pro Ala Asn Thr His Asn Asn Asn Ile Glu Gly Gln Ala Ile
    450                 455                 460

Val Tyr Gln Asn Lys Phe Leu Thr Leu Asn Gly Lys Lys Tyr Tyr Phe
465                 470                 475                 480

Asp Asn Asp Ser Lys Ala Val Thr Gly Trp Gln Thr Ile Asp Gly Lys
                485                 490                 495

Lys Tyr Tyr Phe Asn Leu Asn Thr Ala Glu Ala Ala Thr Gly Trp Gln
            500                 505                 510

Thr Ile Asp Gly Lys Lys Tyr Tyr Phe Asn Leu Asn Thr Ala Glu Ala
        515                 520                 525

Ala Thr Gly Trp Gln Thr Ile Asp Gly Lys Lys Tyr Tyr Phe Asn Thr
    530                 535                 540

Asn Thr Phe Ile Ala Ser Thr Gly Tyr Thr Ser Ile Asn Gly Lys His
545                 550                 555                 560

Phe Tyr Phe Asn Thr Asp Gly Ile Met Gln Ile Gly Val Phe Lys Gly
                565                 570                 575

Pro Asn Gly Phe Glu Tyr Phe Ala Pro Ala Asn Thr Asp Ala Asn Asn
            580                 585                 590

Ile Glu Gly Gln Ala Ile Leu Tyr Gln Asn Lys Phe Leu Thr Leu Asn
        595                 600                 605

Gly Lys Lys Tyr Tyr Phe Gly Ser Asp Ser Lys Ala Val Thr Gly Leu
    610                 615                 620

Arg Thr Ile Asp Gly Lys Lys Tyr Tyr Phe Asn Thr Asn Thr Ala Val
625                 630                 635                 640

Ala Val Thr Gly Trp Gln Thr Ile Asn Gly Lys Lys Tyr Tyr Phe Asn
                645                 650                 655

Thr Asn Thr Ser Ile Ala Ser Thr Gly Tyr Thr Ile Ile Ser Gly Lys
            660                 665                 670

His Phe Tyr Phe Asn Thr Asp Gly Ile Met Gln Ile Gly Val Phe Lys
```

675                 680                 685
Gly Pro Asp Gly Phe Glu Tyr Phe Ala Pro Asn Thr Asp Ala Asn
690                 695                 700

Asn Ile Glu Gly Gln Ala Ile Arg Tyr Gln Asn Arg Phe Leu Tyr Leu
705                 710                 715                 720

His Asp Asn Ile Tyr Tyr Phe Gly Asn Asn Ser Lys Ala Ala Thr Gly
                    725                 730                 735

Trp Val Thr Ile Asp Gly Asn Arg Tyr Tyr Phe Glu Pro Asn Thr Ala
                740                 745                 750

Met Gly Ala Asn Gly Tyr Lys Thr Ile Asp Asn Lys Asn Phe Tyr Phe
            755                 760                 765

Arg Asn Gly Leu Pro Gln Ile Gly Val Phe Lys Gly Ser Asn Gly Phe
770                 775                 780

Glu Tyr Phe Ala Pro Ala Asn Thr Asp Ala Asn Asn Ile Glu Gly Gln
785                 790                 795                 800

Ala Ile Arg Tyr Gln Asn Arg Phe Leu His Leu Leu Gly Lys Ile Tyr
                805                 810                 815

Tyr Phe Gly Asn Asn Ser Lys Ala Val Thr Gly Trp Gln Thr Ile Asn
                820                 825                 830

Gly Lys Val Tyr Tyr Phe Met Pro Asp Thr Ala Met Ala Ala Ala Gly
            835                 840                 845

Gly Leu Phe Glu Ile Asp Gly Val Ile Tyr Phe Phe Gly Val Asp Gly
850                 855                 860

Val Lys Ala Pro Gly Ile Tyr Gly
865                 870

<210> SEQ ID NO 3
<211> LENGTH: 2710
<212> TYPE: PRT
<213> ORGANISM: Clostridium difficile

<400> SEQUENCE: 3

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

```
Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
            195                 200                 205

Leu Val Ser Glu Tyr Asn Arg Asp Glu Thr Val Leu Glu Ser Tyr Arg
            210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Asn Ile Tyr Ser Gln
            245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
            275                 280                 285

Leu Pro Gly Ile His Ser Asp Leu Phe Lys Thr Ile Ser Arg Pro Ser
            290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
            325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
            355                 360                 365

Asp Leu Glu Ile Lys Ile Ala Phe Ala Leu Gly Ser Val Ile Asn Gln
            370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
            405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
            435                 440                 445

Ile Ala Pro Tyr Leu Gln Val Gly Phe Met Pro Glu Ala Arg Ser Thr
            450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
            485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
            515                 520                 525

Gln Phe Glu Lys Tyr Val Arg Asp Tyr Thr Gly Gly Ser Leu Ser Glu
            530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
            565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
```

```
                595                 600                 605
Ile Ile Gln Arg Asn Met Asn Glu Ser Ala Lys Ser Tyr Phe Leu Ser
            610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
                675                 680                 685

Ser Pro Lys Asn Val Glu Val Asn Leu Leu Gly Cys Asn Met Phe Ser
690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
                755                 760                 765

Ala Ile Met Ser Asp Leu Ser Ser Lys Glu Tyr Ile Phe Phe Asp Ser
770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
            820                 825                 830

Ser Ile Gly Asp Tyr Ile Tyr Tyr Glu Lys Leu Glu Pro Val Lys Asn
                835                 840                 845

Ile Ile His Asn Ser Ile Asp Asp Leu Ile Asp Glu Phe Asn Leu Leu
            850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
                900                 905                 910

Val Glu Thr Glu Lys Glu Ile Phe Ser Lys Tyr Ser Glu His Ile Thr
            915                 920                 925

Lys Glu Ile Ser Thr Ile Lys Asn Ser Ile Ile Thr Asp Val Asn Gly
            930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
            980                 985                 990

Ala Gln Leu Phe Ser Thr Gly Leu  Asn Thr Ile Tyr Asp  Ser Ile Gln
            995                1000                1005

Leu Val  Asn Leu Ile Ser Asn  Ala Val Asn Asp Thr  Ile Asn Val
    1010                1015                1020
```

```
Leu Pro Thr Ile Thr Glu Gly Ile Pro Ile Val Ser Thr Ile Leu
1025                1030                1035

Asp Gly Ile Asn Leu Gly Ala Ala Ile Lys Glu Leu Leu Asp Glu
1040                1045                1050

His Asp Pro Leu Leu Lys Lys Glu Leu Glu Ala Lys Val Gly Val
1055                1060                1065

Leu Ala Ile Asn Met Ser Leu Ser Ile Ala Ala Thr Val Ala Ser
1070                1075                1080

Ile Val Gly Ile Gly Ala Glu Val Thr Ile Phe Leu Leu Pro Ile
1085                1090                1095

Ala Gly Ile Ser Ala Gly Ile Pro Ser Leu Val Asn Asn Glu Leu
1100                1105                1110

Ile Leu His Asp Lys Ala Thr Ser Val Val Asn Tyr Phe Asn His
1115                1120                1125

Leu Ser Glu Ser Lys Lys Tyr Gly Pro Leu Lys Thr Glu Asp Asp
1130                1135                1140

Lys Ile Leu Val Pro Ile Asp Asp Leu Val Ile Ser Glu Ile Asp
1145                1150                1155

Phe Asn Asn Asn Ser Ile Lys Leu Gly Thr Cys Asn Ile Leu Ala
1160                1165                1170

Met Glu Gly Gly Ser Gly His Thr Val Thr Gly Asn Ile Asp His
1175                1180                1185

Phe Phe Ser Ser Pro Ser Ile Ser Ser His Ile Pro Ser Leu Ser
1190                1195                1200

Ile Tyr Ser Ala Ile Gly Ile Glu Thr Glu Asn Leu Asp Phe Ser
1205                1210                1215

Lys Lys Ile Met Met Leu Pro Asn Ala Pro Ser Arg Val Phe Trp
1220                1225                1230

Trp Glu Thr Gly Ala Val Pro Gly Leu Arg Ser Leu Glu Asn Asp
1235                1240                1245

Gly Thr Arg Leu Leu Asp Ser Ile Arg Asp Leu Tyr Pro Gly Lys
1250                1255                1260

Phe Tyr Trp Arg Phe Tyr Ala Phe Phe Asp Tyr Ala Ile Thr Thr
1265                1270                1275

Leu Lys Pro Val Tyr Glu Asp Thr Asn Ile Lys Ile Lys Leu Asp
1280                1285                1290

Lys Asp Thr Arg Asn Phe Ile Met Pro Thr Ile Thr Thr Asn Glu
1295                1300                1305

Ile Arg Asn Lys Leu Ser Tyr Ser Phe Asp Gly Ala Gly Gly Thr
1310                1315                1320

Tyr Ser Leu Leu Leu Ser Ser Tyr Pro Ile Ser Thr Asn Ile Asn
1325                1330                1335

Leu Ser Lys Asp Asp Leu Trp Ile Phe Asn Ile Asp Asn Glu Val
1340                1345                1350

Arg Glu Ile Ser Ile Glu Asn Gly Thr Ile Lys Lys Gly Lys Leu
1355                1360                1365

Ile Lys Asp Val Leu Ser Lys Ile Asp Ile Asn Lys Asn Lys Leu
1370                1375                1380

Ile Ile Gly Asn Gln Thr Ile Asp Phe Ser Gly Asp Ile Asp Asn
1385                1390                1395

Lys Asp Arg Tyr Ile Phe Leu Thr Cys Glu Leu Asp Asp Lys Ile
1400                1405                1410
```

```
Ser Leu Ile Ile Glu Ile Asn Leu Val Ala Lys Ser Tyr Ser Leu
1415                1420                1425

Leu Leu Ser Gly Asp Lys Asn Tyr Leu Ile Ser Asn Leu Ser Asn
1430                1435                1440

Thr Ile Glu Lys Ile Asn Thr Leu Gly Leu Asp Ser Lys Asn Ile
1445                1450                1455

Ala Tyr Asn Tyr Thr Asp Glu Ser Asn Asn Lys Tyr Phe Gly Ala
1460                1465                1470

Ile Ser Lys Thr Ser Gln Lys Ser Ile Ile His Tyr Lys Lys Asp
1475                1480                1485

Ser Lys Asn Ile Leu Glu Phe Tyr Asn Asp Ser Thr Leu Glu Phe
1490                1495                1500

Asn Ser Lys Asp Phe Ile Ala Glu Asp Ile Asn Val Phe Met Lys
1505                1510                1515

Asp Asp Ile Asn Thr Ile Thr Gly Lys Tyr Tyr Val Asp Asn Asn
1520                1525                1530

Thr Asp Lys Ser Ile Asp Phe Ser Ile Ser Leu Val Ser Lys Asn
1535                1540                1545

Gln Val Lys Val Asn Gly Leu Tyr Leu Asn Glu Ser Val Tyr Ser
1550                1555                1560

Ser Tyr Leu Asp Phe Val Lys Asn Ser Asp Gly His His Asn Thr
1565                1570                1575

Ser Asn Phe Met Asn Leu Phe Leu Asp Asn Ile Ser Phe Trp Lys
1580                1585                1590

Leu Phe Gly Phe Glu Asn Ile Asn Phe Val Ile Asp Lys Tyr Phe
1595                1600                1605

Thr Leu Val Gly Lys Thr Asn Leu Gly Tyr Val Glu Phe Ile Cys
1610                1615                1620

Asp Asn Asn Lys Asn Ile Asp Ile Tyr Phe Gly Glu Trp Lys Thr
1625                1630                1635

Ser Ser Ser Lys Ser Thr Ile Phe Ser Gly Asn Gly Arg Asn Val
1640                1645                1650

Val Val Glu Pro Ile Tyr Asn Pro Asp Thr Gly Glu Asp Ile Ser
1655                1660                1665

Thr Ser Leu Asp Phe Ser Tyr Glu Pro Leu Tyr Gly Ile Asp Arg
1670                1675                1680

Tyr Ile Asn Lys Val Leu Ile Ala Pro Asp Leu Tyr Thr Ser Leu
1685                1690                1695

Ile Asn Ile Asn Thr Asn Tyr Tyr Ser Asn Glu Tyr Tyr Pro Glu
1700                1705                1710

Ile Ile Val Leu Asn Pro Asn Thr Phe His Lys Lys Val Asn Ile
1715                1720                1725

Asn Leu Asp Ser Ser Ser Phe Glu Tyr Lys Trp Ser Thr Glu Gly
1730                1735                1740

Ser Asp Phe Ile Leu Val Arg Tyr Leu Glu Glu Ser Asn Lys Lys
1745                1750                1755

Ile Leu Gln Lys Ile Arg Ile Lys Gly Ile Leu Ser Asn Thr Gln
1760                1765                1770

Ser Phe Asn Lys Met Ser Ile Asp Phe Lys Asp Ile Lys Lys Leu
1775                1780                1785

Ser Leu Gly Tyr Ile Met Ser Asn Phe Lys Ser Phe Asn Ser Glu
1790                1795                1800

Asn Glu Leu Asp Arg Asp His Leu Gly Phe Lys Ile Ile Asp Asn
```

```
                1805                1810                1815

Lys Thr Tyr Tyr Tyr Asp Glu Asp Ser Lys Leu Val Lys Gly Leu
    1820                1825                1830

Ile Asn Ile Asn Asn Ser Leu Phe Tyr Phe Asp Pro Ile Glu Phe
    1835                1840                1845

Asn Leu Val Thr Gly Trp Gln Thr Ile Asn Gly Lys Lys Tyr Tyr
    1850                1855                1860

Phe Asp Ile Asn Thr Gly Ala Ala Leu Thr Ser Tyr Lys Ile Ile
    1865                1870                1875

Asn Gly Lys His Phe Tyr Phe Asn Asn Asp Gly Val Met Gln Leu
    1880                1885                1890

Gly Val Phe Lys Gly Pro Asp Gly Phe Glu Tyr Phe Ala Pro Ala
    1895                1900                1905

Asn Thr Gln Asn Asn Asn Ile Glu Gly Gln Ala Ile Val Tyr Gln
    1910                1915                1920

Ser Lys Phe Leu Thr Leu Asn Gly Lys Lys Tyr Tyr Phe Asp Asn
    1925                1930                1935

Asn Ser Lys Ala Val Thr Gly Trp Arg Ile Ile Asn Asn Glu Lys
    1940                1945                1950

Tyr Tyr Phe Asn Pro Asn Asn Ala Ile Ala Ala Val Gly Leu Gln
    1955                1960                1965

Val Ile Asp Asn Asn Lys Tyr Tyr Phe Asn Pro Asp Thr Ala Ile
    1970                1975                1980

Ile Ser Lys Gly Trp Gln Thr Val Asn Gly Ser Arg Tyr Tyr Phe
    1985                1990                1995

Asp Thr Asp Thr Ala Ile Ala Phe Asn Gly Tyr Lys Thr Ile Asp
    2000                2005                2010

Gly Lys His Phe Tyr Phe Asp Ser Asp Cys Val Val Lys Ile Gly
    2015                2020                2025

Val Phe Ser Thr Ser Asn Gly Phe Glu Tyr Phe Ala Pro Ala Asn
    2030                2035                2040

Thr Tyr Asn Asn Asn Ile Glu Gly Gln Ala Ile Val Tyr Gln Ser
    2045                2050                2055

Lys Phe Leu Thr Leu Asn Gly Lys Lys Tyr Tyr Phe Asp Asn Asn
    2060                2065                2070

Ser Lys Ala Val Thr Gly Trp Gln Thr Ile Asp Ser Lys Lys Tyr
    2075                2080                2085

Tyr Phe Asn Thr Asn Thr Ala Glu Ala Ala Thr Gly Trp Gln Thr
    2090                2095                2100

Ile Asp Gly Lys Lys Tyr Tyr Phe Asn Thr Asn Thr Ala Glu Ala
    2105                2110                2115

Ala Thr Gly Trp Gln Thr Ile Asp Gly Lys Lys Tyr Tyr Phe Asn
    2120                2125                2130

Thr Asn Thr Ala Ile Ala Ser Thr Gly Tyr Thr Ile Ile Asn Gly
    2135                2140                2145

Lys His Phe Tyr Phe Asn Thr Asp Gly Ile Met Gln Ile Gly Val
    2150                2155                2160

Phe Lys Gly Pro Asn Gly Phe Glu Tyr Phe Ala Pro Ala Asn Thr
    2165                2170                2175

Asp Ala Asn Asn Ile Glu Gly Gln Ala Ile Leu Tyr Gln Asn Glu
    2180                2185                2190

Phe Leu Thr Leu Asn Gly Lys Lys Tyr Tyr Phe Gly Ser Asp Ser
    2195                2200                2205
```

-continued

Lys Ala Val Thr Gly Trp Arg Ile Ile Asn Asn Lys Lys Tyr Tyr
2210            2215                2220

Phe Asn Pro Asn Asn Ala Ile Ala Ala Ile His Leu Cys Thr Ile
2225            2230                2235

Asn Asn Asp Lys Tyr Tyr Phe Ser Tyr Asp Gly Ile Leu Gln Asn
2240            2245                2250

Gly Tyr Ile Thr Ile Glu Arg Asn Asn Phe Tyr Phe Asp Ala Asn
2255            2260                2265

Asn Glu Ser Lys Met Val Thr Gly Val Phe Lys Gly Pro Asn Gly
2270            2275                2280

Phe Glu Tyr Phe Ala Pro Ala Asn Thr His Asn Asn Asn Ile Glu
2285            2290                2295

Gly Gln Ala Ile Val Tyr Gln Asn Lys Phe Leu Thr Leu Asn Gly
2300            2305                2310

Lys Lys Tyr Tyr Phe Asp Asn Asp Ser Lys Ala Val Thr Gly Trp
2315            2320                2325

Gln Thr Ile Asp Gly Lys Lys Tyr Tyr Phe Asn Leu Asn Thr Ala
2330            2335                2340

Glu Ala Ala Thr Gly Trp Gln Thr Ile Asp Gly Lys Lys Tyr Tyr
2345            2350                2355

Phe Asn Leu Asn Thr Ala Glu Ala Ala Thr Gly Trp Gln Thr Ile
2360            2365                2370

Asp Gly Lys Lys Tyr Tyr Phe Asn Thr Asn Thr Phe Ile Ala Ser
2375            2380                2385

Thr Gly Tyr Thr Ser Ile Asn Gly Lys His Phe Tyr Phe Asn Thr
2390            2395                2400

Asp Gly Ile Met Gln Ile Gly Val Phe Lys Gly Pro Asn Gly Phe
2405            2410                2415

Glu Tyr Phe Ala Pro Ala Asn Thr Asp Ala Asn Asn Ile Glu Gly
2420            2425                2430

Gln Ala Ile Leu Tyr Gln Asn Lys Phe Leu Thr Leu Asn Gly Lys
2435            2440                2445

Lys Tyr Tyr Phe Gly Ser Asp Ser Lys Ala Val Thr Gly Leu Arg
2450            2455                2460

Thr Ile Asp Gly Lys Lys Tyr Tyr Phe Asn Thr Asn Thr Ala Val
2465            2470                2475

Ala Val Thr Gly Trp Gln Thr Ile Asn Gly Lys Lys Tyr Tyr Phe
2480            2485                2490

Asn Thr Asn Thr Ser Ile Ala Ser Thr Gly Tyr Thr Ile Ile Ser
2495            2500                2505

Gly Lys His Phe Tyr Phe Asn Thr Asp Gly Ile Met Gln Ile Gly
2510            2515                2520

Val Phe Lys Gly Pro Asp Gly Phe Glu Tyr Phe Ala Pro Ala Asn
2525            2530                2535

Thr Asp Ala Asn Asn Ile Glu Gly Gln Ala Ile Arg Tyr Gln Asn
2540            2545                2550

Arg Phe Leu Tyr Leu His Asp Asn Ile Tyr Tyr Phe Gly Asn Asn
2555            2560                2565

Ser Lys Ala Ala Thr Gly Trp Val Thr Ile Asp Gly Asn Arg Tyr
2570            2575                2580

Tyr Phe Glu Pro Asn Thr Ala Met Gly Ala Asn Gly Tyr Lys Thr
2585            2590                2595

```
Ile Asp Asn Lys Asn Phe Tyr Phe Arg Asn Gly Leu Pro Gln Ile
2600                2605                2610

Gly Val Phe Lys Gly Ser Asn Gly Phe Glu Tyr Phe Ala Pro Ala
    2615                2620                2625

Asn Thr Asp Ala Asn Asn Ile Glu Gly Gln Ala Ile Arg Tyr Gln
2630                2635                2640

Asn Arg Phe Leu His Leu Leu Gly Lys Ile Tyr Tyr Phe Gly Asn
    2645                2650                2655

Asn Ser Lys Ala Val Thr Gly Trp Gln Thr Ile Asn Gly Lys Val
2660                2665                2670

Tyr Tyr Phe Met Pro Asp Thr Ala Met Ala Ala Ala Gly Gly Leu
    2675                2680                2685

Phe Glu Ile Asp Gly Val Ile Tyr Phe Phe Gly Val Asp Gly Val
2690                2695                2700

Lys Ala Pro Gly Ile Tyr Gly
    2705                2710

<210> SEQ ID NO 4
<211> LENGTH: 872
<212> TYPE: PRT
<213> ORGANISM: Clostridium difficile

<400> SEQUENCE: 4

Ser Leu Phe Tyr Phe Asp Pro Ile Glu Phe Asn Leu Val Thr Gly Trp
1               5                   10                  15

Gln Thr Ile Asn Gly Lys Lys Tyr Tyr Phe Asp Ile Asn Thr Gly Ala
            20                  25                  30

Ala Leu Thr Ser Tyr Lys Ile Ile Asn Gly Lys His Phe Tyr Phe Asn
        35                  40                  45

Asn Asp Gly Val Met Gln Leu Gly Val Phe Lys Gly Pro Asp Gly Phe
    50                  55                  60

Glu Tyr Phe Ala Pro Ala Asn Thr Gln Asn Asn Asn Ile Glu Gly Gln
65                  70                  75                  80

Ala Ile Val Tyr Gln Ser Lys Phe Leu Thr Leu Asn Gly Lys Lys Tyr
                85                  90                  95

Tyr Phe Asp Asn Asn Ser Lys Ala Val Thr Gly Trp Arg Ile Ile Asn
            100                 105                 110

Asn Glu Lys Tyr Tyr Phe Asn Pro Asn Asn Ala Ile Ala Ala Val Gly
        115                 120                 125

Leu Gln Val Ile Asp Asn Asn Lys Tyr Tyr Phe Asn Pro Asp Thr Ala
    130                 135                 140

Ile Ile Ser Lys Gly Trp Gln Thr Val Asn Gly Ser Arg Tyr Tyr Phe
145                 150                 155                 160

Asp Thr Asp Thr Ala Ile Ala Phe Asn Gly Tyr Lys Thr Ile Asp Gly
                165                 170                 175

Lys His Phe Tyr Phe Asp Ser Asp Cys Val Val Lys Ile Gly Val Phe
            180                 185                 190

Ser Thr Ser Asn Gly Phe Glu Tyr Phe Ala Pro Ala Asn Thr Tyr Asn
        195                 200                 205

Asn Asn Ile Glu Gly Gln Ala Ile Val Tyr Gln Ser Lys Phe Leu Thr
    210                 215                 220

Leu Asn Gly Lys Lys Tyr Tyr Phe Asp Asn Asn Ser Lys Ala Val Thr
225                 230                 235                 240

Gly Trp Gln Thr Ile Asp Ser Lys Lys Tyr Tyr Phe Asn Thr Asn Thr
                245                 250                 255
```

```
Ala Glu Ala Ala Thr Gly Trp Gln Thr Ile Asp Gly Lys Lys Tyr Tyr
            260                 265                 270

Phe Asn Thr Asn Thr Ala Glu Ala Thr Gly Trp Gln Thr Ile Asp
            275                 280                 285

Gly Lys Lys Tyr Tyr Phe Asn Thr Asn Thr Ala Ile Ala Ser Thr Gly
            290                 295                 300

Tyr Thr Ile Ile Asn Gly Lys His Phe Tyr Phe Asn Thr Asp Gly Ile
305                 310                 315                 320

Met Gln Ile Gly Val Phe Lys Gly Pro Asn Gly Phe Glu Tyr Phe Ala
                325                 330                 335

Pro Ala Asn Thr Asp Ala Asn Asn Ile Glu Gly Gln Ala Ile Leu Tyr
            340                 345                 350

Gln Asn Glu Phe Leu Thr Leu Asn Gly Lys Lys Tyr Tyr Phe Gly Ser
            355                 360                 365

Asp Ser Lys Ala Val Thr Gly Trp Arg Ile Ile Asn Asn Lys Lys Tyr
            370                 375                 380

Tyr Phe Asn Pro Asn Asn Ala Ile Ala Ala Ile His Leu Cys Thr Ile
385                 390                 395                 400

Asn Asn Asp Lys Tyr Tyr Phe Ser Tyr Asp Gly Ile Leu Gln Asn Gly
                405                 410                 415

Tyr Ile Thr Ile Glu Arg Asn Asn Phe Tyr Phe Asp Ala Asn Asn Glu
                420                 425                 430

Ser Lys Met Val Thr Gly Val Phe Lys Gly Pro Asn Gly Phe Glu Tyr
            435                 440                 445

Phe Ala Pro Ala Asn Thr His Asn Asn Asn Ile Glu Gly Gln Ala Ile
            450                 455                 460

Val Tyr Gln Asn Lys Phe Leu Thr Leu Asn Gly Lys Lys Tyr Tyr Phe
465                 470                 475                 480

Asp Asn Asp Ser Lys Ala Val Thr Gly Trp Gln Thr Ile Asp Gly Lys
                485                 490                 495

Lys Tyr Tyr Phe Asn Leu Asn Thr Ala Glu Ala Ala Thr Gly Trp Gln
            500                 505                 510

Thr Ile Asp Gly Lys Lys Tyr Tyr Phe Asn Leu Asn Thr Ala Glu Ala
            515                 520                 525

Ala Thr Gly Trp Gln Thr Ile Asp Gly Lys Lys Tyr Tyr Phe Asn Thr
            530                 535                 540

Asn Thr Phe Ile Ala Ser Thr Gly Tyr Thr Ser Ile Asn Gly Lys His
545                 550                 555                 560

Phe Tyr Phe Asn Thr Asp Gly Ile Met Gln Ile Gly Val Phe Lys Gly
                565                 570                 575

Pro Asn Gly Phe Glu Tyr Phe Ala Pro Ala Asn Thr Asp Ala Asn Asn
            580                 585                 590

Ile Glu Gly Gln Ala Ile Leu Tyr Gln Asn Lys Phe Leu Thr Leu Asn
            595                 600                 605

Gly Lys Lys Tyr Tyr Phe Gly Ser Asp Ser Lys Ala Val Thr Gly Leu
            610                 615                 620

Arg Thr Ile Asp Gly Lys Lys Tyr Tyr Phe Asn Thr Asn Thr Ala Val
625                 630                 635                 640

Ala Val Thr Gly Trp Gln Thr Ile Asn Gly Lys Lys Tyr Tyr Phe Asn
                645                 650                 655

Thr Asn Thr Ser Ile Ala Ser Thr Gly Tyr Thr Ile Ile Ser Gly Lys
            660                 665                 670
```

```
His Phe Tyr Phe Asn Thr Asp Gly Ile Met Gln Ile Gly Val Phe Lys
            675                 680                 685

Gly Pro Asp Gly Phe Glu Tyr Phe Ala Pro Ala Asn Thr Asp Ala Asn
        690                 695                 700

Asn Ile Glu Gly Gln Ala Ile Arg Tyr Gln Asn Arg Phe Leu Tyr Leu
705                 710                 715                 720

His Asp Asn Ile Tyr Tyr Phe Gly Asn Asn Ser Lys Ala Ala Thr Gly
                725                 730                 735

Trp Val Thr Ile Asp Gly Asn Arg Tyr Tyr Phe Glu Pro Asn Thr Ala
            740                 745                 750

Met Gly Ala Asn Gly Tyr Lys Thr Ile Asp Asn Lys Asn Phe Tyr Phe
        755                 760                 765

Arg Asn Gly Leu Pro Gln Ile Gly Val Phe Lys Gly Ser Asn Gly Phe
770                 775                 780

Glu Tyr Phe Ala Pro Ala Asn Thr Asp Ala Asn Asn Ile Glu Gly Gln
785                 790                 795                 800

Ala Ile Arg Tyr Gln Asn Arg Phe Leu His Leu Leu Gly Lys Ile Tyr
                805                 810                 815

Tyr Phe Gly Asn Asn Ser Lys Ala Val Thr Gly Trp Gln Thr Ile Asn
            820                 825                 830

Gly Lys Val Tyr Tyr Phe Met Pro Asp Thr Ala Met Ala Ala Ala Gly
        835                 840                 845

Gly Leu Phe Glu Ile Asp Gly Val Ile Tyr Phe Phe Gly Val Asp Gly
        850                 855                 860

Val Lys Ala Pro Gly Ile Tyr Gly
865                 870

<210> SEQ ID NO 5
<211> LENGTH: 2710
<212> TYPE: PRT
<213> ORGANISM: Clostridium difficile

<400> SEQUENCE: 5

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175
```

```
Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Lys Ser His
        195                 200                 205

Leu Val Ser Glu Tyr Asn Arg Asp Glu Thr Val Leu Glu Ser Tyr Arg
            210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ser Asp Ile Val Arg
            260                 265                 270

Leu Leu Ala Leu Lys Asn Phe Gly Gly Val Tyr Leu Asp Val Asp Met
            275                 280                 285

Leu Pro Gly Ile His Ser Asp Leu Phe Lys Thr Ile Ser Arg Pro Ser
            290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
            355                 360                 365

Asp Leu Glu Ile Lys Ile Ala Phe Ala Leu Gly Ser Val Ile Asn Gln
            370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
            435                 440                 445

Ile Ala Pro Tyr Leu Gln Val Gly Phe Met Pro Glu Ala Arg Ser Thr
            450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
            515                 520                 525

Gln Phe Glu Lys Tyr Val Arg Asp Tyr Thr Gly Gly Ser Leu Ser Glu
            530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590
```

```
Tyr Glu Ala Thr Cys Asn Leu Phe Ser Lys Asn Pro Lys Asn Ser Ile
            595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
                660                 665                 670

Leu Ser Asn Glu Ile Ser Ser Phe Leu Asp Thr Ile Lys Leu Asp Ile
    675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
                740                 745                 750

Arg Lys Glu Leu Leu Ala His Ser Gly Lys Trp Ile Asn Lys Glu Glu
    755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Asp Ala Ser Val Ser
                805                 810                 815

Pro Asp Thr Lys Phe Ile Leu Asn Asn Leu Lys Leu Asn Ile Glu Ser
                820                 825                 830

Ser Ile Gly Asp Tyr Ile Tyr Tyr Glu Lys Leu Glu Pro Val Lys Asn
    835                 840                 845

Ile Ile His Asn Ser Ile Asp Asp Leu Ile Asp Glu Phe Asn Leu Leu
    850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
                900                 905                 910

Val Glu Thr Glu Lys Glu Ile Phe Ser Lys Tyr Ser Glu His Ile Thr
    915                 920                 925

Lys Glu Ile Ser Thr Ile Lys Asn Ser Ile Ile Thr Asp Val Asn Gly
    930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
                980                 985                 990

Ala Gln Leu Phe Ser Thr Gly Leu Asn Thr Ile Tyr Asp Ser Ile Gln
    995                 1000                1005

Leu Val  Asn Leu Ile Ser Asn  Ala Val Asn Asp Thr  Ile Asn Val
```

```
                  1010                1015                1020
Leu Pro Thr Ile Thr Glu Gly Ile Pro Ile Val Ser Thr Ile Leu
         1025                1030                1035

Asp Gly Ile Asn Leu Gly Ala Ala Ile Lys Glu Leu Leu Asp Glu
         1040                1045                1050

His Asp Pro Leu Leu Lys Lys Glu Leu Glu Ala Lys Val Gly Val
         1055                1060                1065

Leu Ala Ile Asn Met Ser Leu Ser Ile Ala Ala Thr Val Ala Ser
         1070                1075                1080

Ile Val Gly Ile Gly Ala Glu Val Thr Ile Phe Leu Leu Pro Ile
         1085                1090                1095

Ala Gly Ile Ser Ala Gly Ile Pro Ser Leu Val Asn Asn Glu Leu
         1100                1105                1110

Ile Leu His Asp Lys Ala Thr Ser Val Val Asn Tyr Phe Asn His
         1115                1120                1125

Leu Ser Glu Ser Lys Lys Tyr Gly Pro Leu Lys Thr Glu Asp Asp
         1130                1135                1140

Lys Ile Leu Val Pro Ile Asp Asp Leu Val Ile Ser Glu Ile Asp
         1145                1150                1155

Phe Asn Asn Asn Ser Ile Lys Leu Gly Thr Cys Asn Ile Leu Ala
         1160                1165                1170

Met Glu Gly Gly Ser Gly His Thr Val Thr Gly Asn Ile Asp His
         1175                1180                1185

Phe Phe Ser Ser Pro Ser Ile Ser Ser His Ile Pro Ser Leu Ser
         1190                1195                1200

Ile Tyr Ser Ala Ile Gly Ile Glu Thr Glu Asn Leu Asp Phe Ser
         1205                1210                1215

Lys Lys Ile Met Met Leu Pro Asn Ala Pro Ser Arg Val Phe Trp
         1220                1225                1230

Trp Glu Thr Gly Ala Val Pro Gly Leu Arg Ser Leu Glu Asn Asp
         1235                1240                1245

Gly Thr Arg Leu Leu Asp Ser Ile Arg Asp Leu Tyr Pro Gly Lys
         1250                1255                1260

Phe Tyr Trp Arg Phe Tyr Ala Phe Phe Asp Tyr Ala Ile Thr Thr
         1265                1270                1275

Leu Lys Pro Val Tyr Glu Asp Thr Asn Ile Lys Ile Lys Leu Asp
         1280                1285                1290

Lys Asp Thr Arg Asn Phe Ile Met Pro Thr Ile Thr Thr Asn Glu
         1295                1300                1305

Ile Arg Asn Lys Leu Ser Tyr Ser Phe Asp Gly Ala Gly Gly Thr
         1310                1315                1320

Tyr Ser Leu Leu Leu Ser Ser Tyr Pro Ile Ser Thr Asn Ile Asn
         1325                1330                1335

Leu Ser Lys Asp Asp Leu Trp Ile Phe Asn Ile Asp Asn Glu Val
         1340                1345                1350

Arg Glu Ile Ser Ile Glu Asn Gly Thr Ile Lys Lys Gly Lys Leu
         1355                1360                1365

Ile Lys Asp Val Leu Ser Lys Ile Asp Ile Asn Lys Asn Lys Leu
         1370                1375                1380

Ile Ile Gly Asn Gln Thr Ile Asp Phe Ser Gly Asp Ile Asp Asn
         1385                1390                1395

Lys Asp Arg Tyr Ile Phe Leu Thr Cys Glu Leu Asp Asp Lys Ile
         1400                1405                1410
```

-continued

```
Ser Leu Ile Ile Glu Ile Asn Leu Val Ala Lys Ser Tyr Ser Leu
1415                1420                1425

Leu Leu Ser Gly Asp Lys Asn Tyr Leu Ile Ser Asn Leu Ser Asn
1430                1435                1440

Thr Ile Glu Lys Ile Asn Thr Leu Gly Leu Asp Ser Lys Asn Ile
1445                1450                1455

Ala Tyr Asn Tyr Thr Asp Glu Ser Asn Asn Lys Tyr Phe Gly Ala
1460                1465                1470

Ile Ser Lys Thr Ser Gln Lys Ser Ile Ile His Tyr Lys Lys Asp
1475                1480                1485

Ser Lys Asn Ile Leu Glu Phe Tyr Asn Asp Ser Thr Leu Glu Phe
1490                1495                1500

Asn Ser Lys Asp Phe Ile Ala Glu Asp Ile Asn Val Phe Met Lys
1505                1510                1515

Asp Asp Ile Asn Thr Ile Thr Gly Lys Tyr Tyr Val Asp Asn Asn
1520                1525                1530

Thr Asp Lys Ser Ile Asp Phe Ser Ile Ser Leu Val Ser Lys Asn
1535                1540                1545

Gln Val Lys Val Asn Gly Leu Tyr Leu Asn Glu Ser Val Tyr Ser
1550                1555                1560

Ser Tyr Leu Asp Phe Val Lys Asn Ser Asp Gly His His Asn Thr
1565                1570                1575

Ser Asn Phe Met Asn Leu Phe Leu Asp Asn Ile Ser Phe Trp Lys
1580                1585                1590

Leu Phe Gly Phe Glu Asn Ile Asn Phe Val Ile Asp Lys Tyr Phe
1595                1600                1605

Thr Leu Val Gly Lys Thr Asn Leu Gly Tyr Val Glu Phe Ile Cys
1610                1615                1620

Asp Asn Asn Lys Asn Ile Asp Ile Tyr Phe Gly Glu Trp Lys Thr
1625                1630                1635

Ser Ser Ser Lys Ser Thr Ile Phe Ser Gly Asn Gly Arg Asn Val
1640                1645                1650

Val Val Glu Pro Ile Tyr Asn Pro Asp Thr Gly Glu Asp Ile Ser
1655                1660                1665

Thr Ser Leu Asp Phe Ser Tyr Glu Pro Leu Tyr Gly Ile Asp Arg
1670                1675                1680

Tyr Ile Asn Lys Val Leu Ile Ala Pro Asp Leu Tyr Thr Ser Leu
1685                1690                1695

Ile Asn Ile Asn Thr Asn Tyr Tyr Ser Asn Glu Tyr Tyr Pro Glu
1700                1705                1710

Ile Ile Val Leu Asn Pro Asn Thr Phe His Lys Lys Val Asn Ile
1715                1720                1725

Asn Leu Asp Ser Ser Phe Glu Tyr Lys Trp Ser Thr Glu Gly
1730                1735                1740

Ser Asp Phe Ile Leu Val Arg Tyr Leu Glu Glu Ser Asn Lys Lys
1745                1750                1755

Ile Leu Gln Lys Ile Arg Ile Lys Gly Ile Leu Ser Asn Thr Gln
1760                1765                1770

Ser Phe Asn Lys Met Ser Ile Asp Phe Lys Asp Ile Lys Lys Leu
1775                1780                1785

Ser Leu Gly Tyr Ile Met Ser Asn Phe Lys Ser Phe Asn Ser Glu
1790                1795                1800
```

```
Asn Glu Leu Asp Arg Asp His Leu Gly Phe Lys Ile Ile Asp Asn
    1805                1810                1815

Lys Thr Tyr Tyr Tyr Asp Glu Asp Ser Lys Leu Val Lys Gly Leu
    1820                1825                1830

Ile Asn Ile Asn Asn Ser Leu Phe Tyr Phe Asp Pro Ile Glu Phe
    1835                1840                1845

Asn Leu Val Thr Gly Trp Gln Thr Ile Asn Gly Lys Lys Tyr Tyr
    1850                1855                1860

Phe Asp Ile Asn Thr Gly Ala Ala Leu Thr Ser Tyr Lys Ile Ile
    1865                1870                1875

Asn Gly Lys His Phe Tyr Phe Asn Asn Asp Gly Val Met Gln Leu
    1880                1885                1890

Gly Val Phe Lys Gly Pro Asp Gly Phe Glu Tyr Phe Ala Pro Ala
    1895                1900                1905

Asn Thr Gln Asn Asn Asn Ile Glu Gly Gln Ala Ile Val Tyr Gln
    1910                1915                1920

Ser Lys Phe Leu Thr Leu Asn Gly Lys Lys Tyr Tyr Phe Asp Asn
    1925                1930                1935

Asn Ser Lys Ala Val Thr Gly Trp Arg Ile Ile Asn Asn Glu Lys
    1940                1945                1950

Tyr Tyr Phe Asn Pro Asn Asn Ala Ile Ala Ala Val Gly Leu Gln
    1955                1960                1965

Val Ile Asp Asn Asn Lys Tyr Tyr Phe Asn Pro Asp Thr Ala Ile
    1970                1975                1980

Ile Ser Lys Gly Trp Gln Thr Val Asn Gly Ser Arg Tyr Tyr Phe
    1985                1990                1995

Asp Thr Asp Thr Ala Ile Ala Phe Asn Gly Tyr Lys Thr Ile Asp
    2000                2005                2010

Gly Lys His Phe Tyr Phe Asp Ser Asp Cys Val Val Lys Ile Gly
    2015                2020                2025

Val Phe Ser Thr Ser Asn Gly Phe Glu Tyr Phe Ala Pro Ala Asn
    2030                2035                2040

Thr Tyr Asn Asn Asn Ile Glu Gly Gln Ala Ile Val Tyr Gln Ser
    2045                2050                2055

Lys Phe Leu Thr Leu Asn Gly Lys Lys Tyr Tyr Phe Asp Asn Asn
    2060                2065                2070

Ser Lys Ala Val Thr Gly Trp Gln Thr Ile Asp Ser Lys Lys Tyr
    2075                2080                2085

Tyr Phe Asn Thr Asn Thr Ala Glu Ala Ala Thr Gly Trp Gln Thr
    2090                2095                2100

Ile Asp Gly Lys Lys Tyr Tyr Phe Asn Thr Asn Thr Ala Glu Ala
    2105                2110                2115

Ala Thr Gly Trp Gln Thr Ile Asp Gly Lys Lys Tyr Tyr Phe Asn
    2120                2125                2130

Thr Asn Thr Ala Ile Ala Ser Thr Gly Tyr Thr Ile Ile Asn Gly
    2135                2140                2145

Lys His Phe Tyr Phe Asn Thr Asp Gly Ile Met Gln Ile Gly Val
    2150                2155                2160

Phe Lys Gly Pro Asn Gly Phe Glu Tyr Phe Ala Pro Ala Asn Thr
    2165                2170                2175

Asp Ala Asn Asn Ile Glu Gly Gln Ala Ile Leu Tyr Gln Asn Glu
    2180                2185                2190

Phe Leu Thr Leu Asn Gly Lys Lys Tyr Tyr Phe Gly Ser Asp Ser
```

-continued

```
                    2195                2200                 2205

Lys  Ala  Val  Thr  Gly  Trp  Arg  Ile  Ile  Asn  Asn  Lys  Lys  Tyr  Tyr
          2210                2215                2220

Phe  Asn  Pro  Asn  Asn  Ala  Ile  Ala  Ala  Ile  His  Leu  Cys  Thr  Ile
          2225                2230                2235

Asn  Asn  Asp  Lys  Tyr  Tyr  Phe  Ser  Tyr  Asp  Gly  Ile  Leu  Gln  Asn
          2240                2245                2250

Gly  Tyr  Ile  Thr  Ile  Glu  Arg  Asn  Asn  Phe  Tyr  Phe  Asp  Ala  Asn
          2255                2260                2265

Asn  Glu  Ser  Lys  Met  Val  Thr  Gly  Val  Phe  Lys  Gly  Pro  Asn  Gly
          2270                2275                2280

Phe  Glu  Tyr  Phe  Ala  Pro  Ala  Asn  Thr  His  Asn  Asn  Asn  Ile  Glu
          2285                2290                2295

Gly  Gln  Ala  Ile  Val  Tyr  Gln  Asn  Lys  Phe  Leu  Thr  Leu  Asn  Gly
          2300                2305                2310

Lys  Lys  Tyr  Tyr  Phe  Asp  Asn  Asp  Ser  Lys  Ala  Val  Thr  Gly  Trp
          2315                2320                2325

Gln  Thr  Ile  Asp  Gly  Lys  Lys  Tyr  Tyr  Phe  Asn  Leu  Asn  Thr  Ala
          2330                2335                2340

Glu  Ala  Ala  Thr  Gly  Trp  Gln  Thr  Ile  Asp  Gly  Lys  Lys  Tyr  Tyr
          2345                2350                2355

Phe  Asn  Leu  Asn  Thr  Ala  Glu  Ala  Ala  Thr  Gly  Trp  Gln  Thr  Ile
          2360                2365                2370

Asp  Gly  Lys  Lys  Tyr  Tyr  Phe  Asn  Thr  Asn  Thr  Phe  Ile  Ala  Ser
          2375                2380                2385

Thr  Gly  Tyr  Thr  Ser  Ile  Asn  Gly  Lys  His  Phe  Tyr  Phe  Asn  Thr
          2390                2395                2400

Asp  Gly  Ile  Met  Gln  Ile  Gly  Val  Phe  Lys  Gly  Pro  Asn  Gly  Phe
          2405                2410                2415

Glu  Tyr  Phe  Ala  Pro  Ala  Asn  Thr  Asp  Ala  Asn  Asn  Ile  Glu  Gly
          2420                2425                2430

Gln  Ala  Ile  Leu  Tyr  Gln  Asn  Lys  Phe  Leu  Thr  Leu  Asn  Gly  Lys
          2435                2440                2445

Lys  Tyr  Tyr  Phe  Gly  Ser  Asp  Ser  Lys  Ala  Val  Thr  Gly  Leu  Arg
          2450                2455                2460

Thr  Ile  Asp  Gly  Lys  Lys  Tyr  Tyr  Phe  Asn  Thr  Asn  Thr  Ala  Val
          2465                2470                2475

Ala  Val  Thr  Gly  Trp  Gln  Thr  Ile  Asn  Gly  Lys  Lys  Tyr  Tyr  Phe
          2480                2485                2490

Asn  Thr  Asn  Thr  Ser  Ile  Ala  Ser  Thr  Gly  Tyr  Thr  Ile  Ile  Ser
          2495                2500                2505

Gly  Lys  His  Phe  Tyr  Phe  Asn  Thr  Asp  Gly  Ile  Met  Gln  Ile  Gly
          2510                2515                2520

Val  Phe  Lys  Gly  Pro  Asp  Gly  Phe  Glu  Tyr  Phe  Ala  Pro  Ala  Asn
          2525                2530                2535

Thr  Asp  Ala  Asn  Asn  Ile  Glu  Gly  Gln  Ala  Ile  Arg  Tyr  Gln  Asn
          2540                2545                2550

Arg  Phe  Leu  Tyr  Leu  His  Asp  Asn  Ile  Tyr  Tyr  Phe  Gly  Asn  Asn
          2555                2560                2565

Ser  Lys  Ala  Ala  Thr  Gly  Trp  Val  Thr  Ile  Asp  Gly  Asn  Arg  Tyr
          2570                2575                2580

Tyr  Phe  Glu  Pro  Asn  Thr  Ala  Met  Gly  Ala  Asn  Gly  Tyr  Lys  Thr
          2585                2590                2595
```

```
Ile Asp Asn Lys Asn Phe Tyr Phe Arg Asn Gly Leu Pro Gln Ile
2600                2605                2610

Gly Val Phe Lys Gly Ser Asn Gly Phe Glu Tyr Phe Ala Pro Ala
        2615                2620                2625

Asn Thr Asp Ala Asn Asn Ile Glu Gly Gln Ala Ile Arg Tyr Gln
2630                2635                2640

Asn Arg Phe Leu His Leu Leu Gly Lys Ile Tyr Tyr Phe Gly Asn
2645                2650                2655

Asn Ser Lys Ala Val Thr Gly Trp Gln Thr Ile Asn Gly Lys Val
2660                2665                2670

Tyr Tyr Phe Met Pro Asp Thr Ala Met Ala Ala Ala Gly Gly Leu
2675                2680                2685

Phe Glu Ile Asp Gly Val Ile Tyr Phe Phe Gly Val Asp Gly Val
2690                2695                2700

Lys Ala Pro Gly Ile Tyr Gly
2705                2710

<210> SEQ ID NO 6
<211> LENGTH: 872
<212> TYPE: PRT
<213> ORGANISM: Clostridium difficile

<400> SEQUENCE: 6

Ser Leu Phe Tyr Phe Asp Pro Ile Glu Phe Asn Leu Val Thr Gly Trp
1               5                   10                  15

Gln Thr Ile Asn Gly Lys Lys Tyr Tyr Phe Asp Ile Asn Thr Gly Ala
            20                  25                  30

Ala Leu Thr Ser Tyr Lys Ile Ile Asn Gly Lys His Phe Tyr Phe Asn
        35                  40                  45

Asn Asp Gly Val Met Gln Leu Gly Val Phe Lys Gly Pro Asp Gly Phe
    50                  55                  60

Glu Tyr Phe Ala Pro Ala Asn Thr Gln Asn Asn Asn Ile Glu Gly Gln
65                  70                  75                  80

Ala Ile Val Tyr Gln Ser Lys Phe Leu Thr Leu Asn Gly Lys Lys Tyr
                85                  90                  95

Tyr Phe Asp Asn Asn Ser Lys Ala Val Thr Gly Trp Arg Ile Ile Asn
            100                 105                 110

Asn Glu Lys Tyr Tyr Phe Asn Pro Asn Asn Ala Ile Ala Ala Val Gly
        115                 120                 125

Leu Gln Val Ile Asp Asn Asn Lys Tyr Tyr Phe Asn Pro Asp Thr Ala
    130                 135                 140

Ile Ile Ser Lys Gly Trp Gln Thr Val Asn Gly Ser Arg Tyr Tyr Phe
145                 150                 155                 160

Asp Thr Asp Thr Ala Ile Ala Phe Asn Gly Tyr Lys Thr Ile Asp Gly
                165                 170                 175

Lys His Phe Tyr Phe Asp Ser Asp Cys Val Val Lys Ile Gly Val Phe
            180                 185                 190

Ser Thr Ser Asn Gly Phe Glu Tyr Phe Ala Pro Ala Asn Thr Tyr Asn
        195                 200                 205

Asn Asn Ile Glu Gly Gln Ala Ile Val Tyr Gln Ser Lys Phe Leu Thr
    210                 215                 220

Leu Asn Gly Lys Lys Tyr Tyr Phe Asp Asn Asn Ser Lys Ala Val Thr
225                 230                 235                 240

Gly Trp Gln Thr Ile Asp Ser Lys Lys Tyr Tyr Phe Asn Thr Asn Thr
```

-continued

```
                        245                 250                 255
Ala Glu Ala Ala Thr Gly Trp Gln Thr Ile Asp Gly Lys Lys Tyr Tyr
                    260                 265                 270

Phe Asn Thr Asn Thr Ala Glu Ala Ala Thr Gly Trp Gln Thr Ile Asp
                275                 280                 285

Gly Lys Lys Tyr Tyr Phe Asn Thr Asn Thr Ala Ile Ala Ser Thr Gly
            290                 295                 300

Tyr Thr Ile Ile Asn Gly Lys His Phe Tyr Phe Asn Thr Asp Gly Ile
305                 310                 315                 320

Met Gln Ile Gly Val Phe Lys Gly Pro Asn Gly Phe Glu Tyr Phe Ala
                325                 330                 335

Pro Ala Asn Thr Asp Ala Asn Asn Ile Glu Gly Gln Ala Ile Leu Tyr
                340                 345                 350

Gln Asn Glu Phe Leu Thr Leu Asn Gly Lys Lys Tyr Tyr Phe Gly Ser
                355                 360                 365

Asp Ser Lys Ala Val Thr Gly Trp Arg Ile Ile Asn Asn Lys Lys Tyr
            370                 375                 380

Tyr Phe Asn Pro Asn Asn Ala Ile Ala Ala Ile His Leu Cys Thr Ile
385                 390                 395                 400

Asn Asn Asp Lys Tyr Tyr Phe Ser Tyr Asp Gly Ile Leu Gln Asn Gly
                405                 410                 415

Tyr Ile Thr Ile Glu Arg Asn Asn Phe Tyr Phe Asp Ala Asn Asn Glu
                420                 425                 430

Ser Lys Met Val Thr Gly Val Phe Lys Gly Pro Asn Gly Phe Glu Tyr
                435                 440                 445

Phe Ala Pro Ala Asn Thr His Asn Asn Ile Glu Gly Gln Ala Ile
            450                 455                 460

Val Tyr Gln Asn Lys Phe Leu Thr Leu Asn Gly Lys Lys Tyr Tyr Phe
465                 470                 475                 480

Asp Asn Asp Ser Lys Ala Val Thr Gly Trp Gln Thr Ile Asp Gly Lys
                485                 490                 495

Lys Tyr Tyr Phe Asn Leu Asn Thr Ala Glu Ala Ala Thr Gly Trp Gln
            500                 505                 510

Thr Ile Asp Gly Lys Lys Tyr Tyr Phe Asn Leu Asn Thr Ala Glu Ala
            515                 520                 525

Ala Thr Gly Trp Gln Thr Ile Asp Gly Lys Lys Tyr Tyr Phe Asn Thr
            530                 535                 540

Asn Thr Phe Ile Ala Ser Thr Gly Tyr Thr Ser Ile Asn Gly Lys His
545                 550                 555                 560

Phe Tyr Phe Asn Thr Asp Gly Ile Met Gln Ile Gly Val Phe Lys Gly
                565                 570                 575

Pro Asn Gly Phe Glu Tyr Phe Ala Pro Ala Asn Thr Asp Ala Asn Asn
            580                 585                 590

Ile Glu Gly Gln Ala Ile Leu Tyr Gln Asn Lys Phe Leu Thr Leu Asn
            595                 600                 605

Gly Lys Lys Tyr Tyr Phe Gly Ser Asp Ser Lys Ala Val Thr Gly Leu
            610                 615                 620

Arg Thr Ile Asp Gly Lys Lys Tyr Tyr Phe Asn Thr Asn Thr Ala Val
625                 630                 635                 640

Ala Val Thr Gly Trp Gln Thr Ile Asn Gly Lys Lys Tyr Tyr Phe Asn
                645                 650                 655

Thr Asn Thr Ser Ile Ala Ser Thr Gly Tyr Thr Ile Ile Ser Gly Lys
            660                 665                 670
```

```
His Phe Tyr Phe Asn Thr Asp Gly Ile Met Gln Ile Gly Val Phe Lys
            675                 680                 685

Gly Pro Asp Gly Phe Glu Tyr Phe Ala Pro Ala Asn Thr Asp Ala Asn
690                 695                 700

Asn Ile Glu Gly Gln Ala Ile Arg Tyr Gln Asn Arg Phe Leu Tyr Leu
705                 710                 715                 720

His Asp Asn Ile Tyr Tyr Phe Gly Asn Ser Lys Ala Ala Thr Gly
                725                 730                 735

Trp Val Thr Ile Asp Gly Asn Arg Tyr Tyr Phe Glu Pro Asn Thr Ala
                740                 745                 750

Met Gly Ala Asn Gly Tyr Lys Thr Ile Asp Asn Lys Asn Phe Tyr Phe
            755                 760                 765

Arg Asn Gly Leu Pro Gln Ile Gly Val Phe Lys Gly Ser Asn Gly Phe
770                 775                 780

Glu Tyr Phe Ala Pro Ala Asn Thr Asp Ala Asn Asn Ile Glu Gly Gln
785                 790                 795                 800

Ala Ile Arg Tyr Gln Asn Arg Phe Leu His Leu Leu Gly Lys Ile Tyr
                805                 810                 815

Tyr Phe Gly Asn Asn Ser Lys Ala Val Thr Gly Trp Gln Thr Ile Asn
            820                 825                 830

Gly Lys Val Tyr Tyr Phe Met Pro Asp Thr Ala Met Ala Ala Ala Gly
            835                 840                 845

Gly Leu Phe Glu Ile Asp Gly Val Ile Tyr Phe Phe Gly Val Asp Gly
            850                 855                 860

Val Lys Ala Pro Gly Ile Tyr Gly
865                 870

<210> SEQ ID NO 7
<211> LENGTH: 2710
<212> TYPE: PRT
<213> ORGANISM: Clostridium difficile

<400> SEQUENCE: 7

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
                20                  25                  30

Tyr Asn Lys Leu Thr Thr Asn Asn Asn Glu Asn Lys Tyr Leu Gln Leu
            35                  40                  45

Lys Lys Leu Asn Glu Ser Ile Asp Val Phe Met Asn Lys Tyr Lys Thr
50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
```

```
                    165                 170                 175
Phe Ile Tyr Asp Arg Gln Lys Arg Phe Ile Asn Tyr Tyr Lys Ser Gln
                180                 185                 190

Ile Asn Lys Pro Thr Val Pro Thr Ile Asp Asp Ile Ile Lys Ser His
            195                 200                 205

Leu Val Ser Glu Tyr Asn Arg Asp Glu Thr Val Leu Glu Ser Tyr Arg
        210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590
```

```
Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
        610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
                660                 665                 670

Leu Ser Asn Glu Ile Ser Ser Phe Leu Asp Thr Ile Lys Leu Asp Ile
                675                 680                 685

Ser Pro Lys Asn Val Glu Val Asn Leu Leu Gly Cys Asn Met Phe Ser
        690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
                740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
        770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
                820                 825                 830

Ser Ile Gly Asp Tyr Ile Tyr Tyr Glu Lys Leu Glu Pro Val Lys Asn
        835                 840                 845

Ile Ile His Asn Ser Ile Asp Asp Leu Ile Asp Glu Phe Asn Leu Leu
        850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
                900                 905                 910

Val Glu Thr Glu Lys Glu Ile Phe Ser Lys Tyr Ser Glu His Ile Thr
        915                 920                 925

Lys Glu Ile Ser Thr Ile Lys Asn Ser Ile Ile Thr Asp Val Asn Gly
        930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
                980                 985                 990

Ala Gln Leu Phe Ser Thr Gly Leu Asn Thr Ile Tyr Asp Ser Ile Gln
        995                 1000                1005
```

-continued

```
Leu Val Asn Leu Ile Ser Asn Ala Val Asn Asp Thr Ile Asn Val
    1010                1015                1020

Leu Pro Thr Ile Thr Glu Gly Ile Pro Ile Val Ser Thr Ile Leu
    1025                1030                1035

Asp Gly Ile Asn Leu Gly Ala Ala Ile Lys Glu Leu Leu Asp Glu
    1040                1045                1050

His Asp Pro Leu Leu Lys Lys Glu Leu Glu Ala Lys Val Gly Val
    1055                1060                1065

Leu Ala Ile Asn Met Ser Leu Ser Ile Ala Ala Thr Val Ala Ser
    1070                1075                1080

Ile Val Gly Ile Gly Ala Glu Val Thr Ile Phe Leu Leu Pro Ile
    1085                1090                1095

Ala Gly Ile Ser Ala Gly Ile Pro Ser Leu Val Asn Asn Glu Leu
    1100                1105                1110

Ile Leu His Asp Lys Ala Thr Ser Val Val Asn Tyr Phe Asn His
    1115                1120                1125

Leu Ser Glu Ser Lys Lys Tyr Gly Pro Leu Lys Thr Glu Asp Asp
    1130                1135                1140

Lys Ile Leu Val Pro Ile Asp Asp Leu Val Ile Ser Glu Ile Asp
    1145                1150                1155

Phe Asn Asn Asn Ser Ile Lys Leu Gly Thr Cys Asn Ile Leu Ala
    1160                1165                1170

Met Glu Gly Gly Ser Gly His Thr Val Thr Gly Asn Ile Asp His
    1175                1180                1185

Phe Phe Ser Ser Pro Ser Ile Ser Ser His Ile Pro Ser Leu Ser
    1190                1195                1200

Ile Tyr Ser Ala Ile Gly Ile Glu Thr Glu Asn Leu Asp Phe Ser
    1205                1210                1215

Lys Lys Ile Met Met Leu Pro Asn Ala Pro Ser Arg Val Phe Trp
    1220                1225                1230

Trp Glu Thr Gly Ala Val Pro Gly Leu Arg Ser Leu Glu Asn Asp
    1235                1240                1245

Gly Thr Arg Leu Leu Asp Ser Ile Arg Asp Leu Tyr Pro Gly Lys
    1250                1255                1260

Phe Tyr Trp Arg Phe Tyr Ala Phe Phe Asp Tyr Ala Ile Thr Thr
    1265                1270                1275

Leu Lys Pro Val Tyr Glu Asp Thr Asn Ile Lys Ile Lys Leu Asp
    1280                1285                1290

Lys Asp Thr Arg Asn Phe Ile Met Pro Thr Ile Thr Thr Asn Glu
    1295                1300                1305

Ile Arg Asn Lys Leu Ser Tyr Ser Phe Asp Gly Ala Gly Gly Thr
    1310                1315                1320

Tyr Ser Leu Leu Leu Ser Ser Tyr Pro Ile Ser Thr Asn Ile Asn
    1325                1330                1335

Leu Ser Lys Asp Asp Leu Trp Ile Phe Asn Ile Asp Asn Glu Val
    1340                1345                1350

Arg Glu Ile Ser Ile Glu Asn Gly Thr Ile Lys Lys Gly Lys Leu
    1355                1360                1365

Ile Lys Asp Val Leu Ser Lys Ile Asp Ile Asn Lys Asn Lys Leu
    1370                1375                1380

Ile Ile Gly Asn Gln Thr Ile Asp Phe Ser Gly Asp Ile Asp Asn
    1385                1390                1395

Lys Asp Arg Tyr Ile Phe Leu Thr Cys Glu Leu Asp Asp Lys Ile
```

-continued

```
             1400              1405              1410

Ser Leu Ile Ile Glu Ile Asn Leu Val Ala Lys Ser Tyr Ser Leu
    1415              1420              1425

Leu Leu Ser Gly Asp Lys Asn Tyr Leu Ile Ser Asn Leu Ser Asn
    1430              1435              1440

Thr Ile Glu Lys Ile Asn Thr Leu Gly Leu Asp Ser Lys Asn Ile
    1445              1450              1455

Ala Tyr Asn Tyr Thr Asp Glu Ser Asn Asn Lys Tyr Phe Gly Ala
    1460              1465              1470

Ile Ser Lys Thr Ser Gln Lys Ser Ile Ile His Tyr Lys Lys Asp
    1475              1480              1485

Ser Lys Asn Ile Leu Glu Phe Tyr Asn Asp Ser Thr Leu Glu Phe
    1490              1495              1500

Asn Ser Lys Asp Phe Ile Ala Glu Asp Ile Asn Val Phe Met Lys
    1505              1510              1515

Asp Asp Ile Asn Thr Ile Thr Gly Lys Tyr Tyr Val Asp Asn Asn
    1520              1525              1530

Thr Asp Lys Ser Ile Asp Phe Ser Ile Ser Leu Val Ser Lys Asn
    1535              1540              1545

Gln Val Lys Val Asn Gly Leu Tyr Leu Asn Glu Ser Val Tyr Ser
    1550              1555              1560

Ser Tyr Leu Asp Phe Val Lys Asn Ser Asp Gly His His Asn Thr
    1565              1570              1575

Ser Asn Phe Met Asn Leu Phe Leu Asp Asn Ile Ser Phe Trp Lys
    1580              1585              1590

Leu Phe Gly Phe Glu Asn Ile Asn Phe Val Ile Asp Lys Tyr Phe
    1595              1600              1605

Thr Leu Val Gly Lys Thr Asn Leu Gly Tyr Val Glu Phe Ile Cys
    1610              1615              1620

Asp Asn Asn Lys Asn Ile Asp Ile Tyr Phe Gly Glu Trp Lys Thr
    1625              1630              1635

Ser Ser Ser Lys Ser Thr Ile Phe Ser Gly Asn Gly Arg Asn Val
    1640              1645              1650

Val Val Glu Pro Ile Tyr Asn Pro Asp Thr Gly Glu Asp Ile Ser
    1655              1660              1665

Thr Ser Leu Asp Phe Ser Tyr Glu Pro Leu Tyr Gly Ile Asp Arg
    1670              1675              1680

Tyr Ile Asn Lys Val Leu Ile Ala Pro Asp Leu Tyr Thr Ser Leu
    1685              1690              1695

Ile Asn Ile Asn Thr Asn Tyr Tyr Ser Asn Glu Tyr Tyr Pro Glu
    1700              1705              1710

Ile Ile Val Leu Asn Pro Asn Thr Phe His Lys Lys Val Asn Ile
    1715              1720              1725

Asn Leu Asp Ser Ser Ser Phe Glu Tyr Lys Trp Ser Thr Glu Gly
    1730              1735              1740

Ser Asp Phe Ile Leu Val Arg Tyr Leu Glu Glu Ser Asn Lys Lys
    1745              1750              1755

Ile Leu Gln Lys Ile Arg Ile Lys Gly Ile Leu Ser Asn Thr Gln
    1760              1765              1770

Ser Phe Asn Lys Met Ser Ile Asp Phe Lys Asp Ile Lys Lys Leu
    1775              1780              1785

Ser Leu Gly Tyr Ile Met Ser Asn Phe Lys Ser Phe Asn Ser Glu
    1790              1795              1800
```

-continued

```
Asn Glu Leu Asp Arg Asp His Leu Gly Phe Lys Ile Ile Asp Asn
1805                1810                1815

Lys Thr Tyr Tyr Tyr Asp Glu Asp Ser Lys Leu Val Lys Gly Leu
1820                1825                1830

Ile Asn Ile Asn Asn Ser Leu Phe Tyr Phe Asp Pro Ile Glu Phe
1835                1840                1845

Asn Leu Val Thr Gly Trp Gln Thr Ile Asn Gly Lys Lys Tyr Tyr
1850                1855                1860

Phe Asp Ile Asn Thr Gly Ala Ala Leu Thr Ser Tyr Lys Ile Ile
1865                1870                1875

Asn Gly Lys His Phe Tyr Phe Asn Asn Asp Gly Val Met Gln Leu
1880                1885                1890

Gly Val Phe Lys Gly Pro Asp Gly Phe Glu Tyr Phe Ala Pro Ala
1895                1900                1905

Asn Thr Gln Asn Asn Asn Ile Glu Gly Gln Ala Ile Val Tyr Gln
1910                1915                1920

Ser Lys Phe Leu Thr Leu Asn Gly Lys Lys Tyr Tyr Phe Asp Asn
1925                1930                1935

Asn Ser Lys Ala Val Thr Gly Trp Arg Ile Ile Asn Asn Glu Lys
1940                1945                1950

Tyr Tyr Phe Asn Pro Asn Asn Ala Ile Ala Ala Val Gly Leu Gln
1955                1960                1965

Val Ile Asp Asn Asn Lys Tyr Tyr Phe Asn Pro Asp Thr Ala Ile
1970                1975                1980

Ile Ser Lys Gly Trp Gln Thr Val Asn Gly Ser Arg Tyr Tyr Phe
1985                1990                1995

Asp Thr Asp Thr Ala Ile Ala Phe Asn Gly Tyr Lys Thr Ile Asp
2000                2005                2010

Gly Lys His Phe Tyr Phe Asp Ser Asp Cys Val Val Lys Ile Gly
2015                2020                2025

Val Phe Ser Thr Ser Asn Gly Phe Glu Tyr Phe Ala Pro Ala Asn
2030                2035                2040

Thr Tyr Asn Asn Asn Ile Glu Gly Gln Ala Ile Val Tyr Gln Ser
2045                2050                2055

Lys Phe Leu Thr Leu Asn Gly Lys Lys Tyr Tyr Phe Asp Asn Asn
2060                2065                2070

Ser Lys Ala Val Thr Gly Leu Gln Thr Ile Asp Ser Lys Lys Tyr
2075                2080                2085

Tyr Phe Asn Thr Asn Thr Ala Glu Ala Ala Thr Gly Trp Gln Thr
2090                2095                2100

Ile Asp Gly Lys Lys Tyr Tyr Phe Asn Thr Asn Thr Ala Glu Ala
2105                2110                2115

Ala Thr Gly Trp Gln Thr Ile Asp Gly Lys Lys Tyr Tyr Phe Asn
2120                2125                2130

Thr Asn Thr Ala Ile Ala Ser Thr Gly Tyr Thr Ile Ile Asn Gly
2135                2140                2145

Lys His Phe Tyr Phe Asn Thr Asp Gly Ile Met Gln Ile Gly Val
2150                2155                2160

Phe Lys Gly Pro Asn Gly Phe Glu Tyr Phe Ala Pro Ala Asn Thr
2165                2170                2175

Asp Ala Asn Asn Ile Glu Gly Gln Ala Ile Leu Tyr Gln Asn Glu
2180                2185                2190
```

-continued

Phe Leu Thr Leu Asn Gly Lys Lys Tyr Tyr Phe Gly Ser Asp Ser
2195                2200                2205

Lys Ala Val Thr Gly Trp Arg Ile Ile Asn Asn Lys Lys Tyr Tyr
2210                2215                2220

Phe Asn Pro Asn Asn Ala Ile Ala Ala Ile His Leu Cys Thr Ile
2225                2230                2235

Asn Asn Asp Lys Tyr Tyr Phe Ser Tyr Asp Gly Ile Leu Gln Asn
2240                2245                2250

Gly Tyr Ile Thr Ile Glu Arg Asn Asn Phe Tyr Phe Asp Ala Asn
2255                2260                2265

Asn Glu Ser Lys Met Val Thr Gly Val Phe Lys Gly Pro Asn Gly
2270                2275                2280

Phe Glu Tyr Phe Ala Pro Ala Asn Thr His Asn Asn Asn Ile Glu
2285                2290                2295

Gly Gln Ala Ile Val Tyr Gln Asn Lys Phe Leu Thr Leu Asn Gly
2300                2305                2310

Lys Lys Tyr Tyr Phe Asp Asn Asp Ser Lys Ala Val Thr Gly Trp
2315                2320                2325

Gln Thr Ile Asp Gly Lys Lys Tyr Tyr Phe Asn Leu Asn Thr Ala
2330                2335                2340

Glu Ala Ala Thr Gly Trp Gln Thr Ile Asp Gly Lys Lys Tyr Tyr
2345                2350                2355

Phe Asn Leu Asn Thr Ala Glu Ala Ala Thr Gly Trp Gln Thr Ile
2360                2365                2370

Asp Gly Lys Lys Tyr Tyr Phe Asn Thr Asn Thr Phe Ile Ala Ser
2375                2380                2385

Thr Gly Tyr Thr Ser Ile Asn Gly Lys His Phe Tyr Phe Asn Thr
2390                2395                2400

Asp Gly Ile Met Gln Ile Gly Val Phe Lys Gly Pro Asn Gly Phe
2405                2410                2415

Glu Tyr Phe Ala Pro Ala Asn Thr Asp Ala Asn Asn Ile Glu Gly
2420                2425                2430

Gln Ala Ile Leu Tyr Gln Asn Lys Phe Leu Thr Leu Asn Gly Lys
2435                2440                2445

Lys Tyr Tyr Phe Gly Ser Asp Ser Lys Ala Val Thr Gly Leu Arg
2450                2455                2460

Thr Ile Asp Gly Lys Lys Tyr Tyr Phe Asn Thr Asn Thr Ala Val
2465                2470                2475

Ala Val Thr Gly Trp Gln Thr Ile Asn Gly Lys Lys Tyr Tyr Phe
2480                2485                2490

Asn Thr Asn Thr Ser Ile Ala Ser Thr Gly Tyr Thr Ile Ile Ser
2495                2500                2505

Gly Lys His Phe Tyr Phe Asn Thr Asp Gly Ile Met Gln Ile Gly
2510                2515                2520

Val Phe Lys Gly Pro Asp Gly Phe Glu Tyr Phe Ala Pro Ala Asn
2525                2530                2535

Thr Asp Ala Asn Asn Ile Glu Gly Gln Ala Ile Arg Tyr Gln Asn
2540                2545                2550

Arg Phe Leu Tyr Leu His Asp Asn Ile Tyr Tyr Phe Gly Asn Asn
2555                2560                2565

Ser Lys Ala Ala Thr Gly Trp Val Thr Ile Asp Gly Asn Arg Tyr
2570                2575                2580

Tyr Phe Glu Pro Asn Thr Ala Met Gly Ala Asn Gly Tyr Lys Thr

```
                    2585                2590                2595
Ile Asp Asn Lys Asn Phe Tyr Phe Arg Asn Gly Leu Pro Gln Ile
    2600                2605                2610
Gly Val Phe Lys Gly Ser Asn Gly Phe Glu Tyr Phe Ala Pro Ala
    2615                2620                2625
Asn Thr Asp Ala Asn Asn Ile Glu Gly Gln Ala Ile Arg Tyr Gln
    2630                2635                2640
Asn Arg Phe Leu His Leu Leu Gly Lys Ile Tyr Tyr Phe Gly Asn
    2645                2650                2655
Asn Ser Lys Ala Val Thr Gly Trp Gln Thr Ile Asn Gly Lys Val
    2660                2665                2670
Tyr Tyr Phe Met Pro Asp Thr Ala Met Ala Ala Ala Gly Gly Leu
    2675                2680                2685
Phe Glu Ile Asp Gly Val Ile Tyr Phe Phe Gly Val Asp Gly Val
    2690                2695                2700
Lys Ala Pro Gly Ile Tyr Gly
    2705                2710

<210> SEQ ID NO 8
<211> LENGTH: 872
<212> TYPE: PRT
<213> ORGANISM: Clostridium difficile

<400> SEQUENCE: 8

Ser Leu Phe Tyr Phe Asp Pro Ile Glu Phe Asn Leu Val Thr Gly Trp
1               5                   10                  15
Gln Thr Ile Asn Gly Lys Lys Tyr Tyr Phe Asp Ile Asn Thr Gly Ala
                20                  25                  30
Ala Leu Thr Ser Tyr Lys Ile Ile Asn Gly Lys His Phe Tyr Phe Asn
                35                  40                  45
Asn Asp Gly Val Met Gln Leu Gly Val Phe Lys Gly Pro Asp Gly Phe
            50                  55                  60
Glu Tyr Phe Ala Pro Ala Asn Thr Gln Asn Asn Asn Ile Glu Gly Gln
65                  70                  75                  80
Ala Ile Val Tyr Gln Ser Lys Phe Leu Thr Leu Asn Gly Lys Lys Tyr
                85                  90                  95
Tyr Phe Asp Asn Asn Ser Lys Ala Val Thr Gly Trp Arg Ile Ile Asn
                100                 105                 110
Asn Glu Lys Tyr Tyr Phe Asn Pro Asn Asn Ala Ile Ala Ala Val Gly
            115                 120                 125
Leu Gln Val Ile Asp Asn Asn Lys Tyr Tyr Phe Asn Pro Asp Thr Ala
            130                 135                 140
Ile Ile Ser Lys Gly Trp Gln Thr Val Asn Gly Ser Arg Tyr Tyr Phe
145                 150                 155                 160
Asp Thr Asp Thr Ala Ile Ala Phe Asn Gly Tyr Lys Thr Ile Asp Gly
                165                 170                 175
Lys His Phe Tyr Phe Asp Ser Asp Cys Val Val Lys Ile Gly Val Phe
                180                 185                 190
Ser Thr Ser Asn Gly Phe Glu Tyr Phe Ala Pro Ala Asn Thr Tyr Asn
            195                 200                 205
Asn Asn Ile Glu Gly Gln Ala Ile Val Tyr Gln Ser Lys Phe Leu Thr
            210                 215                 220
Leu Asn Gly Lys Lys Tyr Tyr Phe Asp Asn Asn Ser Lys Ala Val Thr
225                 230                 235                 240
```

```
Gly Leu Gln Thr Ile Asp Ser Lys Lys Tyr Phe Asn Thr Asn Thr
                    245                 250                 255

Ala Glu Ala Ala Thr Gly Trp Gln Thr Ile Asp Gly Lys Lys Tyr Tyr
                260                 265                 270

Phe Asn Thr Asn Thr Ala Glu Ala Ala Thr Gly Trp Gln Thr Ile Asp
                275                 280                 285

Gly Lys Lys Tyr Tyr Phe Asn Thr Asn Thr Ala Ile Ala Ser Thr Gly
                290                 295                 300

Tyr Thr Ile Ile Asn Gly Lys His Phe Tyr Phe Asn Thr Asp Gly Ile
305                 310                 315                 320

Met Gln Ile Gly Val Phe Lys Gly Pro Asn Gly Phe Glu Tyr Phe Ala
                    325                 330                 335

Pro Ala Asn Thr Asp Ala Asn Asn Ile Glu Gly Gln Ala Ile Leu Tyr
                340                 345                 350

Gln Asn Glu Phe Leu Thr Leu Asn Gly Lys Lys Tyr Tyr Phe Gly Ser
                355                 360                 365

Asp Ser Lys Ala Val Thr Gly Trp Arg Ile Ile Asn Asn Lys Lys Tyr
                370                 375                 380

Tyr Phe Asn Pro Asn Asn Ala Ile Ala Ala Ile His Leu Cys Thr Ile
385                 390                 395                 400

Asn Asn Asp Lys Tyr Tyr Phe Ser Tyr Asp Gly Ile Leu Gln Asn Gly
                405                 410                 415

Tyr Ile Thr Ile Glu Arg Asn Asn Phe Tyr Phe Asp Ala Asn Asn Glu
                420                 425                 430

Ser Lys Met Val Thr Gly Val Phe Lys Gly Pro Asn Gly Phe Glu Tyr
                435                 440                 445

Phe Ala Pro Ala Asn Thr His Asn Asn Asn Ile Glu Gly Gln Ala Ile
                450                 455                 460

Val Tyr Gln Asn Lys Phe Leu Thr Leu Asn Gly Lys Lys Tyr Tyr Phe
465                 470                 475                 480

Asp Asn Asp Ser Lys Ala Val Thr Gly Trp Gln Thr Ile Asp Gly Lys
                485                 490                 495

Lys Tyr Tyr Phe Asn Leu Asn Thr Ala Glu Ala Ala Thr Gly Trp Gln
                500                 505                 510

Thr Ile Asp Gly Lys Lys Tyr Tyr Phe Asn Leu Asn Thr Ala Glu Ala
                515                 520                 525

Ala Thr Gly Trp Gln Thr Ile Asp Gly Lys Lys Tyr Tyr Phe Asn Thr
                530                 535                 540

Asn Thr Phe Ile Ala Ser Thr Gly Tyr Thr Ser Ile Asn Gly Lys His
545                 550                 555                 560

Phe Tyr Phe Asn Thr Asp Gly Ile Met Gln Ile Gly Val Phe Lys Gly
                565                 570                 575

Pro Asn Gly Phe Glu Tyr Phe Ala Pro Ala Asn Thr Asp Ala Asn Asn
                580                 585                 590

Ile Glu Gly Gln Ala Ile Leu Tyr Gln Asn Lys Phe Leu Thr Leu Asn
                595                 600                 605

Gly Lys Lys Tyr Tyr Phe Gly Ser Asp Ser Lys Ala Val Thr Gly Leu
                610                 615                 620

Arg Thr Ile Asp Gly Lys Lys Tyr Tyr Phe Asn Thr Asn Thr Ala Val
625                 630                 635                 640

Ala Val Thr Gly Trp Gln Thr Ile Asn Gly Lys Lys Tyr Tyr Phe Asn
                    645                 650                 655

Thr Asn Thr Ser Ile Ala Ser Thr Gly Tyr Thr Ile Ile Ser Gly Lys
```

```
           660             665             670
His Phe Tyr Phe Asn Thr Asp Gly Ile Met Gln Ile Gly Val Phe Lys
            675                 680                 685
Gly Pro Asp Gly Phe Glu Tyr Phe Ala Pro Ala Asn Thr Asp Ala Asn
690                 695                 700
Asn Ile Glu Gly Gln Ala Ile Arg Tyr Gln Asn Arg Phe Leu Tyr Leu
705                 710                 715                 720
His Asp Asn Ile Tyr Tyr Phe Gly Asn Asn Ser Lys Ala Ala Thr Gly
                725                 730                 735
Trp Val Thr Ile Asp Gly Asn Arg Tyr Tyr Phe Glu Pro Asn Thr Ala
            740                 745                 750
Met Gly Ala Asn Gly Tyr Lys Thr Ile Asp Asn Lys Asn Phe Tyr Phe
            755                 760                 765
Arg Asn Gly Leu Pro Gln Ile Gly Val Phe Lys Gly Ser Asn Gly Phe
770                 775                 780
Glu Tyr Phe Ala Pro Ala Asn Thr Asp Ala Asn Asn Ile Glu Gly Gln
785                 790                 795                 800
Ala Ile Arg Tyr Gln Asn Arg Phe Leu His Leu Leu Gly Lys Ile Tyr
            805                 810                 815
Tyr Phe Gly Asn Asn Ser Lys Ala Val Thr Gly Trp Gln Thr Ile Asn
                820                 825                 830
Gly Lys Val Tyr Tyr Phe Met Pro Asp Thr Ala Met Ala Ala Ala Gly
            835                 840                 845
Gly Leu Phe Glu Ile Asp Gly Val Ile Tyr Phe Phe Gly Val Asp Gly
            850                 855                 860
Val Lys Ala Pro Gly Ile Tyr Gly
865                 870

<210> SEQ ID NO 9
<211> LENGTH: 2619
<212> TYPE: DNA
<213> ORGANISM: Artificial Sequence
<220> FEATURE:
<223> OTHER INFORMATION: synthetic nucleotide sequence

<400> SEQUENCE: 9
agcctgttct acttcgaccc catcgagttc aacctggtga ccggctggca gaccatcaac      60
ggcaagaagt actacttcga catcaacacc ggcgccgccc tgaccagcta caagatcatc     120
aacggcaagc acttctactt caacaacgac ggcgtgatgc agctgggcgt gttcaagggc     180
cccgacggct cgagtacttt cgcccccgcc aacacccaga caacaacat cgagggccag      240
gccatcgtgt accagagcaa gttcctgacc ctgaacggca gaagtacta cttcgacaac      300
aacagcaagg ccgtgaccgg ctggagaatc atcaacaacg agaagtacta cttcaacccc      360
aacaacgcca tcgccgccgt gggcctgcag gtgatcgaca caacaagta ctacttcaac       420
cccgacaccg ccatcatcag caagggctgg cagaccgtga acggcagcag atactacttc      480
gacaccgaca ccgccatcgc cttcaacggc tacaagacca tcgacggcaa gcacttctac      540
ttcgacagcg actgtgtggt gaagatcggc gtgttcagca ccagcaacgg cttcgagtac      600
ttcgcccccg ccaacaccta acaacaacaa catcgagggc caggccatcgt gtaccagagc      660
aagttcctga ccctgaacgg caagaagtac tacttcgaca acaacagcaa ggccgtgacc      720
ggcctgcaga ccatcgacag caagaagtac tacttcaaca ccaacaccgc cgaggccgcc      780
accggctggc agaccatcga cggcaagaag tactacttca caccaacac cgccgaggcc      840
```

```
gccaccggct ggcagaccat cgacggcaag aagtactact tcaacaccaa caccgccatc    900
gccagcaccg gctacaccat catcaacggc aagcacttct acttcaacac cgacggcatc    960
atgcagatcg gcgtgttcaa gggccccaac ggcttcgagt acttcgcccc cgccaacacc   1020
gacgccaaca acatcgaggg ccaggccatc ctgtaccaga cgagttcct gaccctgaac    1080 ggcaagaagt actacttcgg cagcgacagc aaggccgtga ccggctggag aatcatcaac   1140
aacaagaagt actacttcaa ccccaacaac gccatcgccg ccatccacct gtgtaccatc   1200
aacaacgaca agtactactt cagctacgac ggcatcctgc agaacggcta catcaccatc   1260
gagagaaaca acttctactt cgacgccaac aacgagagca agatggtgac cggcgtgttc   1320
aagggcccca acggcttcga gtacttcgcc cccgccaaca cccacaacaa caacatcgag   1380
ggccaggcca tcgtgtacca gaacaagttc ctgaccctga acggcaagaa gtactacttc   1440
gacaacgaca gcaaggccgt gaccggctgg cagaccatcg acggcaagaa gtactacttc   1500
aacctgaaca ccgccgaggc cgccaccggc tggcagacca tcgacggcaa gaagtactac   1560
ttcaacctga caccgccga ggccgccacc ggctggcaga ccatcgacgg caagaagtac   1620
tacttcaaca ccaacacctt catcgccagc accggctaca ccagcatcaa cggcaagcac   1680
ttctacttca acaccgacgg catcatgcag atcggcgtgt tcaagggccc caacggcttc   1740
gagtacttcg cccccgccaa caccgacgcc aacaacatcg agggccaggc catcctgtac   1800
cagaacaagt tcctgaccct gaacggcaag aagtactact cggcagcga cagcaaggcc    1860 gtgaccggcc tgagaaccat cgacggcaag aagtactact tcaacaccaa caccgccgtg   1920
gccgtgaccg gctggcagac catcaacggc aagaagtact acttcaacac caacaccagc   1980
atcgccagca ccggctacac catcatcagc ggcaagcact tctacttcaa caccgacggc   2040
atcatgcaga tcggcgtgtt caagggcccc gacggcttcg agtacttcgc ccccgccaac   2100
accgacgcca acaacatcga gggccaggcc atcagatacc agaacagatt cctgtacctg   2160
cacgacaaca tctactactt cggcaacaac agcaaggccg ccaccggctg ggtgaccatc   2220
gacggcaaca gatactactt cgagcccaac accgccatgg gcgccaacgg ctacaagacc   2280
atcgacaaca gaacttcta cttcagaaac ggcctgcccc agatcggcgt gttcaagggc    2340
agcaacggct tcgagtactt cgcccccgcc aacaccgacg ccaacaacat cgagggccag   2400
gccatcagat accagaacag attcctgcac ctgctgggca agatctacta cttcggcaac   2460
aacagcaagg ccgtgaccgg ctggcagacc atcaacggca aggtgtacta cttcatgccc   2520
gacaccgcca tggccgccgc cggcggcctg ttcgagatcg acggcgtgat ctacttcttc   2580
ggcgtggacg gcgtgaaggc ccccggcatc tacggctaa                          2619
```

<210> SEQ ID NO 10
<211> LENGTH: 44
<212> TYPE: PRT
<213> ORGANISM: Clostridium difficile

<400> SEQUENCE: 10

```
Ala Thr Gly Trp Gln Thr Ile Asp Gly Lys Lys Tyr Tyr Phe Asn Thr
1               5                   10                  15

Asn Thr Ala Glu Ala Ala Thr Gly Trp Gln Thr Ile Asp Gly Lys Lys
            20                  25                  30

Tyr Tyr Phe Asn Thr Asn Thr Ala Ile Ala Ser Thr
        35                  40
```

<210> SEQ ID NO 11

<211> LENGTH: 2681
<212> TYPE: DNA
<213> ORGANISM: Artificial Sequence
<220> FEATURE:
<223> OTHER INFORMATION: synthetic nucleotide sequence

<400> SEQUENCE: 11

| | | | | | |
|---|---|---|---|---|---|
| ggcgccgtgt | tcgtgagccc | cagccgcaga | cgcaagaagc | gcgccggagg | atccagcctg | 60 |
| ttctacttcg | accccatcga | gttcaacctg | gtgaccggct | ggcagaccat | caacggcaag | 120 |
| aagtactact | tcgacatcaa | caccggcgcc | gccctgacca | gctacaagat | catcaacggc | 180 |
| aagcacttct | acttcaacaa | cgacggcgtg | atgcagctgg | gcgtgttcaa | gggccccgac | 240 |
| ggcttcgagt | acttcgcccc | cgccaacacc | cagaacaaca | catcgaggg | ccaggccatc | 300 |
| gtgtaccaga | gcaagttcct | gaccctgaac | ggcaagaagt | actacttcga | caacaacagc | 360 |
| aaggccgtga | ccggctggag | aatcatcaac | aacgagaagt | actacttcaa | ccccaacaac | 420 |
| gccatcgccg | ccgtgggcct | gcaggtgatc | gacaacaaca | agtactactt | caaccccgac | 480 |
| accgccatca | tcagcaaggg | ctggcagacc | gtgaacggca | gcagatacta | cttcgacacc | 540 |
| gacaccgcca | tcgccttcaa | cggctacaag | accatcgacg | gcaagcactt | ctacttcgac | 600 |
| agcgactgtg | tggtgaagat | cggcgtgttc | agcaccagca | acggcttcga | gtacttcgcc | 660 |
| cccgccaaca | cctacaacaa | caacatcgag | ggccaggcca | tcgtgtacca | gagcaagttc | 720 |
| ctgaccctga | acggcaagaa | gtactacttc | gacaacaaca | gcaaggccgt | gaccggcctg | 780 |
| cagaccatcg | acagcaagaa | gtactacttc | aacaccaaca | ccgccgaggc | cgccaccggc | 840 |
| tggcagacca | tcgacggcaa | gaagtactac | ttcaaccacca | acaccgccga | ggccgccacc | 900 |
| ggctggcaga | ccatcgacgg | caagaagtac | tacttcaaca | ccaacaccgc | catcgccagc | 960 |
| accggctaca | ccatcatcaa | cggcaagcac | ttctacttca | acaccgacgg | catcatgcag | 1020 |
| atcggcgtgt | tcaagggccc | caacggcttc | gagtacttcg | ccccgccaa | caccgacgcc | 1080 |
| aacaacatcg | agggccaggc | catcctgtac | cagaacgagt | tcctgaccct | gaacggcaag | 1140 |
| aagtactact | tcggcagcga | cagcaaggcc | gtgaccggct | ggagaatcat | caacaacaag | 1200 |
| aagtactact | tcaaccccaa | caacgccatc | gccgccatcc | acctgtgtac | catcaacaac | 1260 |
| gacaagtact | acttcagcta | cgacggcatc | ctgcagaacg | gctacatcac | catcgagaga | 1320 |
| aacaacttct | acttcgacgc | caacaacgag | agcaagatgg | tgaccggcgt | gttcaagggc | 1380 |
| cccaacggct | tcgagtactt | cgcccccgcc | aacacccaca | caacaacat | cgagggccag | 1440 |
| gccatcgtgt | accagaacaa | gttcctgacc | ctgaacggca | agaagtacta | cttcgacaac | 1500 |
| gacagcaagg | ccgtgaccgg | ctggcagacc | atcgacggca | agaagtacta | cttcaacctg | 1560 |
| aacaccgccg | aggccgccac | cggctggcag | accatcgacg | gcaagaagta | ctacttcaac | 1620 |
| ctgaacaccg | ccgaggccgc | caccggctgg | cagaccatcg | acggcaagaa | gtactacttc | 1680 |
| aacaccaaca | ccttcatcgc | cagcaccggc | tacaccagca | tcaacggcaa | gcacttctac | 1740 |
| ttcaacaccg | acggcatcat | gcagatcggc | gtgttcaagg | gccccaacgg | cttcgagtac | 1800 |
| ttcgcccccg | ccaacaccga | cgccaacaac | atcgagggcc | aggccatcct | gtaccagaac | 1860 |
| aagttcctga | ccctgaacgg | caagaagtac | tacttcggca | cgacagcaa | ggccgtgacc | 1920 |
| ggcctgagaa | ccatcgacgg | caagaagtac | tacttcaaca | ccaacaccgc | cgtggccgtg | 1980 |
| accggctggc | agaccatcaa | cggcaagaag | tactacttca | acaccaacac | cagcatcgcc | 2040 |
| agcaccggct | acaccatcat | cagcggcaag | cacttctact | tcaacaccga | cggcatcatg | 2100 |
| cagatcggcg | tgttcaaggg | ccccgacggc | ttcgagtact | tcgcccccgc | caacaccgac | 2160 |

```
gccaacaaca tcgagggcca ggccatcaga taccagaaca gattcctgta cctgcacgac    2220
aacatctact acttcggcaa caacagcaag gccgccaccg gctgggtgac catcgacggc    2280
aacagatact acttcgagcc caacaccgcc atgggcgcca acggctacaa gaccatcgac    2340
aacaagaact tctacttcag aaacggcctg ccccagatcg gcgtgttcaa gggcagcaac    2400
ggcttcgagt acttcgcccc cgccaacacc gacgccaaca acatcgaggg ccaggccatc    2460
agataccaga acagattcct gcacctgctg ggcaagatct actacttcgg caacaacagc    2520
aaggccgtga ccggctggca gaccatcaac ggcaaggtgt actacttcat gcccgacacc    2580
gccatggccg ccgccggcgg cctgttcgag atcgacggcg tgatctactt cttcggcgtg    2640
gacggcgtga aggcccccgg catctacggc taagaattct a                       2681

<210> SEQ ID NO 12
<211> LENGTH: 2648
<212> TYPE: DNA
<213> ORGANISM: Artificial Sequence
<220> FEATURE:
<223> OTHER INFORMATION: synthetic nucleotide sequence

<400> SEQUENCE: 12
gctagccgcc accatgggat ccgcctgttc tacttcgacc ccatcgagtt caacctggtg      60
accggctggc agaccatcaa cggcaagaag tactacttcg acatcaacac cggcgccgcc     120
ctgaccagct acagatcat caacggcaag cacttctact tcaacaacga cggcgtgatg      180
cagctgggcg tgttcaaggg ccccgacggc ttcgagtact cgccccgc caacacccag       240 aacaacaaca tcgagggcca ggccatcgtg taccagagca agttcctgac cctgaacggc     300
aagaagtact acttcgacaa caacagcaag gccgtgaccg gctggagaat catcaacaac     360
gagaagtact acttcaaccc caacaacgcc atcgccgccg tgggcctgca ggtgatcgac     420
aacaacaagt actacttcaa ccccgacacc gccatcatca gcaagggctg gcagaccgtg     480
aacggcagca gatactactt cgacaccgac accgccatcg ccttcaacgg ctacaagacc     540
atcgacggca gcacttcta cttcgacagc gactgtgtgg tgaagatcgg cgtgttcagc     600
accagcaacg gcttcgagta cttcgccccc gccaacacct acaacaacaa catcgagggc     660
caggccatcg tgtaccagag caagttcctg accctgaacg gcaagaagta ctacttcgac     720
aacaacagca aggccgtgac cggcctgcag accatcgaca gcaagaagta ctacttcaac     780
accaacaccg ccgaggccgc caccggctgg cagaccatcg acggcaagaa gtactacttc     840
aacaccaaca ccgccgaggc cgccaccggc tggcagacca tcgacggcaa gaagtactac     900
ttcaacacca acaccgccat cgccagcacc ggctacacca tcatcaacgg caagcacttc     960
tacttcaaca ccgacggcat catgcagatc ggcgtgttca agggcccaa cggcttcgag    1020 tacttcgccc ccgccaacac cgacgccaac aacatcgagg ccaggccat cctgtaccag     1080 aacgagttcc tgaccctgaa cggcaagaag tactacttcg cagcgacag caaggccgtg     1140 accggctgga gaatcatcaa caacaagaag tactacttca ccccaacaa cgccatcgcc     1200 gccatccacc tgtgtaccat caacaacgac aagtactact tcagctacga cggcatcctg    1260
cagaacggct acatcaccat cgagagaaac aacttctact tcgacgccaa caacgagagc    1320
aagatggtga ccggcgtgtt caagggcccc aacggcttcg agtacttcgc cccgccaac     1380 acccacaaca caacatcga gggccaggcc atcgtgtacc agaacaagtt cctgaccctg     1440
aacggcaaga agtactactt cgacaacgac agcaaggccg tgaccggctg gcagaccatc    1500
```

| | |
|---|---|
| gacggcaaga agtactactt caacctgaac accgccgagg ccgccaccgg ctggcagacc | 1560 |
| atcgacggca agaagtacta cttcaacctg aacaccgccg aggccgccac cggctggcag | 1620 |
| accatcgacg gcaagaagta ctacttcaac accaacacct tcatcgccag caccggctac | 1680 |
| accagcatca acggcaagca cttctacttc aacaccgacg gcatcatgca gatcggcgtg | 1740 |
| ttcaagggcc ccaacggctt cgagtacttc gcccccgcca acaccgacgc caacaacatc | 1800 |
| gagggccagg ccatcctgta ccagaacaag ttcctgaccc tgaacggcaa gaagtactac | 1860 |
| ttcggcagcg acagcaaggc cgtgaccggc ctgagaacca tcgacggcaa gaagtactac | 1920 |
| ttcaacacca caccgccgt ggccgtgacc ggctggcaga ccatcaacgg caagaagtac | 1980 |
| tacttcaaca ccaacaccag catcgccagc accggctaca ccatcatcag cggcaagcac | 2040 |
| ttctacttca acaccgacgg catcatgcag atcggcgtgt tcaagggccc cgacggcttc | 2100 |
| gagtacttcg cccccgccaa caccgacgcc aacaacatcg agggccaggc catcagatac | 2160 |
| cagaacagat tcctgtacct gcacgacaac atctactact tcggcaacaa cagcaaggcc | 2220 |
| gccaccggct gggtgaccat cgacggcaac agatactact tcgagcccaa caccgccatg | 2280 |
| ggcgccaacg gctacaagac catcgacaac aagaacttct acttcagaaa cggcctgccc | 2340 |
| cagatcggcg tgttcaaggg cagcaacggc ttcgagtact tcgcccccgc caacaccgac | 2400 |
| gccaacaaca tcgagggcca ggccatcaga taccagaaca gattcctgca cctgctgggc | 2460 |
| aagatctact acttcggcaa caacagcaag gccgtgaccg gctggcagac catcaacggc | 2520 |
| aaggtgtact acttcatgcc cgacaccgcc atggccgccg ccggcggcct gttcgagatc | 2580 |
| gacggcgtga tctacttctt cggcgtggac ggcgtgaagg cccccggcat ctacggctaa | 2640 |
| gaattcta | 2648 |

<210> SEQ ID NO 13
<211> LENGTH: 2400
<212> TYPE: DNA
<213> ORGANISM: Clostridium difficile

<400> SEQUENCE: 13

| | |
|---|---|
| tcattattct attttgatcc tatagaattt aacttagtaa ctggatggca aactatcaat | 60 |
| ggtaaaaaat attattttga tataaatact ggagcagctt taactagtta taaaattatt | 120 |
| aatggtaaac acttttattt taataatgat ggtgtgatgc agttgggagt atttaaagga | 180 |
| cctgatggat ttgaatattt tgcacctgcc aatactcaaa ataataacat agaaggtcag | 240 |
| gctatagttt atcaaagtaa attcttaact ttgaatggca aaaaatatta ttttgataat | 300 |
| aactcaaaag cagtcactgg atggagaatt attaacaatg agaaatatta ctttaatcct | 360 |
| aataatgcta ttgctgcagt cggattgcaa gtaattgaca ataataagta ttatttcaat | 420 |
| cctgacactg ctatcatctc aaaaggttgg cagactgtta atggtagtag atactacttt | 480 |
| gatactgata ccgctattgc ctttaatggt tataaaacta ttgatggtaa acacttttat | 540 |
| tttgatagtg attgtgtagt gaaaataggt gtgtttagta cctctaatgg atttgaatat | 600 |
| tttgcacctg ctaatactta taataataac atagaaggtc aggctatagt ttatcaaagt | 660 |
| aaattcttaa ctttgaatgg taaaaaatat actttgata taactcaaa agcagttacc | 720 |
| ggatggcaaa ctattgatag taaaaaatat tactttaata ctaacactgc tgaagcagct | 780 |
| actggatggc aaactattga tggtaaaaaa tattacttta atactaacac tgctgaagca | 840 |
| gctactggat ggcaaactat tgatggtaaa aatattact ttaatactaa cactgctata | 900 |
| gcttcaactg gttatacaat tattaatggt aaacattttt attttaatac tgatggtatt | 960 |

```
atgcagatag gagtgtttaa aggacctaat ggatttgaat attttgcacc tgctaatacg    1020
gatgctaaca acatagaagg tcaagctata ctttaccaaa atgaattctt aactttgaat    1080
ggtaaaaaat attactttgg tagtgactca aaagcagtta ctggatggag aattattaac    1140
aataagaaat attactttaa tcctaataat gctattgctg caattcatct atgcactata    1200
aataatgaca agtattactt tagttatgat ggaattcttc aaaatggata tattactatt    1260
gaaagaaata atttctattt tgatgctaat aatgaatcta aatggtaac aggagtattt     1320 aaaggaccta atggatttga gtattttgca cctgctaata ctcacaataa taacatagaa    1380
ggtcaggcta tagtttacca gaacaaattc ttaactttga atggcaaaaa atattatttt    1440
gataatgact caaaagcagt tactggatgg caaaccattg atggtaaaaa atattacttt    1500
aatcttaaca ctgctgaagc agctactgga tggcaaacta ttgatggtaa aaatattac    1560 tttaatctta acactgctga agcagctact ggatggcaaa ctattgatgg taaaaaatat    1620
tactttaata ctaacacttt catagcctca actggttata caagtattaa tggtaaacat    1680
ttttatttta atactgatgg tattatgcag ataggagtgt taaaggacc taatggattt     1740 gaatactttg cacctgctaa tacgatgct aacaacatag aaggtcaagc tatactttac     1800
caaaataaat tcttaacttt gaatggtaaa aaatattact ttggtagtga ctcaaaagca    1860
gttaccggac tgcgaactat tgatggtaaa aaatattact ttaatactaa cactgctgtt    1920
gcagttactg gatggcaaac tattaatggt aaaaaatact actttaatac taacacttct    1980
atagcttcaa ctggttatac aattattagt ggtaaacatt tttatttaa tactgatggt     2040 attatgcaga taggagtgtt taaaggacct gatggatttg aatactttgc acctgctaat    2100
acagatgcta acaatataga aggtcaagct atacgttatc aaaatagatt cctatattta    2160
catgacaata tatattattt tggtaataat tcaaaagcgg ctactggttg ggtaactatt    2220
gatggtaata gatattactt cgagcctaat acagctatgg gtgcgaatgg ttataaaact    2280
attgataata aaaattttta ctttagaaat ggtttacctc agataggagt gtttaaaggg    2340
tctaatggat ttgaatactt tgcacctgct aatacggatg ctaacaatat agaaggtcaa    2400
```

<210> SEQ ID NO 14
<211> LENGTH: 2400
<212> TYPE: DNA
<213> ORGANISM: Clostridium difficile

<400> SEQUENCE: 14

```
tcattattct attttgatcc tatagaattt aactagtaa ctggatggca aactatcaat      60
ggtaaaaaat attatttga tataaatact ggagcagctt aactagttta taaaattatt     120
aatggtaaac acttttattt taataatgat ggtgtgatgc agttgggagt atttaaagga    180
cctgatggat ttgaatattt tgcacctgcc aatactcaaa ataataacat agaaggtcag    240
gctatagttt atcaaagtaa attcttaact ttgaatggca aaaaatatta ttttgataat    300
aactcaaaag cagtcactgg atggagaatt attaacaatg agaaatatta ctttaatcct    360
aataatgcta ttgctgcagt cggattgcaa gtaattgaca ataataagta ttatttcaat    420
cctgacactg ctatcatctc aaaaggttgg cagactgtta atggtagtag atactacttt    480
gatactgata ccgctattgc ctttaatggt tataaaacta ttgatggtaa acacttttat    540
tttgatagtg attgtgtagt gaaaataggt gtgtttagta cctctaatgg atttgaatat    600
tttgcacctg ctaatactta taataataac atagaaggtc aggctatagt ttatcaaagt    660
```

```
aaattcttaa ctttgaatgg taaaaaatat tactttgata taactcaaa agcagttacc    720
ggatggcaaa ctattgatag taaaaaatat tactttaata ctaacactgc tgaagcagct    780
actggatggc aaactattga tggtaaaaaa tattacttta atactaacac tgctgaagca    840
gctactggat ggcaaactat tgatggtaaa aaatattact ttaatactaa cactgctata    900
gcttcaactg ttatacaat tattaatggt aaacattttt attttaatac tgatggtatt    960
atgcagatag gagtgtttaa aggacctaat ggatttgaat attttgcacc tgctaatacg   1020
gatgctaaca acatagaagg tcaagctata ctttaccaaa atgaattctt aactttgaat   1080
ggtaaaaaat attactttgg tagtgactca aaagcagtta ctggatggag aattattaac   1140
aataagaaat attactttaa tcctaataat gctattgctg caattcatct atgcactata   1200
aataatgaca gtattactt tagttatgat ggaattcttc aaaatggata tattactatt   1260
gaaagaaata atttctattt tgatgctaat aatgaatcta aatggtaac aggagtattt   1320
aaaggaccta atggatttga gtattttgca cctgctaata ctcacaataa aacatagaa    1380
ggtcaggcta tagtttacca gaacaaattc ttaactttga atggcaaaaa atattatttt   1440
gataatgact caaaagcagt tactggatgg caaaccattg atggtaaaaa atattacttt   1500
aatcttaaca ctgctgaagc agctactgga tggcaaacta ttgatggtaa aaaatattac   1560
tttaatctta cactgctga agcagctact ggatggcaaa ctattgatgg taaaaaatat   1620
tactttaata ctaacacttt catagcctca actggtata caagtattaa tggtaaacat   1680
ttttatttta atactgatgg tattatgcag ataggagtgt ttaaaggacc taatggattt   1740
gaatactttg cacctgctaa tacgatgct aacaacatag aaggtcaagc tatactttac   1800
caaaataaat tcttaacttt gaatggtaaa aaatattact ttggtagtga ctcaaaagca   1860
gttaccggac tgcgaactat tgatggtaaa aaatattact taatactaa cactgctgtt   1920
gcagttactg gatggcaaac tattaatggt aaaaaatact actttaatac taacacttct   1980
atagcttcaa ctggttatac aattattagt ggtaaacatt tttattttaa tactgatggt   2040
attatgcaga taggagtgtt taaaggacct gatggatttg aatactttgc acctgctaat   2100
acagatgcta acaatataga aggtcaagct atacgttatc aaaatagatt cctatattta   2160
catgacaata tatattattt tggtaataat tcaaaagcgg ctactggttg ggtaactatt   2220
gatggtaata gatattactt cgagcctaat acagctatgg gtgcgaatgg ttataaaact   2280
attgataata aaaattttta ctttagaaat ggtttacctc agataggagt gtttaagggg   2340
tctaatggat ttgaatactt tgcacctgct aatacggatg ctaacaatat agaaggtcaa   2400
```

<210> SEQ ID NO 15
<211> LENGTH: 2366
<212> TYPE: PRT
<213> ORGANISM: Clostridium difficile

<400> SEQUENCE: 15

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val

-continued

```
             65                  70                  75                  80
        Thr Glu Val Leu Glu Leu Lys Asn Asn Asn Leu Thr Pro Val Glu Lys
                         85                  90                  95

Asn Leu His Phe Val Trp Ile Gly Gly Gln Ile Asn Asp Thr Ala Ile
                        100                 105                 110

Asn Tyr Ile Asn Gln Trp Lys Asp Val Asn Ser Asp Tyr Asn Val Asn
                        115                 120                 125

Val Phe Tyr Asp Ser Asn Ala Phe Leu Ile Asn Thr Leu Lys Lys Thr
        130                 135                 140

Val Val Glu Ser Ala Ile Asn Asp Thr Leu Glu Ser Phe Arg Glu Asn
        145                 150                 155                 160

Leu Asn Asp Pro Arg Phe Asp Tyr Asn Lys Phe Arg Lys Arg Met
                        165                 170                 175

Glu Ile Ile Tyr Asp Lys Gln Lys Asn Phe Ile Asn Tyr Tyr Lys Ala
                        180                 185                 190

Gln Arg Glu Glu Asn Pro Glu Leu Ile Ile Asp Asp Ile Val Lys Thr
                        195                 200                 205

Tyr Leu Ser Asn Glu Tyr Ser Lys Glu Ile Asp Glu Leu Asn Thr Tyr
                        210                 215                 220

Ile Glu Glu Ser Leu Asn Lys Ile Thr Gln Asn Ser Gly Asn Asp Val
        225                 230                 235                 240

Arg Asn Phe Glu Glu Phe Lys Asn Gly Glu Ser Phe Asn Leu Tyr Glu
                        245                 250                 255

Gln Glu Leu Val Glu Arg Trp Asn Leu Ala Ala Ala Ser Asp Ile Leu
                        260                 265                 270

Arg Ile Ser Ala Leu Lys Glu Ile Gly Gly Met Tyr Leu Asp Val Asp
                        275                 280                 285

Met Leu Pro Gly Ile Gln Pro Asp Leu Phe Glu Ser Ile Glu Lys Pro
                        290                 295                 300

Ser Ser Val Thr Val Asp Phe Trp Glu Met Thr Lys Leu Glu Ala Ile
        305                 310                 315                 320

Met Lys Tyr Lys Glu Tyr Ile Pro Glu Tyr Thr Ser Glu His Phe Asp
                        325                 330                 335

Met Leu Asp Glu Glu Val Gln Ser Ser Phe Glu Ser Val Leu Ala Ser
                        340                 345                 350

Lys Ser Asp Lys Ser Glu Ile Phe Ser Ser Leu Gly Asp Met Glu Ala
                        355                 360                 365

Ser Pro Leu Glu Val Lys Ile Ala Phe Asn Ser Lys Gly Ile Ile Asn
                        370                 375                 380

Gln Gly Leu Ile Ser Val Lys Asp Ser Tyr Cys Ser Asn Leu Ile Val
        385                 390                 395                 400

Lys Gln Ile Glu Asn Arg Tyr Lys Ile Leu Asn Asn Ser Leu Asn Pro
                        405                 410                 415

Ala Ile Ser Glu Asp Asn Asp Phe Asn Thr Thr Thr Asn Thr Phe Ile
                        420                 425                 430

Asp Ser Ile Met Ala Glu Ala Asn Ala Asp Asn Gly Arg Phe Met Met
                        435                 440                 445

Glu Leu Gly Lys Tyr Leu Arg Val Gly Phe Phe Pro Asp Val Lys Thr
                        450                 455                 460

Thr Ile Asn Leu Ser Gly Pro Glu Ala Tyr Ala Ala Ala Tyr Gln Asp
        465                 470                 475                 480

Leu Leu Met Phe Lys Glu Gly Ser Met Asn Ile His Leu Ile Glu Ala
                        485                 490                 495
```

```
Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
            515                 520                 525

Ala Gln Phe Glu Glu Tyr Lys Arg Asn Tyr Phe Glu Gly Ser Leu Gly
        530                 535                 540

Glu Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Ile Asn Val Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Ser Ile
        755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
        835                 840                 845

Ser Asp Ser Ile Asn Tyr Ile Lys Asp Glu Phe Lys Leu Ile Glu Ser
    850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910
```

```
Thr Glu Lys Thr Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
    930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
        995                 1000                1005

Glu Leu Val Ser Thr Ala Leu Asp Glu Thr Ile Asp Leu Leu Pro
    1010                1015                1020

Thr Leu Ser Glu Gly Leu Pro Ile Ile Ala Thr Ile Ile Asp Gly
    1025                1030                1035

Val Ser Leu Gly Ala Ala Ile Lys Glu Leu Ser Glu Thr Ser Asp
    1040                1045                1050

Pro Leu Leu Arg Gln Glu Ile Glu Ala Lys Ile Gly Ile Met Ala
    1055                1060                1065

Val Asn Leu Thr Thr Ala Thr Thr Ala Ile Ile Thr Ser Ser Leu
    1070                1075                1080

Gly Ile Ala Ser Gly Phe Ser Ile Leu Leu Val Pro Leu Ala Gly
    1085                1090                1095

Ile Ser Ala Gly Ile Pro Ser Leu Val Asn Asn Glu Leu Val Leu
    1100                1105                1110

Arg Asp Lys Ala Thr Lys Val Val Asp Tyr Phe Lys His Val Ser
    1115                1120                1125

Leu Val Glu Thr Glu Gly Val Phe Thr Leu Leu Asp Asp Lys Ile
    1130                1135                1140

Met Met Pro Gln Asp Asp Leu Val Ile Ser Glu Ile Asp Phe Asn
    1145                1150                1155

Asn Asn Ser Ile Val Leu Gly Lys Cys Glu Ile Trp Arg Met Glu
    1160                1165                1170

Gly Gly Ser Gly His Thr Val Thr Asp Asp Ile Asp His Phe Phe
    1175                1180                1185

Ser Ala Pro Ser Ile Thr Tyr Arg Glu Pro His Leu Ser Ile Tyr
    1190                1195                1200

Asp Val Leu Glu Val Gln Lys Glu Glu Leu Asp Leu Ser Lys Asp
    1205                1210                1215

Leu Met Val Leu Pro Asn Ala Pro Asn Arg Val Phe Ala Trp Glu
    1220                1225                1230

Thr Gly Trp Thr Pro Gly Leu Arg Ser Leu Glu Asn Asp Gly Thr
    1235                1240                1245

Lys Leu Leu Asp Arg Ile Arg Asp Asn Tyr Glu Gly Glu Phe Tyr
    1250                1255                1260

Trp Arg Tyr Phe Ala Phe Ile Ala Asp Ala Leu Ile Thr Thr Leu
    1265                1270                1275

Lys Pro Arg Tyr Glu Asp Thr Asn Ile Arg Ile Asn Leu Asp Ser
    1280                1285                1290

Asn Thr Arg Ser Phe Ile Val Pro Ile Ile Thr Thr Glu Tyr Ile
    1295                1300                1305

Arg Glu Lys Leu Ser Tyr Ser Phe Tyr Gly Ser Gly Gly Thr Tyr
```

-continued

```
            1310                1315                1320

Ala Leu Ser Leu Ser Gln Tyr Asn Met Gly Ile Asn Ile Glu Leu
            1325                1330                1335

Ser Glu Ser Asp Val Trp Ile Ile Asp Val Asp Asn Val Val Arg
            1340                1345                1350

Asp Val Thr Ile Glu Ser Asp Lys Ile Lys Lys Gly Asp Leu Ile
            1355                1360                1365

Glu Gly Ile Leu Ser Thr Leu Ser Ile Glu Glu Asn Lys Ile Ile
            1370                1375                1380

Leu Asn Ser His Glu Ile Asn Phe Ser Gly Glu Val Asn Gly Ser
            1385                1390                1395

Asn Gly Phe Val Ser Leu Thr Phe Ser Ile Leu Glu Gly Ile Asn
            1400                1405                1410

Ala Ile Ile Glu Val Asp Leu Leu Ser Lys Ser Tyr Lys Leu Leu
            1415                1420                1425

Ile Ser Gly Glu Leu Lys Ile Leu Met Leu Asn Ser Asn His Ile
            1430                1435                1440

Gln Gln Lys Ile Asp Tyr Ile Gly Phe Asn Ser Glu Leu Gln Lys
            1445                1450                1455

Asn Ile Pro Tyr Ser Phe Val Asp Ser Glu Gly Lys Glu Asn Gly
            1460                1465                1470

Phe Ile Asn Gly Ser Thr Lys Glu Gly Leu Phe Val Ser Glu Leu
            1475                1480                1485

Pro Asp Val Val Leu Ile Ser Lys Val Tyr Met Asp Asp Ser Lys
            1490                1495                1500

Pro Ser Phe Gly Tyr Tyr Ser Asn Asn Leu Lys Asp Val Lys Val
            1505                1510                1515

Ile Thr Lys Asp Asn Val Asn Ile Leu Thr Gly Tyr Tyr Leu Lys
            1520                1525                1530

Asp Asp Ile Lys Ile Ser Leu Ser Leu Thr Leu Gln Asp Glu Lys
            1535                1540                1545

Thr Ile Lys Leu Asn Ser Val His Leu Asp Glu Ser Gly Val Ala
            1550                1555                1560

Glu Ile Leu Lys Phe Met Asn Arg Lys Gly Asn Thr Asn Thr Ser
            1565                1570                1575

Asp Ser Leu Met Ser Phe Leu Glu Ser Met Asn Ile Lys Ser Ile
            1580                1585                1590

Phe Val Asn Phe Leu Gln Ser Asn Ile Lys Phe Ile Leu Asp Ala
            1595                1600                1605

Asn Phe Ile Ile Ser Gly Thr Thr Ser Ile Gly Gln Phe Glu Phe
            1610                1615                1620

Ile Cys Asp Glu Asn Asp Asn Ile Gln Pro Tyr Phe Ile Lys Phe
            1625                1630                1635

Asn Thr Leu Glu Thr Asn Tyr Thr Leu Tyr Val Gly Asn Arg Gln
            1640                1645                1650

Asn Met Ile Val Glu Pro Asn Tyr Asp Leu Asp Asp Ser Gly Asp
            1655                1660                1665

Ile Ser Ser Thr Val Ile Asn Phe Ser Gln Lys Tyr Leu Tyr Gly
            1670                1675                1680

Ile Asp Ser Cys Val Asn Lys Val Val Ile Ser Pro Asn Ile Tyr
            1685                1690                1695

Thr Asp Glu Ile Asn Ile Thr Pro Val Tyr Glu Thr Asn Asn Thr
            1700                1705                1710
```

```
Tyr Pro Glu Val Ile Val Leu Asp Ala Asn Tyr Ile Asn Glu Lys
1715                1720                1725

Ile Asn Val Asn Ile Asn Asp Leu Ser Ile Arg Tyr Val Trp Ser
1730                1735                1740

Asn Asp Gly Asn Asp Phe Ile Leu Met Ser Thr Ser Glu Glu Asn
1745                1750                1755

Lys Val Ser Gln Val Lys Ile Arg Phe Val Asn Val Phe Lys Asp
1760                1765                1770

Lys Thr Leu Ala Asn Lys Leu Ser Phe Asn Phe Ser Asp Lys Gln
1775                1780                1785

Asp Val Pro Val Ser Glu Ile Ile Leu Ser Phe Thr Pro Ser Tyr
1790                1795                1800

Tyr Glu Asp Gly Leu Ile Gly Tyr Asp Leu Gly Leu Val Ser Leu
1805                1810                1815

Tyr Asn Glu Lys Phe Tyr Ile Asn Asn Phe Gly Met Met Val Ser
1820                1825                1830

Gly Leu Ile Tyr Ile Asn Asp Ser Leu Tyr Tyr Phe Lys Pro Pro
1835                1840                1845

Val Asn Asn Leu Ile Thr Gly Phe Val Thr Val Gly Asp Asp Lys
1850                1855                1860

Tyr Tyr Phe Asn Pro Ile Asn Gly Gly Ala Ala Ser Ile Gly Glu
1865                1870                1875

Thr Ile Ile Asp Asp Lys Asn Tyr Tyr Phe Asn Gln Ser Gly Val
1880                1885                1890

Leu Gln Thr Gly Val Phe Ser Thr Glu Asp Gly Phe Lys Tyr Phe
1895                1900                1905

Ala Pro Ala Asn Thr Leu Asp Glu Asn Leu Glu Gly Glu Ala Ile
1910                1915                1920

Asp Phe Thr Gly Lys Leu Ile Ile Asp Glu Asn Ile Tyr Tyr Phe
1925                1930                1935

Asp Asp Asn Tyr Arg Gly Ala Val Glu Trp Lys Glu Leu Asp Gly
1940                1945                1950

Glu Met His Tyr Phe Ser Pro Glu Thr Gly Lys Ala Phe Lys Gly
1955                1960                1965

Leu Asn Gln Ile Gly Asp Tyr Lys Tyr Tyr Phe Asn Ser Asp Gly
1970                1975                1980

Val Met Gln Lys Gly Phe Val Ser Ile Asn Asp Asn Lys His Tyr
1985                1990                1995

Phe Asp Asp Ser Gly Val Met Lys Val Gly Tyr Thr Glu Ile Asp
2000                2005                2010

Gly Lys His Phe Tyr Phe Ala Glu Asn Gly Glu Met Gln Ile Gly
2015                2020                2025

Val Phe Asn Thr Glu Asp Gly Phe Lys Tyr Phe Ala His His Asn
2030                2035                2040

Glu Asp Leu Gly Asn Glu Glu Gly Glu Glu Ile Ser Tyr Ser Gly
2045                2050                2055

Ile Leu Asn Phe Asn Asn Lys Ile Tyr Tyr Phe Asp Asp Ser Phe
2060                2065                2070

Thr Ala Val Val Gly Trp Lys Asp Leu Glu Asp Gly Ser Lys Tyr
2075                2080                2085

Tyr Phe Asp Glu Asp Thr Ala Glu Ala Tyr Ile Gly Leu Ser Leu
2090                2095                2100
```

```
Ile Asn Asp Gly Gln Tyr Tyr Phe Asn Asp Asp Gly Ile Met Gln
    2105                2110                2115

Val Gly Phe Val Thr Ile Asn Asp Lys Val Phe Tyr Phe Ser Asp
    2120                2125                2130

Ser Gly Ile Ile Glu Ser Gly Val Gln Asn Ile Asp Asp Asn Tyr
    2135                2140                2145

Phe Tyr Ile Asp Asp Asn Gly Ile Val Gln Ile Gly Val Phe Asp
    2150                2155                2160

Thr Ser Asp Gly Tyr Lys Tyr Phe Ala Pro Ala Asn Thr Val Asn
    2165                2170                2175

Asp Asn Ile Tyr Gly Gln Ala Val Glu Tyr Ser Gly Leu Val Arg
    2180                2185                2190

Val Gly Glu Asp Val Tyr Tyr Phe Gly Glu Thr Tyr Thr Ile Glu
    2195                2200                2205

Thr Gly Trp Ile Tyr Asp Met Glu Asn Glu Ser Asp Lys Tyr Tyr
    2210                2215                2220

Phe Asn Pro Glu Thr Lys Lys Ala Cys Lys Gly Ile Asn Leu Ile
    2225                2230                2235

Asp Asp Ile Lys Tyr Tyr Phe Asp Glu Lys Gly Ile Met Arg Thr
    2240                2245                2250

Gly Leu Ile Ser Phe Glu Asn Asn Asn Tyr Tyr Phe Asn Glu Asn
    2255                2260                2265

Gly Glu Met Gln Phe Gly Tyr Ile Asn Ile Glu Asp Lys Met Phe
    2270                2275                2280

Tyr Phe Gly Glu Asp Gly Val Met Gln Ile Gly Val Phe Asn Thr
    2285                2290                2295

Pro Asp Gly Phe Lys Tyr Phe Ala His Gln Asn Thr Leu Asp Glu
    2300                2305                2310

Asn Phe Glu Gly Glu Ser Ile Asn Tyr Thr Gly Trp Leu Asp Leu
    2315                2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Tyr Phe Asp Pro Asp
    2345                2350                2355

Thr Ala Gln Leu Val Ile Ser Glu
    2360                2365

<210> SEQ ID NO 16
<211> LENGTH: 612
<212> TYPE: PRT
<213> ORGANISM: Clostridium difficile

<400> SEQUENCE: 16

Ser Glu Glu Asn Lys Val Ser Gln Val Lys Ile Arg Phe Val Asn Val
1               5                   10                  15

Phe Lys Asp Lys Thr Leu Ala Asn Lys Leu Ser Phe Asn Phe Ser Asp
            20                  25                  30

Lys Gln Asp Val Pro Val Ser Glu Ile Ile Leu Ser Phe Thr Pro Ser
        35                  40                  45

Tyr Tyr Glu Asp Gly Leu Ile Gly Tyr Asp Leu Gly Leu Val Ser Leu
    50                  55                  60

Tyr Asn Glu Lys Phe Tyr Ile Asn Asn Phe Gly Met Met Val Ser Gly
65                  70                  75                  80

Leu Ile Tyr Ile Asn Asp Ser Leu Tyr Tyr Phe Lys Pro Pro Val Asn
                85                  90                  95
```

```
Asn Leu Ile Thr Gly Phe Val Thr Val Gly Asp Asp Lys Tyr Tyr Phe
            100                 105                 110
Asn Pro Ile Asn Gly Gly Ala Ala Ser Ile Gly Glu Thr Ile Ile Asp
            115                 120                 125
Asp Lys Asn Tyr Tyr Phe Asn Gln Ser Gly Val Leu Gln Thr Gly Val
130                 135                 140
Phe Ser Thr Glu Asp Gly Phe Lys Tyr Phe Ala Pro Ala Asn Thr Leu
145                 150                 155                 160
Asp Glu Asn Leu Glu Gly Glu Ala Ile Asp Phe Thr Gly Lys Leu Ile
                165                 170                 175
Ile Asp Glu Asn Ile Tyr Tyr Phe Asp Asp Asn Tyr Arg Gly Ala Val
                180                 185                 190
Glu Trp Lys Glu Leu Asp Gly Glu Met His Tyr Phe Ser Pro Glu Thr
            195                 200                 205
Gly Lys Ala Phe Lys Gly Leu Asn Gln Ile Gly Asp Tyr Lys Tyr Tyr
            210                 215                 220
Phe Asn Ser Asp Gly Val Met Gln Lys Gly Phe Val Ser Ile Asn Asp
225                 230                 235                 240
Asn Lys His Tyr Phe Asp Asp Ser Gly Val Met Lys Val Gly Tyr Thr
                245                 250                 255
Glu Ile Asp Gly Lys His Phe Tyr Phe Ala Glu Asn Gly Glu Met Gln
                260                 265                 270
Ile Gly Val Phe Asn Thr Glu Asp Gly Phe Lys Tyr Phe Ala His His
            275                 280                 285
Asn Glu Asp Leu Gly Asn Glu Glu Gly Glu Glu Ile Ser Tyr Ser Gly
            290                 295                 300
Ile Leu Asn Phe Asn Asn Lys Ile Tyr Tyr Phe Asp Asp Ser Phe Thr
305                 310                 315                 320
Ala Val Val Gly Trp Lys Asp Leu Glu Asp Gly Ser Lys Tyr Tyr Phe
                325                 330                 335
Asp Glu Asp Thr Ala Glu Ala Tyr Ile Gly Leu Ser Leu Ile Asn Asp
                340                 345                 350
Gly Gln Tyr Tyr Phe Asn Asp Asp Gly Ile Met Gln Val Gly Phe Val
            355                 360                 365
Thr Ile Asn Asp Lys Val Phe Tyr Phe Ser Asp Ser Gly Ile Ile Glu
            370                 375                 380
Ser Gly Val Gln Asn Ile Asp Asp Asn Tyr Phe Tyr Ile Asp Asp Asn
385                 390                 395                 400
Gly Ile Val Gln Ile Gly Val Phe Asp Thr Ser Asp Gly Tyr Lys Tyr
                405                 410                 415
Phe Ala Pro Ala Asn Thr Val Asn Asp Asn Ile Tyr Gly Gln Ala Val
                420                 425                 430
Glu Tyr Ser Gly Leu Val Arg Val Gly Glu Asp Val Tyr Tyr Phe Gly
            435                 440                 445
Glu Thr Tyr Thr Ile Glu Thr Gly Trp Ile Tyr Asp Met Glu Asn Glu
            450                 455                 460
Ser Asp Lys Tyr Tyr Phe Asn Pro Glu Thr Lys Lys Ala Cys Lys Gly
465                 470                 475                 480
Ile Asn Leu Ile Asp Asp Ile Lys Tyr Tyr Phe Asp Glu Lys Gly Ile
                485                 490                 495
Met Arg Thr Gly Leu Ile Ser Phe Glu Asn Asn Asn Tyr Tyr Phe Asn
            500                 505                 510
```

| | | | | | | | | | | | | |
|---|---|---|---|---|---|---|---|---|---|---|---|---|
|Glu|Asn|Gly|Glu|Met|Gln|Phe|Gly|Tyr|Ile|Asn|Ile|Glu|Asp|Lys|Met|
| |515| | | |520| | | |525| | | | | | |

| | | | | | | | | | | | |
|---|---|---|---|---|---|---|---|---|---|---|---|
|Phe|Tyr|Phe|Gly|Glu|Asp|Gly|Val|Met|Gln|Ile|Gly|Val|Phe|Asn|Thr|
| | |530| | | |535| | | |540| | | | | |

Pro Asp Gly Phe Lys Tyr Phe Ala His Gln Asn Thr Leu Asp Glu Asn
545                 550                 555                 560

Phe Glu Gly Glu Ser Ile Asn Tyr Thr Gly Trp Leu Asp Leu Asp Glu
                565                 570                 575

Lys Arg Tyr Tyr Phe Thr Asp Glu Tyr Ile Ala Ala Thr Gly Ser Val
                580                 585                 590

Ile Ile Asp Gly Glu Glu Tyr Tyr Phe Asp Pro Asp Thr Ala Gln Leu
                595                 600                 605

Val Ile Ser Glu
    610

<210> SEQ ID NO 17
<211> LENGTH: 1441
<212> TYPE: DNA
<213> ORGANISM: Clostridium difficile

<400> SEQUENCE: 17

```
agtgaagaaa ataaggtgtc acaagttaaa ataagattcg ttaatgtttt taaagataag     60
actttggcaa ataagctatc ttttaacttt agtgataaac aagatgtacc tgtaagtgaa    120
ataatcttat catttacacc ttcatattat gaggatggat tgattggcta tgatttgggt    180
ctagtttctt tatataatga gaaattttat attaataact ttggaatgat ggtatctgga    240
ttaatatata ttaatgattc attatattat tttaaaccac cagtaaataa tttgataact    300
ggatttgtga ctgtaggcga tgataaatac tactttaatc caattaatgg tggagctgct    360
tcaattggag agacaataat tgatgacaaa aattattatt tcaaccaaag tggagtgtta    420
caaacaggtg tatttagtac agaagatgga tttaaatatt ttgccccagc taatacactt    480
gatgaaaacc tagaaggaga agcaattgat tttactggaa aattaattat tgacgaaaat    540
atttattatt ttgatgataa ttatagagga gctgtagaat ggaaagaatt agatggtgaa    600
atgcactatt ttagcccaga aacaggtaaa gcttttaaag gtctaaatca ataggtgat    660
tataaatact atttcaattc tgatggagtt atgcaaaaag gatttgttag tataaatgat    720
aataaacact attttgatga ttctggtgtt atgaaagtag gttacactga atagatggc    780
aagcatttct actttgctga aaacggagaa atgcaaatag gagtatttaa tacagaagat    840
ggatttaaat attttgctca tcataatgaa gatttaggaa atgaagaagg tgaagaaatc    900
tcatattctg gtatattaaa tttcaataat aaaatttact attttgatga ttcatttaca    960
gctgtagttg gatggaaaga tttagaggat ggttcaaagt attatttga tgaagataca   1020
gcagaagcat atataggttt gtcattaata aatgatggtc aatattattt taatgatgat   1080
ggaattatgc aagttggatt tgtcactata atgataaag tcttctactt ctctgactct   1140
ggaattatag aatctggagt acaaaacata gatgacaatt atttctatat agatgataat   1200
ggtatagttc aaattggtgt atttgatact tcagatggat ataaatattt tgcacctgct   1260
aatactgtaa atgataatat ttacggacaa gcagttgaat atagtggttt agttagagtt   1320
ggggaagatg tatattattt tggagaaaca tatacaattg agactggatg gatatatgat   1380
atggaaaatg aaagtgataa atattatttc aatccagaaa ctaaaaaagc atgcaaaggt   1440
a                                                                  1441
```

<210> SEQ ID NO 18
<211> LENGTH: 1441
<212> TYPE: DNA
<213> ORGANISM: Clostridium difficile

<400> SEQUENCE: 18

| | | | | | |
|---|---|---|---|---|---|
| agtgaagaaa | ataaggtgtc | acaagttaaa | ataagattcg | ttaatgtttt | taaagataag | 60 |
| actttggcaa | ataagctatc | ttttaacttt | agtgataaac | aagatgtacc | tgtaagtgaa | 120 |
| ataatcttat | catttacacc | ttcatattat | gaggatggat | tgattggcta | tgatttgggt | 180 |
| ctagtttctt | tatataatga | gaaattttat | attaataact | ttggaatgat | ggtatctgga | 240 |
| ttaatatata | ttaatgattc | attatattat | tttaaaccac | cagtaaataa | tttgataact | 300 |
| ggatttgtga | ctgtaggcga | tgataaatac | tactttaatc | caattaatgg | tggagctgct | 360 |
| tcaattggag | agacaataat | tgatgacaaa | aattattatt | tcaaccaaag | tggagtgtta | 420 |
| caaacaggtg | tatttagtac | agaagatgga | tttaaatatt | ttgccccagc | taatacactt | 480 |
| gatgaaaacc | tagaaggaga | agcaattgat | tttactggaa | aattaattat | tgacgaaaat | 540 |
| atttattatt | ttgatgataa | ttatagagga | gctgtagaat | ggaaagaatt | agatggtgaa | 600 |
| atgcactatt | ttagcccaga | aacaggtaaa | gcttttaaag | gtctaaatca | ataggtgat | 660 |
| tataaatact | atttcaattc | tgatggagtt | atgcaaaaag | gatttgttag | tataaatgat | 720 |
| aataaacact | attttgatga | ttctggtgtt | atgaaagtag | gttacactga | aatagatggc | 780 |
| aagcatttct | actttgctga | aaacggagaa | atgcaaatag | gagtatttaa | tacagaagat | 840 |
| ggatttaaat | attttgctca | tcataatgaa | gatttaggaa | atgaagaagg | tgaagaaatc | 900 |
| tcatattctg | gtatattaaa | tttcaataat | aaaatttact | attttgatga | ttcatttaca | 960 |
| gctgtagttg | gatggaaaga | tttagaggat | ggttcaaagt | attatttga | tgaagataca | 1020 |
| gcagaagcat | ataggtttt | gtcattaata | aatgatggtc | aatattattt | taatgatgat | 1080 |
| ggaattatgc | aagttggatt | tgtcactata | aatgataaag | tcttctactt | ctctgactct | 1140 |
| ggaattatag | aatctggagt | acaaaacata | gatgacaatt | atttctatat | agatgataat | 1200 |
| ggtatagttc | aaattggtgt | atttgatact | tcagatggat | ataaatttt | tgcacctgct | 1260 |
| aatactgtaa | atgataatat | ttacggacaa | gcagttgaat | atagtggttt | agttagagtt | 1320 |
| ggggaagatg | tatattattt | tggagaaaca | tatacaattg | agactggatg | gatatatgat | 1380 |
| atggaaaatg | aaagtgataa | atattatttc | aatccagaaa | ctaaaaaagc | atgcaaaggt | 1440 |
| a | | | | | | 1441 |

<210> SEQ ID NO 19
<211> LENGTH: 2649
<212> TYPE: DNA
<213> ORGANISM: Artificial Sequence
<220> FEATURE:
<223> OTHER INFORMATION: synthetic nucleotide sequence

<400> SEQUENCE: 19

| | | | | | |
|---|---|---|---|---|---|
| gctagccgcc | accatgggat | ccagcctgtt | ctacttcgac | cccatcgagt | tcaacctggt | 60 |
| gaccggctgg | cagaccatca | cggcaagaa | gtactacttc | gacatcaaca | ccggcgccgc | 120 |
| cctgaccagc | tacaagatca | tcaacggcaa | gcacttctac | ttcaacaacg | acggcgtgat | 180 |
| gcagctgggc | gtgttcaagg | gccccgacgg | cttcgagtac | ttcgcccccg | ccaacaccca | 240 |
| gaacaacaac | atcgagggcc | aggccatcgt | gtaccagagc | aagttcctga | ccctgaacgg | 300 |
| caagaagtac | tacttcgaca | acaacagcaa | ggccgtgacc | ggctggcaga | tcatcaacaa | 360 |

-continued

```
cgagaagtac tacttcaacc ccaacaacgc catcgccgcc gtgggcctgc aggtgatcga      420
caacaacaag tactacttca accccgacac cgccatcatc agcaagggct ggcagaccgt      480
gaacggcagc agatactact tcgacaccga caccgccatc gccttcaacg gctacaagac      540
catcgacggc aagcacttct acttcgacag cgactgtgtg gtgaagatcg gcgtgttcag      600
caccagcaac ggcttcgagt acttcgcccc cgccaacacc tacaacaaca acatcgaggg      660
ccaggccatc gtgtaccaga gcaagttcct gaccctgaac ggcaagaagt actacttcga      720
caacaacagc aaggccgtga ccggcctgca gaccatcgac agcaagaagt actacttcaa      780
caccaacacc gccgaggccg ccaccggctg gcagaccatc gacggcaaga agtactactt      840
caacaccaac accgccgagg ccgccaccgg ctggcagacc atcgacggca agaagtacta      900
cttcaacacc aacaccgcca tcgccagcac cggctacacc atcatcaacg gcaagcactt      960
ctacttcaac accgacggca tcatgcagat cggcgtgttc aagggcccca acggcttcga     1020
gtacttcgcc cccgccaaca ccgacgccaa caacatcgag ggccaggcca tcctgtacca     1080
gaacgagttc ctgaccctga cggcaagaa gtactacttc ggcagcgaca gcaaggccgt     1140
gaccggctgg agaatcatca acaacaagaa gtactacttc aaccccaaca cgccatcgc     1200 cgccatccac ctgtgtacca tcaacaacga caagtactac ttcagctacg acggcatcct     1260
gcagaacggc tacatcacca tcgagagaaa caacttctac ttcgacgcca caacgagag     1320 caagatggtg accggcgtgt tcaagggccc caacggcttc gagtacttcg cccccgccaa     1380
cacccacaac aacaacatcg agggccaggc catcgtgtac cagaacaagt tcctgaccct     1440
gaacggcaag aagtactact tcgacaacga cagcaaggcc gtgaccggct ggcagaccat     1500
cgacggcaag aagtactact tcaacctgaa caccgccgag ccgccaccg gctggcagac     1560 catcgacggc aagaagtact acttcaacct gaacaccgcc gaggccgcca ccggctggca     1620
gaccatcgac ggcaagaagt actacttcaa caccaacacc ttcatcgcca gcaccggcta     1680
caccagcatc aacggcaagc acttctactt caacaccgac ggcatcatgc agatcggcgt     1740
gttcaagggc cccaacggct tcgagtactt cgcccccgcc aacaccgacg ccaacaacat     1800
cgagggccag gccatcctgt accagaacaa gttcctgacc ctgaacggca agaagtacta     1860
cttcggcagc gacagcaagg ccgtgaccgg cctgagaacc atcgacggca agaagtacta     1920
cttcaacacc aacaccgccg tggccgtgac cggctggcag accatcaacg gcaagaagta     1980
ctacttcaac accaacacca gcatcgccag caccggctac accatcatca gcggcaagca     2040
cttctacttc aacaccgacg gcatcatgca gatcggcgtg ttcaagggcc ccgacggctt     2100
cgagtacttc gcccccgcca acaccgacgc caacaacatc gagggccagg ccatcagata     2160
ccagaacaga ttcctgtacc tgcacgacaa catctactac ttcggcaaca acagcaaggc     2220
cgccaccggc tgggtgacca tcgacggcaa cagatactac ttcgagccca caccgccat     2280 gggcgccaac ggctacaaga ccatcgacaa caagaacttc tacttcagaa acggcctgcc     2340
ccagatcggc gtgttcaagg gcagcaacgg cttcgagtac ttcgcccccg ccaacaccga     2400
cgccaacaac atcgagggcc aggccatcag ataccagaac agattcctgc acctgctggg     2460
caagatctac tacttcggca caacagcaa ggccgtgacc ggctggcaga ccatcaacgg     2520
caaggtgtac tacttcatgc ccgacaccgc catggccgcc gccggcggcc tgttcgagat     2580
cgacggcgtg atctacttct tcggcgtgga cggcgtgaag gccccggca tctacggcta     2640 agaattcta                                                             2649
```

<210> SEQ ID NO 20
<211> LENGTH: 1957
<212> TYPE: DNA
<213> ORGANISM: Artificial Sequence
<220> FEATURE:
<223> OTHER INFORMATION: synthetic nucleotide sequence

<400> SEQUENCE: 20

```
gctagccgcc accatggacg ccatgctgcg cggactgtgc tgcgtgctgc tgctgtgcgg      60
cgccgtgttc gtgagcccca gccgcagacg caagaagcgc gccggaggat ccagcgagga     120
gaacaaggtg agccaagtga agattagatt cgtgaacgtg ttcaaggaca agacactggc     180
caacaagctg agcttcaact tcagcgacaa gcaagacgtg cctgtgagcg agattattct     240
gagcttcaca cctagctatt atgaggacgc cctgattggc tatgacctgg gcctggtgag     300
cctgtataac gagaagttct atattaacaa cttcggcatg atggtgagcg gcctgattta     360
tattaacgac agcctgtact acttcaagcc tcctgtgaac aacctgatca ccggcttcgt     420
gaccgtgggc gacgacaagt actacttcaa ccctatcaac ggcggcgcag ccagcatcgg     480
cgagaccatc atcgacgaca gaactacta cttcaaccag agcggcgtgc tgcagaccgg     540
cgtgttcagc accgaggacg gcttcaagta cttcgcccct gccaacaccc tggacgagaa     600
cctggagggc gaggccatcg acttcaccgg caagctgatc atcgacgaga acatctacta     660
cttcgacgac aactacagag cgccgtggaa gtggaaggag ctggacggcg agatgcatta     720
cttcagccct gagaccggca aggccttcaa gggcctgaac cagatcggcg acgacaagta     780
ctacttcaac agcgacggcg tgatgcagaa gggcttcgtg agcatcaacg acaacaagca     840
ttacttcgac gacagcggcg tgatgaaggt gggctacacc gagatcgacg gcaagcattt     900
ctacttcgcc gagaacggcg agatgcagat cggcgtgttc aacaccgagg acggcttcaa     960
gtacttcgcc catcataacg aggacctggg caacgaggag ggcgaggaga tcagctacag    1020
cggcatcctg aacttcaaca acaagatcta cttcgac gacagcttca ccgccgtggt     1080
gggctggaag gacctggagg acggcagcaa gtactacttc gacgaggaca ccgccgaggc    1140
ctacatcggc ctgagcctga tcaacgacgg ccagtactac ttcaacgacg acggcatcat    1200
gcaggtgggc ttcgtgacca tcaacgacaa ggtgttctac ttcagcgaca gcggcatcat    1260
cgagagcggc gtgcagaaca tcgacgacaa ctacttctac atcgacgaca cggcatcgt    1320
gcagatcggc gtgttcgaca ccagcgacgg ctacaagtac ttcgcccctg ccaacaccgt    1380
gaacgacaac atctacggcc aggccgtgga gtacagcggc ctggtgagag tgggcgagga    1440
cgtgtactac ttcggcgaga cctacaccat cgagaccggc tggatctacg acatggagaa    1500
cgagagcgac aagtactact tcaaccctga gaccaagaag gcctgcaagg gcatcaacct    1560
gatcgacgac atcaagtact acttcgacga aagggcatc atgagaaccg gcctgatcag    1620
cttcgagaat aacaactact acttcaacga gaacggcgag atgcagttcg gctacatcaa    1680
catcgaggac aagatgttct acttcggcga ggacggcgtg atgcagatcg gcgtgttcaa    1740
cacccctgac ggcttcaagt acttcgccca tcagaacacc ctggacgaga cttcgaggg    1800
cgagagcatc aactacaccg ctggctgga cctggacgaga aagagatact acttcaccga    1860
cgagtacatc gccgccaccg gcagcgtgat catcgacggc gaggagtact acttcgaccc    1920
tgacaccgcc cagctggtga tcagcgagta agaattc                              1957
```

<210> SEQ ID NO 21
<211> LENGTH: 2619

<212> TYPE: DNA
<213> ORGANISM: Artificial Sequence
<220> FEATURE:
<223> OTHER INFORMATION: synthetic nucleotide sequence

<400> SEQUENCE: 21

```
tcactgtttt actttgatcc aattgagttt aatctggtga ccggctggca gaccattaat      60
ggcaaaaaat actactttga tattaatacc ggcgccgccc tgaccagcta caaaattatt     120
aatggcaaac acttttactt taataatgat ggcgtgatgc agctgggcgt gtttaaaggc     180
ccagatggct ttgagtactt tgccccagcc aatacccaga ataataatat tgagggccag     240
gccattgtgt accagagcaa atttctgact ttgaatggca aaaaatatta ttttgataat     300
aactcaaaag cagtcactgg atggagaatt attaacaatg agaaatatta ctttaatcct     360
aataatgcta ttgctgcagt cggattgcaa gtaattgaca ataataagta ttatttcaat     420
cctgacactg ctatcatctc aaaaggttgg cagactgtta atggtagtag atactacttt     480
gatactgata ccgctattgc ctttaatggt tataaaacta ttgatggtaa acacttttat     540
tttgatagtg attgtgtagt gaaaataggt gtgtttagta cctctaatgg atttgaatat     600
tttgcacctg ctaatactta taataataac atagaaggtc aggctatagt ttatcaaagt     660
aaattcttaa ctttgaatgg taaaaaatat tactttgata ataactcaaa agcagttacc     720
ggatggcaaa ctattgatag taaaaaatat tactttaata ctaacactgc tgaagcagct     780
actggatggc aaactattga tggtaaaaaa tattacttta atactaacac tgctgaagca     840
gctactggat ggcaaactat tgatggtaaa aaatattact taatactaa cactgctata     900
gcttcaactg gttatacaat tattaatggt aaacattttt attttaatac tgatggtatt     960
atgcagatag gagtgtttaa aggacctaat ggatttgaat attttgcacc tgctaatacg    1020
gatgctaaca acatagaagg tcaagctata ctttaccaaa atgaattctt aactttgaat    1080
ggtaaaaaat attactttgg tagtgactca aaagcagtta ctggatggag aattattaac    1140
aataagaaat attactttaa tcctaataat gctattgctg caattcatct atgcactata    1200
aataatgaca gtattactt tagttatgat ggaattcttc aaaatggata tattactatt    1260
gaaagaaata atttctattt tgatgctaat aatgaatcta aaatggtaac aggagtattt    1320
aaaggaccta atggatttga gtattttgca cctgctaata ctcacaataa taacatagaa    1380
ggtcaggcta tagtttacca gaacaaattc ttaactttga atggcaaaaa atattatttt    1440
gataatgact caaaagcagt tactggatgg caaaccattg atggtaaaaa atattacttt    1500
aatcttaaca ctgctgaagc agctactgga tggcaaacta ttgatggtaa aaaatattac    1560
tttaatctta acactgctga agcagctact ggatggcaaa ctattgatgg taaaaaatat    1620
tactttaata ctaacacttt catagcctca actggttata caagtattaa tggtaaacat    1680
ttttattttg atactgatgg tattatgcag ataggagtgt taaaggacc taatggattt    1740
gaatactttg cacctgctaa tacgatgct aacaacatag aaggtcaagc tatactttac    1800
caaaataaat tcttaacttt gaatggtaaa aaatattact ttggtagtga ctcaaaagca    1860
gttaccggac tgcgaactat tgatggtaaa aaatattact taatactaa cactgctgtt    1920
gcagttactg gatggcaaac tattaatggt aaaaaatact actttaatac taacacttct    1980
atagcttcaa ctggttatac aattattagt ggtaaacatt tttattttaa tactgatggt    2040
attatgcaga taggagtgtt taaaggacct gatggatttg aatactttgc acctgctaat    2100
acagatgcta acaatataga aggtcaagct atacgttatc aaaatagatt cctatattta    2160
```

| | |
|---|---|
| catgacaata tatattattt tggtaataat tcaaaagcgg ctactggttg ggtaactatt | 2220 |
| gatggtaata gatattactt cgagcctaat acagctatgg gtgcgaatgg ttataaaact | 2280 |
| attgataata aaaatttta ctttagaaat ggtttacctc agataggagt gtttaaaggg | 2340 |
| tctaatggat ttgaatactt tgcacctgct aatacggatg ctaacaatat agaaggtcaa | 2400 |
| gctatacgtt atcaaaatag attcctacat ttacttggaa aaatatatta ctttggtaat | 2460 |
| aattcaaaag cagttactgg atggcaaact attaatggta agtatatta ctttatgcct | 2520 |
| gatactgcta tggctgcagc tggtggactt ttcgagattg atggtgttat atatttcttt | 2580 |
| ggtgttgatg gagtaaaagc ccctgggata tatggctaa | 2619 |

<210> SEQ ID NO 22
<211> LENGTH: 2619
<212> TYPE: DNA
<213> ORGANISM: Artificial Sequence
<220> FEATURE:
<223> OTHER INFORMATION: synthetic nucleotide sequence

<400> SEQUENCE: 22

| | |
|---|---|
| tcattattct attttgatcc tatagaattt aacttagtaa ctggatggca aactatcaat | 60 |
| ggtaaaaat attattttga tataaatact ggagcagctt aactagtta taaaattatt | 120 |
| aatggtaaac acttttattt taataatgat ggtgtgatgc agctgggcgt gttcaagggc | 180 |
| cccgacggct tcgagtactt cgcccccgcc aacacccaga caacaacat cgagggccag | 240 |
| gccatcgtgt accagagcaa gttcctgacc ctgaacggca agaagtacta cttcgacaac | 300 |
| aacagcaagg ccgtgaccgg ctggagaatc atcaacaacg agaagtacta cttcaacccc | 360 |
| aacaacgcca tcgccgccgt gggcctgcag gtgatcgaca acaacaagta ctacttcaac | 420 |
| cccgacaccg ccatcatcag caagggctgg cagaccgtga acggcagcag atactacttc | 480 |
| gacaccgaca ccgccatcgc cttcaacggc tacaagacca tcgacggcaa gcacttctac | 540 |
| ttcgacagcg actgcgtggt gaagatcggc gtgttcagca ccagcaacgg cttcgagtac | 600 |
| ttcgcccccg ccaacaccta caacaacaac atcgagggcc aggccatcgt gtaccagagc | 660 |
| aagttcctga ccctgaacgg caaaaaatat tactttgata taactcaaa agcagttacc | 720 |
| ggatggcaaa ctattgatag taaaaaatat tactttaata ctaacactgc tgaagcagct | 780 |
| actggatggc aaactattga tggtaaaaaa tattactttta atactaacac tgctgaagca | 840 |
| gctactggat ggcaaactat tgatggtaaa aaatattact ttaatactaa cactgctata | 900 |
| gcttcaactg ttatacaat tattaatggt aaacattttt attttaatac tgatggtatt | 960 |
| atgcagatag gagtgtttaa aggacctaat ggatttgaat attttgcacc tgctaatacg | 1020 |
| gatgctaaca acatagaagg tcaagctata ctttaccaaa atgaattctt aactttgaat | 1080 |
| ggtaaaaaat attactttgg tagtgactca aaagcagtta ctggatggag aattattaac | 1140 |
| aataagaaat attactttaa tcctaataat gctattgctg caattcatct atgcactata | 1200 |
| aataatgaca agtattactt tagttatgat ggaattcttc aaaatggata tattactatt | 1260 |
| gaaagaaata atttctattt tgatgctaat aatgaatcta aaatggtaac aggagtattt | 1320 |
| aaaggaccta atggatttga gtattttgca cctgctaata ctcacaataa taacatagaa | 1380 |
| ggtcaggcta tagtttacca gaacaaattc ttaactttga atggcaaaaa atattatttt | 1440 |
| gataatgact caaaagcagt tactggatgg caaaccattg atggtaaaaa atattacttt | 1500 |
| aatcttaaca ctgctgaagc agctactgga tggcaaacta ttgatggtaa aaaatattac | 1560 |
| tttaatctta acactgctga agcagctact ggatggcaaa ctattgatgg taaaaaatat | 1620 |

```
tactttaata ctaacacttt catagcctca actggttata caagtattaa tggtaaacat    1680
ttttatttta atactgatgg tattatgcag ataggagtgt ttaaaggacc taatggattt    1740
gaatactttg cacctgctaa tacggatgct aacaacatag aaggtcaagc tatactttac    1800 caaataaat tcttaacttt gaatggtaaa aaatattact ttggtagtga ctcaaaagca     1860
gttaccggac tgcgaactat tgatggtaaa aaatattact ttaatactaa cactgctgtt    1920
gcagttactg gatggcaaac tattaatggt aaaaaatact actttaatac taacacttct    1980
atagcttcaa ctggttatac aattattagt ggtaaacatt tttattttaa tactgatggt    2040
attatgcaga taggagtgtt taaggaccct gatggatttg aatactttgc acctgctaat    2100
acagatgcta acaatataga aggtcaagct atacgttatc aaaatagatt cctatattta    2160
catgacaata tatattattt tggtaataat tcaaaagcgg ctactggttg ggtaactatt    2220
gatggtaata gatattactt cgagcctaat acagctatgg gtgcgaatgg ttataaaact    2280
attgataata aaattttta ctttagaaat ggtttacctc agataggagt gtttaaaggg     2340
tctaatggat ttgaatactt tgcacctgct aatacggatg ctaacaatat agaaggtcaa    2400
gctatacgtt atcaaaatag attcctacat ttacttggaa aaatatatta ctttggtaat    2460
aattcaaaag cagttactgg atggcaaact attaatggta agtatatta ctttatgcct     2520 gatactgcta tggctgcagc tggtggactt ttcgagattg atggtgttat atatttcttt    2580
ggtgttgatg gagtaaaagc ccctgggata tatggctaa                           2619
```

<210> SEQ ID NO 23
<211> LENGTH: 2619
<212> TYPE: DNA
<213> ORGANISM: Artificial Sequence
<220> FEATURE:
<223> OTHER INFORMATION: synthetic nucleotide sequence

<400> SEQUENCE: 23

```
tcattattct attttgatcc tatagaattt aacttagtaa ctggatggca aactatcaat     60
ggtaaaaaat attatttga tataaatact ggagcagctt taactagtta taaaattatt     120
aatggtaaac acttttattt taataatgat ggtgtgatgc agttgggagt atttaaagga    180
cctgatggat ttgaatattt tgcacctgcc aatactcaaa ataataacat agaaggtcag    240
gctatagttt atcaaagtaa attcttaact ttgaatggca aaaaatatta ttttgataat    300
aactcaaaag cagtcactgg atggagaatt attaacaatg agaaatatta ctttaatcct    360
aataatgcta ttgctgcagt cggattgcaa gtaattgaca taataagta ttatttcaat    420 cctgacactg ctatcatctc aaaaggttgg cagactgtta atggtagtag atactacttt    480
gatactgata ccgctattgc ctttaatggt tataaaacta ttgatggtaa acactttta     540 tttgatagtg attgtgtagt gaaaataggt gtgtttagta cctctaatgg atttgaatat    600
tttgcacctg ctaatactta taataataac atagaaggtc aggctatagt ttatcaaagt    660
aaattcctga ccctgaacgg caagaagtac tacttcgata caacagcaa ggccgtgacc     720 ggctggcaga ccatcgatag caagaagtac tacttcaaca ccaacaccgc cgaggccgcc    780
accggctggc agaccatcga tggcaagaag tactacttca caccaacac cgccgaggcc    840 gccaccggct ggcagaccat cgatggcaag aagtactact tcaacaccaa caccgccatc    900
gccagcaccg gctacaccat catcaacggc aagcacttct acttcaacac cgatggcatc    960
atgcagatcg gcgtgttcaa gggccccaac ggcttcgagt acttcgcccc cgccaacacc   1020
```

```
gatgccaaca acatcgaggg ccaggccatc ctgtaccaga acgagttcct gaccctgaac    1080
ggcaagaagt actacttcgg cagcgatagc aaggccgtga ccggctggag aatcatcaac    1140
aacaagaagt actacttcaa ccccaacaac gccatcgccg ccatccacct gtgcaccatc    1200
aacaacgata agtactactt cagctacgat ggcatcctgc agaacggcta catcaccatc    1260
gagagaaaca acttctactt cgatgccaac aacgagagca agatggtgac cggcgtgttc    1320
aagggcccca acggcttcga gtacttcgcc cccgccaaca cccacaacaa caacatcgag    1380
ggccaggcca tcgtgtacca gaacaagttc ctgaccctga acggcaagaa gtactacttc    1440
gataacgata gcaaggccgt tactggatgg caaaccattg atggtaaaaa atattacttt    1500
aatcttaaca ctgctgaagc agctactgga tggcaaacta ttgatggtaa aaaatattac    1560
tttaatctta acactgctga agcagctact ggatggcaaa ctattgatgg taaaaaatat    1620
tactttaata ctaacacttt catagcctca actggttata caagtattaa tggtaaacat    1680
ttttatttta atactgatgg tattatgcag ataggagtgt ttaaaggacc taatggattt    1740
gaatactttg cacctgctaa tacggatgct aacaacatag aaggtcaagc tatactttac    1800
caaaataaat tcttaacttt gaatggtaaa aatattactt tggtagtga ctcaaaagca    1860 gttaccggac tgcgaactat tgatggtaaa aatattactt taatactaa cactgctgtt    1920 gcagttactg gatggcaaac tattaatggt aaaaaatact actttaatac taacacttct    1980
atagcttcaa ctggttatac aattattagt ggtaaacatt tttattttaa tactgatggt    2040
attatgcaga taggagtgtt taaaggacct gatggatttg aatactttgc acctgctaat    2100
acagatgcta acaatataga aggtcaagct atacgttatc aaaatagatt cctatattta    2160
catgacaata tatattattt tggtaataat tcaaaagcgg ctactggttg ggtaactatt    2220
gatggtaata gatattactt cgagcctaat acagctatgg gtgcgaatgg ttataaaact    2280
attgataata aaattttta ctttagaaat ggtttacctc agataggagt gtttaagggg    2340
tctaatggat ttgaatactt tgcacctgct aatacggatg ctaacaatat agaaggtcaa    2400
gctatacgtt atcaaaatag attcctacat ttacttggaa aaatatatta ctttggtaat    2460
aattcaaaag cagttactgg atggcaaact attaatggta agtatatta ctttatgcct    2520 gatactgcta tggctgcagc tggtggactt ttcgagattg atggtgttat atatttctttt   2580 ggtgttgatg agtaaaaagc ccctgggata tatggctaa                           2619

<210> SEQ ID NO 24
<211> LENGTH: 2619
<212> TYPE: DNA
<213> ORGANISM: Artificial Sequence
<220> FEATURE:
<223> OTHER INFORMATION: synthetic nucleotide sequence

<400> SEQUENCE: 24
tcattattct attttgatcc tatagaattt aacttagtaa ctggatggca aactatcaat      60
ggtaaaaaat attattttga tataaatact ggagcagctt taactagtta taaaattatt     120
aatggtaaac acttttattt taataatgat ggtgtgatgc agttgggagt atttaaagga     180
cctgatggat ttgaatattt tgcacctgcc aatactcaaa ataataacat agaaggtcag     240
gctatagttt atcaaagtaa attcttaact ttgaatggca aaaaatatta ttttgataat     300
aactcaaaag cagtcactgg atggagaatt attaacaatg agaaatatta ctttaatcct     360
aataatgcta ttgctgcagt cggattgcaa gtaattgaca ataataagta ttatttcaat     420
cctgacactg ctatcatctc aaaaggttgg cagactgtta atggtagtag atactacttt     480
```

```
gatactgata ccgctattgc ctttaatggt tataaaacta ttgatggtaa acacttttat      540
tttgatagtg attgtgtagt gaaaataggt gtgtttagta cctctaatgg atttgaatat      600
tttgcacctg ctaatactta taataataac atagaaggtc aggctatagt ttatcaaagt      660
aaattcttaa ctttgaatgg taaaaaatat tactttgata taaactcaaa agcagttacc      720
ggatggcaaa ctattgatag taaaaaatat tactttaata ctaacactgc cgaggccgcc      780
accggctggc agaccatcga cggcaagaag tactacttca acaccaacac cgccgaggcc      840
gccaccggct ggcagaccat cgacggcaag aagtactact tcaacaccaa caccgccatc      900
gccagcaccg gctacaccat catcaacggc aagcatttct acttcaacac cgacggcatc      960
atgcagatcg gcgtgttcaa gggcccaaac ggcttcgagt acttcgcccc agccaacacc     1020
gacgccaaca catcgagggc caggccatc ctgtaccaga cgagttcct gaccctgaac       1080 ggcaagaagt actacttcgg cagcgacagc aaggccgtga ccggctggag aatcatcaac     1140
aacaagaagt actacttcaa cccaaacaac gccatcgccg ccatccatct gtgcaccatc     1200
aacaacgaca gtactactt cagctacgac ggcatcctgc agaacggcta catcaccatc      1260
gagagaaaca acttctactt cgacgccaac aacgagagca agatggtgac cggcgtgttc     1320
aagggcccaa acggcttcga gtacttcgcc ccagccaaca cccataacaa caacatcgag     1380
ggccaggcca tcgtgtacca gaacaagttc ctgaccctga acggcaagaa gtactacttc     1440
gacaacgaca gcaaggccgt gaccggctgg cagaccatcg acggcaagaa gtactacttc     1500
aacctgaaca ccgccgaggc cgccaccggc tggcagacca tcgacggcaa gaagtactac     1560
ttcaacctga caccgccga ggccgccacc ggctggcaga ccatcgacgg caagaagtac      1620
tacttcaaca ccaacacctt catcgccagc accggctaca ccagcatcaa cggcaagcat     1680
ttctacttca acaccgacgg catcatgcag atcggcgtgt tcaagggccc aaacggcttc     1740
gagtacttcg ccccagccaa caccgacgcc aacaacatcg agggccaggc catcctgtac     1800
cagaacaagt tcctgaccct gaacggtaaa aaatattact ttggtagtga ctcaaaagca     1860
gttaccggac tgcgaactat tgatggtaaa aaatattact ttaatactaa cactgctgtt     1920
gcagttactg gatggcaaac tattaatggt aaaaaatact actttaatac taacacttct     1980
atagcttcaa ctggttatac aattattagt ggtaaacatt tttattttaa tactgatggt     2040
attatgcaga taggagtgtt taaaggacct gatggatttg aatactttgc acctgctaat     2100
acagatgcta acaatataga aggtcaagct atacgttatc aaaatagatt cctatattta     2160
catgacaata tatattattt tggtaataat tcaaaagcgg ctactggttg ggtaactatt     2220
gatggtaata gatattactt cgagcctaat acagctatgg gtgcgaatgg ttataaaact     2280
attgataata aaaattttta ctttagaaat ggtttacctc agataggagt gtttaaaggg     2340
tctaatggat ttgaatactt tgcacctgct aatacggatg ctaacaatat agaaggtcaa     2400
gctatacgtt atcaaaatag attcctacat ttacttggaa aaatatatta ctttggtaat     2460
aattcaaaag cagttactgg atggcaaact attaatggta agtatatta ctttatgcct      2520 gatactgcta tggctgcagc tggtggactt ttcgagattg atggtgttat atatttctt      2580 ggtgttgatg gagtaaaagc ccctgggata tatggctaa                            2619

<210> SEQ ID NO 25
<211> LENGTH: 2619
<212> TYPE: DNA
<213> ORGANISM: Artificial Sequence
<220> FEATURE:
```

<223> OTHER INFORMATION: synthetic nucleotide sequence

<400> SEQUENCE: 25

```
tcattattct attttgatcc tatagaattt aacctggtga ccggctggca gaccatcaac    60
ggcaagaagt actacttcga catcaacacc ggcgccgccc tgaccagcta caagatcatc   120
aacggcaagc atttctactt caacaacgac ggcgtgatgc agctgggcgt gttcaagggc   180
cctgacggct tcgagtactt cgcccctgcc aacacccaga caacaacat cgagggccag    240
gccatcgtgt accagagcaa gttcctgacc ctgaacggca agaagtacta cttcgacaac   300
aacagcaagg ccgtgaccgg ctggagaatc atcaacaacg agaagtacta cttcaaccct   360
aacaacgcca tcgccgccgt gggcctgcag gtgatcgaca acaacaagta ctacttcaac   420
cctgacaccg ccatcatcag caagggctgg cagaccgtga acggcagcag atactacttc   480
gacaccgaca ccgccatcgc cttcaacggc tacaagacca tcgacggcaa gcatttctac   540
ttcgacagcg actgtgtggt gaagatcggc gtgttcagca ccagcaacgg cttcgagtac   600
ttcgcccctg ccaacaccta caacaacaac atcgagggcc aggccatcgt gtaccagagc   660
aagttcctga ccctgaacgg caagaagtac tacttcgaca acaacagcaa ggccgtgacc   720
ggctggcaga ccatcgacag caagaagtac tacttcaaca ccaacaccgc cgaggccgcc   780
accggctggc agaccatcga cggcaagaag tactacttca acaccaacac cgccgaggcc   840
gccaccggct ggcagaccat cgacggcaag aagtactact tcaacaccaa caccgccatc   900
gccagcaccg gctacaccat catcaacggc aagcatttct acttcaacac cgacggcatc   960
atgcagatcg gcgtgttcaa gggccctaac ggcttcgagt acttcgcccc tgccaacacc  1020
gacgccaaca acatcgaggg ccaggccatc ctgtaccaga cgagttcct gaccctgaac    1080
ggcaagaagt actacttcgg cagcgacagc aaggccgtga ccggctggag aatcatcaac  1140
aacaagaagt actacttcaa ccctaacaac gccatcgccg ccatccatct gtgtaccatc  1200
aacaacgaca gtactactt cagctacgac ggcatcctgc agaacggcta catcaccatc   1260
gagagaaaca acttctactt cgacgccaac aacgagagca agatggtgac cggcgtgttc  1320
aagggcccta acggcttcga gtacttcgcc cctgctaata ctcacaataa taacatagaa  1380
ggtcaggcta tagtttacca gaacaaattc ttaactttga atggcaaaaa atattatttt  1440
gataatgact caaaagcagt tactggatgg caaaccattg atggtaaaaa atattacttt  1500
aatcttaaca ctgctgaagc agctactgga tggcaaacta ttgatggtaa aaaatattac  1560
tttaatctta acactgctga agcagctact ggatggcaaa ctattgatgg taaaaaatat  1620
tactttaata ctaacacttt catagcctca actggttata caagtattaa tggtaaacat  1680
ttttatttta atactgatgg tattatgcag ataggagtgt ttaaaggacc taatggattt  1740
gaatactttg cacctgctaa tacggatgct aacaacatag aaggtcaagc tatactttac  1800
caaaataaat tcttaacttt gaatggtaaa aatattact ttggtagtga ctcaaaagca   1860
gttaccggac tgcgaactat tgatggtaaa aaatattact ttaatactaa cactgctgtt  1920
gcagttactg gatggcaaac tattaatggt aaaaaatact actttaatac taacacttct  1980
atagcttcaa ctggttatac aattattagt ggtaaacatt tttattttaa tactgatggt  2040
attatgcaga taggagtgtt taaaggacct gatggatttg aatactttgc acctgctaat  2100
acagatgcta acaatataga aggtcaagct atacgttatc aaaatagatt cctatattta  2160
catgacaata tatattattt tggtaataat tcaaaagcgg ctactggttg gtaactatt   2220
gatggtaata gatattactt cgagcctaat acagctatgg gtgcgaatgg ttataaaact  2280
```

```
attgataata aaaatttta ctttagaaat ggtttacctc agataggagt gtttaaaggg     2340
tctaatggat ttgaatactt tgcacctgct aatacggatg ctaacaatat agaaggtcaa    2400
gctatacgtt atcaaaatag attcctacat ttacttggaa aaatatatta ctttggtaat    2460
aattcaaaag cagttactgg atggcaaact attaatggta aagtatatta ctttatgcct    2520
gatactgcta tggctgcagc tggtggactt ttcgagattg atggtgttat atatttcttt    2580
ggtgttgatg gagtaaaagc ccctgggata tatggctaa                           2619
```

<210> SEQ ID NO 26
<211> LENGTH: 2619
<212> TYPE: DNA
<213> ORGANISM: Artificial Sequence
<220> FEATURE:
<223> OTHER INFORMATION: synthetic nucleotide sequence

<400> SEQUENCE: 26

```
tcattattct attttgatcc tatagaattt aacttagtaa ctggatggca aactatcaat      60
ggtaaaaaat attattttga tataaatact ggagcagctt aactagtta taaaattatt      120 aatggtaaac acttttattt taataatgat ggtgtgatgc agttgggagt atttaaagga     180
cctgatggat ttgaatattt tgcacctgcc aatactcaaa ataataacat agaaggtcag     240
gctatagttt atcaaagtaa attcttaact ttgaatggca aaaaatatta ttttgataat     300
aactcaaaag cagtcactgg atggagaatt attaacaatg agaaatatta ctttaatcct    360
aataatgcta ttgctgcagt cggattgcaa gtaattgaca ataataagta ttatttcaac    420
cctgacaccg ccatcatcag caagggctgg cagaccgtga acggcagcag atactacttc    480
gacaccgaca ccgccatcgc cttcaacggc tacaagacca tcgacggcaa gcacttctac    540
ttcgacagcg actgtgtggt gaagatcggc gtgttcagca ccagcaacgg cttcgagtac    600
ttcgcccctg ccaacaccta caacaacaac atcgagggcc aggccatcgt gtaccagagc    660
aagttcctga ccctgaacgg caagaagtac tacttcgaca caacagcaa ggccgtgacc     720 ggctggcaga ccatcgacag caagaagtac tacttcaaca ccaacaccgc cgaggccgcc    780
accggctggc agaccatcga cggcaagaag tactacttca caccaacac cgccgaggcc    840 gccaccggct ggcagaccat cgacggcaag agtactact tcaacaccaa caccgccatc     900
gccagcaccg gctacaccat catcaacggc aagcacttct acttcaacac cgacggcatc    960
atgcagatcg gcgtgttcaa gggccctaac ggcttcgagt acttcgcccc tgccaacacc   1020
gacgccaaca acatcgaggg ccaggccatc ctgtaccaga cgagttcct gaccctgaac    1080 ggcaagaagt actacttcgg cagcgacagc aaggccgtga ccggctggag aatcatcaac    1140
aacaagaagt actacttcaa ccctaacaac gccatcgccg ccatccacct gtgtaccatc    1200
aacaacgaca gtactactt cagctacgac ggcatcctgc agaacggcta catcaccatc    1260
gagagaaaca acttctactt cgacgccaac aacgagagca agatggtgac cggcgtgttc    1320
aagggcccta acggcttcga gtacttcgcc cctgccaaca cccacaacaa caacatcgag   1380
ggccaggcca tcgtgtacca gaacaagttc ctgaccctga acggcaagaa gtactacttc   1440
gacaacgaca gcaaggccgt gaccggctgg cagaccatcg acggcaagaa gtactacttc   1500
aacctgaaca ccgccgaggc cgccaccggc tggcagacca tcgacggcaa gaagtactac   1560
ttcaacctga caccgccga ggccgccacc ggctggcaga ccatcgacgg caagaagtac    1620
tacttcaaca ccaacaccct tcatcgccagc accggctaca ccagcatcaa cggcaagcac    1680
```

| ttctacttca acaccgacgg catcatgcag atcggcgtgt tcaagggccc taacggcttc | 1740 |
| gagtacttcg cccctgccaa caccgacgcc aacaacatcg agggccaggc catcctgtac | 1800 |
| cagaacaagt tcctgaccct gaacggcaag aagtactact tcggcagcga cagcaaggcc | 1860 |
| gtgaccggcc tgagaaccat cgacggcaag aagtactact tcaacaccaa caccgccgtg | 1920 |
| gccgtgaccg gctggcagac catcaacggc aagaagtact acttcaacac caacaccagc | 1980 |
| atcgccagca ccggctacac aattattagt ggtaaacatt tttattttaa tactgatggt | 2040 |
| attatgcaga taggagtgtt taaaggacct gatggatttg aatactttgc acctgctaat | 2100 |
| acagatgcta acaatataga aggtcaagct atacgttatc aaaatagatt cctatattta | 2160 |
| catgacaata tatattattt tggtaataat tcaaaagcgg ctactggttg ggtaactatt | 2220 |
| gatggtaata gatattactt cgagcctaat acagctatgg gtgcgaatgg ttataaaact | 2280 |
| attgataata aaaattttta ctttagaaat ggtttacctc agataggagt gtttaaaggg | 2340 |
| tctaatggat ttgaatactt tgcacctgct aatacggatg ctaacaatat agaaggtcaa | 2400 |
| gctatacgtt atcaaaatag attcctacat ttacttggaa aaatatatta ctttggtaat | 2460 |
| aattcaaaag cagttactgg atggcaaact attaatggta agtatatta ctttatgcct | 2520 |
| gatactgcta tggctgcagc tggtggactt ttcgagattg atggtgttat atatttctttt | 2580 |
| ggtgttgatg gagtaaaagc ccctgggata tatggctaa | 2619 |

<210> SEQ ID NO 27
<211> LENGTH: 2618
<212> TYPE: DNA
<213> ORGANISM: Artificial Sequence
<220> FEATURE:
<223> OTHER INFORMATION: synthetic nucleotide sequence

<400> SEQUENCE: 27

| tcattattct attttgatcc tatagaattt aacttagtaa ctggatggca aactatcaat | 60 |
| ggtaaaaaat attattttga tataaatact ggagcagctt taactagtta taaaattatt | 120 |
| aatggtaaac acttttattt taataatgat ggtgtgatgc agttgggata tttaaaggac | 180 |
| ctgatggatt tgaatatttt gcacctgcca atactcaaaa taataacatc gagggccagg | 240 |
| ccatcgtgta ccagagcaag ttcctgaccc tgaacggcaa gaagtactac ttcgacaaca | 300 |
| acagcaaggc cgtgaccggc tggagaatca tcaacaacga gaagtactac ttcaacccca | 360 |
| acaacgccat cgccgccgtg ggcctgcagg tgatcgacaa caacaagtac tacttcaacc | 420 |
| ccgacaccgc catcatcagc aagggctgga gaccgtgaa cggcagcaga tactacttcg | 480 |
| acaccgacac cgccatcgcc ttcaacggct acaagaccat cgacggcaag catttctact | 540 |
| tcgacagcga ctgtgtggtg aagatcggcg tgttcagcac cagcaacggc ttcgagtact | 600 |
| tcgcccccgc caacacctac aacaacaaca tcgagggcca ggccatcgtg taccagagca | 660 |
| agttcctgac cctgaacggc aagaagtact acttcgacaa caacagcaag gccgtgaccg | 720 |
| gctggcagac catcgacagc aagaagtact acttcaacac caacaccgcc gaggccgcca | 780 |
| ccggctggca gaccatcgac ggcaagaagt actacttcaa caccaacacc gccgaggccg | 840 |
| ccaccggctg gcagaccatc gacggcaaga agtactactt caacaccaac accgccatcg | 900 |
| ccagcaccgg ctacaccatc atcaacggca gcatttctca cttcaacacc gacggcatca | 960 |
| tgcagatcgg cgtgttcaag ggccccaacg gcttcgagta cttcgccccc gccaacaccg | 1020 |
| acgccaacaa catcgagggc caggccatcc tgtaccagag cgagttcctg accctgaacg | 1080 |
| gcaagaagta ctacttcggc agcgacagca aggccgtgac cggctggaga atcatcaaca | 1140 |

```
acaagaagta ctacttcaac cccaacaacg ccatcgccgc catccatctg tgtaccatca    1200
acaacgacaa gtactacttc agctacgacg gcatcctgca gaacggctac atcaccatcg    1260
agagaaacaa cttctacttc gacgccaaca acgagagcaa gatggtgacc ggcgtgttca    1320
agggccccaa cggcttcgag tacttcgccc ccgccaacac cctaacaac aacatcgagg     1380 gccaggccat cgtgtaccag aacaagttcc tgaccctgaa cggcaagaag tactacttcg    1440
acaacgacag caaggccgtg accggctggc agaccatcga cggcaagaag tactacttca    1500
acctgaacac cgccgaggcc gccaccggct ggcagaccat cgacggcaag aagtactact    1560
tcaacctgaa caccgccgag gccgccaccg gctggcagac catcgacggc aagaagtact    1620
acttcaacac caacaccttc atcgccagca ccggctacac cagcatcaac ggcaagcatt    1680
tctacttcaa caccgacggc atcatgcaga tcggcgtgtt caagggcccc aacggcttcg    1740
agtacttcgc ccccgccaac accgacgcca acaacatcga gggccaggcc atcctgtacc    1800
agaacaagtt cctgaccctg aacgcaaga agtactactt cggcagcgac agcaaggccg    1860
tgaccggcct gagaaccatc gacggcaaga agtactactt caacaccaac accgccgtgg    1920
ccgtgaccgg ctggcagacc atcaacggca agaagtacta cttcaacacc aacaccagca    1980
tcgccagcac cggctacacc atcatcagcg gcaagcattt ctacttcaac accgacggca    2040
tcatgcagat cggcgtgttc aagggccccg acggatttga atactttgca cctgctaata    2100
cagatgctaa caatatagaa ggtcaagcta tacgttatca aaatagattc ctatatttac    2160 atgcacaatat atattatttt ggtaataatt caaaagcggc tactggttgg gtaactattg    2220
atggtaatag atattacttc gagcctaata cagctatggg tgcgaatggt tataaaacta    2280
ttgataataa aaattttac tttagaaatg gtttacctca gataggagtg tttaaagggt      2340
ctaatggatt tgaatacttt gcacctgcta atacggatgc taacaatata gaaggtcaag    2400
ctatacgtta tcaaaataga ttcctacatt tacttggaaa aatatattac tttggtaata    2460
attcaaaagc agttactgga tggcaaacta ttaatggtaa agtatattac tttatgcctg    2520
atactgctat ggctgcagct ggtggacttt cgagattga tggtgttata tatttctttg     2580
gtgttgatgg agtaaaagcc cctgggatat atggctaa                            2618
```

<210> SEQ ID NO 28
<211> LENGTH: 2619
<212> TYPE: DNA
<213> ORGANISM: Artificial Sequence
<220> FEATURE:
<223> OTHER INFORMATION: synthetic nucleotide sequence

<400> SEQUENCE: 28

```
tcattattct attttgatcc tatagaattt aacttagtaa ctggatggca aactatcaat     60
ggtaaaaaat attattttga tataaatact ggagcagctt aactagtta taaaattatt     120 aatggtaaac acttttattt taataatgat ggtgtgatgc agttgggagt atttaaagga    180
cctgatggat ttgagtactt cgccccagcc aacacccaga caacaacat cgagggccag     240 gccatcgtgt accagagcaa gttcctgacc ctgaacggca agaagtacta cttcgacaac    300
aacagcaagg ccgtgaccgg ctggagaatc atcaacaacg agaagtacta cttcaaccca    360
aacaacgcca tcgccgccgt gggcctgcag gtgatcgaca acaacaagta ctacttcaac    420
ccagacaccg ccatcatcag caagggctgg cagaccgtga acggcagcag atactacttc    480
gacaccgaca ccgccatcgc cttcaacggc tacaagacca tcgacggcaa gcacttctac    540
```

```
ttcgacagcg actgtgtggt gaagatcggc gtgttcagca ccagcaacgg cttcgagtac      600
ttcgccccag ccaacaccta caacaacaac atcgagggcc aggccatcgt gtaccagagc      660
aagttcctga ccctgaacgg caagaagtac tacttcgaca caacagcaa ggccgtgacc       720 ggctggcaga ccatcgacag caagaagtac tacttcaaca ccaacaccgc cgaggccgcc      780
accggctggc agaccatcga cggcaagaag tactacttca caccaacac cgccgaggcc       840 gccaccggct ggcagaccat cgacggcaag aagtactact tcaacaccaa caccgccatc      900
gccagcaccg gctacaccat catcaacggc aagcacttct acttcaacac cgacggcatc      960
atgcagatcg gcgtgttcaa gggcccaaac ggcttcgagt acttcgcccc agccaacacc      1020
gacgccaaca acatcgaggg ccaggccatc ctgtaccaga cgagttcct gaccctgaac        1080 ggcaagaagt actacttcgg cagcgacagc aaggccgtga ccggctggag aatcatcaac      1140
aacaagaagt actacttcaa cccaaacaac gccatcgccg ccatccacct gtgtaccatc      1200
aacaacgaca gtactactt cagctacgac ggcatcctgc agaacggcta catcaccatc       1260
gagagaaaca acttctactt cgacgccaac aacgagagca gatggtgac cggcgtgttc       1320 aagggcccaa acggcttcga gtacttcgcc ccagccaaca cccacaacaa caacatcgag      1380
ggccaggcca tcgtgtacca gaacaagttc ctgaccctga cggcaagaa gtactacttc       1440 gacaacgaca gcaaggccgt gaccggctgg cagaccatcg acggcaagaa gtactacttc      1500
aacctgaaca ccgccgaggc cgccaccggc tggcagacca tcgacggcaa gaagtactac      1560
ttcaacctga caccgccga ggccgccacc ggctggcaga ccatcgacgg caagaagtac       1620
tacttcaaca ccaacacctt catcgccagc accggctaca ccagcatcaa cggcaagcac      1680
ttctacttca caccgacgg catcatgcag atcggcgtgt tcaagggccc aaacggcttc       1740
gagtacttcg ccccagccaa caccgacgcc aacaacatcg agggccaggc catcctgtac      1800
cagaacaagt tcctgacccct gaacggcaag aagtactact tcggcagcga cagcaaggcc     1860
gtgaccggcc tgagaaccat cgacggcaag aagtactact tcaacaccaa caccgccgtg      1920
gccgtgaccg gctggcagac catcaacggc aagaagtact acttcaacac caacaccagc      1980
atcgccagca ccggctacac catcatcagc ggcaagcact tctacttcaa caccgacggc      2040
atcatgcaga tcggcgtgtt caagggccca gacggcttcg agtacttcgc cccagccaac      2100
accgacgcca acatcga gggccaggcc atcagatacc agaacagatt cctgtacctg         2160
cacgacaaca tctactactt cggcaacaac agcaaggccg ccaccggctg ggtgaccatc      2220
gacggcaaca gatactactt cgagccaaac accgccatgg cgccaacgg ctacaagacc       2280 atcgacaaca agaacttcta cttcagaaat ggtttacctc agataggagt gtttaaaggg      2340
tctaatggat ttgaatactt tgcacctgct aatacggatg ctaacaatat agaaggtcaa      2400
gctatacgtt atcaaaatag attcctacat ttacttggaa aaatatatta ctttggtaat      2460
aattcaaaag cagttactgg atggcaaact attaatggta agtatatta ctttatgcct        2520 gatactgcta tggctgcagc tggtggactt ttcgagattg atggtgttat atatttcttt      2580
ggtgttgatg gagtaaaagc ccctgggata tatggctaa                             2619
```

<210> SEQ ID NO 29
<211> LENGTH: 2619
<212> TYPE: DNA
<213> ORGANISM: Artificial Sequence
<220> FEATURE:
<223> OTHER INFORMATION: synthetic nucleotide sequence

<400> SEQUENCE: 29

-continued

```
tcattattct attttgaccc catcgagttc aacctggtga ccggctggca gaccatcaac     60
ggcaagaagt actacttcga catcaacacc ggcgccgccc tgaccagcta caagatcatc    120
aacggcaagc acttctactt caacaacgac ggcgtgatgc agctgggcgt gttcaagggc    180
cccgacggct tcgagtactt cgcccccgcc aacacccaga caacaacat cgagggccag     240
gccatcgtgt accagagcaa gttcctgacc ctgaacggca agaagtacta cttcgacaac    300
aacagcaagg ccgtgaccgg ctggagaatc atcaacaacg agaagtacta cttcaacccc    360
aacaacgcca tcgccgccgt gggcctgcag gtgatcgaca caacaagta ctacttcaac     420
cccgacaccg ccatcatcag caagggctgg cagaccgtga acggcagcag atactacttc    480
gacaccgaca ccgccatcgc cttcaacggc tacaagacca tcgacggcaa gcacttctac    540
ttcgacagcg actgtgtggt gaagatcggc gtgttcagca ccagcaacgg cttcgagtac    600
ttcgcccccg ccaacaccta caacaacaac atcgagggcc aggccatcgt gtaccagagc    660
aagttcctga ccctgaacgg caagaagtac tacttcgaca acaacagcaa ggccgtgacc    720
ggctggcaga ccatcgacag caagaagtac tacttcaaca ccaacaccgc cgaggccgcc    780
accggctggc agaccatcga cggcaagaag tactacttca acaccaacac cgccgaggcc    840
gccaccggct ggcagaccat cgacggcaag aagtactact tcaacaccaa caccgccatc    900
gccagcaccg gctacaccat catcaacggc aagcacttct acttcaacac cgacggcatc    960
atgcagatcg gcgtgttcaa gggccccaac ggcttcgagt acttcgcccc cgccaacacc   1020
gacgccaaca catcgaggg ccaggccatc ctgtaccaga cgagttcct gaccctgaac     1080
ggcaagaagt actacttcgg cagcgacagc aaggccgtga ccggctggag aatcatcaac   1140
aacaagaagt actacttcaa ccccaacaac gccatcgccg ccatccacct gtgtaccatc   1200
aacaacgaca agtactactt cagctacgac ggcatcctgc agaacggcta catcaccatc   1260
gagagaaaca acttctactt cgacgccaac aacgagagca agatggtgac cggcgtgttc   1320
aagggcccca acggcttcga gtacttcgcc cccgccaaca cccacaacaa caacatcgag   1380
ggccaggcca tcgtgtacca gaacaagttc ctgaccctga acggcaagaa gtactacttc   1440
gacaacgaca gcaaggccgt gaccggctgg cagaccatcg acggcaagaa gtactacttc   1500
aacctgaaca ccgccgaggc cgccaccggc tggcagacca tcgacggcaa gaagtactac   1560
ttcaacctga caccgccga ggccgccacc ggctggcaga ccatcgacgg caagaagtac   1620
tacttcaaca ccaacacctt catcgccagc accggctaca ccagcatcaa cggcaagcac   1680
ttctacttca acaccgacgg catcatgcag atcggcgtgt tcaagggccc caacggcttc   1740
gagtacttcg cccccgccaa caccgacgcc aacaacatcg agggccaggc catcctgtac   1800
cagaacaagt tcctgaccct gaacggcaag aagtactact tcggcagcga cagcaaggcc   1860
gtgaccggcc tgagaaccat cgacggcaag aagtactact tcaacaccaa caccgccgtg   1920
gccgtgaccg gctggcagac catcaacggc aagaagtact acttcaacac caacaccagc   1980
atcgccagca ccggctacac catcatcagc ggcaagcact tctacttcaa caccgacggc   2040
atcatgcaga tcggcgtgtt caagggcccc gacggcttcg agtacttcgc ccccgccaac   2100
accgacgcca caacatcga gggccaggcc atcagatacc agaacagatt cctgtacctg   2160
cacgacaaca tctactactt cggcaacaac agcaaggccg ccaccggctg ggtgaccatc   2220
gacggcaaca gatactactt cgagcccaac accgccatgg cgccaacgg ctacaagacc   2280
atcgacaaca agaacttcta cttcagaaac ggcctgcccc agatcggcgt gttcaagggc   2340
```

| agcaacggct tcgagtactt cgcccccgcc aacaccgacg ccaacaacat cgaaggtcaa | 2400 |
| gctatacgtt atcaaaatag attcctacat ttacttggaa aaatatatta ctttggtaat | 2460 |
| aattcaaaag cagttactgg atggcaaact attaatggta aagtatatta ctttatgcct | 2520 |
| gatactgcta tggctgcagc tggtggactt ttcgagattg atggtgttat atatttcttt | 2580 |
| ggtgttgatg gagtaaaagc ccctgggata tatggctaa | 2619 |

<210> SEQ ID NO 30
<211> LENGTH: 1839
<212> TYPE: DNA
<213> ORGANISM: Artificial Sequence
<220> FEATURE:
<223> OTHER INFORMATION: synthetic nucleotide sequence

<400> SEQUENCE: 30

| agtgaagaaa ataaggtgtc acaagttaaa ataagattcg ttaatgtttt taaagataag | 60 |
| actttggcaa ataagctatc ttttaacttt agtgataaac aagatgtacc tgtaagtgaa | 120 |
| ataatcttat catttacacc ttcatattat gaggatggat tgattggcta tgatttgggt | 180 |
| ctagtttctt tatataatga gaaattttat attaataact ttggaatgat ggtatctgga | 240 |
| ttaatatata ttaatgattc attatattat tttaaaccac cagtaaataa tttgataact | 300 |
| ggatttgtga ctgtaggcga tgataaatac tactttaatc caattaatgg tggagctgct | 360 |
| tcaattggag agacaataat tgatgacaaa aattattatt caaccaaag tggagtgtta | 420 |
| caaacaggtg tatttagtac agaagatgga tttaaatatt ttgccccagc taatacactt | 480 |
| gatgaaaacc tagaaggaga agcaattgat tttactggaa aattaattat tgacgaaaat | 540 |
| atttattatt ttgatgataa ttatagagga gctgtagaat ggaaagaatt agatggtgaa | 600 |
| atgcactatt ttagcccaga aacaggtaaa gcttttaaag gtctaaatca ataggtgat | 660 |
| tataaatact atttcaattc tgatggagtt atgcaaaaag gatttgttag tataaatgat | 720 |
| aataaacact attttgatga ttctggtgtt atgaaagtag gttacactga aatagatggc | 780 |
| aagcatttct actttgctga aaacggagaa atgcaaatag gagtatttaa tacagaagat | 840 |
| ggatttaaat attttgctca tcataatgaa gatttaggaa atgaagaagg tgaagaaatc | 900 |
| tcatattctg gtatattaaa tttcaataat aaaatttact attttgatga ttcatttaca | 960 |
| gctgtagttg gatggaaaga tttagaggat ggttcaaagt attattttga tgaagataca | 1020 |
| gcagaagcat ataggtttt gtcattaata aatgatggtc aatattattt taatgatgat | 1080 |
| ggaatcatgc aggtgggatt tgtgacaatc aatgataaag tgttttactt tagcgatagc | 1140 |
| ggaatcatcg agagcggagt gcagaatatc gatgataatt acttttacat cgatgataat | 1200 |
| ggaatcgtgc agatcggagt gtttgataca agcgatggat acaaatactt tgctcccgct | 1260 |
| aatactgtaa atgataatat ttacggacaa gcagttgaat atagtggttt agttagagtt | 1320 |
| ggggaagatg tatattattt tggagaaaca tatacaattg agactggatg gatatatgat | 1380 |
| atggaaaatg aaagtgataa atattatttc aatccagaaa ctaaaaaagc atgcaaaggt | 1440 |
| attaatttaa ttgatgatat aaaatattat tttgatgaga agggcataat gagaacgggt | 1500 |
| cttatatcat ttgaaaataa taattattac tttaatgaga atggtgaaat gcaatttggt | 1560 |
| tatataaata tagaagataa gatgttctat tttggtgaag atggtgtcat gcagattgga | 1620 |
| gtatttaata caccagatgg atttaaatac tttgcacatc aaaatacttt ggatgagaat | 1680 |
| tttgagggag aatcaataaa ctatactggt tggttagatt tagatgaaaa gagatattat | 1740 |
| tttacagatg aatatattgc agcaactggt tcagttatta ttgatggtga ggagtattat | 1800 |

```
tttgatcctg atacagctca attagtgatt agtgaatag                              1839

<210> SEQ ID NO 31
<211> LENGTH: 1839
<212> TYPE: DNA
<213> ORGANISM: Artificial Sequence
<220> FEATURE:
<223> OTHER INFORMATION: synthetic nucleotide sequence

<400> SEQUENCE: 31
agtgaagaaa ataaggtgag ccaagtgaag atcagatttg tgaacgtgtt taaggataag        60
accctggcaa acaagctgag ctttaacttt agcgataagc aagatgtgcc cgtgagcgaa       120
atcatcctga gctttacccc cagctactac gaagatggac tgatcggata cgatctggga       180
ctggtgagcc tgtacaacga aaagttttac atcaacaact tggaatgat ggtgagcgga       240
ctgatctaca tcaacgatag cctgtactac tttaagcccc ccgtgaacaa cctgatcacc       300
ggatttgtga ccgtgggaga tgataagtac tactttaacc ccatcaacgg aggagcagca       360
agcatcggag aaaccatcat cgatgataaa aattattatt caaccaaag tggagtgtta        420
caaacaggtg tatttagtac agaagatgga tttaaatatt tgccccagc taatacactt        480
gatgaaaacc tagaaggaga agcaattgat tttactggaa aattaattat tgacgaaaat       540
atttattatt ttgatgataa ttatagagga gctgtagaat ggaaagaatt agatggtgaa       600
atgcactatt ttagcccaga aacaggtaaa gcttttaaag gtctaaatca aataggtgat       660
tataaatact atttcaattc tgatggagtt atgcaaaaag gatttgttag tataaatgat       720
aataaacact attttgatga ttctggtgtt atgaaagtag gttacactga aatagatggc       780
aagcatttct actttgctga aaacggagaa atgcaaatag gagtatttaa tacagaagat       840
ggatttaaat attttgctca tcataatgaa gatttaggaa atgaagaagg tgaagaaatc       900
tcatattctg gtatattaaa tttcaataat aaaatttact attttgatga ttcatttaca       960
gctgtagttg gatggaaaga tttagaggat ggttcaaagt attattttga tgaagataca      1020
gcagaagcat atataggttt gtcattaata aatgatggtc aatattttt taatgatgat      1080
ggaattatgc aagttggatt tgtcactata aatgataaag tcttctactt ctctgactct      1140
ggaattatag aatctggagt acaaaacata gatgacaatt atttctatat agatgataat      1200
ggtatagttc aaattggtgt atttgatact tcagatggat ataaatattt tgcacctgct      1260
aatactgtaa atgataatat ttacggacaa gcagttgaat atagtggttt agttagagtt      1320
ggggaagatg tatattattt tggagaaaca tatacaattg agactggatg gatatatgat      1380
atggaaaatg aaagtgataa atattatttc aatccagaaa ctaaaaaagc atgcaaaggt      1440
attaattaa ttgatgatat aaaatattat tttgatgaga agggcataat gagaacgggt      1500
cttatatcat ttgaaaataa taattattac tttaatgaga atggtgaaat gcaatttggt      1560
tatataaata tagaagataa gatgttctat tttggtgaag atggtgtcat gcagattgga      1620
gtatttaata caccagatgg atttaaatac tttgcacatc aaaatacttt ggatgagaat      1680
tttgagggag aatcaataaa ctatactggt tggttagatt tagatgaaaa gagatattat      1740
tttacagatg aatatattgc agcaactggt tcagttatta ttgatggtga ggagtattat      1800
tttgatcctg atacagctca attagtgatt agtgaatag                              1839

<210> SEQ ID NO 32
<211> LENGTH: 1839
<212> TYPE: DNA
```

<213> ORGANISM: Artificial Sequence
<220> FEATURE:
<223> OTHER INFORMATION: synthetic nucleotide sequence

<400> SEQUENCE: 32

```
agtgaagaaa ataaggtgtc acaagttaaa ataagattcg ttaatgtttt taaagataag      60
actttggcaa ataagctatc ttttaacttt agtgataaac aagatgtacc tgtaagtgaa     120
ataatcttat catttacacc ttcatactat gaggatggac tgataggcta tgacctgggc     180
ctggtttcat tgtataatga aagttttac atcaacaatt ttgggatgat ggtctctggg      240
ctaatctaca tcaatgattc gctttactat tttaaacccc ctgtgaacaa tctgattact     300
ggtttcgtta cagtggggga cgataaatac tatttcaacc caataaacgg cggagccgct     360
agtattggag aaactatcat agatgacaag aactactatt tcaatcagtc cggagtgctc     420
cagacaggag tctttagcac cgaagatggc ttcaagtatt tcgcccccgc gaataccctc     480
gatgagaacc ttgaggggga agccattgat ttcacgggca agctgatcat tgacgaaaac     540
atttactatt tcgacgataa ctacagaggt gcagtggagg ggaaagagtt agacggcgag     600
atgcattact ttagcccgga aaccggtaaa gcttttaaag gattgaatca aatcggtgac     660
tacaagtact attttaactc tgacggggtg atgcagaagg gcttcgtatc catcaacgac     720
aataagcact actttgatga ttctggtgtt atgaaagtag gttacactga aatagatggc     780
aagcatttct actttgctga aaacggagaa atgcaaatag gagtatttaa tacagaagat     840
ggatttaaat attttgctca tcataatgaa gatttaggaa atgaagaagg tgaagaaatc     900
tcatattctg gtatattaaa tttcaataat aaaaattact attttgatga ttcatttaca     960
gctgtagttg gatggaaaga tttagaggat ggttcaaagt attattttga tgaagataca    1020
gcagaagcat atataggttt gtcattaata aatgatggtc aatattattt taatgatgat    1080
ggaattatgc aagttggatt tgtcactata aatgataaag tcttctactt ctctgactct    1140
ggaattatag aatctggagt acaaaacata gatgacaatt atttctatat agatgataat    1200
ggtatagttc aaattggtgt atttgatact tcagatggat ataaatattt tgcacctgct    1260
aatactgtaa atgataatat ttacggacaa gcagttgaat atagtggttt agttagagtt    1320
ggggaagatg tatattattt tggagaaaca tatacaattg agactggatg gatatatgat    1380
atggaaaatg aaagtgataa atattatttc aatccagaaa ctaaaaaagc atgcaaaggt    1440
attaattaa ttgatgatat aaaatattat tttgatgaga agggcataat gagaacgggt    1500
cttatatcat ttgaaaataa taattattac tttaatgaga atggtgaaat gcaatttggt    1560
tatataaata tagaagataa gatgttctat tttggtgaag atggtgtcat gcagattgga    1620
gtatttaata caccagatgg atttaaatac tttgcacatc aaaatacttt ggatgagaat    1680
tttgagggag aatcaataaa ctatactggt tggttagatt tagatgaaaa gagatattat    1740
tttacagatg aatatattgc agcaactggt tcagttatta ttgatggtga ggagtattat    1800
tttgatcctg atacagctca attagtgatt agtgaatag                           1839
```

<210> SEQ ID NO 33
<211> LENGTH: 1839
<212> TYPE: DNA
<213> ORGANISM: Artificial Sequence
<220> FEATURE:
<223> OTHER INFORMATION: synthetic nucleotide sequence

<400> SEQUENCE: 33

```
agtgaagaaa ataaggtgtc acaagttaaa ataagattcg ttaatgtttt taaagataag      60
```

```
actttggcaa ataagctatc ttttaacttt agtgataaac aagatgtacc tgtaagtgaa        120
ataatcttat catttacacc ttcatattat gaggatggat tgattggcta tgatttgggt        180
ctagtttctt tatataatga gaaattttat attaataact ttggaatgat ggtatctgga        240
ttaatatata ttaatgattc attatattat tttaaaccac cagtaaataa tttgataact        300
ggatttgtga ctgtaggcga tgataagtat tacttcaatc ctattaacgg cggggcggct        360
tcaatcgggg aaaccataat tgacgataag aactactatt tcaaccaatc cggggtcctg        420
cagacaggag tgttttctac cgaggatgga ttcaaatact tgctcccgc caacacatta         480 gacgagaatc tagagggcga agccattgat tttacaggga aactcatcat tgacgagaac        540
atctactatt tcgatgacaa ttacagaggc gccgtcgaat ggaaagagct cgacggtgag        600
atgcattact ttagcccaga gaccggtaaa gccttcaaag gactgaacca gatcggcgac        660
tacaagtatt actttaacag tgatggagtg atgcagaagg gtttcgtgtc aataaatgac        720
aataaacatt actttgacga tagcggtgta atgaaggttg gctacactga aatcgatggc        780
aagcacttct attttgcaga aaacggcgag atgcagatag gcgtgtttaa cacggaggat        840
ggatttaagt acttcgccca ccacaatgaa gaccttggaa atgaggaagg tgaagagatt        900
tcttattcgg ggatcttgaa cttaacaat aaaatttact atttcgatga cagcttcacc         960
gcagtcgttg gtggaagga cctggaagac gggtccaagt attcttcga tgaggacact        1020 gcagaggctt atatcggact gagtcttatc aatgacggcc agtattattt caatgatgat       1080
ggaatcatgc aagtgggctt tgtcactata aatgataaag tcttctactt ctctgactct       1140
ggaattatag aatctggagt acaaaacata gatgacaatt atttctatat agatgataat       1200
ggtatagttc aaattggtgt atttgatact tcagatggat ataaatttt tgcacctgct        1260 aatactgtaa atgataatat ttacggacaa gcagttgaat atagtggttt agttagagtt       1320
ggggaagatg tatattattt tggagaaaca tatacaattg agactggatg gatatatgat       1380
atggaaaatg aaagtgataa atattatttc aatccagaaa ctaaaaaagc atgcaaaggt       1440
attaatttaa ttgatgatat aaaatattat tttgatgaga agggcataat gagaacgggt       1500
cttatatcat ttgaaaataa taattattac tttaatgaga atggtgaaat gcaatttggt       1560
tatataaata tagaagataa gatgttctat tttggtgaag atggtgtcat gcagattgga       1620
gtatttaata caccagatgg atttaaatac tttgcacatc aaaatacttt ggatgagaat       1680
tttgagggag aatcaataaa ctatactggt tggttagatt tagatgaaaa gagatattat       1740
tttacagatg aaatatattgc agcaactggt tcagttatta ttgatggtga ggagtattat       1800
tttgatcctg atacagctca attagtgatt agtgaatag                              1839
```

<210> SEQ ID NO 34
<211> LENGTH: 1748
<212> TYPE: DNA
<213> ORGANISM: Artificial Sequence
<220> FEATURE:
<223> OTHER INFORMATION: synthetic nucleotide sequence

<400> SEQUENCE: 34

```
agtgaagaaa ataaggtgtc acaagttaaa ataagattcg ttaatgtttt taaagataag         60
actttggcaa ataagctatc ttttaacttt agtgataaac aagatgtacc tgtaagtgaa        120
ataatcttat catttacacc ttcatattat gaggatggat tgattggcta tgatttgggt        180
ctagtttctt tatataatga gaaattttat attaataact ttggaatgat ggtatctgga        240
```

```
ttaatatata ttaatgattc attatattat tttaaaccac cagtaaataa tttgataact    300
ggatttgtga ctgtaggcga tgataaatac tactttaatc caattaatgg tggagctgct    360
tcaattggag agacaataat tgatgacaaa aattattatt tcaaccaaag tggagtgtta    420
caaacaggtg tatttagtac agaagataat atttactatt ttgatgacaa ctataggggc    480
gcagtggagt ggaaagaact ggatggagag atgcactatt ttagccctga acaggcaaa     540 gcattcaagg gattaaacca aatttgggga tacaaatact atttcaatag cgacggagta    600
atgcagaagg ggttcgtctc catcaatgat aacaagcatt actttgacga ttcaggcgtt    660
atgaaagtgg gctatactga gatcgatggg aagcacttct actttgctga gaacggcgaa    720
atgcagattg gtgtgttcaa tactgaagac ggttttaaat atttcgcaca tcacaatgag    780
gatcttggca atgaagaggg agaagagata agttactctg gtatcctgaa cttcaacaat    840
aaaatctact atttcgacga ttcgttcacc gccgtggtcg gatggaagga ccttgaagat    900
gggagcaagt attactttga cgaagataca gccgaggcgt atattggcct cagtctgatt    960
aacgacggac agtattactt taacgacgat ggcatcatgc aggtcggatt cgtgacaatc   1020
aatgacaagg tattttactt ttctgactct ggaataatcg aatcaggagt gcagaacatt   1080
gacgataact acttttacat cgatgacaat ggcatcgtcc agatcggcgt gtttgacaca   1140
tccgacgggt ataagtactt cgccccagct aacactgtta acgacaacat ttacggccaa   1200
gccgttgagt attccggtct agtgagagtg ggggaggacg tctactattt cggtgagacc   1260
tacaccatag agaccgggtg gatttatgat atggaaaatg aaagtgataa atattatttc   1320
aatccagaaa ctaaaaaagc atgcaaaggt attaatttaa ttgatgatat aaaatattat   1380
tttgatgaga agggcataat gagaacggtc ttatatcatt tgaaaataat aattattact   1440
ttaatgaaaa tggtgaaatg caatttggtt atataaatat agaagataag atgttctatt   1500
ttggtgaaga tggtgtcatg cagattggag tatttaatac accagatgga tttaaatact   1560
ttgcacatca aaatactttg gatgagaatt ttgagggaga atcaataaac tatactggtt   1620
ggttagattt agatgaaaag agatattatt ttacagatga atatattgca gcaactggtt   1680
cagttattat tgatggtgag gagtattatt ttgatcctga tacagctcaa ttagtgatta   1740
gtgaatag                                                             1748
```

<210> SEQ ID NO 35
<211> LENGTH: 1839
<212> TYPE: DNA
<213> ORGANISM: Artificial Sequence
<220> FEATURE:
<223> OTHER INFORMATION: synthetic nucleotide sequence

<400> SEQUENCE: 35

```
agtgaagaaa ataaggtgtc acaagttaaa ataagattcg ttaatgtttt taaagataag     60
actttggcaa ataagctatc ttttaacttt agtgataaac aagatgtacc tgtaagtgaa    120
ataatcttat catttacacc ttcatattat gaggatggat tgattggcta tgatttgggt    180
ctagtttctt tatataatga gaaatttttat attaataact ttggaatgat ggtatctgga    240
ttaatatata ttaatgattc attatattat tttaaaccac cagtaaataa tttgataact    300
ggatttgtga ctgtaggcga tgataaatac tactttaatc caattaatgg tggagctgct    360
tcaattggag agacaataat tgatgacaaa aattattatt tcaaccaaag tggagtgtta    420
caaacaggtg tatttagtac agaagatgga tttaaatatt ttgccccagc taatacactt    480
gatgaaaacc tagaaggaga agcaattgat tttactggaa aattaattat tgacgaaaat    540
```

```
atttattatt ttgatgataa ttatagagga gctgtagaat ggaaagaatt agatggtgaa      600
atgcactatt ttagcccaga acaggtaaag cttttaaag gtctaaatca aataggtgat      660
tataaatact atttcaacag tgacggggtt atgcagaaag gtttcgtgag tattaatgac     720
aataagcatt atttcgacga tagcggagtg atgaaggtcg gctacaccga aatcgatggg    780
aaacactttt actttgcaga aaatggagaa atgcaaatag gcgtgttcaa taccgaggat    840
ggcttcaagt atttcgcaca ccataatgag gatctgggga acgaagaggg ggaggaaata   900
agctattctg gcatcctcaa ctttaacaat aagatttact atttcgacga ttcgttcacc    960
gccgttgtcg gctggaaaga cttagaggat ggctctaaat actatttcga tgaggacacg   1020
gccgaggcgt atatcggcct gtcacttatc aatgacggcc agtactattt caatgatgac   1080
gggatcatgc aggtggggtt cgtcactatt aacgataaag ttttctactt ttccgatagc   1140
ggaatcatag aatccggagt acagaacatt gacgataact attttttacat tgacgataat  1200 gggattgtcc agatcggggt attcgacaca tctgacggat acaaatactt tgccccagct   1260
aacaccgtga acgacaatat ttatggacag gccgtggagt atagcggttt ggtacgggtg   1320
ggcgaagatg tgtactattt tggagagact tacaccattg agaccgggtg gatttatgac   1380
atggagaacg agtccgataa gtattacttt aatccggaga caaaaaaggc ttgcaagggc    1440
atcaacctga tcgatgacat caaatactat tttgacgaga agggaataat gaggactgga    1500
cttatatcat ttgaaaacaa taactactat tttaacgaaa atggggaaat gcaatttggt    1560
tacattaata tcgaggataa gatgttttac tttggcgaag atggtgtgat gcagattggt    1620
gtctttaaca cacccgacgg cttcaagtat ttcgcacacc aaaacacgct ggacgaaaac   1680
ttcgagggcg agtccatcaa ttacactggt tggctcgacc tggatgaaaa gagatattac    1740
ttcacagatg agtacatcgc tgccactgga agtgttatca ttgacggtga ggaatactac    1800
ttcgaccctg acacagctca gctagtgatc tcagagtag                            1839
```

<210> SEQ ID NO 36
<211> LENGTH: 1839
<212> TYPE: DNA
<213> ORGANISM: Artificial Sequence
<220> FEATURE:
<223> OTHER INFORMATION: synthetic nucleotide sequence

<400> SEQUENCE: 36

```
agtgaagaaa ataaggtgtc acaagttaaa ataagattcg ttaatgtttt taaagataag    60
actttggcaa ataagctatc ttttaacttt agtgataaac aagatgtacc tgtaagtgaa   120
ataatcttat catttacacc ttcatattat gaggatggat tgattggcta tgatttgggt    180
ctagtttctt tatataacga aaaattttac attaataact ttgggatgat ggtgtcaggg    240
cttatctaca tcaacgactc cctgtattac tttaagccgc ccgtcaacaa tttaatcacg    300
ggattcgtca ctgtcgggga cgataaatac tatttcaacc caattaacgg cggggcagcc   360
tctataggtg agactatcat tgacgataag aattactatt tcaatcagag cggggtgcta    420
caaaccggtg tgtttagcac tgaggacggt tttaaatact tcgcccccgc caacacactg    480
gacgaaaacc tcgaaggaga ggccatcgat ttcactgaaa aactgatcat tgacgaaaac   540
atttattact ttgatgacaa ctacagggga gccgttgaat ggaaggagct ggatggggag   600
atgcactact tctctcctga aactggtaag gcgtttaagg gacttaatca gatagggat     660 tataaatact atttcaactc cgacggagta atgcagaaag gctttgtgag catcaatgat   720
```

```
aataaacatt atttcgacga ttcaggcgtg atgaaagtgg gctacacaga aattgacggc    780
aagcactttt acttcgctga gaacggtgag atgcagatcg gcgtcttcaa cacagaagac    840
ggatttaaat atttcgctca ccataatgag gacctgggca acgaggaagg cgaagagatc    900
tcctactctg gcatcttgaa ttttaacaat aagatttatt actttgatga cagcttcaca    960
gctgtcgttg gctggaagga tctggaagat gggtcaaaat actatttcga cgaggacaca   1020
gcagaggcat acatcgggct cagtttgata acgacgggc aatattactt caatgatgac   1080
ggaattatgc aagtaggctt cgtgaccatt aatgacaagg tgttctactt ctctgatagc   1140
ggaattatcg agagtggtgt gcagaatatc gacgataact attttatat tgacgataac   1200 gggatagtcc agatcggcgt gtttgatacc tcggatggat acaagtactt cgcgccagct   1260
aataccgtga atgacaacat ctacggccag gccgttgaat atagtggtct cgtgagagta   1320
ggcgaggacg tttattactt tggcgagacc tatacgattg agaccggctg gatatacgac   1380
atggagaatg aatccgataa gtattacttc aatcctgaga ccaaaaaggc atgcaaggga   1440
ataaacctga tcgatgacat caagtattat tttgatgaga agggtattat gcggacaggt   1500
cttatatcat ttgaaaataa taattattac tttaatgaga atggtgaaat gcaatttggt   1560
tatataaata tagaagataa gatgttctat tttggtgaag atggtgtcat gcagattgga   1620
gtatttaata caccagatgg atttaaatac tttgcacatc aaaatacttt ggatgagaat   1680
tttgagggag aatcaataaa ctatactggt tggttagatt tagatgaaaa gagatattat   1740
tttacagatg aatatattgc agcaactggt tcagttatta ttgatggtga ggagtattat   1800
tttgatcctg atacagctca attagtgatt agtgaatag                          1839

<210> SEQ ID NO 37
<211> LENGTH: 1839
<212> TYPE: DNA
<213> ORGANISM: Artificial Sequence
<220> FEATURE:
<223> OTHER INFORMATION: synthetic nucleotide sequence

<400> SEQUENCE: 37
agtgaagaaa ataaggtgtc acaagtgaag atcagattcg tgaatgtttt taaagacaaa     60
acgttggcga acaagctttc attcaacttt agtgacaaac aagacgtgcc cgtgtccgaa    120
ataatcctga gcttcacccc cagctattac gaggacggac ttatcggata cgaccttgga    180
ctggtatcct tatataacga gaaattctat attaacaatt ttgggatgat ggtctccggc    240
ctgatttaca taaatgacag tctatattac tttaagccgc ccgtcaacaa tctcatcacg    300
ggcttcgtaa ctgtcggcga cgataagtat tactttaacc ctatcaacgg aggggcagct    360
agtatagggg agacgatcat tgatgacaaa aattactatt ttaatcagtc tggagttctc    420
cagacaggcg tgttttcaac agaagacggg ttcaagtact tcgcaccagc taacacattg    480
gatgagaacc tggagggaga agctatcgat tttactggca agctgatcat agatgagaac    540
atttattact tcgatgacaa ctatcggggt gccgttgaat ggaaggagct cgatggggag    600
atgcactact ctctcctga acaggcaag gccttcaaag gctcaatca gattggagac    660 tataaatact atttcaactc cgatggcgtg atgcaaaaag gttttgtgtc tattaatgac    720
aacaagcact attttgatga ctctggcgtt atgaaggtag gctacacaga gatcgatggc    780
aagcatttct atttcgcaga aaacggcgag atgcagattg gtgtgttcaa taccgaagat    840
ggcttcaagt atttcgccca ccataatgag gatctgggga atgaggaagg cgaagagata    900
agctatagcg gaattctgaa tttcaacaat aagatctatt actttgatga cagcttcacc    960
```

```
gccgttgtgg gttggaaaga tttagaagat gggtcgaaat actattttga tgaggatacc      1020
gcggaagcct acatcggtct ctccttgata acgacggtc  agtactattt caatgacgat      1080
gggatcatgc aggtggggtt tgtcaccatt aacgataagg tcttttattt tagtgattca      1140
ggaattatcg agagcggggt gcagaatatc gacgataatt atttctacat cgacgataat      1200
ggaatcgtcc agatcggagt atttgacact tccgatggct acaaatactt cgctccagcc      1260
aacaccgtta acgacaatat ctacggacag gccgtgaat  actctggtct ggtgcgcgtc      1320
ggcgaggacg tgtactattt tggtgaaacc tacactattg agaccggctg gatctacgac      1380
atggagaatg aatcagacaa gtactatttc aaccctgaga ctaagaaagc atgcaagggc      1440
attaacctga tagacgacat taaatactac tttgacgaga agggaattat gaggacaggg      1500
ctaattagct ttgaaaataa taattattac tttaatgaga atggtgaaat gcaatttggt      1560
tatataaata tagaagataa gatgttctat tttggtgaag atggtgtcat gcagattgga      1620
gtatttaata caccagatgg atttaaatac tttgcacatc aaaatacttt ggatgagaat      1680
tttgagggag aatcaataaa ctatactggt tggttagatt tagatgaaaa gagatattat      1740
tttacagatg aatatattgc agcaactggt tcagttatta ttgatggtga ggagtattat      1800
tttgatcctg atacagctca attagtgatt agtgaatag                              1839

<210> SEQ ID NO 38
<211> LENGTH: 1839
<212> TYPE: DNA
<213> ORGANISM: Artificial Sequence
<220> FEATURE:
<223> OTHER INFORMATION: synthetic nucleotide sequence

<400> SEQUENCE: 38
agtgaagaaa ataaggtgtc acaagttaaa ataagattcg ttaatgtttt taaagataag        60
actttggcaa ataagctttc attcaacttc agcgataaac aggacgtccc ggtatccgaa       120
attatcctgt cctttacccc cagctactat gaggacggcc tgatcggata tgatctaggg       180
ctggtgtcat tatacaatga gaagttttac atcaacaatt tcggaatgat ggtgagtggt       240
ctgatctaca tcaatgatag cctttactat ttcaagcctc ccgttaataa ccttataacc       300
ggatttgtaa cagtgggcga tgacaaatac tattttaacc caatcaacgg aggtgccgca       360
tcgatagggg aaactattat agacgataaa aactattact tcaatcaaag tggcgtgttg       420
caaactggcg tgtttagcac ggaggatggg ttcaagtact tgctcccgc  taacacactg       480 gacgaaaacc tcgagggtga ggcgattgat tttacaggga agctgatcat tgacgagaac       540
atttattact tcgacgataa ttacaggggt gccgttgaat ggaaggagtt agacggcgag       600
atgcattact tttcacctga aacggggaag gcattcaaag gactcaatca gatcgggat       660 tacaagtatt actttaacag tgatggcgtc atgcagaaag gattcgtttc tattaacgac       720
aataagcact acttcgatga ctccggagtc atgaaagtgg gtatacgga  aatagacggg       780 aagcatttct atttttgcaga gaacggagaa atgcaaattg gagtctttaa tacagaggat       840
ggctttaagt atttcgccca ccataacgag gacctaggta atgaagaggg agaggaaatt       900
tcctactctg ggatattgaa tttcaacaat aaaatctact attttgacga ttcctttaca       960
gccgtggtag ggtggaaaga cctggaagat ggatctaaat actattttga cgaggacaca      1020
gccgaggcct acattggcct ctctctgatc aatgacggcc agtactattt caacgacgat      1080
gggatcatgc aggtgggatt cgtcaccatc aatgacaaag tgttctactt tagcgatagc      1140
```

| | |
|---|---|
| gggatcattg aatcaggcgt ccaaaacatt gatgacaact attttatat cgacgataac | 1200 |
| ggcattgtgc agataggtgt gttcgacacc tcggatgggt acaaatattt cgctcctgcg | 1260 |
| aacaccgtta atgataatat ttacggccag gccgtagaat acagtggcct cgtgagagtt | 1320 |
| ggtgaggacg tgtattactt tggagagacc tatactatcg agactggctg gatttatgac | 1380 |
| atggagaatg agtctgacaa atattacttt aacccagaga ctaagaaagc ttgcaaggga | 1440 |
| atcaacttga ttgatgacat taagtactat tttgacgaaa agggcatcat gcgcacaggc | 1500 |
| ctgatatcct ttgagaacaa taactattac ttcaatgaga atggcgaaat gcagttcggt | 1560 |
| tacatcaaca tcgaggacaa gatgttctac ttcggtgaag acggcgtcat gcagatcggc | 1620 |
| gtgtttaaca ccccagatgg attcaagtat ttcgcacacc agaatactct tgatgaaaac | 1680 |
| ttcgaaggcg aaagcatcaa ttacaccggg tggctggatc tcgatgagaa gcggtattac | 1740 |
| ttcacagatg aatatattgc agcaactggt tcagttatta ttgatggtga ggagtattat | 1800 |
| tttgatcctg atacagctca attagtgatt agtgaatag | 1839 |

<210> SEQ ID NO 39
<211> LENGTH: 2619
<212> TYPE: DNA
<213> ORGANISM: Clostridium difficile

<400> SEQUENCE: 39

| | |
|---|---|
| tcattattct attttgatcc tatagaattt aacttagtaa ctggatggca aactatcaat | 60 |
| ggtaaaaaat attatttga tataaatact ggagcagctt aactagtta taaaattatt | 120 |
| aatggtaaac acttttattt taataatgat ggtgtgatgc agttgggagt atttaaagga | 180 |
| cctgatggat ttgaatattt tgcacctgcc aatactcaaa ataataacat agaaggtcag | 240 |
| gctatagttt atcaaagtaa attcttaact ttgaatggca aaaaatatta ttttgataat | 300 |
| aactcaaaag cagtcactgg atggagaatt attaacaatg agaaatatta ctttaatcct | 360 |
| aataatgcta ttgctgcagt cggattgcaa gtaattgaca ataataagta ttatttcaat | 420 |
| cctgacactg ctatcatctc aaaaggttgg cagactgtta atggtagtag atactacttt | 480 |
| gatactgata ccgctattgc ctttaatggt tataaaacta ttgatggtaa acactttat | 540 |
| tttgatagtg attgtgtagt gaaataggt gtgtttagta cctctaatgg atttgaatat | 600 |
| tttgcacctg ctaatactta taataataac atagaaggtc aggctatagt ttatcaaagt | 660 |
| aaattcttaa ctttgaatgg taaaaaatat tactttgata taactcaaa agcagttacc | 720 |
| ggatggcaaa ctattgatag taaaaaatat tactttaata ctaacactgc tgaagcagct | 780 |
| actggatggc aaactattga tggtaaaaaa tattacttta atactaacac tgctgaagca | 840 |
| gctactggat ggcaaactat tgatggtaaa aatatattact ttaatactaa cactgctata | 900 |
| gcttcaactg gttatacaat tattaatggt aaacattttt attttaatac tgatggtatt | 960 |
| atgcagatag gagtgtttaa aggacctaat ggatttgaat attttgcacc tgctaatacg | 1020 |
| gatgctaaca acatagaagg tcaagctata ctttaccaaa atgaattctt aactttgaat | 1080 |
| ggtaaaaaat attactttgg tagtgactca aaagcagtta ctggatggag aattattaac | 1140 |
| aataagaaat attactttaa tcctaataat gctattgctg caattcatct atgcactata | 1200 |
| aataatgaca agtattactt tagttatgat ggaattcttc aaaatggata tattactatt | 1260 |
| gaaagaaata atttctatt tgatgctaat aatgaatcta aatggtaac aggagtattt | 1320 |
| aaaggaccta atggatttga gtattttgca cctgctaata ctcacaataa taacatagaa | 1380 |
| ggtcaggcta tagttaccaa gaacaaattc ttaactttga atggcaaaaa atattatttt | 1440 |

```
gataatgact caaaagcagt tactggatgg caaaccattg atggtaaaaa atattacttt    1500
aatcttaaca ctgctgaagc agctactgga tggcaaacta ttgatggtaa aaatattac    1560 tttaatctta acactgctga agcagctact ggatggcaaa ctattgatgg taaaaaatat    1620
tactttaata ctaacacttt catagcctca actggttata caagtattaa tggtaaacat    1680
ttttatttta atactgatgg tattatgcag ataggagtgt ttaaaggacc taatggattt    1740
gaatactttg cacctgctaa tacgatgct aacaacatag aaggtcaagc tatactttac    1800
caaaataaat tcttaacttt gaatggtaaa aaatattact tggtagtga ctcaaaagca    1860 gttaccggac tgcgaactat tgatggtaaa aaatattact taatactaa cactgctgtt    1920 gcagttactg gatggcaaac tattaatggt aaaaaatact actttaatac taacacttct    1980
atagcttcaa ctggttatac aattattagt ggtaaacatt tttatttaa tactgatggt    2040 attatgcaga taggagtgtt taaaggacct gatggatttg aatactttgc acctgctaat    2100
acagatgcta acaatataga aggtcaagct atacgttatc aaaatagatt cctatattta    2160
catgacaata tatattattt tggtaataat tcaaaagcgg ctactggttg ggtaactatt    2220
gatggtaata gatattactt cgagcctaat acagctatgg gtgcgaatgg ttataaaact    2280
attgataata aaattttta ctttagaaat ggtttacctc agataggagt gtttaaaggg    2340
tctaatggat ttgaatactt tgcacctgct aatacggatg ctaacaatat agaaggtcaa    2400
gctatacgtt atcaaaatag attcctacat ttacttggaa aaatatatta ctttggtaat    2460
aattcaaaag cagttactgg atggcaaact attaatggta agtatatta ctttatgcct    2520 gatactgcta tggctgcagc tggtggactt ttcgagattg atggtgttat atatttcttt    2580
ggtgttgatg gagtaaaagc ccctgggata tatggctaa                          2619

<210> SEQ ID NO 40
<211> LENGTH: 1839
<212> TYPE: DNA
<213> ORGANISM: Clostridium difficile

<400> SEQUENCE: 40
agtgaagaaa ataaggtgtc acaagttaaa ataagattcg ttaatgtttt taaagataag      60
actttggcaa ataagctatc ttttaacttt agtgataaac aagatgtacc tgtaagtgaa     120
ataatcttat catttacacc ttcatattat gaggatggat tgattggcta tgatttgggt     180
ctagtttctt tatataatga gaaatttat attaataact ttggaatgat ggtatctgga     240
ttaatatata ttaatgattc attatattat tttaaaccac cagtaaataa tttgataact     300
ggatttgtga ctgtaggcga tgataaatac tactttaatc caattaatgg tggagctgct     360
tcaattggag agacaataat tgatgacaaa attattatt tcaaccaaag tggagtgtta     420
caaacaggtg tatttagtac agaagatgga tttaaatatt ttgccccagc taatacactt     480
gatgaaaacc tagaaggaga agcaattgat tttactggaa aattaattat tgacgaaaat     540
atttattatt ttgatgataa ttatagagga gctgtagaat ggaaagaatt agatggtgaa     600
atgcactatt ttagcccaga aacaggtaaa gcttttaaag gtctaaatca aataggtgat     660
tataaatact atttcaattc tgatggagtt atgcaaaaag gatttgttag tataaatgat     720
aataaacact attttgatga ttctggtgtt atgaaagtag gttacactga aatagatggc     780
aagcatttct actttgctga aaacggagaa atgcaaatag gagtatttaa tacagaagat     840
ggatttaaat attttgctca tcataatgaa gatttaggaa atgaagaagg tgaagaaatc     900
```

```
tcatattctg gtatattaaa tttcaataat aaaatttact attttgatga ttcatttaca    960
gctgtagttg gatggaaaga tttagaggat ggttcaaagt attattttga tgaagataca   1020
gcagaagcat ataggtttt gtcattaata aatgatggtc aatattattt taatgatgat    1080
ggaattatgc aagttggatt tgtcactata aatgataaag tcttctactt ctctgactct   1140
ggaattatag aatctggagt acaaaacata gatgacaatt atttctatat agatgataat   1200
ggtatagttc aaattggtgt atttgatact tcagatggat ataaatattt tgcacctgct   1260
aatactgtaa atgataatat ttacggacaa gcagttgaat atagtggttt agttagagtt   1320
ggggaagatg tatattattt tggagaaaca tatacaattg agactggatg gatatatgat   1380
atggaaaatg aaagtgataa atattatttc aatccagaaa ctaaaaaagc atgcaaaggt   1440
attaatttaa ttgatgatat aaaatattat tttgatgaga agggcataat gagaacgggt   1500
cttatatcat ttgaaaataa taattattac tttaatgaga atggtgaaat gcaatttggt   1560 tatataaaata tagaagataa gatgttctat tttggtgaag atggtgtcat gcagattgga   1620
gtatttaata caccagatgg atttaaatac tttgcacatc aaaatacttt ggatgagaat   1680
tttgagggag aatcaataaa ctatactggt tggttagatt tagatgaaaa gagatattat   1740
tttacagatg aaatatattgc agcaactggt tcagttatta ttgatggtga ggagtattat   1800
tttgatcctg atacagctca attagtgatt agtgaatag                          1839
```

<210> SEQ ID NO 41
<211> LENGTH: 1839
<212> TYPE: DNA
<213> ORGANISM: Artificial Sequence
<220> FEATURE:
<223> OTHER INFORMATION: synthetic nucleotide sequence

<400> SEQUENCE: 41

```
agcgaggaga acaaggtgag ccaagtgaag attagattcg tgaacgtgtt caaggacaag     60
acactggcca acaagctgag cttcaacttc agcgacaagc aagacgtgcc tgtgagcgag    120
attattctga gcttcacacc tagctattat gaggacggcc tgattggcta tgacctgggc    180
ctggtgagcc tgtataacga gaagttctat attaacaact tcggcatgat ggtgagcggc    240
ctgatttata ttaacgacag cctgtactac ttcaagcctc tgtgaacaa cctgatcacc     300 ggcttcgtga ccgtgggcga cgacaagtac tacttcaacc ctatcaacgg cggcgcagcc    360
agcatcggcg agaccatcat cgacgacaag aactactact caaccagag cggcgtgctg     420 cagaccggcg tgttcagcac cgaggacggc ttcaagtact tcgcccctgc caacaccctg    480
gacgagaacc tggagggcga ggccatcgac ttcaccggca agctgatcat cgacgagaac    540
atctactact tcgacgacaa ctacagaggc gccgtggagt ggaaggagct ggacggcgag    600
atgcattact tcagccctga gaccggcaag gccttcaagg gcctgaacca gatcggcgac    660
gacaagtact acttcaacag cgacggcgtg atgcagaagg gcttcgtgag catcaacgac    720
aacaagcatt acttcgacga cagcggcgtg atgaaggtgg gctacaccga gatcgacggc    780
aagcatttct acttcgccga gaacggcgag atgcagatcg gcgtgttcaa caccgaggac    840
ggcttcaagt acttcgccca tcataacgag gacctgggca acgaggaggg cgaggagatc    900
agctacagcg gcatcctgaa cttcaacaac aagatctact acttcgacga cagcttcacc    960
gccgtggtgg gctggaagga cctggaggac ggcagcaagt actacttcga cgaggacacc   1020
gccgaggcct acatcggcct gagcctgatc aacgacggcc agtactactt caacgacgac   1080
ggcatcatgc aggtgggctt cgtgaccatc aacgacaagg tgttctactt cagcgacagc   1140
```

```
ggcatcatcg agagcggcgt gcagaacatc gacgacaact acttctacat cgacgacaac   1200
ggcatcgtgc agatcggcgt gttcgacacc agcgacggct acaagtactt cgcccctgcc   1260
aacaccgtga acgacaacat ctacggccag gccgtggagt acagcggcct ggtgagagtg   1320
ggcgaggacg tgtactactt cggcgagacc tacaccatcg agaccggctg gatctacgac   1380
atggagaacg agagcgacaa gtactacttc aaccctgaga ccaagaaggc ctgcaagggc   1440
atcaacctga tcgacgacat caagtactac ttcgacgaga agggcatcat gagaaccggc   1500
ctgatcagct tcgagaataa caactactac ttcaacgaga acggcgagat gcagttcggc   1560
tacatcaaca tcgaggacaa gatgttctac ttcggcgagg acggcgtgat gcagatcggc   1620
gtgttcaaca cccctgacgg cttcaagtac ttcgcccatc agaacacccct ggacgagaac   1680 ttcgagggcg agagcatcaa ctacaccggc tggctggacc tggacgagaa gagatactac   1740
ttcaccgacg agtacatcgc cgccaccggc agcgtgatca tcgacggcga ggagtactac   1800
ttcgaccctg acaccgccca gctggtgatc agcgagtaa                           1839
```

What is claimed is:

1. A method for reducing the risk of a *Clostridium difficile* infection in a human, the method comprising administering to the human an effective amount of a DNA molecule comprising the receptor binding domain of toxin A codon-optimized gene represented by SEQ ID NO: 9 and the receptor binding domain of toxin B codon-optimized gene represented by SEQ ID NO: 41.

* * * * *